United States Patent
Weiss et al.

(10) Patent No.: US 11,351,271 B2
(45) Date of Patent: Jun. 7, 2022

(54) RNA-BASED LOGIC CIRCUITS WITH RNA BINDING PROTEINS, APTAMERS AND SMALL MOLECULES

(71) Applicants: Massachusetts Institute of Technology, Cambridge, MA (US); Kyoto University, Kyoto (JP)

(72) Inventors: Ron Weiss, Newton, MA (US); Liliana Wroblewska, Wilmington, MA (US); Velia Siciliano, Cambridge, MA (US); Tasuku Kitada, Ghent (BE); Maria Hottelet Foley, Cambridge, MA (US); Katie Bodner, Stanford, CA (US); Hirohide Saito, Kyoto (JP); Kei Endo, Chiba (JP); Darrell J. Irvine, Arlington, MA (US); Tyler Wagner, Bel Air, MD (US); Jacob Becraft, Boston, MA (US)

(73) Assignees: Massachusetts Institute of Technology, Cambridge, MA (US); Kyoto University, Kyoto (JP)

( * ) Notice: Subject to any disclaimer, the term of this patent is extended or adjusted under 35 U.S.C. 154(b) by 772 days.

(21) Appl. No.: 15/509,258

(22) PCT Filed: Sep. 8, 2015

(86) PCT No.: PCT/US2015/049045
§ 371 (c)(1),
(2) Date: Mar. 7, 2017

(87) PCT Pub. No.: WO2016/040395
PCT Pub. Date: Mar. 17, 2016

(65) Prior Publication Data
US 2018/0296702 A1    Oct. 18, 2018
US 2019/0151474 A2    May 23, 2019

Related U.S. Application Data

(60) Provisional application No. 62/195,747, filed on Jul. 22, 2015, provisional application No. 62/047,137, filed on Sep. 8, 2014.

(51) Int. Cl.
| | |
|---|---|
| *C12N 15/11* | (2006.01) |
| *A61K 48/00* | (2006.01) |
| *C12N 15/63* | (2006.01) |
| *C12N 15/10* | (2006.01) |
| *C12N 15/85* | (2006.01) |

(52) U.S. Cl.
CPC .......... *A61K 48/0066* (2013.01); *C12N 15/10* (2013.01); *C12N 15/63* (2013.01); *C12N 15/85* (2013.01); *C12N 2840/102* (2013.01)

(58) Field of Classification Search
CPC .... A61K 48/0066; C12N 15/63; C12N 15/85; C12N 2840/102
See application file for complete search history.

(56) References Cited

U.S. PATENT DOCUMENTS

| | | |
|---|---|---|
| 2009/0098561 A1 | 4/2009 | Smolke et al. |
| 2011/0040077 A1* | 2/2011 | Inoue ............ C12N 15/67 |
| | | 530/409 |

FOREIGN PATENT DOCUMENTS

| | | |
|---|---|---|
| EP | 2221367 A1 | 8/2010 |
| EP | 2390324 A1 | 11/2011 |
| WO | WO 2002/062949 A2 | 8/2002 |
| WO | WO 2006/056825 A1 | 6/2006 |
| WO | WO 2008/134593 A1 | 11/2008 |
| WO | WO 2012/012739 A2 | 1/2012 |

OTHER PUBLICATIONS

Qi Dissertation (2012) (Year: 2012).*
Nissim et al. in "Multiplexed and Programmable Regulation of Gene Networks with an Integrated RNA and CRISPR/Cas Toolkit in Human Cells" (Molecular Cell vol. 54, Issue 4, May 22, 2014, pp. 698-710). (Year: 2014).*
Qi et al ("RNA processing enables predictable programming of gene expression." Nat Biotechnol. 2012 vol. 30, pp. 1002-1006). (Year: 2012).*
Xie et al in "Multi-input RNAi-based logic circuit for identification of specific cancer cells". (Science 333, 1307-1311, 2011) (Year: 2011).*
Davidson & Ellington "Synthetic RNA circuits" (Nature Chemical Biology vol. 3, No. 1: Jan. 1, 2007, pp. 23-28). (Year: 2007).*
Patel Dissertation (Drexel University, Oct. 2010 entitled: "microRNA mediated regulation of APP gene expression"). (Year: 2010).*
Benenson, Synthetic biology with RNA: progress report. Curr Opin Chem Biol. 2012; 16:278-84.
Caban et al., The L7Ae RNA binding motif is a multifunctional domain required for the ribosome-dependent Sec incorporation activity of Sec insertion sequence binding protein 2. Mol Cell Biol. Sep. 2007;27(18):6350-60. doi:10.1128/MCB.00632-07. Epub Jul. 16, 2007.
Leisner et al., Rationally-designed logic integration of regulatory signals in mammalian cells. Nat Nanotechnol. Sep. 2010;5(9):666-70. doi: 10.1038/nnano.2010.135. Epub Jul. 11, 2010.
Rinaudo et al., A universal RNAi-based logic evaluator that operates in mammalian cells. Nat Biotechnol. Jul. 2007;25(7):795-801. doi:10.1038/nbt1307. Epub May 21, 2007.
Saito et al., Synthetic translational regulation by an L7Ae-kink-turn RNP switch. Nat Chem Biol. Jan. 2010;6(1):71-8. doi: 10.1038/nchembio.273. Epub Dec. 13, 2009.
Siciliano et al., miRNAs confer phenotypic robustness to gene networks by suppressing biological noise. Nat Commun. 2013;4:2364. doi: 10.1038/ncomms3364.
Xie et al., Multi-input RNAi-based logic circuit for identification of specific cancer cells. Science. Sep. 2, 2011;333(6047):1307-11. doi: 10.1126/science.1205527. Supplemental Information.

(Continued)

*Primary Examiner* — Catherine S Hibbert
(74) *Attorney, Agent, or Firm* — Wolf, Greenfield & Sacks, P.C.

(57) ABSTRACT

Engineered synthetic RNA-based genetic circuits are provided that are regulated exclusively at the post-transcriptional level.

15 Claims, 95 Drawing Sheets
Specification includes a Sequence Listing.

(56) References Cited

OTHER PUBLICATIONS

Ai et al., Exploration of new chromophore structures leads to the identification of improved blue fluorescent proteins. Biochemistry. May 22, 2007;46(20):5904-10.
An et al., Artificial control of gene expression in mammalian cells by modulating RNA interference through aptamer-small molecule interaction. RNA. May 2006;12(5):710-6.
Anderson et al., Incorporation of pseudouridine into mRNA enhances translation by diminishing PKR activation. Nucleic Acids Res. Sep. 2010;38(17):5884-92. doi: 10.1093/nar/gkq347. Epub May 10, 2010.
Anderson et al., Nucleoside modifications in RNA limit activation of 2'-5'-oligoadenylate synthetase and increase resistance to cleavage by RNase L. Nucleic Acids Res. Nov. 2011;39(21):9329-38. doi: 10.1093/nar/gkr586.
Andries et al., Synthetic biology devices and circuits for RNA-based 'smart vaccines': a propositional review. Expert Rev Vaccines. Feb. 2015;14(2):313-31.
Aubel et al., Mammalian synthetic biology—from tools to therapies. BioEssays : news and reviews in molecular, cellular and developmental biology 32,332-345 (2010).
Ausländer et al. A general design strategy for protein-responsive riboswitches in mammalian cells. Nature Methods 11, 1154-1160 (2014).
Ausländer et al., Programmable single-cell mammalian biocomputers. Nature 487, 123-127 (2012).
Azizgolshani, et al., Reconstituted plant viral capsids can release genes to mammalian cells. Virology 441, 12-17 (2013).
Banaszynski et al., DD-Shield Domain Sequence Mammalian Codon Optimized and Adapted from: LA Banaszynski, et al. "A Rapid, Reversible, and Tunable Method to Regulate Protein Function in Living Cells Using Synthetic Small Molecules." Cell, 2006, 126, 995-1004.
Beal et al. Model-Driven Engineering of Gene Expression from RNA Replicons. ACS Synth. Biol. 4, 48-56 (2015).
Belmont et al., Engineering a direct and inducible protein-RNA interaction to regulate RNA biology. ACS Chem. Biol. 5, 851-861 (2010).
Benenson, Synthetic biology with RNA: progress report. Current opinion in chemical biology 16, 278-284 (2012).
Berglund et al., Immunization with recombinant Semliki Forest virus induces protection against influenza challenge in mice. Vaccine 17, 497-507 (1999).
Bessis et al., Immune responses to gene therapy vectors: influence on vector function and effector mechanisms. Gene Ther. 11 Suppl 1, S10-17 (2004).
Bleris et al. Synthetic incoherent feedforward circuits show adaptation to the amount of their genetic template. Molecular Systems Biology 7, 1-12 (2011).
Bouard et al., Viral vectors: from virology to transgene expression. Br. J. Pharmacol. 157, 153-165 (2009).
Chalancon, G. et al. Interplay between gene expression noise and regulatory network architecture. Trends Genet. 28, 221-232 (2012).
Chen et al., Silencing of episomal transgene expression by plasmid bacterial DNA elements in vivo. Gene Ther. 11, 856-864 (2004).
Chen et al., Silencing of Episomal Transgene Expression in Liver by Plasmid Bacterial Backbone DNA is Independent of CpG Methylation. Mol. Ther. 16, 548-556 (2008).
Cohen et al., Quantification of plasmid DNA copies in the nucleus after lipoplex and polyplex transfection. Journal of controlled release 135, 166-174 (2009).
Culler et al., Reprogramming cellular behavior with RNA controllers responsive to endogenous proteins. Science 330, 1251-1255 (2010).
Donnelly et al. Analysis of the aphthovirus 2A/2B polyprotein 'cleavage' mechanism indicates not a proteolytic reaction, but a novel translational effect: a putative ribosomal 'skip'. J. Gen. Virol. 82, 1013-1025 (2001).
Dubensky et al., Delivery systems for gene-based vaccines. Mol. Med. Camb. Mass 6, 723-732 (2000).
Endo et al., Quantitative and simultaneous translational control of distinct mammalian mRNAs. Nucleic acids research 41, e135 (2013).
Firth et al., Non-canonical translation in RNA viruses. J. Gen. Virol. 93, 1385-1409 (2012).
Frolov et al. Alphavirus-based expression vectors: strategies and applications. Proc. Natl. Acad. Sci. U. S. A. 93, 11371-11377 (1996).
Frolov et al. Selection of RNA replicons capable of persistent noncytopathic replication in mammalian cells. J. Virol. 73, 3854-3865 (1999).
Frolov et al., Cis-acting RNA elements at the 5' end of Sindbis virus genome RNA regulate minus- and plus-strand RNA synthesis. RNA 7, 1638-1651 (2001).
Frolova et al., Functional Sindbis virus replicative complexes are formed at the plasma membrane. J. Virol. 84, 11679-11695 (2010).
Gallie, The cap and poly(A) tail function synergistically to regulate mRNA translational efficiency. Genes Dev. 5, 2108-2116 (1991).
Gardner et al., Construction of a genetic toggle switch in Escherichia coli. Nature 403, 339-342 (2000).
Geall et al. Nonviral delivery of self-amplifying RNA vaccines. Proc. Natl. Acad. Sci. U. S. A. 109, 14604-14609 (2012).
Geall et al., RNA: the new revolution in nucleic acid vaccines. Semin. Immunol. 25, 152-159 (2013).
Gibson et al. Dermal fibroblasts convert to a myogenic lineage in mdx mouse muscle. J. Cell Sci. 108 ( Pt 1), 207-214 (1995).
Glover et al., The efficiency of nuclear plasmid DNA delivery is a critical determinant of transgene expression at the single cell level. J. Gene Med. 12, 77-85 (2010).
Goldfless et al. Direct and specific chemical control of eukaryotic translation with a synthetic RNA-protein interaction. Nucl.Acids Res. (2012) vol. 40, No. 9.
Green et al., Toehold switches: de-novo-designed regulators of gene expression. Cell 159, 925-939 (2014).
Haase et al. Generation of a tumor- and tissue-specific episomal non-viral vector system. BMC Biotechnol. 13, 49 (2013).
Hahn et al., Infectious Sindbis virus transient expression vectors for studying antigen processing and presentation. Proc. Natl. Acad. Sci. U. S. A. 89, 2679-2683 (1992).
Haurwitz et al., Csy4 relies on an unusual catalytic dyad to position and cleave CRISPR RNA. EMBO J. 31, 2824-2832 (2012).
Haurwitz et al., Sequence- and structure-specific RNA processing by a CRISPR endonuclease. Science 329, 1355-1358 (2010).
Inagaki et al., Frequency and spectrum of genomic integration of recombinant adeno-associated virus serotype 8 vector in neonatal mouse liver. J. Virol. 82, 9513-9524 (2008).
Iwamoto et al., A general chemical method to regulate protein stability in the mammalian central nervous system. Chem. Biol. 17, 981-988 (2010).
Jafari et al., Nonviral approach for targeted nucleic acid delivery. Curr. Med. Chem. 19, 197-208 (2012).
Jose et al., A structural and functional perspective of alphavirus replication and assembly. Future Microbiol. 4, 837-856 (2009).
Kallio et al. Template RNA length determines the size of replication complex spherules for Semliki Forest virus. J. Virol. 87, 9125-9134 (2013).
Karikó et al. Incorporation of pseudouridine into mRNA yields superior nonimmunogenic vector with increased translational capacity and biological stability. Mol. Ther. J. Am. Soc. Gene Ther. 16, 1833-1840 (2008).
Karikó et al., Suppression of RNA recognition by Toll-like receptors: the impact of nucleoside modification and the evolutionary origin of RNA. Immunity 23, 165-175 (2005).
Karpati et al. Myoblast transfer in Duchenne muscular dystrophy. Ann. Neurol. 34, 8-17 (1993).
Kay, State-of-the-art gene-based therapies: the road ahead. Nat. Rev. Genet. 12, 316-328 (2011).
Khalil et al., Synthetic biology: applications come of age. Nature reviews. Genetics 11, 367-379 (2010).
Kim et al. High cleavage efficiency of a 2A peptide derived from porcine teschovirus-1 in human cell lines, zebrafish and mice. PloS One 6, e18556 (2011).

(56) References Cited

OTHER PUBLICATIONS

Klinman et al., (1997) DNA vaccines: safety and efficacy issues. Springer Semin. Immunopathol. 19, 245-256.
Kormann et al. Expression of therapeutic proteins after delivery of chemically modified mRNA in mice. Nat. Biotechnol. 29, 154-157 (2011).
Kramer et al. An engineered epigenetic transgene switch in mammalian cells. Nat Biotechnol 22, 867-870 (2004).
Kramps et al., Messenger RNA-based vaccines: progress, challenges, applications. Wiley interdisciplinary reviews. RNA (2013).
Kulasegaran-Shylini et al., The 5'UTR-specific mutation in VEEV TC-83 genome has a strong effect on RNA replication and subgenomic RNA synthesis, but not on translation of the encoded proteins. Virology 387, 211-221 (2009).
Lattanzi et al. High efficiency myogenic conversion of human fibroblasts by adenoviral vector-mediated MyoD gene transfer. An alternative strategy for ex vivo gene therapy of primary myopathies. J. Clin. Invest. 101, 2119-2128 (1998).
Liu et al., Experimental Studies on the Differentiation of Fibroblasts into Myoblasts induced by MyoD Genes in vitro. Int. J. Biomed. Sci. IJBS 4, 14-19 (2008).
Livet et al. Transgenic strategies for combinatorial expression of fluorescent proteins in the nervous system. Nature 450, 56-62 (2007).
Ljungberg et al., Self-replicating alphavirus RNA vaccines. Expert Rev. Vaccines 14, 177-194 (2015).
Lundstrom, Alphavirus Vectors in Vaccine Development. J Vaccines Vaccin. 2012;3:139. doi: 10.4172/2157-7560.1000139.
Lundstrom, Alphavirus-Based Vaccines. Viruses 6, 2392-2415 (2014).
Lundstrom, Alphaviruses in Gene Therapy. Viruses 1, 13-25 (2009).
Lustig et al. Molecular basis of Sindbis virus neurovirulence in mice. J. Virol. 62, 2329-2336 (1988).
Mendell et al. A phase 1/2a follistatin gene therapy trial for becker muscular dystrophy. Mol. Ther. J. Am. Soc. Gene Ther. 23, 192-201 (2015).
Middleton et al., Retention of plasmid DNA in mammalian cells is enhanced by binding of the Epstein—Barr virus replication protein EBNA1. J. Virol. 68, 4067-4071 (1994).
Miller et al., Tissue-specific and transcription factor-mediated nuclear entry of DNA. Adv. Drug Deliv. Rev. 61, 603-613 (2009).
Mittal et al., Dissecting the expression dynamics of RNA-binding proteins in posttranscriptional regulatory networks. Proc. Natl. Acad. Sci. U.S.A. 106, 20300-20305 (2009).
Miyazaki et al., Destabilizing Domains Derived from the Human Estrogen Receptor. J. Am. Chem. Soc. 134, 3942-3945 (2012).
Mortimer et al. Cationic lipid-mediated transfection of cells in culture requires mitotic activity. Gene Ther. 6, 403-411 (1999).
Nechushtan et al., Conformation of the Bax C—terminus regulates subcellular location and cell death. EMBO J. 18, 2330-2341 (1999).
Nowak et al., Duchenne muscular dystrophy and dystrophin: pathogenesis and opportunities for treatment. EMBO Rep. 5, 872-876 (2004).
Opalinska et al., Nucleic-acid therapeutics: basic principles and recent applications. Nat. Rev. Drug Discov. 1, 503-514 (2002).
Pascolo, Vaccination with messenger RNA. DNA Vaccines, Methods Mol Med. 127, 23-40 (2006).
Peabody, The RNA binding site of bacteriophage MS2 coat protein. EMBO J. 12, 595-600 (1993).
Pedraza et al., Noise propagation in gene networks. Science 307, 1965-1969 (2005).
Pegoraro et al. Genetic and biochemical normalization in female carriers of Duchenne muscular dystrophy: evidence for failure of dystrophin production in dystrophin-competent myonuclei. Neurology 45, 677-690 (1995).
Petrakova et al. Noncytopathic replication of Venezuelan equine encephalitis virus and eastern equine encephalitis virus replicons in Mammalian cells. J. Virol. 79, 7597-7608 (2005).
Pollard et al., Challenges and advances towards the rational design of mRNA vaccines. Trends Mol. Med. 19, 705-713 (2013).
Qian et al., Scaling up digital circuit computation with DNA strand displacement cascades. Science 332, 1196-1201 (2011).
Rapti et al. Neutralizing Antibodies Against AAV Serotypes 1, 2, 6, and 9 in Sera of Commonly Used Animal Models. Mol. Ther. 20, 73-83 (2012).
Rechsteiner et al., PEST sequences and regulation by proteolysis. Trends in Biochemical Sciences 21, 267-271 (1996).
Robertson, (1994) Safety considerations for nucleic acid vaccines. Vaccine 12, 1526-1528.
Rodrigo et al., De novo automated design of small RNA circuits for engineering synthetic riboregulation in living cells. Proc. Natl. Acad. Sci. U.S.A. 109, 15271-15276 (2012).
Sahin et al., mRNA-based therapeutics—developing a new class of drugs. Nat Rev Drug Discov 13, 759-780 (2014).
Saito et al. Synthetic translational regulation by an L7Ae-kink-turn RNP switch. Nat. Chem. Biol. 6, 71-78 (2010).
Sanz et al., Dual mechanism for the translation of subgenomic mRNA from Sindbis virus in infected and uninfected cells. PloS One 4, e4772 (2009).
Schwanhäusser et al. Global quantification of mammalian gene expression control. Nature 473, 337-342 (2011).
Shcherbo et al., Bright far-red fluorescent protein for whole-body imaging. Nature Methods 4, 741-746 (2007).
Shimoga et al., Synthetic mammalian transgene negative autoregulation. Molecular Systems Biology 9, 670 (2013).
Siciliano et al. MiRNAs confer phenotypic robustness to gene networks by suppressing biological noise. Nat Commun 4, 2364 (2013).
Stewart et al. Lentivirus-delivered stable gene silencing by RNAi in primary cells. RNA 9, 493-501 (2003).
Strauss et al., The alphaviruses: gene expression, replication, and evolution. Microbiol. Rev. 58, 491-562 (1994).
Szymczak et al. Correction of multi-gene deficiency in vivo using a single 'self-cleaving' 2A peptide-based retroviral vector. Nat Biotechnol 22, 589-594 (2004).
Tavernier et al. mRNA as gene therapeutic: how to control protein expression. Journal of controlled release : official journal of the Controlled Release Society 150, 238-247 (2011).
Thomas et al., Progress and problems with the use of viral vectors for gene therapy. Nat. Rev. Genet. 4, 346-358 (2003).
Thomas et al., Sindbis virus vectors designed to express a foreign protein as a cleavable component of the viral structural polyprotein. J. Virol. 77, 5598-5606 (2003).
Uematsu et al. Lack of Interference with Immunogenicity of a Chimeric Alphavirus Replicon Particle-Based Influenza Vaccine by Preexisting Antivector Immunity. Clin. Vaccine Immunol. CVI 19, 991-998 (2012).
Van Etten et al. Human Pumilio proteins recruit multiple deadenylases to efficiently repress messenger RNAs. J. Biol. Chem. 287, 36370-36383 (2012).
Wahlfors et al., Evaluation of recombinant alphaviruses as vectors in gene therapy. Gene Ther. 7, 472-480 (2000).
Wang et al. Systemic delivery of modified mRNA encoding herpes simplex virus 1thymidine kinase for targeted cancer gene therapy. Molecular therapy: the journal of the American Society of Gene Therapy 21, 358-367 (2013).
Warren et al. Highly efficient reprogramming to pluripotency and directed differentiation of human cells with synthetic modified mRNA. Cell stem cell 1, 618-630 (2010).
Weber et al., A Modular Cloning System for Standardized Assembly of Multigene Constructs. PLoS ONE 6, e16765 (2011).
Webster et al., Accelerated age-related decline in replicative lifespan of Duchenne muscular dystrophy myoblasts: implications for cell and gene therapy. Somat. Cell Mol. Genet. 16, 557-565 (1990).
Weidmann et al., *Drosophila pumilio* protein contains multiple autonomous repression domains that regulate mRNAs independently of Nanos and brain tumor. Molecular and cellular biology 32, 527-540 (2012).
Wielgosz et al., Sequence Requirements for Sindbis Virus Subgenomic mRNA Promoter Function in Cultured Cells. J. Virol. 75, 3509-3519 (2001).

(56) References Cited

OTHER PUBLICATIONS

Wiley et al., Double subgenomic alphaviruses expressing multiple fluorescent proteins using a Rhopalosiphum padi virus internal ribosome entry site element. PloS One 5, e13924 (2010).
Wolff et al. Direct gene transfer into mouse muscle in vivo. Science 247, 1465-1468 (1990).
Wooddell et al., Sustained liver-specific transgene expression from the albumin promoter in mice following hydrodynamic plasmid DNA delivery. J. Gene Med. 10, 551-563 (2008).
Xie et al., Multi-input RNAi-based logic circuit for identification of specific cancer cells. Science 333, 1307-1311 (2011).
Yin et al. Non-viral vectors for gene-based therapy. Nat. Rev. Genet. 15, 541-555 (2014).
Yoshioka et al. Efficient generation of human iPSCs by a synthetic self-replicative RNA. Cell Stem Cell 13, 246-254 (2013).
[No Author Listed] Trimethoprim. Sigma Aldrich. Retrieved from: <www.sigmaaldrich.com/catalog/product/sigma /t7883?lang=en &region=US>. Accessed on Jul. 31, 2019. 4 pages.
[No Author Listed] Shield1 Ligand. Takara. Retrieved from: <https://www.takarabio.com/products/inducible-systems/inducible-protein-stabilization/shield1>. Accessed on Jul. 31, 2019. 2 pages.

\* cited by examiner

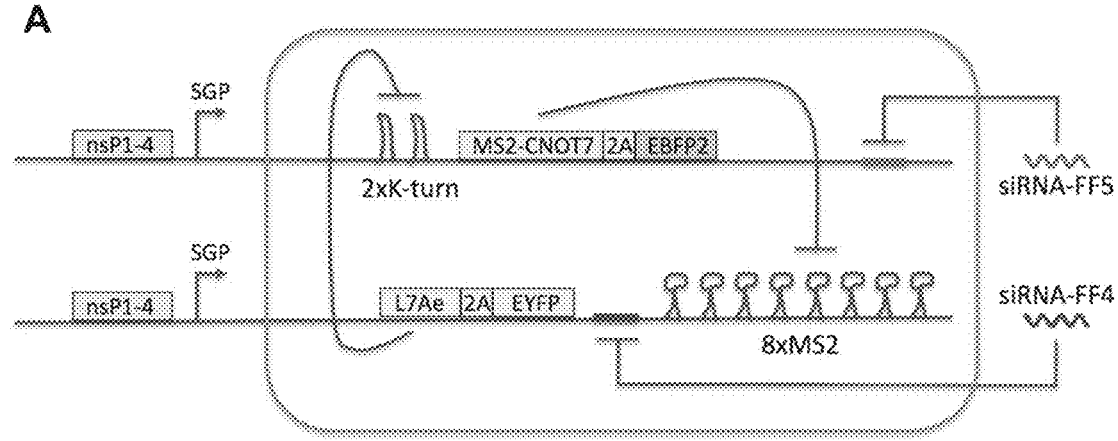
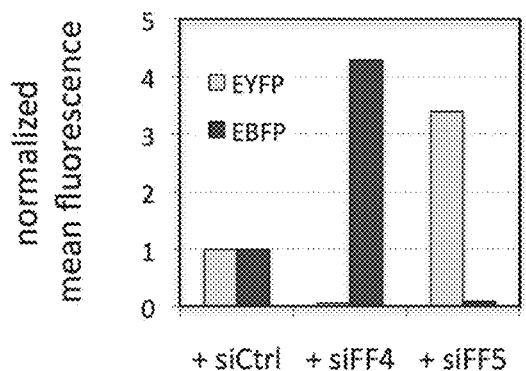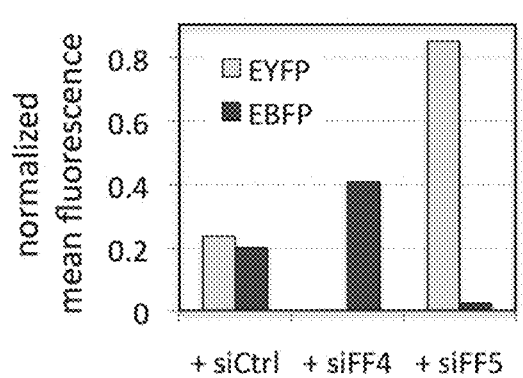
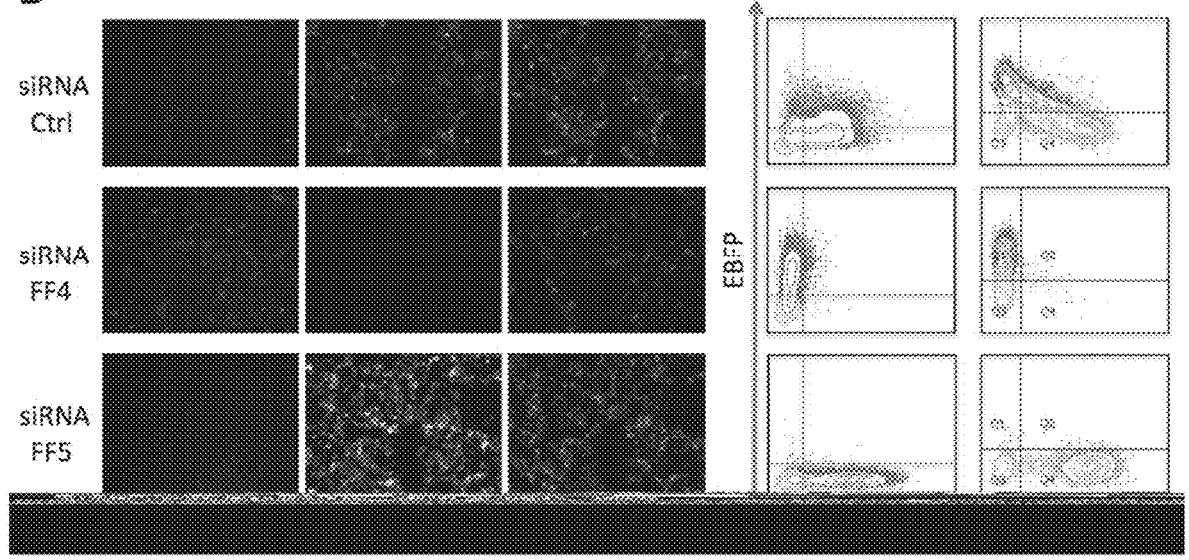
FIGs. 3A-3E

A

B

C

A
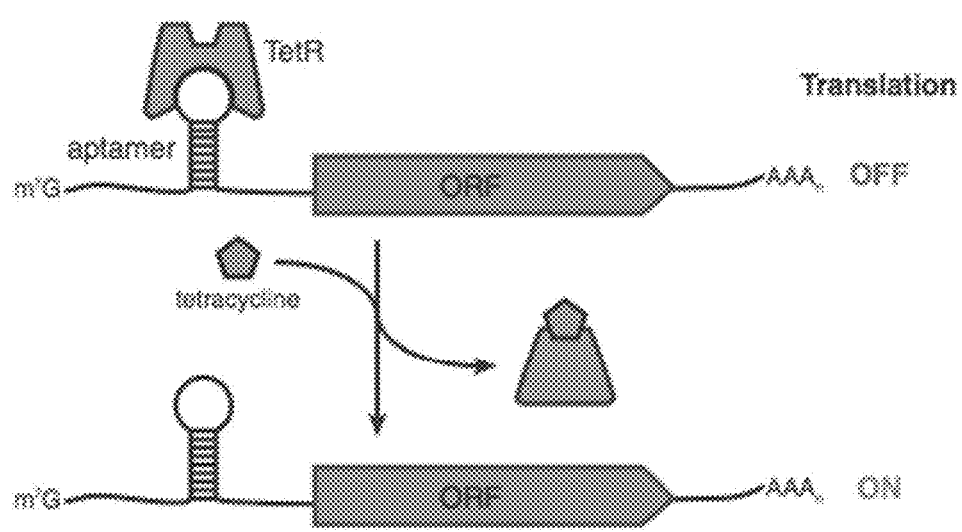
B
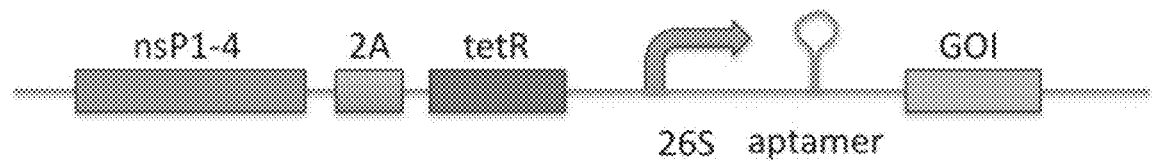
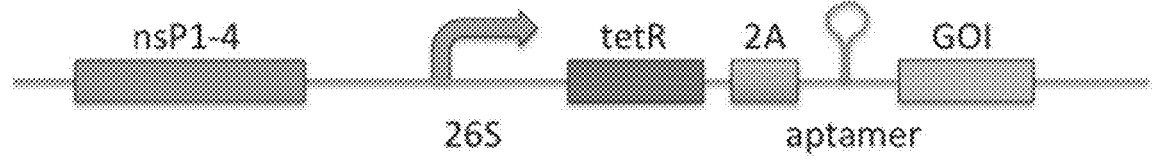
FIGs. 6A-6B a b c a pDNA schema
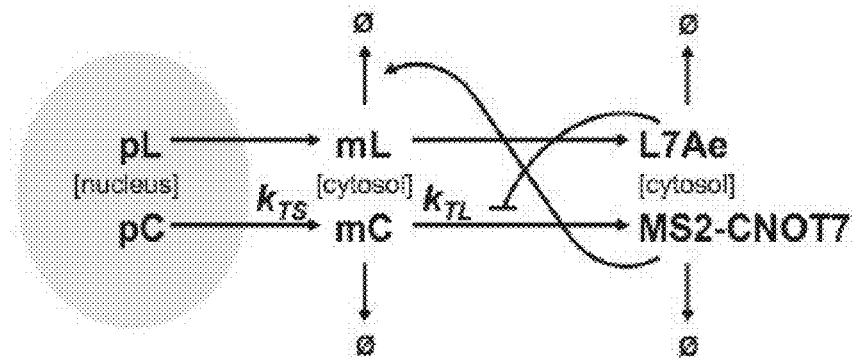
b Replicon schema
> 4 hours:
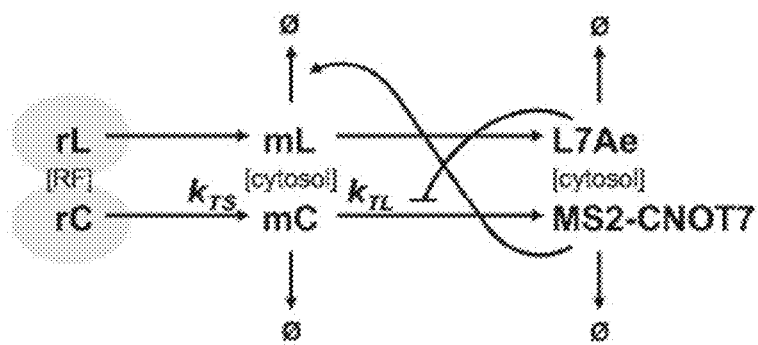
< 4 hours:
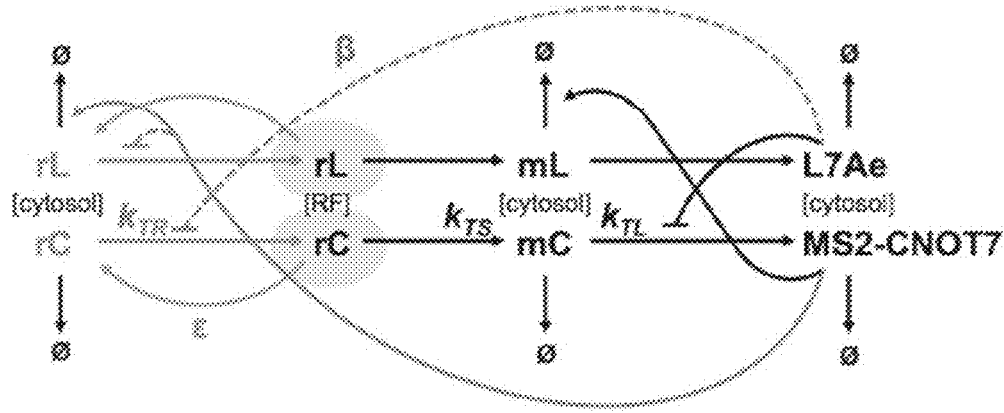
FIGs. 31A-31B

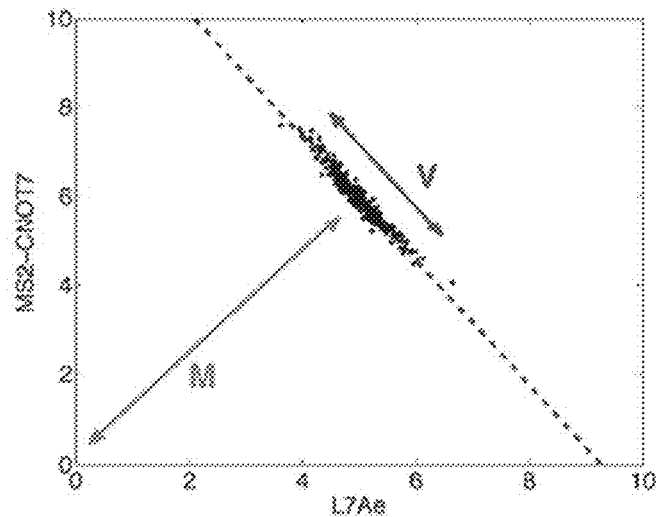
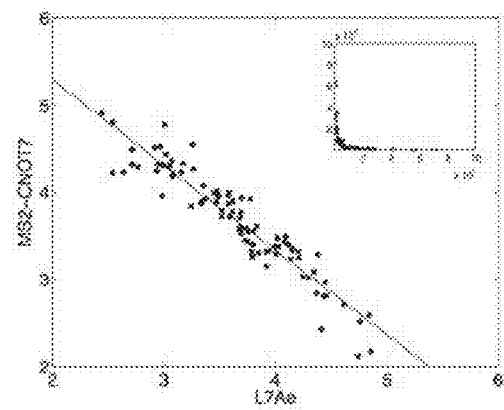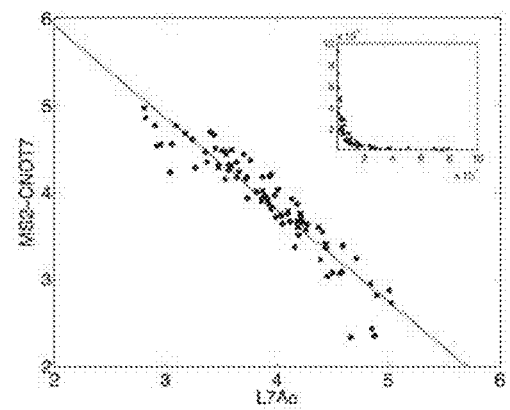
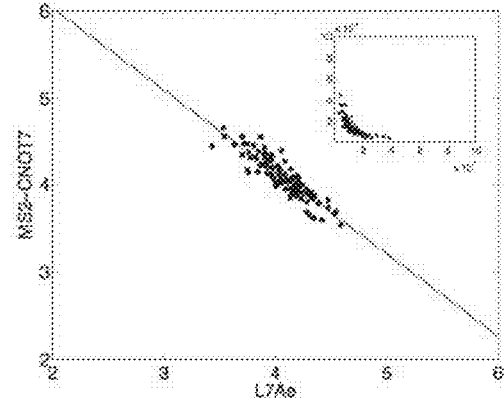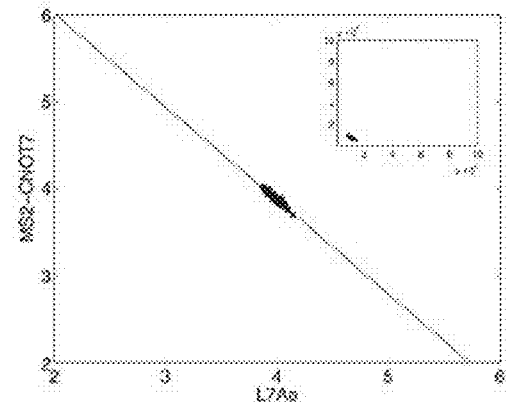
FIGs. 32A-32B a b a b

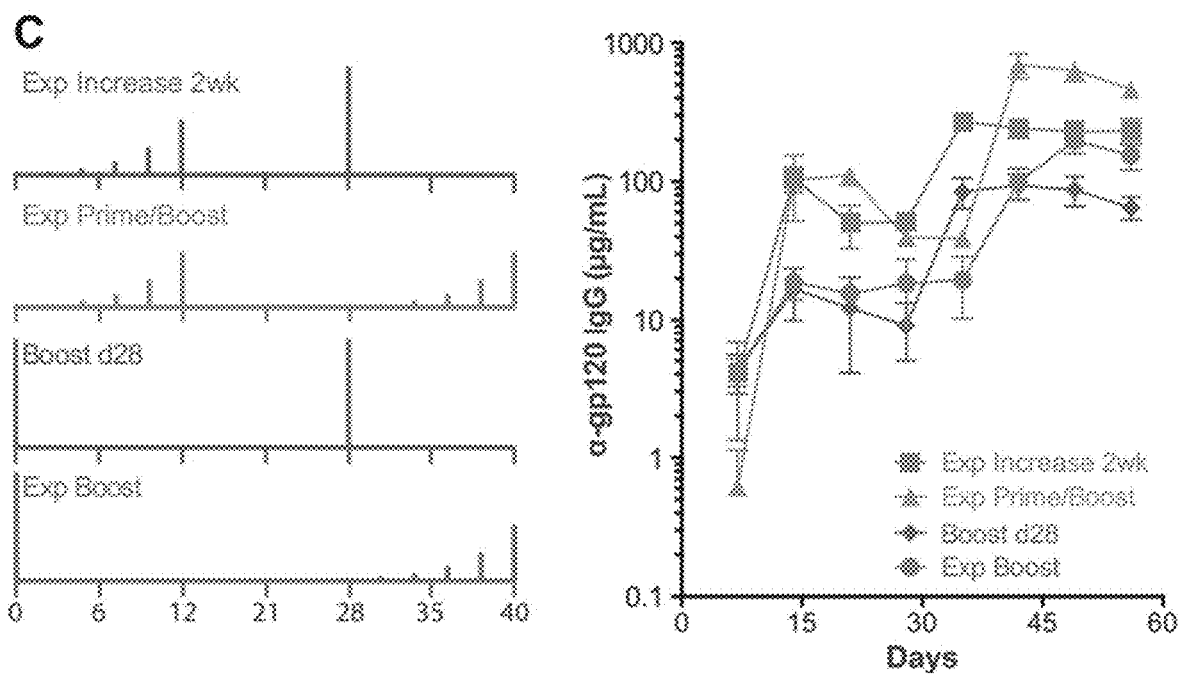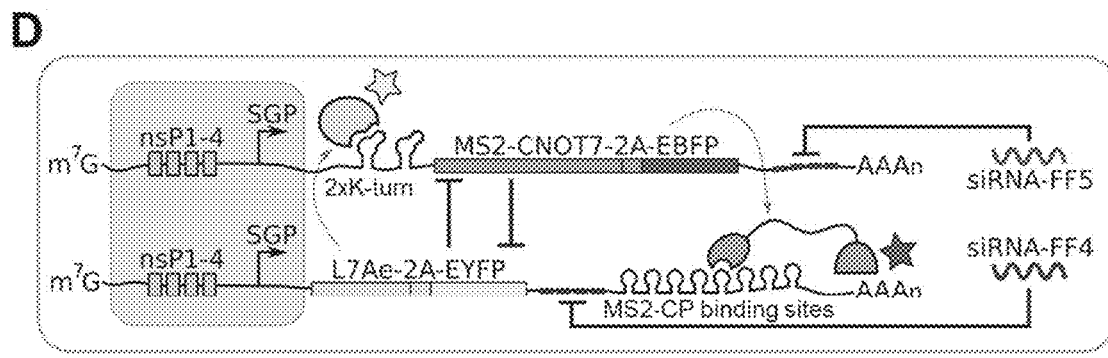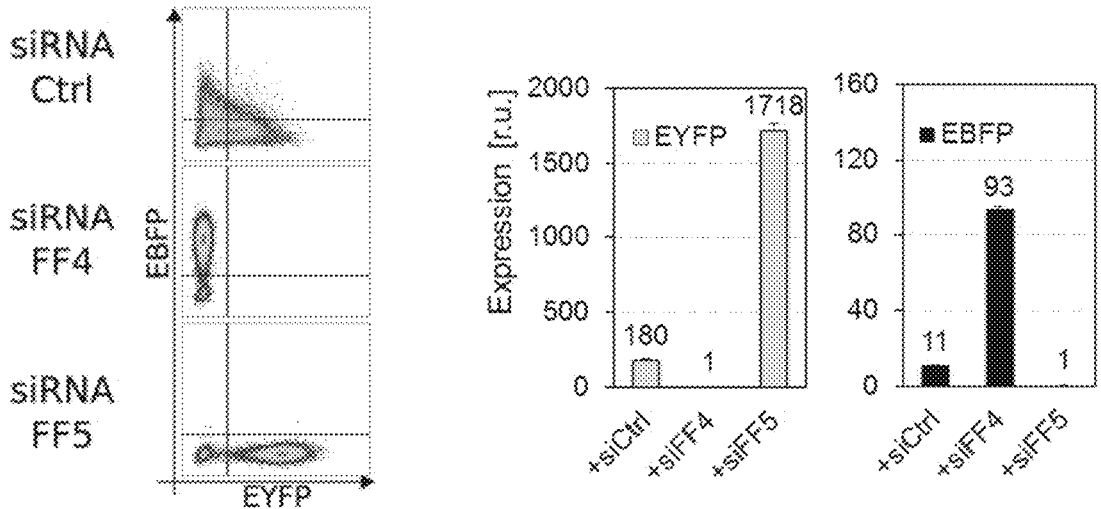
FIGs. 37C-37D

Low-mKate

|  | | mVenus | | | | | |
|---|---|---|---|---|---|---|---|
|  | | Low | Medium | High | Low+UTR | Medium+UTR | High+UTR |
| EBFP | Low | 0.01 0.03 | 0.02 0.02 | 0.02 0.03 | 0.02 0.03 | 0.16 0.02 | 0.13 0.02 |
|  | Medium | 0.01 0.06 | 0.01 0.04 | 0.02 0.05 | 0.02 0.05 | 0.12 0.04 | 0.14 0.05 |
|  | High | 0.01 0.07 | 0.01 0.05 | 0.02 0.05 | 0.02 0.05 | 0.12 0.04 | 0.14 0.04 |
|  | Low+UTR | 0.01 0.08 | 0.02 0.08 | 0.02 0.07 | 0.04 0.07 | 0.13 0.07 | 0.15 0.07 |
|  | Medium+UTR | 0.01 0.28 | 0.01 0.22 | 0.01 0.17 | 0.02 0.18 | 0.10 0.22 | 0.09 0.25 |
|  | High+UTR | 0.01 0.32 | 0.02 0.31 | 0.02 0.24 | 0.02 0.19 | 0.11 0.28 | 0.11 0.26 |

Med.-mKate

|  | | mVenus | | | | | |
|---|---|---|---|---|---|---|---|
|  | | Low | Medium | High | Low+UTR | Medium+UTR | High+UTR |
| EBFP | Low | 0.01 0.48 | 0.01 0.37 | 0.02 0.40 | 0.02 0.32 | 0.12 0.36 | 0.15 0.36 |
|  | Medium | 0.00 0.44 | 0.01 0.33 | 0.01 0.37 | 0.02 0.43 | 0.10 0.35 | 0.09 0.25 |
|  | High | 0.01 0.46 | 0.03 0.35 | 0.02 0.45 | 0.04 0.31 | 0.10 0.34 | 0.11 0.30 |
|  | Low+UTR | 0.01 0.44 | 0.02 0.37 | 0.02 0.32 | 0.05 0.40 | 0.12 0.34 | 0.11 0.32 |
|  | Medium+UTR | 0.01 0.34 | 0.01 0.27 | 0.01 0.29 | 0.02 0.28 | 0.09 0.32 | 0.09 0.33 |
|  | High+UTR | 0.01 0.41 | 0.01 0.33 | 0.01 0.32 | 0.02 0.29 | 0.09 0.28 | 0.09 0.31 |

High-mKate

|  | | mVenus | | | | | |
|---|---|---|---|---|---|---|---|
|  | | Low | Medium | High | Low+UTR | Medium+UTR | High+UTR |
| EBFP | Low | 0.02 0.70 | 0.02 0.51 | 0.02 0.56 | 0.02 0.37 | 0.11 0.60 | 0.13 0.39 |
|  | Medium | 0.05 0.62 | 0.04 0.29 | 0.05 0.80 | 0.04 0.32 | 0.10 0.49 | 0.11 0.42 |
|  | High | 0.05 0.65 | 0.04 0.48 | 0.04 0.53 | 0.05 0.43 | 0.11 0.50 | 0.11 0.41 |
|  | Low+UTR | 0.06 0.50 | 0.06 0.48 | 0.06 0.48 | 0.04 0.38 | 0.12 0.50 | 0.11 0.38 |
|  | Medium+UTR | 0.21 0.45 | 0.18 0.39 | 0.20 0.44 | 0.17 0.37 | 0.09 0.44 | 0.09 0.39 |
|  | High+UTR | 0.25 0.45 | 0.25 0.43 | 0.21 0.38 | 0.17 0.28 | 0.22 0.38 | 0.08 0.25 0.40 |

FIG. 52B

|  | L7Ae | TetR | mVenus-PEST |
|---|---|---|---|
| -TMP/-Dox | 0 | 1 | 0 |
| +TMP/+Dox | 1 | 0 | 1 |

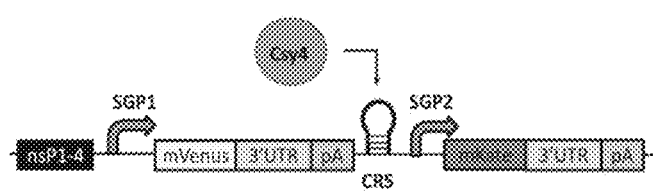
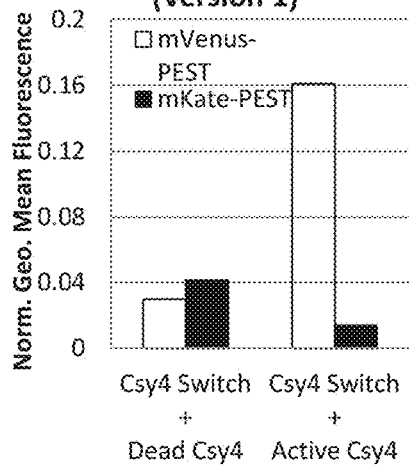
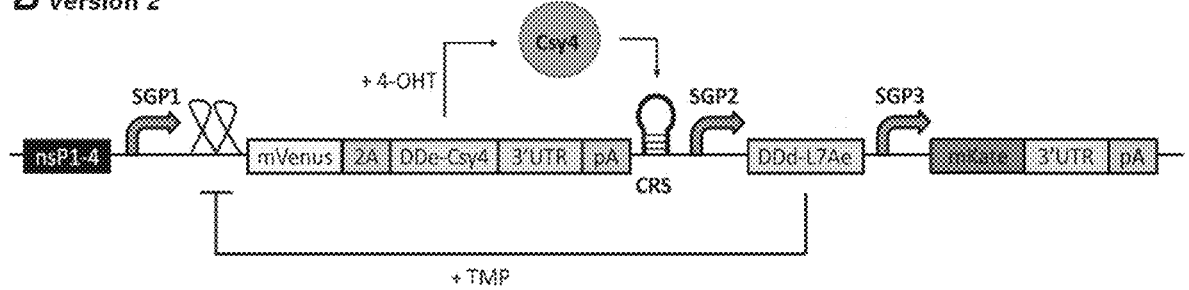
| State | mVenus | DDe-Csy4 | DDd-L7Ae | mKate |
|---|---|---|---|---|
| + TMP / - 4-OHT | 0 | 0 | 1 | 1 |
| - TMP / + 4-OHT | 1 | 1 | 0 | 0 |
FIGs. 63A-63B (Initial in vivo repression weak ->to further improve repression of SGP(30) 2xKt, SGP(16) 2xKt)
Screen #2: NxKt tuning 100 ng RNA normalized to pXZ065

Circuit:
SGP1(15) DDdL7Ae --| SGP2(X) NxKt Fluc (X=30,16, N=3,4)
Best:
SGP1(15) DDdL7Ae --| SGP2(30) 3xKt Fluc (pTK417)
SGP1(15) DDdL7Ae --| SGP2(30) 4xKt Fluc (pTK420)
SGP1(15) DDdL7Ae --| SGP2(16) 3xKt Fluc (pTK465)
SGP1(15) DDdL7Ae --|SGP2(16) 4xKt Fluc (pTK468)

(To improve the expression level of the ON state of SGP(16) 3xKt, SGP(16) 4xKt)
Screen #3: 2xDDd tuning (20150506)100 ng RNA normalized to pXZ065

Circuit:
SGP1(15) 2xDDdL7Ae –| SGP2(X) NxKt Fluc (X=16, N=3,4)
Best:
SGP1(15) 2xDDdL7Ae –| SGP2(16) 4xKt Fluc (pTK439)

(To improve the expression level and ON/OFF ratio of the best circuits above)
Screen #4: sidebyside -/+ IRES E3L 100 ng RNA normalized to pXZ065

Circuit:
SGP1(15) (2x)DDdL7Ae --| SGP2(16) NxKt Fluc IRES E3L (N=2,3,4)
SGP1(15) DDdL7Ae --| SGP2(30) NxKt Fluc IRES E3L (N=3,4)
Best:
SGP1(15) DDd-L7Ae SGP2(16) 3xKt Fluc2 IRES E3L (pTK477)
SGP1(15) DDd-L7Ae SGP2(16) 4xKt Fluc2 IRES E3L (pTK478)
SGP1(15) DDd-L7Ae SGP2(30)-3xK Fluc2 IRES E3L (pTK489)
SGP1(15) DDd-L7Ae SGP2(30)-4xK Fluc2 IRES E3L (pTK492)

TetR-DDX6 can replace the cascade for small molecule "ON" switch

SEQUENCE LISTING

```
<160> NUMBER OF SEQ ID NOS: 56

<210> SEQ ID NO 1
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 1
aagggcatcg acttcaagg                                              19

<210> SEQ ID NO 2
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 2
tgcttgtcgg ccatgatata g                                           21

<210> SEQ ID NO 3
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 3
ctgacctgga aactgagact atg                                         23

<210> SEQ ID NO 4
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 4
ggcgactcta actcccttat tg                                          22

<210> SEQ ID NO 5
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 5
ccctataact ctctacggct aac                                         23

<210> SEQ ID NO 6
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 6
agaagtcgtg ctgcttca                                               18
```

<210> SEQ ID NO 7
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 7
ggcgtggttt agagtaggta taa                                        23

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8
tcgtctcgtt ggtacctttc                                            20

<210> SEQ ID NO 9
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 9
gctgaatgga tcagctctaa ct                                         22

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
cagtctgggt tgccacttta                                            20

<210> SEQ ID NO 11
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 11
acctgtagcg ttcgtcagtc ctct                                       24

<210> SEQ ID NO 12
<211> LENGTH: 849
<212> TYPE: RNA
<213> ORGANISM: Artificial Sequence
<220> FEATURE:
<223> OTHER INFORMATION: Synthetic Polynucleotide

<400> SEQUENCE: 12
gggcgaauua agagagaaaa gaagaguaag aagaaauaua agacaccggu cgccaccaug      60
gacggguccg gggagcagcc cagaggcggg gggcccacca gcucugagca gaucaugaag     120 acagggccc uuuugcuuca ggguuucauc caggaucgag cagggcgaau ggggggggag     180
gcacccgagc uggcccugga cccggugccu caggaugcgu ccaccaagaa gcugagcgag     240
ugucucaagc gcaucgggga cgaacuggac aguaacaugg agcugcagag gaugauugcc     300

```
gccguggaca cagacucccc ccgagagguc uuuuuccgag uggcagcuga cauguuuucu        360
gacggcaacu ucaacugggg ccggguuguc gcccuuuucu acuuugccag caaacugggug      420 cucaaggccc ugugcaccaa ggugccggaa cugaucagaa ccaucauggg cuggacauug       480
gacuuccucc gggagcggcu guugggcugg auccaagacc aggugguug ggacggccuc        540 cucuccuacu uugggacgcc cacguggcag accgugacca ucuuugugc gggagugcuc        600 accgccucgc ucaccaucug aagaagaug ggcugacucu agaccuucug cggggcuugc        660
cuucuggcca ugcccuucuu cucucccuug caccuguacc ucuuggucuu ugaauaaagc       720
cugaguagga aaaaaaaaa aaaaaaaaaa aaaaaaaaaa aaaaaaaaaa aaaaaaaaaa        780
aaaaaaaaaa aaaaaaaaaa aaaaaaaaaa aaaaaaaaaa aaaaaaaaaa aaaaaaaaaa       840
aaaaaaaaa                                                                849
```

<210> SEQ ID NO 13
<211> LENGTH: 1158
<212> TYPE: RNA
<213> ORGANISM: Artificial Sequence
<220> FEATURE:
<223> OTHER INFORMATION: Synthetic Polynucleotide

<400> SEQUENCE: 13

```
ggauccguga ucggaaacgu gagauccacc ucagauccgc uaggacaccc gcagaucgag        60
aagaaggcga auuaagagag aaaagaagag uaagaagaaa uauaagacac cggucgccac       120
cauggacggg uccggggagc agcccagagg cggggggccc accagcucug agcagaucau       180
gaagacaggg gcccuuuugc uucagggguuu cauccaggau cgagcagggc gaauggggggg     240 ggaggcaccc gagcuggccc uggaccccggu gccucaggau gcguccacca agaagcugag      300
cgagugucuc aagcgcaucg gggacgaacu ggacaguaac auggagcugc agaggaugau       360
ugccgccgug gacacagacu ccccccgaga ggucuuuuuc cgaguggcag cugacauguu       420
uucugacggc aacuucaacu ggggccgggu ugucgcccuu uucuacuuug ccagcaaacu       480
ggugcucaag gcccugugca ccaaggugcc ggaacugauc agaaccauca ugggcuggac       540
auuggacuuc cucgggagc ggcuguuggg cuggauccaa gaccagggug uuggggacgg        600 ccucccucucc uacuugggga cgcccacgug gcagaccgug accaucuuug uggcgggagu     660
gcucaccgcc ucgcucacca ucuggaagaa gaugggcuga gcggccgcua aaccaucuuu      720
accagacagu guuaccaucu uuaccagaca guguuaccau cuuuaccaga cagucuuacc      780
aucuuuacca gacaguguua aucgauucca uaaaguagga acacuacau ccauaaagua       840 ggaaacacua cauccauaaa guaggaaaca cuacauccau aaaguaggaa acacuacaaa      900
gcuuaaccca uggaauucag uucucaaacc caugggaauuc aguucucaaa cccauggaau     960
ucaguucuca aacccaugga auucaguucu cagucgaagc uucgaauucu gcagucgacu     1020
gaauaaagcc ugaguaggaa aaaaaaaaa aaaaaaaaaa aaaaaaaaa aaaaaaaaaa       1080 aaaaaaaaaa aaaaaaaaaa aaaaaaaaaa aaaaaaaaaa aaaaaaaaaa aaaaaaaaaa     1140
aaaaaaaaaa aaaaaaaa                                                    1158
```

<210> SEQ ID NO 14
<211> LENGTH: 1509
<212> TYPE: RNA
<213> ORGANISM: Artificial Sequence
<220> FEATURE:
<223> OTHER INFORMATION: Synthetic Polynucleotide

<400> SEQUENCE: 14

```
gggcgaauua agagagaaaa gaagaguaag aagaaauaua agacaccggu cgccaccaug       60
uacgugagau uugagguucc ugaggacaug cagaacgaag cucugagucu gcuggagaag      120
guuagggaga gcgguaaggu aaagaaaggu accaacgaga cgacaaaggc uggagagg        180
ggacuggcaa agcucguuua caucgcagag gauguugacc cgccugagau cguugcucau      240
cugccccucc ucugcgagga gaagaaugug ccguacauuu acguuaaaag caagaacgac      300
cuuggaaggg cuguggcau ugaggugcca ugcgcuucgg cagcgauaau caacgaggga       360
gagcugagaa aggagcuugg aagccuugug gagaagauua aaggccuuca gaagggaucu      420
ggcgccacca acuucucucu gcugaagcag gccggcgacg uggaggagaa cccaggccca      480
auggcgcacg cugggagaac ggguacgau aaccggaga uagugaugaa guacauccau        540
uauaagcugu cgcagagggg cuacgagugg gaugcggag augugggcgc cgcgcccccg       600
ggggccgccc ccgcaccggg caucuucucc ucccagcccg gcacacgcc ccauccagcc       660
gcaucccggg acccgucgc caggaccucg ccgcugcaga ccccggcugc ccccggcgcc      720
gccgcgggc cugcgcucag cccggugcca ccugguguc accugacccu ccgccaggcc       780
ggcgacgacu ucucccgccg cuaccgccgc gacuucgccg agaugccag ccagcugcac      840
cugacgcccu ucaccgcgcg gggacgcuuu gccacggugg uggaggagcu cuucagggac      900
ggggugaacu gggggaggau uguggccuuc uuugaguucg gugggucau ugugugguggag      960
agcgucaacc gggagauguc gcccuggug acaacaucg cccugguggau gacugaguac     1020
cugaaccggc accugcacac cuggauccag gauaacggag gcugggaugc cuuugugaa      1080
cguacggcc ccagcaugcg gccucuguuu gauuucuccu ggcugucucu gaagacucug      1140
cucaguuugg cccugguggg agcuugcauc acccugggug ccuaucuggg ccacaaguga     1200
gucuagaccu ucugcgggc gacgagcugu acaaguaauu cuagaagauc ccaaaucaac      1260
aucagucuga uaagcuauca acaucagucu gauaagcuau caacaucagu cugauaagcu     1320
aucaacauca gucugauaag cuaagaucuc ccgggcguac aaguaaagcg ugaauaaagc     1380
cugaguagga aaaaaaaaa aaaaaaaaa aaaaaaaaaa aaaaaaaaaa aaaaaaaaaa        1440
aaaaaaaaaa aaaaaaaaaa aaaaaaaaaa aaaaaaaaaa aaaaaaaaaa aaaaaaaaaa     1500
aaaaaaaaa                                                              1509
```

<210> SEQ ID NO 15
<211> LENGTH: 1413
<212> TYPE: RNA
<213> ORGANISM: Artificial Sequence
<220> FEATURE:
<223> OTHER INFORMATION: Synthetic Polynucleotide

<400> SEQUENCE: 15

```
gggcgaauua agagagaaaa gaagaguaag aagaaauaua agacaccggu cgccaccaug        60
uacgugagau uugagguucc ugaggacaug cagaacgaag cucugagucu gcuggagaag       120
guuagggaga gcgguaaggu aaagaaaggu accaacgaga cgacaaaggc uggagagg         180
ggacuggcaa agcucguuua caucgcagag gauguugacc cgccugagau cguugcucau       240
cugccccucc ucugcgagga gaaugug ccguacauuu acguuaaaag caagaacgac          300
cuuggaaggg cuguggcau ugaggugcca ugcgcuucgg cagcgauaau caacgaggga        360
gagcugagaa aggagcuugg aagccuugug gagaagauua aaggccuuca gaagggaucu       420
ggcgccacca acuucucucu gcugaagcag gccggcgacg uggaggagaa cccaggccca       480
```

```
auggcgcacg cugggagaac ggggguacgau aaccgggaga uagugaugaa guacauccau    540
uauaagcugu cgcagagggg cuacgagugg gaugcgggag auguggggcg cgcgcccccg    600
ggggccgccc ccgcaccggg caucuucucc ucccagcccg ggcacacgcc ccauccagcc    660
gcaucccggg acccggucgc caggaccucg ccgcugcaga ccccggcugc ccccggcgcc    720
gccgcggggc cugcgcucag cccggugcca ccugugguoc accugacccu ccgccaggcc    780
ggcgacgacu ucucccgccg cuaccgccgc gacuucgccg agauguccag ccagcugcac    840
cugacgcccu ucaccgcgcg gggacgcuuu gccacggugg uggaggagcu cuucagggac    900
ggggugaacu gggggaggau uguggccuuc uuugaguucg gugggguucau gugugugag    960 agcgucaacc gggagauguc gccccuggug gacaacaucg cccugggau gacugaguac   1020 cugaaccggc accugcacac cuggauccag gauaacggag gcgggaugc cuuuguggaa   1080 cguacggcc ccagcaugcg gccucuguuu gauuucuccu ggcugucucu gaagacucug   1140
cucaguuugg cccuggugg agcuugcauc acccuggug ccuaucuggg ccacaaguga   1200
gucuagaccu ucugcggggc uugccuucug gccaugcccu ucuucucucc cuugcaccug   1260
uaccucuugg ucuuugaaua aagccugagu aggaaaaaaa aaaaaaaaa aaaaaaaaa   1320 aaaaaaaaaa aaaaaaaaa aaaaaaaaa aaaaaaaaa aaaaaaaaa aaaaaaaaa   1380 aaaaaaaaaa aaaaaaaaa aaaaaaaaa aaa                                 1413

<210> SEQ ID NO 16
<211> LENGTH: 984
<212> TYPE: RNA
<213> ORGANISM: Artificial Sequence
<220> FEATURE:
<223> OTHER INFORMATION: Synthetic Polynucleotide

<400> SEQUENCE: 16
gggcgaauua agagagaaaa gaagaguaag aagaaauaua agacaccggu cgccaccaug     60
gugucuaagg gcgaagagcu gauuaaggag aacaugcaca ugaagcugua cauggagggc    120
accgugaaca accaccacuu caagugcaca uccgagggcg aaggcaagcc cuacgagggc    180
acccagacca ugagaaucaa gguggucgag ggcggcccuc uccccuucgc cuucgacauc    240
cuggcuacca gcuucaugua cggcagcaaa accuucauca accacaccca gggcauccoc    300 gacuucuuua agcagucouu cccugagggc uucacauggg agagaguoac cacauacgaa    360 gacgggggcg ugcugaccgc uacccaggac accagccucc aggacggcug ccucaucuac    420
aacgucaaga ucagaggggu gaacuuccca uccaacggcc cugugaugca gaagaaaaca    480
cucggcuggg aggccuccac cgagaugcug uacccogcug acggcggccu ggaaggcaga    540
agcgacaugg cccugaagcu cguggggggg ggccaccuga ucugcaacuu gaagaccaca    600
uacagaucca gaaacccgc uaagaaccuc aagaugcccg gcgucuacua uguggacaga    660
agacuggaaa gaaucaagga ggccgacaaa gagaccuacg ucgagcagca cgagguggcu    720
guggccagau acugcgaccu ccccuagcaaa cuggggcaca aacuuaauug auucuagacc    780
uucugcgggg cuugccuucu ggccaugccc uucuucucuc ccuugcaccu guaccucuug    840
gucuuugauu aaagccugag uaggaaaaa aaaaaaaa aaaaaaaa aaaaaaaa    900 aaaaaaaaaa aaaaaaaa aaaaaaaa aaaaaaaa aaaaaaaa aaaaaaaa    960 aaaaaaaaaa aaaaaaaa aaaa                                           984

<210> SEQ ID NO 17
```

```
<211> LENGTH: 1239
<212> TYPE: RNA
<213> ORGANISM: Artificial Sequence
<220> FEATURE:
<223> OTHER INFORMATION: Synthetic Polynucleotide

<400> SEQUENCE: 17
gggcgaauua agagagaaaa gaagaguaag aagaaauaua agacaccggu cgccaccaug      60
gugagcaagg gcgaggagcu guucaccggg guggugccca uccuggucga gcuggacggc     120
gacguaaacg gccacaaguu cagcgugucc ggcgagggcg agggcgaugc caccuacggc     180
aagcugaccc ugaaguucau cugcaccacc ggcaagcugc ccgugcccug gcccacccuc     240
gugaccaccc ugaccuacgg cgugcagugc uucagccgcu accccgacca caugaagcag     300
cacgacuucu ucaaguccgc caugcccgaa ggcuacgucc aggagcgcac caucuucuuc     360
aaggacgacg gcaacuacaa gacccgcgcc gaggugaagu cgagggcga cacccuggug     420 aaccgcaucg agcugaaggg caucgacuuc aaggaggacg gcaacauccu ggggcacaag     480
cuggaguaca acuacaacag ccacaacguc uauaucaugg ccgacaagca gaagaacggc     540
aucaagguga acuucaagau ccgccacaac aucgaggacg gcagcgugca gcucgccgac     600
cacuaccagc agaacacccc caucggcgac ggccccgugc ugcugcccga caaccacuac     660
cugagcaccc aguccgcccu gagcaaagac cccaacgaga gcgcgauca cauggaccug     720 cuggaguucu ugaccgccgc cgggaucacu cucggcaugg acgagcugua caaguaauuc     780
uaggcgaucg cucgaaaaac augaggauca cccaugucug caggucgacu cuagaaaaca     840
ugaggaucac ccaugaccug caggucgacu cuagaaaaca ugaggaucac ccaugucugc     900
aggucgacuc uagaaaacau gaggaucacc caugaccucg aaaaacauga ggaucaccca     960
ugucugcagg ucgacucuag aaaacaugag gaucacccau guucugcagg ucgacucuag    1020
aaaacaugag gaucacccau gucugcaggu cgacucuaga aaacaugagg aucacccaug    1080
uccucgaggu gucggccgc ugaauaaagc cugaguagga aaaaaaaaa aaaaaaaaa      1140 aaaaaaaaaa aaaaaaaaaa aaaaaaaaa aaaaaaaaaa aaaaaaaaaa aaaaaaaaaa    1200
aaaaaaaaaa aaaaaaaaaa aaaaaaaaa aaaaaaaaa                             1239

<210> SEQ ID NO 18
<211> LENGTH: 653
<212> TYPE: RNA
<213> ORGANISM: Artificial Sequence
<220> FEATURE:
<223> OTHER INFORMATION: Synthetic Polynucleotide

<400> SEQUENCE: 18
gggcgaauua agagagaaaa gaagaguaag aagaaauaua agacaccggu cgccaccaug      60
ggauccgcuu cuaacuuuac ucaguucguu cucgucgaca auggcggaac uggcgacgug     120
acugucgccc caagcaacuu cgcuaacggg gucgcugaau ggaucagcuc uaacucgcga     180
ucacaggcuu acaaaguaac cuguagcguu cgucagagcu cugcgcagaa ucgcaaauac     240
accaucaaag ucgaggugcc uaaaggcgca uggaggucuu acuuaaauau ggaacuaacc     300
auccaauuuu ucgccacgaa uuccgacugc gagcuuauug uuaaggcaau gcaaggucuc     360
cuaaaagaug gaaacccgau ucccucggcc aucgcggcca acuccggcau cuacagaucu     420
cauaugcauc ucgagugaua gucuagaccu ucugcggggc uugccuucug gccaugcccu     480
ucuucucucc cuugcaccug uaccucuugg ucuuugaauu aagccugagu aggaaaaaaa     540
aaaaaaaaaa aaaaaaaaaa aaaaaaaaa aaaaaaaaa aaaaaaaaaa aaaaaaaaaa      600
```

| aaaaaaaaaa aaaaaaaaaa aaaaaaaaaa aaaaaaaaaa aaaaaaaaaa aaa | 653 |

<210> SEQ ID NO 19
<211> LENGTH: 1594
<212> TYPE: RNA
<213> ORGANISM: Artificial Sequence
<220> FEATURE:
<223> OTHER INFORMATION: Synthetic Polynucleotide

<400> SEQUENCE: 19

| ggauccguga ucggaaacgu gagauccacc ucagauccgc uaggacaccc gcagaucgag | 60 |
| aagaaggcga auuaagagag aaaagaagag uaagaagaaa uauaagacac cggucgccac | 120 |
| cauggcuucu aacuuuacuc aguucguucu cgucgacaau ggcggaacug cgacgugac | 180 |
| ugucgcccca agcaacuucg cuaacggggu cgcugaaugg aucagcucua acucgcguuc | 240 |
| acaggcuuac aaaguaaccu guagcguucg ucagagcucu gcgcagaagc gcaaauacac | 300 |
| caucaaaguc gaggugccua aguggcaacc cagacuguu ggugguguag agcuuccugu | 360 |
| agccgcaugg cguucguacu uaaauaugga acuaaccauu ccaauuuucg ccacgaauuc | 420 |
| cgacugcgag cuuauuguua aggcaaugca aggucuccua aaagauggaa acccgauucc | 480 |
| cucggccauc gcagcaaacu ccggcaucua cucgaucgcc augccagcgg caacuguaga | 540 |
| ucauagccaa agaauuugug aaguuugggc uugcaacuug gaugaagaga ugaagaaaau | 600 |
| ucgucaaguu auccgaaaau auaauuacgu ugcuauggac accgaguuuc caggugguggu | 660 |
| ugcaagaccc auuggagaau ucaggagcaa ugcugacuau caauaccaac uauugcggug | 720 |
| uaauguagac uuguuaaaga uaauucagcu aggacugaca uuuaugaaug agcaaggaga | 780 |
| auaccccucca ggaacuucaa cuuggcaguu uaauuuuaaa uuuaauuuga cggaggacau | 840 |
| guaugcccag gacucuauag agcuacuaac aacaucuggu uccaguuuua aaaacauga | 900 |
| ggaggaagga auugaaaccc aguacuuugc agaacuucuu augacuucug gagugguccu | 960 |
| cugugaaggg gucaaauggu ugucauuuca uagcgguuac gacuuuggcu acuuaaucaa | 1020 |
| aauccuaacc aacucuaacu ugccugaaga agaacuugac uucuuugaga uccuucgauu | 1080 |
| guuuuuccu gucauuuaug augugaagua ccucaugaag agcugcaaaa aucucaaagg | 1140 |
| uggauuacag gagguggcag aacaguuaga gcuggaacgg auaggaccac aacaucaggc | 1200 |
| aggaucugau ucauugcuca caggaauggc cuuuuucaaa augagagaaa uguucuuuga | 1260 |
| agaucauauu gaugaugcca aauauugugg ucauuguau ggccuugguu cugguucauc | 1320 |
| cuauguacag aauggcacag ggaaugcaua ugaagaggaa gccaacaagc agucaguuua | 1380 |
| aaucuagacc uucugcgggg cuugccuucu ggccaugccc uucuucucuc ccuugcaccu | 1440 |
| guaccucuug gucuuugaau aaagccugag uaggaaaaaa aaaaaaaaa aaaaaaaaa | 1500 |
| aaaaaaaaaa aaaaaaaaaa aaaaaaaaaa aaaaaaaaaa aaaaaaaaaa aaaaaaaaaa | 1560 |
| aaaaaaaaaa aaaaaaaaaa aaaaaaaaaa aaaa | 1594 |

<210> SEQ ID NO 20
<211> LENGTH: 680
<212> TYPE: RNA
<213> ORGANISM: Artificial Sequence
<220> FEATURE:
<223> OTHER INFORMATION: Synthetic Polynucleotide

<400> SEQUENCE: 20

| gggcgaauua agagagaaaa gaagaguaag aagaaauaua agacaccggu cgccaccaug | 60 |

| | |
|---|---|
| uacgugagau uugagguucc ugaggacaug cagaacgaag cucugagucu gcuggagaag | 120 |
| guuagggaga gcgguaaggu aaagaaaggu accaacgaga cgacaaaggc guggagagg | 180 |
| ggacuggcaa agcucguuua caucgcagag gauguugacc cgccugagau cguugcucau | 240 |
| cugcccccucc ucugcgagga gaagaaugug ccguacauuu acguuaaaag caagaacgac | 300 |
| cuuggaaggg cuguggggcau ugaggugcca ugcgcuucgg cagcgauaau caacgaggga | 360 |
| gagcugagaa aggagcuugg aagccuugug gagaagauua aaggccuuca gaaguaaggc | 420 |
| gcgccccgcu ugaagucuuu aauuaaaccg cuugaagucu uuaauuaaac cgcuugaagu | 480 |
| cuuuaauuaa accgcuugaa gucuuuaauu aaagcuaguu acccagcuuu cuuguacaaa | 540 |
| gugaauaaag ccugaguagg aaaaaaaaaa aaaaaaaaaa aaaaaaaaaa aaaaaaaaaa | 600 |
| aaaaaaaaaa aaaaaaaaaa aaaaaaaaaa aaaaaaaaaa aaaaaaaaaa aaaaaaaaaa | 660 |
| aaaaaaaaaa aaaaaaaaaa | 680 |

<210> SEQ ID NO 21
<211> LENGTH: 990
<212> TYPE: RNA
<213> ORGANISM: Artificial Sequence
<220> FEATURE:
<223> OTHER INFORMATION: Synthetic Polynucleotide

<400> SEQUENCE: 21

| | |
|---|---|
| gggcgaauua agagagaaaa gaagaguaag aagaaauaua agacaccggu cgccaccaug | 60 |
| gugagcaagg gcgaggagcu guucaccggg guggugccca uccuggucga gcuggacggc | 120 |
| gacguaaacg gccacaaguu cagcgugucc ggcgagggcg agggcgaugc caccuacggc | 180 |
| aagcugaccc ugaaguucau cugcaccacc ggcaagcugc ccgugcccug gcccacccuc | 240 |
| gugaccaccc ugaccuacgg cgugcagugc uucagccgcu accccgacca caugaagcag | 300 |
| cacgacuucu ucaaguccgc caugcccgaa ggcuacgucc aggagcgcac caucuucuuc | 360 |
| aaggacgacg gcaacuacaa gacccgcgcc gaggugaagu ucgagggcga cacccugggug | 420 |
| aaccgcaucg agcugaaggg caucgacuuc aaggaggacg gcaacauccu ggggcacaag | 480 |
| cuggaguaca acuacaacag ccacaacguc uauaucaugg ccgacaagca gaagaacggc | 540 |
| aucaagguga acuucaagau ccgccacaac aucgaggacg gcagcgugca gcucgccgac | 600 |
| cacuaccagc agaacacccc caucggcgac ggccccgugc ugcugcccga caaccacuac | 660 |
| cugagcaccc aguccgcccu gagcaaagac cccaacgaga gcgcgauca caugguccug | 720 |
| cuggaguucg ugaccgccgc cgggaucacu cucggcaugg acgagcugua caaguagguc | 780 |
| uagaccuucu gcggggcuug ccuucuggcc augcccuucu cucucccuu gcaccuguac | 840 |
| cucuuggucu uugaauaaag ccugaguagg aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaa | 990 |

<210> SEQ ID NO 22
<211> LENGTH: 1116
<212> TYPE: RNA
<213> ORGANISM: Artificial Sequence
<220> FEATURE:
<223> OTHER INFORMATION: Synthetic Polynucleotide

<400> SEQUENCE: 22

| | |
|---|---|
| gggcgaauua agagagaaaa gaagaguaag aagaaauaua agacaccggu cgccaccaug | 60 |
| gugagcaagg gcgaggagcu guucaccggg guggugccca uccuggucga gcuggacggc | 120 |

```
gacguaaacg gccacaaguu cagcgugucc ggcgagggcg agggcgaugc caccuacggc    180
aagcugaccc ugaaguucau cugcaccacc ggcaagcugc ccgugcccug gcccacccuc    240
gugaccaccc ugaccuacgg cgugcagugc uucagccgcu accccgacca caugaagcag    300
cacgacuucu ucaagccgc caugcccgaa ggcuacgucc aggagcgcac caucuucuuc    360
aaggacgacg gcaacuacaa gacccgcgcc gaggugaagu ucgagggcga cacccuggug    420
aaccgcaucg agcugaaggg caucgacuuc aaggaggacg gcaacauccu ggggcacaag    480
cuggaguaca acuacaacag ccacaacguc uauaucaugg ccgacaagca gaagaacggc    540
aucaagguga acuucaagau ccgccacaac aucgaggacg gcagcgugca gcucgccgac    600
cacuaccagc agaacacccc caucggcgac ggccccgugc ugcugcccga caaccacuac    660
cugagcaccc aguccgcccu gagcaaagac cccaacgaga agcgcgauca cauggaccug    720
cuggaguucg ugaccgccgc cgggaucacu cucggcaugg acgagcugua caagaagcuu    780
agccauggcu ucccgccgga ggguggaggag caggaugaug gcacgcugcc caugucuugu    840
gcccaggaga gcgggaugga ccgucacccu gcagccugug cuucugcuag gaucaaugug    900
uagcucuaga ccuucgcgg ggcuugccuu cuggccaugc ccuucuucuc ucccuugcac    960
cuguaccucu uggucuuuga auaaagccug aguaggaaaa aaaaaaaaaa aaaaaaaaa    1020 aaaaaaaaaa aaaaaaaaaa aaaaaaaaaa aaaaaaaaaa aaaaaaaaaa aaaaaaaaaa    1080
aaaaaaaaaa aaaaaaaaaa aaaaaaaaaa aaaaaa                               1116
```

<210> SEQ ID NO 23
<211> LENGTH: 1083
<212> TYPE: RNA
<213> ORGANISM: Artificial Sequence
<220> FEATURE:
<223> OTHER INFORMATION: Synthetic Polynucleotide

<400> SEQUENCE: 23

```
ggauccguga ucggaaacgu gagauccacc ucagauccgc uaggacaccc gcagaucgag     60
aagaaggcga auuaagagag aaaagaagag uaagaagaaa uauaagacac cggucgccac    120
caugggaucc gugagcaagg gcgaggagcu guucaccggg guggugccca uccuggucga    180
gcuggacggc gacguaaacg gccacaaguu cagcgugucc ggcgagggcg agggcgaugc    240
caccuacggc aagcugaccc ugaaguucau cugcaccacc ggcaagcugc ccgugcccug    300
gcccacccuc gugaccaccc ugaccuacgg cgugcagugc uucagccgcu accccgacca    360
caugaagcag cacgacuucu ucaagccgc caugcccgaa ggcuacgucc aggagcgcac    420
caucuucuuc aaggacgacg gcaacuacaa gacccgcgcc gaggugaagu ucgagggcga    480
cacccuggug aaccgcaucg agcugaaggg caucgacuuc aaggaggacg gcaacauccu    540
ggggcacaag cuggaguaca acuacaacag ccacaacguc uauaucaugg ccgacaagca    600
gaagaacggc aucaagguga acuucaagau ccgccacaac aucgaggacg gcagcgugca    660
gcucgccgac cacuaccagc agaacacccc caucggcgac ggccccgugc ugcugcccga    720
caaccacuac cugagcaccc aguccgcccu gagcaaagac cccaacgaga agcgcgauca    780 cauguccug cuggaguucg ugaccgccgc cgggaucacu cucggcaugg acgagcugua    840
caagagaucu cauaugcauc ucgagugaua gucuagaccu ucugcggggc uugccuucug    900
gccaugcccu ucuucucucc cuugcaccug uaccucuugg ucuuugaaua aagccugagu    960
aggaaaaaaa aaaaaaaaaa aaaaaaaaaa aaaaaaaaaa aaaaaaaaaa aaaaaaaaaa    1020
```

```
aaaaaaaaaa aaaaaaaaaa aaaaaaaaaa aaaaaaaaaa aaaaaaaaaa aaaaaaaaaa    1080
aaa                                                                   1083

<210> SEQ ID NO 24
<211> LENGTH: 653
<212> TYPE: RNA
<213> ORGANISM: Artificial Sequence
<220> FEATURE:
<223> OTHER INFORMATION: Synthetic Polynucleotide

<400> SEQUENCE: 24
gggcgaauua agagagaaaa gaagaguaag aagaaauaua agacaccggu cgccaccaug      60
uacgugagau uugagguucc ugaggacaug cagaacgaag cucugagucu gcuggagaag     120
guuagggaga gcgguaaggu aaagaaaggu accaacgaga cgacaaaggc uguggagagg     180
ggacuggcaa agcucguuua caucgcagag gauguugacc cgccugagau cguugcucau     240 cugcccclucc ucugcgagga gaagaaugug ccguacauuu acguuaaaag caagaacgac    300
cuuggaaggg cugugggcau ugaggugcca ugcgcuucgg cagcgauaau caacgaggga    360
gagcugagaa aggagcuugg aagccuugug gagaagauua aaggccuuca gaagagaucu    420
cauaugcauc ucgagugaua gucuagaccu ucugcggggc uugccuucug gccaugcccu    480
ucuucucucc cuugcaccug uaccucuugg ucuuugauaa aagccugagu aggaaaaaaa    540
aaaaaaaaaa aaaaaaaaaa aaaaaaaaaa aaaaaaaaaa aaaaaaaaaa aaaaaaaaaa    600
aaaaaaaaaa aaaaaaaaaa aaaaaaaaaa aaaaaaaaaa aaaaaaaaaa aaa            653

<210> SEQ ID NO 25
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 25

Ser Ile Ile Asn Phe Glu Lys Leu
1               5

<210> SEQ ID NO 26
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 26
ggtctccgac tagaagagc                                                   19

<210> SEQ ID NO 27
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 27
gctcttcaca cctgagacc                                                   19

<210> SEQ ID NO 28
<211> LENGTH: 18
<212> TYPE: DNA
<213> ORGANISM: Artificial Sequence
<220> FEATURE:
```

<223> OTHER INFORMATION: Synthetic Polynucleotide

<400> SEQUENCE: 28
ggtctcacac cgaagagc                                                 18

<210> SEQ ID NO 29
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 29
gctcttcaat aatgagacc                                                19

<210> SEQ ID NO 30
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 30
ggtctccata agaagagc                                                 18

<210> SEQ ID NO 31
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 31
gctcttcttc atgagacc                                                 18

<210> SEQ ID NO 32
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 32
ggtctccgac taagtcttc                                                19

<210> SEQ ID NO 33
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 33
gaagacttca cctgagacc                                                19

<210> SEQ ID NO 34
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 34
ggtctcacac caagtcttc                                                19

```
<210> SEQ ID NO 35
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 35
gaagacttat aatgagacc                                               19

<210> SEQ ID NO 36
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 36
ggtctccata aaagtcttc                                               19

<210> SEQ ID NO 37
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 37
gaagactttt catgagacc                                               19

<210> SEQ ID NO 38
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t

<400> SEQUENCE: 38
gctcttcnac t                                                       11

<210> SEQ ID NO 39
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (4)..(4)
<223> OTHER INFORMATION: n is a, c, g, or t

<400> SEQUENCE: 39
cacngaagag c                                                       11

<210> SEQ ID NO 40
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (7)..(7)
<223> OTHER INFORMATION: n is a, c, g, or t
```

```
<400> SEQUENCE: 40
ggtctcngac t                                                          11

<210> SEQ ID NO 41
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (5)..(5)
<223> OTHER INFORMATION: n is a, c, g, or t

<400> SEQUENCE: 41
caccngagac c                                                          11

<210> SEQ ID NO 42
<211> LENGTH: 12
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (7)..(8)
<223> OTHER INFORMATION: n is a, c, g, or t

<400> SEQUENCE: 42
gaagacnnga ct                                                         12

<210> SEQ ID NO 43
<211> LENGTH: 12
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (5)..(6)
<223> OTHER INFORMATION: n is a, c, g, or t

<400> SEQUENCE: 43
caccnngtct tc                                                         12

<210> SEQ ID NO 44
<211> LENGTH: 12
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t

<400> SEQUENCE: 44
gctcttcnca cc                                                         12

<210> SEQ ID NO 45
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 45
ataagaagag c                                                          11
```

```
<210> SEQ ID NO 46
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (7)..(7)
<223> OTHER INFORMATION: n is a, c, g, or t

<400> SEQUENCE: 46
ggtctcncac c                                                          11

<210> SEQ ID NO 47
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (5)..(5)
<223> OTHER INFORMATION: n is a, c, g, or t

<400> SEQUENCE: 47
ataangagac c                                                          11

<210> SEQ ID NO 48
<211> LENGTH: 12
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (7)..(8)
<223> OTHER INFORMATION: n is a, c, g, or t

<400> SEQUENCE: 48
gaagacnnca cc                                                         12

<210> SEQ ID NO 49
<211> LENGTH: 12
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (5)..(6)
<223> OTHER INFORMATION: n is a, c, g, or t

<400> SEQUENCE: 49
ataanngtct tc                                                         12

<210> SEQ ID NO 50
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t

<400> SEQUENCE: 50
```
gctcttcnat a        11

<210> SEQ ID NO 51
<211> LENGTH: 12
<212> TYPE: DNA
<213> ORGANISM: Artificial Sequence
<220> FEATURE:
<223> OTHER INFORMATION: Synthetic Polynucleotide

<400> SEQUENCE: 51
ttcaagaaga gc        12

<210> SEQ ID NO 52
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 52
ggtctcaata aaagtcttc        19

<210> SEQ ID NO 53
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (7)..(7)
<223> OTHER INFORMATION: n is a, c, g, or t

<400> SEQUENCE: 53
ggtctcnata a        11

<210> SEQ ID NO 54
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (5)..(5)
<223> OTHER INFORMATION: n is a, c, g, or t

<400> SEQUENCE: 54
ttcangagac c        11

<210> SEQ ID NO 55
<211> LENGTH: 12
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (7)..(8)
<223> OTHER INFORMATION: n is a, c, g, or t

<400> SEQUENCE: 55
gaagacnnat aa        12

<210> SEQ ID NO 56
<211> LENGTH: 12
<212> TYPE: DNA
<213> ORGANISM: Artificial Sequence

```
<220> FEATURE:
<223> OTHER INFORMATION: Synthetic Polynucleotide
<220> FEATURE:
<221> NAME/KEY: misc_feature
<222> LOCATION: (5)..(6)
<223> OTHER INFORMATION: n is a, c, g, or t

<400> SEQUENCE: 56
ttcanngtct tc                                                         12
```

RNA-BASED LOGIC CIRCUITS WITH RNA BINDING PROTEINS, APTAMERS AND SMALL MOLECULES

RELATED APPLICATIONS

This application is a national stage filing under 35 U.S.C. § 371 of International Application No. PCT/US2015/049045, filed Sep. 8, 2015, which claims the benefit under 35 U.S.C. § 119(e) of U.S. provisional application 62/047,137, entitled "RNA-BASED LOGIC CIRCUITS WITH RNA BINDING PROTEINS, APTAMERS AND SMALL MOLECULES," filed Sep. 8, 2014 and of U.S. provisional application 62/195,747, entitled "RNA-BASED LOGIC CIRCUITS WITH RNA BINDING PROTEINS, APTAMERS AND SMALL MOLECULES," filed Jul. 22, 2015, the entire disclosures of each which are herein incorporated by reference in their entireties.

FEDERALLY SPONSORED RESEARCH

This invention was made with Government support under Contract No. W911NF-11-2-0054 awarded by the Army Research Office. The Government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Mar. 7, 2017, is named M065670359US02-SEQ-JRV and is 30326 bytes in size.

FIELD OF INVENTION

Engineered synthetic RNA-based genetic circuits are provided that are regulated exclusively at the post-transcriptional level.

BACKGROUND OF INVENTION

Messenger RNA (mRNA) as a platform for gene transfer has numerous advantages over plasmid DNA including the lack of requirement for crossing the nuclear envelope, and importantly, negligible risk of genomic integration (1-2). The recent progress in development of chemical mRNA modifications made it possible to use in vitro synthesized mRNA with high stability and low immunogenicity as a powerful tool for gene therapy (3-6). Self-replicating RNA is also gaining interest for biomedical applications (7-8).

However, synthetic biology has remained DNA-centered and genetic circuit design always relies exclusively or partially on transcriptional regulation. The development of parts and devices has also been focused primarily on promoter and transcription factor libraries (9-10).

SUMMARY OF INVENTION

The promise of synthetic biology is that the engineered genetic circuits will provide sophistication of output control that can never be achieved with traditional pharmaceuticals. Encoding the regulation exclusively at post-transcriptional level and RNA delivery of desired logic circuits may enable the benefits of synthetic biology tools while offering the safety of non-DNA therapeutics. However, no control mechanisms have been developed to regulate replicon-based expression. While there have been a number of efforts to engineer post-transcriptional devices based on microRNA, aptamers, or aptazymes (11), most are characterized by a very low dynamic range and importantly, the devices are not suitable for construction of scalable circuits.

Devices based on RNA-binding proteins (RBPs), however, can be easily wired together to create synthetic circuits of various complexities or to interconnect cellular and synthetic signaling pathways.

According to one aspect, synthetic RNA circuits are provided. The circuits include a first RNA molecule comprising at least one sequence recognized by at least one first microRNA that is/are specifically expressed in a first cell type, and a sequence encoding a protein that specifically binds to a RNA motif and inhibits protein production; and a second RNA molecule comprising at least one sequence recognized by at least one second microRNA that is/are not expressed in the first cell type or is expressed at a low level relative to a second cell type, at least one RNA motif and a sequence encoding an output molecule.

In some embodiments, in a cell that expresses the at least one first microRNA but does not express the at least one second microRNA, the at least one first microRNA represses translation of or degrades the sequence encoding the protein that specifically binds to a RNA motif and inhibits protein production, thereby allowing expression of the output molecule.

In some embodiments, the output molecule is a protein. In some embodiments, the protein is a therapeutic protein, a cell death protein, a fluorescent protein, an antigen, a selection protein, or an immunomodulator. In some embodiments, the therapeutic protein is a protein for protein replacement therapy, Myr-Akt, or follistatin. In some embodiments, the selection protein is used for selection or purification of a cell in which it is expressed. In some embodiments, the selection protein is a protein that confers drug resistance to a cell. In some embodiments, the fluorescent protein is EGFP, EYFP, or EBFP. In some embodiments, immunomodulator protein is a cytokine. In some embodiments, the cytokine is IL-12, IL-15 or IL-21. In some embodiments, the immunomodulator protein is a immunosuppressant protein. In some embodiments, the cell death protein is hBax.

In some embodiments, the RNA molecules encode more than one output molecule.

In some embodiments, the output molecules comprise at least one antigen, and optionally, one or more adjuvants.

In some embodiments, the protein that specifically binds to a RNA motif and inhibits protein production is L7Ae or a fusion of MS2 protein and a protein that inhibits protein production. In some embodiments, the protein that specifically binds to a RNA motif and inhibits protein production is L7Ae and the RNA motif is one or more Box C/D, K-turn and/or K-loop motifs. In some embodiments, the RNA motif is two K-turn motifs. In some embodiments, the one or more Box C/D, K-turn and/or K-loop motifs are placed in the 5' untranslated region (UTR) of the second RNA molecule.

In some embodiments, the protein that specifically binds to a RNA motif and inhibits protein production is a fusion of MS2 protein and a protein that inhibits protein production and the RNA motif is one or more MS2 coat protein binding sites. In some embodiments, the RNA motif is eight MS2 coat protein binding sites. In some embodiments, the one or more MS2 coat protein binding sites are placed in the 3' untranslated region (UTR) of the second RNA molecule. In some embodiments, the MS2 fusion protein is a fusion of MS2 protein and CNOT7 protein (MS2-CNOT7) or Dm-POP2 protein (MS2-Dm-POP2).

In some embodiments, the RNA molecules comprise modified RNA. In some embodiments, the RNA molecules comprise 5-methylcytosine-triphosphate and/or pseudouridine-triphosphate.

In some embodiments, the RNA molecules are encoded on one or more RNA replicons. In some embodiments, the one or more RNA replicons is/are one or more alphavirus derived replicons, Venezuelan equine encephalitis virus derived replicons or Sindbis derived virus replicons. In some embodiments, the RNA molecules are expressed from one or more subgenomic promoters of the one or more replicons, optionally wherein the one or more subgenomic promoters are optimized for length or position in the RNA molecule. In some embodiments, the one or more subgenomic promoters are regulated by a small molecule. In some embodiments, the small molecule is trimethoprim (TMP) or 4-hydroxytamoxifin (4-OHT).

In some embodiments, the RNA molecules are encoded on one or more plasmids.

In some embodiments, the first cell type is a cancer cell. In some embodiments, the at least one first microRNA is miR-21. In some embodiments, the at least one second microRNA is selected from the group consisting of miR-141, miR-142 and miR-146.

In some embodiments, the synthetic RNA circuit further includes a sequence encoding Csy4 protein and a Csy4 recognition site. In some embodiments, the Csy4 protein is a fusion of a destabilization domain and Csy4. In some embodiments, the destabilization domain is regulated by trimethoprim (TMP) or 4-hydroxytamoxifen (4-OHT).

In some embodiments, the synthetic RNA circuit further includes one or more internal ribosomal entry sites (IRESs) for improved polycystronic expression. In some embodiments, the synthetic RNA circuit further includes one or more general translation enhancers (GTEs). In some embodiments, the synthetic RNA circuit is encoded on self-cleaving helper-defective interfering RNA, optionally comprising Csy4, wherein Csy4 is expressed from an internal ribosome entry site (IRES).

According to another aspect, methods of treating cancer in a mammal are provided. The methods include administering to a mammal the foregoing synthetic RNA circuits. In some embodiments, the synthetic RNA circuit is administered as a first replicon, and further administering a second replicon as ballast to control expression of a protein encoded by the first replicon.

According to another aspect, methods of inducing an immune response in a mammal are provided. The methods include administering to a mammal the foregoing synthetic RNA circuits. In some embodiments, the synthetic RNA circuit is administered as a first replicon, and further administering a second replicon as ballast to control expression of a protein encoded by the first replicon.

According to another aspect, synthetic RNA circuits are provided. The circuits include a first RNA molecule comprising at least one sequence recognized by a protein that specifically binds to a RNA motif and inhibits protein production, and a sequence encoding an output molecule; a second RNA molecule comprising at least one sequence recognized by a second protein that specifically binds to a RNA motif and inhibits protein production, and a sequence encoding the first protein that specifically binds to a RNA motif and inhibits protein production; and a third RNA molecule comprising at least one sequence recognized by an siRNA molecule or a microRNA molecule, and a sequence encoding the second protein that specifically binds to a RNA motif and inhibits protein production. In some embodiments, the circuits further include the siRNA molecule or microRNA molecule that binds to the third RNA molecule. In some embodiments, the siRNA molecule is a synthetic siRNA molecule, or wherein the microRNA molecule is an endogenously expressed microRNA molecule.

In some embodiments, the output molecule is a protein. In some embodiments, the protein is a therapeutic protein, a cell death protein, a fluorescent protein, an antigen, a selection protein, or an immunomodulator. In some embodiments, the therapeutic protein is a protein for protein replacement therapy, Myr-Akt, or follistatin. In some embodiments, the selection protein is used for selection or purification of a cell in which it is expressed. In some embodiments, the selection protein is a protein that confers drug resistance to a cell. In some embodiments, the fluorescent protein is EGFP, EYFP, or EBFP. In some embodiments, immunomodulator protein is a cytokine. In some embodiments, the cytokine is IL-12, IL-15 or IL-21. In some embodiments, the immunomodulator protein is a immunosuppressant protein. In some embodiments, the cell death protein is hBax.

In some embodiments, the RNA molecules encode more than one output molecule.

In some embodiments, the output molecules comprise at least one antigen, and optionally, one or more adjuvants.

In some embodiments, the protein that specifically binds to a RNA motif and inhibits protein production is L7Ae or a fusion of MS2 protein and a protein that inhibits protein production. In some embodiments, the protein that specifically binds to a RNA motif and inhibits protein production is L7Ae and the RNA motif is one or more Box C/D, K-turn and/or K-loop motifs. In some embodiments, the RNA motif is two K-turn motifs. In some embodiments, the one or more Box C/D, K-turn and/or K-loop motifs are placed in the 5' untranslated region (UTR) of the second RNA molecule.

In some embodiments, the protein that specifically binds to a RNA motif and inhibits protein production is a fusion of MS2 protein and a protein that inhibits protein production and the RNA motif is one or more MS2 coat protein binding sites. In some embodiments, the RNA motif is eight MS2 coat protein binding sites. In some embodiments, the one or more MS2 coat protein binding sites are placed in the 3' untranslated region (UTR) of the second RNA molecule. In some embodiments, the MS2 fusion protein is a fusion of MS2 protein and CNOT7 protein (MS2-CNOT7) or Dm-POP2 protein (MS2-Dm-POP2).

In some embodiments, the RNA molecules comprise modified RNA. In some embodiments, the RNA molecules comprise 5-methylcytosine-triphosphate and/or pseudouridine-triphosphate.

In some embodiments, the RNA molecules are encoded on one or more RNA replicons. In some embodiments, the one or more RNA replicons is/are one or more alphavirus derived replicons, Venezuelan equine encephalitis virus derived replicons or Sindbis derived virus replicons. In some embodiments, the RNA molecules are expressed from one or more subgenomic promoters of the one or more replicons, optionally wherein the one or more subgenomic promoters are optimized for length or position in the RNA molecule. In some embodiments, the one or more subgenomic promoters are regulated by a small molecule. In some embodiments, the small molecule is trimethoprim (TMP) or 4-hydroxytamoxifin (4-OHT).

In some embodiments, the RNA molecules are encoded on one or more plasmids.

In some embodiments, the synthetic RNA circuit further includes a sequence encoding Csy4 protein and a Csy4 recognition site. In some embodiments, the Csy4 protein is a fusion of a destabilization domain and Csy4. In some embodiments, the destabilization domain is regulated by trimethoprim (TMP) or 4-hydroxytamoxifin (4-OHT).

In some embodiments, the synthetic RNA circuit further includes one or more internal ribosomal entry sites (IRESs) for improved polycystronic expression. In some embodiments, the synthetic RNA circuit further includes one or more general translation enhancers (GTEs). In some embodiments, the synthetic RNA circuit is encoded on self-cleaving helper-defective interfering RNA, optionally comprising Csy4, wherein Csy4 is expressed from an internal ribosome entry site (IRES).

According to another aspect, methods of treating cancer in a mammal are provided. The methods include administering to a mammal the foregoing synthetic RNA circuits. In some embodiments, the synthetic RNA circuit is administered as a first replicon, and further administering a second replicon as ballast to control expression of a protein encoded by the first replicon.

According to another aspect, methods of inducing an immune response in a mammal are provided. The methods include administering to a mammal the foregoing synthetic RNA circuits. In some embodiments, the synthetic RNA circuit is administered as a first replicon, and further administering a second replicon as ballast to control expression of a protein encoded by the first replicon.

According to another aspect, synthetic RNA circuits are provided. The circuits include a first RNA molecule comprising at least one sequence recognized by a first protein that specifically binds to a RNA motif and inhibits protein production, and a sequence encoding an output molecule; and a second RNA molecule comprising at least one sequence recognized by an siRNA molecule or a microRNA molecule, and a sequence encoding the first protein that specifically binds to a RNA motif and inhibits protein production. In some embodiments, the circuits further include the siRNA molecule or microRNA molecule that binds to the second RNA molecule. In some embodiments, the siRNA molecule is a synthetic siRNA molecule, or wherein the microRNA molecule is an endogenously expressed microRNA molecule.

In some embodiments, the output molecule is a protein. In some embodiments, the protein is a therapeutic protein, a cell death protein, a fluorescent protein, an antigen, a selection protein, or an immunomodulator. In some embodiments, the therapeutic protein is a protein for protein replacement therapy, Myr-Akt, or follistatin. In some embodiments, the selection protein is used for selection or purification of a cell in which it is expressed. In some embodiments, the selection protein is a protein that confers drug resistance to a cell. In some embodiments, the fluorescent protein is EGFP, EYFP, or EBFP. In some embodiments, immunomodulator protein is a cytokine. In some embodiments, the cytokine is IL-12, IL-15 or IL-21. In some embodiments, the immunomodulator protein is a immunosuppressant protein. In some embodiments, the cell death protein is hBax.

In some embodiments, the RNA molecules encode more than one output molecule.

In some embodiments, the output molecules comprise at least one antigen, and optionally, one or more adjuvants.

In some embodiments, the protein that specifically binds to a RNA motif and inhibits protein production is L7Ae or a fusion of MS2 protein and a protein that inhibits protein production. In some embodiments, the protein that specifically binds to a RNA motif and inhibits protein production is L7Ae and the RNA motif is one or more Box C/D, K-turn and/or K-loop motifs. In some embodiments, the RNA motif is two K-turn motifs. In some embodiments, the one or more Box C/D, K-turn and/or K-loop motifs are placed in the 5' untranslated region (UTR) of the second RNA molecule.

In some embodiments, the protein that specifically binds to a RNA motif and inhibits protein production is a fusion of MS2 protein and a protein that inhibits protein production and the RNA motif is one or more MS2 coat protein binding sites. In some embodiments, the RNA motif is eight MS2 coat protein binding sites. In some embodiments, the one or more MS2 coat protein binding sites are placed in the 3' untranslated region (UTR) of the second RNA molecule. In some embodiments, the MS2 fusion protein is a fusion of MS2 protein and CNOT7 protein (MS2-CNOT7) or Dm-POP2 protein (MS2-Dm-POP2).

In some embodiments, the RNA molecules comprise modified RNA. In some embodiments, the RNA molecules comprise 5-methylcytosine-triphosphate and/or pseudouridine-triphosphate.

In some embodiments, the RNA molecules are encoded on one or more RNA replicons. In some embodiments, the one or more RNA replicons is/are one or more alphavirus derived replicons, Venezuelan equine encephalitis virus derived replicons or Sindbis derived virus replicons. In some embodiments, the RNA molecules are expressed from one or more subgenomic promoters of the one or more replicons, optionally wherein the one or more subgenomic promoters are optimized for length or position in the RNA molecule. In some embodiments, the one or more subgenomic promoters are regulated by a small molecule. In some embodiments, the small molecule is trimethoprim (TMP) or 4-hydroxytamoxifin (4-OHT).

In some embodiments, the RNA molecules are encoded on one or more plasmids.

In some embodiments, the synthetic RNA circuit further includes a sequence encoding Csy4 protein and a Csy4 recognition site. In some embodiments, the Csy4 protein is a fusion of a destabilization domain and Csy4. In some embodiments, the destabilization domain is regulated by trimethoprim (TMP) or 4-hydroxytamoxifin (4-OHT).

In some embodiments, the synthetic RNA circuit further includes one or more internal ribosomal entry sites (IRESs) for improved polycystronic expression. In some embodiments, the synthetic RNA circuit further includes one or more general translation enhancers (GTEs). In some embodiments, the synthetic RNA circuit is encoded on self-cleaving helper-defective interfering RNA, optionally comprising Csy4, wherein Csy4 is expressed from an internal ribosome entry site (IRES).

According to another aspect, methods of treating cancer in a mammal are provided. The methods include administering to a mammal the foregoing synthetic RNA circuits. In some embodiments, the synthetic RNA circuit is administered as a first replicon, and further administering a second replicon as ballast to control expression of a protein encoded by the first replicon.

According to another aspect, methods of inducing an immune response in a mammal are provided. The methods include administering to a mammal the foregoing synthetic RNA circuits. In some embodiments, the synthetic RNA circuit is administered as a first replicon, and further administering a second replicon as ballast to control expression of a protein encoded by the first replicon.

According to another aspect, synthetic RNA circuits are provided. The circuits include a first RNA molecule comprising at least one sequence recognized by a first protein that specifically binds to a RNA motif and inhibits protein production, a sequence encoding a second protein that specifically binds to a RNA motif and inhibits protein production, and at least one sequence recognized by a first siRNA molecule or microRNA molecule; and a second RNA molecule comprising at least one sequence recognized by the second protein that specifically binds to a RNA motif and inhibits protein production, a sequence encoding the first protein that specifically binds to a RNA motif and inhibits protein production, and at least one sequence recognized by a second siRNA molecule or microRNA molecule. In some embodiments, the circuits further include the siRNA molecule or microRNA molecule that binds to the third RNA molecule. In some embodiments, the siRNA molecule is a synthetic siRNA molecule, or wherein the microRNA molecule is an endogenously expressed microRNA molecule. In some embodiments, the first RNA molecule and/or the second RNA molecule further comprise a sequence encoding one or more output molecules that are not a protein that specifically binds to a RNA motif and inhibits protein production.

In some embodiments, the output molecule is a protein. In some embodiments, the protein is a therapeutic protein, a cell death protein, a fluorescent protein, an antigen, a selection protein, or an immunomodulator. In some embodiments, the therapeutic protein is a protein for protein replacement therapy, Myr-Akt, or follistatin. In some embodiments, the selection protein is used for selection or purification of a cell in which it is expressed. In some embodiments, the selection protein is a protein that confers drug resistance to a cell. In some embodiments, the fluorescent protein is EGFP, EYFP, or EBFP. In some embodiments, immunomodulator protein is a cytokine. In some embodiments, the cytokine is IL-12, IL-15 or IL-21. In some embodiments, the immunomodulator protein is a immunosuppressant protein. In some embodiments, the cell death protein is hBax.

In some embodiments, the RNA molecules encode more than one output molecule.

In some embodiments, the output molecules comprise at least one antigen, and optionally, one or more adjuvants.

In some embodiments, the protein that specifically binds to a RNA motif and inhibits protein production is L7Ae or a fusion of MS2 protein and a protein that inhibits protein production. In some embodiments, the protein that specifically binds to a RNA motif and inhibits protein production is L7Ae and the RNA motif is one or more Box C/D, K-turn and/or K-loop motifs. In some embodiments, the RNA motif is two K-turn motifs. In some embodiments, the one or more Box C/D, K-turn and/or K-loop motifs are placed in the 5' untranslated region (UTR) of the second RNA molecule.

In some embodiments, the protein that specifically binds to a RNA motif and inhibits protein production is a fusion of MS2 protein and a protein that inhibits protein production and the RNA motif is one or more MS2 coat protein binding sites. In some embodiments, the RNA motif is eight MS2 coat protein binding sites. In some embodiments, the one or more MS2 coat protein binding sites are placed in the 3' untranslated region (UTR) of the second RNA molecule. In some embodiments, the MS2 fusion protein is a fusion of MS2 protein and CNOT7 protein (MS2-CNOT7) or Dm-POP2 protein (MS2-Dm-POP2).

In some embodiments, the RNA molecules comprise modified RNA. In some embodiments, the RNA molecules comprise 5-methylcytosine-triphosphate and/or pseudouridine-triphosphate.

In some embodiments, the RNA molecules are encoded on one or more RNA replicons. In some embodiments, the one or more RNA replicons is/are one or more alphavirus derived replicons, Venezuelan equine encephalitis virus derived replicons or Sindbis derived virus replicons. In some embodiments, the RNA molecules are expressed from one or more subgenomic promoters of the one or more replicons, optionally wherein the one or more subgenomic promoters are optimized for length or position in the RNA molecule. In some embodiments, the one or more subgenomic promoters are regulated by a small molecule. In some embodiments, the small molecule is trimethoprim (TMP) or 4-hydroxytamoxifin (4-OHT).

In some embodiments, the RNA molecules are encoded on one or more plasmids.

In some embodiments, the synthetic RNA circuit further includes a sequence encoding Csy4 protein and a Csy4 recognition site. In some embodiments, the Csy4 protein is a fusion of a destabilization domain and Csy4. In some embodiments, the destabilization domain is regulated by trimethoprim (TMP) or 4-hydroxytamoxifin (4-OHT).

In some embodiments, the synthetic RNA circuit further includes one or more internal ribosomal entry sites (IRESs) for improved polycystronic expression. In some embodiments, the synthetic RNA circuit further includes one or more general translation enhancers (GTEs). In some embodiments, the synthetic RNA circuit is encoded on self-cleaving helper-defective interfering RNA, optionally comprising Csy4, wherein Csy4 is expressed from an internal ribosome entry site (IRES).

According to another aspect, methods of treating cancer in a mammal are provided. The methods include administering to a mammal the foregoing synthetic RNA circuits. In some embodiments, the synthetic RNA circuit is administered as a first replicon, and further administering a second replicon as ballast to control expression of a protein encoded by the first replicon.

According to another aspect, methods of inducing an immune response in a mammal are provided. The methods include administering to a mammal the foregoing synthetic RNA circuits. In some embodiments, the synthetic RNA circuit is administered as a first replicon, and further administering a second replicon as ballast to control expression of a protein encoded by the first replicon.

According to another aspect, synthetic RNA circuits are provided. The circuits include an RNA molecule comprising a sequence encoding a destabilization domain fused to an output protein, wherein the destabilization domain facilitates degradation of the output protein in the absence of a small molecule that binds to the destabilization domain.

In some embodiments, the protein is a therapeutic protein, a cell death protein, a fluorescent protein, an antigen, a selection protein, or an immunomodulator. In some embodiments, the therapeutic protein is a protein for protein replacement therapy, Myr-Akt, or follistatin. In some embodiments, the selection protein is used for selection or purification of a cell in which it is expressed. In some embodiments, the selection protein is a protein that confers drug resistance to a cell. In some embodiments, the fluorescent protein is EGFP, EYFP, or EBFP. In some embodiments, immunomodulator protein is a cytokine. In some embodiments, the cytokine is IL-12, IL-15 or IL-21. In some embodiments, the immunomodulator protein is a immunosuppressant protein. In some embodiments, the cell death protein is hBax.

In some embodiments, the RNA molecules encode more than one output molecule.

In some embodiments, the output molecules comprise at least one antigen, and optionally, one or more adjuvants.

In some embodiments, the protein that specifically binds to a RNA motif and inhibits protein production is L7Ae or a fusion of MS2 protein and a protein that inhibits protein production. In some embodiments, the protein that specifically binds to a RNA motif and inhibits protein production is L7Ae and the RNA motif is one or more Box C/D, K-turn and/or K-loop motifs. In some embodiments, the RNA motif is two K-turn motifs. In some embodiments, the one or more Box C/D, K-turn and/or K-loop motifs are placed in the 5' untranslated region (UTR) of the second RNA molecule.

In some embodiments, the protein that specifically binds to a RNA motif and inhibits protein production is a fusion of MS2 protein and a protein that inhibits protein production and the RNA motif is one or more MS2 coat protein binding sites. In some embodiments, the RNA motif is eight MS2 coat protein binding sites. In some embodiments, the one or more MS2 coat protein binding sites are placed in the 3' untranslated region (UTR) of the second RNA molecule. In some embodiments, the MS2 fusion protein is a fusion of MS2 protein and CNOT7 protein (MS2-CNOT7) or Dm-POP2 protein (MS2-Dm-POP2).

In some embodiments, the RNA molecules comprise modified RNA. In some embodiments, the RNA molecules comprise 5-methylcytosine-triphosphate and/or pseudouridine-triphosphate.

In some embodiments, the RNA molecules are encoded on one or more RNA replicons. In some embodiments, the one or more RNA replicons is/are one or more alphavirus derived replicons, Venezuelan equine encephalitis virus derived replicons or Sindbis derived virus replicons. In some embodiments, the RNA molecules are expressed from one or more subgenomic promoters of the one or more replicons, optionally wherein the one or more subgenomic promoters are optimized for length or position in the RNA molecule. In some embodiments, the one or more subgenomic promoters are regulated by a small molecule. In some embodiments, the small molecule is trimethoprim (TMP) or 4-hydroxytamoxifin (4-OHT).

In some embodiments, the RNA molecules are encoded on one or more plasmids.

In some embodiments, the synthetic RNA circuit further includes a sequence encoding Csy4 protein and a Csy4 recognition site. In some embodiments, the Csy4 protein is a fusion of a destabilization domain and Csy4. In some embodiments, the destabilization domain is regulated by trimethoprim (TMP) or 4-hydroxytamoxifin (4-OHT).

In some embodiments, the synthetic RNA circuit further includes one or more internal ribosomal entry sites (IRESs) for improved polycystronic expression. In some embodiments, the synthetic RNA circuit further includes one or more general translation enhancers (GTEs). In some embodiments, the synthetic RNA circuit is encoded on self-cleaving helper-defective interfering RNA, optionally comprising Csy4, wherein Csy4 is expressed from an internal ribosome entry site (IRES).

According to another aspect, methods of treating cancer in a mammal are provided. The methods include administering to a mammal the foregoing synthetic RNA circuits. In some embodiments, the synthetic RNA circuit is administered as a first replicon, and further administering a second replicon as ballast to control expression of a protein encoded by the first replicon.

According to another aspect, methods of inducing an immune response in a mammal are provided. The methods include administering to a mammal the foregoing synthetic RNA circuits. In some embodiments, the methods further include administering the small molecule that binds to the destabilization domain to the mammal. In some embodiments, the small molecule that binds to the destabilization domain is administered at different times for expressing the antigen and/or the adjuvant at the different times. In some embodiments, the small molecule that binds to the destabilization domain is administered by oral administration, intramuscular injection of lipid nanoparticles, or by implantation of a polymeric implant for sustained release. In some embodiments, the synthetic RNA circuit is administered as a first replicon, and further administering a second replicon as ballast to control expression of a protein encoded by the first replicon.

According to another aspect, synthetic RNA circuits are provided. The circuits include a first RNA molecule comprising a sequence encoding a destabilization domain fused to a protein that specifically binds to a RNA motif and inhibits protein production; and a second RNA molecule comprising at least one sequence recognized by the protein that specifically binds to a RNA motif and inhibits protein production, and a sequence encoding an output molecule. The destabilization domain facilitates degradation of the protein that specifically binds to a RNA motif and inhibits protein production in the absence of a small molecule that binds to the destabilization domain.

In some embodiments, the output molecule is a protein. In some embodiments, the protein is a therapeutic protein, a cell death protein, a fluorescent protein, an antigen, a selection protein, or an immunomodulator. In some embodiments, the therapeutic protein is a protein for protein replacement therapy, Myr-Akt, or follistatin. In some embodiments, the selection protein is used for selection or purification of a cell in which it is expressed. In some embodiments, the selection protein is a protein that confers drug resistance to a cell. In some embodiments, the fluorescent protein is EGFP, EYFP, or EBFP. In some embodiments, immunomodulator protein is a cytokine. In some embodiments, the cytokine is IL-12, IL-15 or IL-21. In some embodiments, the immunomodulator protein is a immunosuppressant protein. In some embodiments, the cell death protein is hBax.

In some embodiments, the RNA molecules encode more than one output molecule.

In some embodiments, the output molecules comprise at least one antigen, and optionally, one or more adjuvants.

In some embodiments, the protein that specifically binds to a RNA motif and inhibits protein production is L7Ae or a fusion of MS2 protein and a protein that inhibits protein production. In some embodiments, the protein that specifically binds to a RNA motif and inhibits protein production is L7Ae and the RNA motif is one or more Box C/D, K-turn and/or K-loop motifs. In some embodiments, the RNA motif is two K-turn motifs. In some embodiments, the one or more Box C/D, K-turn and/or K-loop motifs are placed in the 5' untranslated region (UTR) of the second RNA molecule.

In some embodiments, the protein that specifically binds to a RNA motif and inhibits protein production is a fusion of MS2 protein and a protein that inhibits protein production and the RNA motif is one or more MS2 coat protein binding sites. In some embodiments, the RNA motif is eight MS2 coat protein binding sites. In some embodiments, the one or more MS2 coat protein binding sites are placed in the 3' untranslated region (UTR) of the second RNA molecule. In some embodiments, the MS2 fusion protein is a fusion of MS2 protein and CNOT7 protein (MS2-CNOT7) or Dm-POP2 protein (MS2-Dm-POP2).

In some embodiments, the RNA molecules comprise modified RNA. In some embodiments, the RNA molecules comprise 5-methylcytosine-triphosphate and/or pseudouridine-triphosphate.

In some embodiments, the RNA molecules are encoded on one or more RNA replicons. In some embodiments, the one or more RNA replicons is/are one or more alphavirus derived replicons, Venezuelan equine encephalitis virus derived replicons or Sindbis derived virus replicons. In some embodiments, the RNA molecules are expressed from one or more subgenomic promoters of the one or more replicons, optionally wherein the one or more subgenomic promoters are optimized for length or position in the RNA molecule. In some embodiments, the one or more subgenomic promoters are regulated by a small molecule. In some embodiments, the small molecule is trimethoprim (TMP) or 4-hydroxytamoxifin (4-OHT).

In some embodiments, the RNA molecules are encoded on one or more plasmids.

In some embodiments, the output molecule is a fusion of a TetR protein and a second protein; and the RNA molecule(s) further includes an aptamer sequence and a second output molecule. The aptamer sequence is bound by the TetR protein in the absence of tetracycline and the aptamer sequence is positioned relative to the second output molecule so that it suppresses translation of the second output molecule in the absence of tetracycline.

In some embodiments, the synthetic RNA circuit further includes a sequence encoding Csy4 protein and a Csy4 recognition site. In some embodiments, the Csy4 protein is a fusion of a destabilization domain and Csy4. In some embodiments, the destabilization domain is regulated by trimethoprim (TMP) or 4-hydroxytamoxifin (4-OHT).

In some embodiments, the synthetic RNA circuit further includes one or more internal ribosomal entry sites (IRESs) for improved polycystronic expression. In some embodiments, the synthetic RNA circuit further includes one or more general translation enhancers (GTEs). In some embodiments, the synthetic RNA circuit is encoded on self-cleaving helper-defective interfering RNA, optionally comprising Csy4, wherein Csy4 is expressed from an internal ribosome entry site (IRES).

According to another aspect, methods of treating cancer in a mammal are provided. The methods include administering to a mammal the foregoing synthetic RNA circuits. In some embodiments, the synthetic RNA circuit is administered as a first replicon, and further administering a second replicon as ballast to control expression of a protein encoded by the first replicon.

According to another aspect, methods of inducing an immune response in a mammal are provided. The methods include administering to a mammal the foregoing synthetic RNA circuits. In some embodiments, the methods further include administering the small molecule that binds to the destabilization domain to the mammal. In some embodiments, the small molecule that binds to the destabilization domain is administered at different times for expressing the antigen and/or the adjuvant at the different times. In some embodiments, the small molecule that binds to the destabilization domain is administered by oral administration, intramuscular injection of lipid nanoparticles, or by implantation of a polymeric implant for sustained release. In some embodiments, the synthetic RNA circuit is administered as a first replicon, and further administering a second replicon as ballast to control expression of a protein encoded by the first replicon.

According to another aspect, synthetic RNA circuits are provided. The circuits include an RNA molecule comprising a sequence encoding a TetR protein and a sequence encoding an output protein, and an aptamer sequence that is bound by the TetR protein in the absence of tetracycline. The aptamer sequence is positioned relative to the sequence encoding the output protein so that it suppresses translation of the output protein in the absence of tetracycline. In some embodiments, the aptamer is positioned in the 5' untranslated region (UTR) of the sequence encoding an output protein.

In some embodiments, the output molecule is a protein. In some embodiments, the protein is a therapeutic protein, a cell death protein, a fluorescent protein, an antigen, a selection protein, or an immunomodulator. In some embodiments, the therapeutic protein is a protein for protein replacement therapy, Myr-Akt, or follistatin. In some embodiments, the selection protein is used for selection or purification of a cell in which it is expressed. In some embodiments, the selection protein is a protein that confers drug resistance to a cell. In some embodiments, the fluorescent protein is EGFP, EYFP, or EBFP. In some embodiments, immunomodulator protein is a cytokine. In some embodiments, the cytokine is IL-12, IL-15 or IL-21. In some embodiments, the immunomodulator protein is a immunosuppressant protein. In some embodiments, the cell death protein is hBax.

In some embodiments, the RNA molecules encode more than one output molecule.

In some embodiments, the output molecules comprise at least one antigen, and optionally, one or more adjuvants.

In some embodiments, the protein that specifically binds to a RNA motif and inhibits protein production is L7Ae or a fusion of MS2 protein and a protein that inhibits protein production. In some embodiments, the protein that specifically binds to a RNA motif and inhibits protein production is L7Ae and the RNA motif is one or more Box C/D, K-turn and/or K-loop motifs. In some embodiments, the RNA motif is two K-turn motifs. In some embodiments, the one or more Box C/D, K-turn and/or K-loop motifs are placed in the 5' untranslated region (UTR) of the second RNA molecule.

In some embodiments, the protein that specifically binds to a RNA motif and inhibits protein production is a fusion of MS2 protein and a protein that inhibits protein production and the RNA motif is one or more MS2 coat protein binding sites. In some embodiments, the RNA motif is eight MS2 coat protein binding sites. In some embodiments, the one or more MS2 coat protein binding sites are placed in the 3' untranslated region (UTR) of the second RNA molecule. In some embodiments, the MS2 fusion protein is a fusion of MS2 protein and CNOT7 protein (MS2-CNOT7) or Dm-POP2 protein (MS2-Dm-POP2).

In some embodiments, the RNA molecules comprise modified RNA. In some embodiments, the RNA molecules comprise 5-methylcytosine-triphosphate and/or pseudouridine-triphosphate.

In some embodiments, the RNA molecules are encoded on one or more RNA replicons. In some embodiments, the one or more RNA replicons is/are one or more alphavirus derived replicons, Venezuelan equine encephalitis virus derived replicons or Sindbis derived virus replicons. In some embodiments, the RNA molecules are expressed from one or more subgenomic promoters of the one or more replicons, optionally wherein the one or more subgenomic promoters are optimized for length or position in the RNA molecule. In some embodiments, the one or more subgenomic promoters are regulated by a small molecule. In some embodiments, the small molecule is trimethoprim (TMP) or 4-hydroxytamoxifin (4-OHT).

In some embodiments, the RNA molecules are encoded on one or more plasmids.

In some embodiments, the synthetic RNA circuit further includes a sequence encoding Csy4 protein and a Csy4 recognition site. In some embodiments, the Csy4 protein is a fusion of a destabilization domain and Csy4. In some embodiments, the destabilization domain is regulated by trimethoprim (TMP) or 4-hydroxytamoxifin (4-OHT).

In some embodiments, the synthetic RNA circuit further includes one or more internal ribosomal entry sites (IRESs) for improved polycystronic expression. In some embodiments, the synthetic RNA circuit further includes one or more general translation enhancers (GTEs). In some embodiments, the synthetic RNA circuit is encoded on self-cleaving helper-defective interfering RNA, optionally comprising Csy4, wherein Csy4 is expressed from an internal ribosome entry site (IRES).

According to another aspect, methods of treating cancer in a mammal are provided. The methods include administering to a mammal the foregoing synthetic RNA circuits. In some embodiments, the synthetic RNA circuit is administered as a first replicon, and further administering a second replicon as ballast to control expression of a protein encoded by the first replicon.

According to another aspect, methods of inducing an immune response in a mammal are provided. The methods include administering to a mammal the foregoing synthetic RNA circuits. In some embodiments, the methods further include administering tetracycline to the mammal. In some embodiments, the tetracycline is administered at different times for expressing the antigen and/or the adjuvant at the different times. In some embodiments, the tetracycline is administered by oral administration, intramuscular injection of lipid nanoparticles, or by implantation of a polymeric implant for sustained release. In some embodiments, the synthetic RNA circuit is administered as a first replicon, and further administering a second replicon as ballast to control expression of a protein encoded by the first replicon.

The invention is not limited in its application to the details of construction and the arrangement of components set forth in the following description or illustrated in the drawings. The invention is capable of other embodiments and of being practiced or of being carried out in various ways. Each of the above embodiments and aspects may be linked to any other embodiment or aspect. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF THE DRAWINGS

The accompanying drawings are not intended to be drawn to scale. For purposes of clarity, not every component may be labeled in every drawing.

FIGS. 3A-3E. Experimental operation of the post-transcriptional switch demonstrated with transient DNA transfection and electroporation of the replicon RNA. (A) Switch design: L7Ae is co-translated with yellow fluorescent protein, EYFP. MS2-CNOT7 is co-translated with blue fluorescent protein, EBFP. The two proteins co-repress each other and addition of a synthetic siRNA (siFF4 or siFF5) was used to set the state of the switch. The logic takes place exclusively at post-transcriptional level, mRNA in the case of DNA co-transfection experiment (boxed) or alphaviral replicon including four non-structural proteins (nsP1-4) and a subgenomic promoter (SGP). Red fluorescent protein, mKate, was used as transfection marker for DNA transfection experiments. (B-C) Mean fluorescence of the two reporters in the different states of the switch encoded on plasmid DNA (B) or alphaviral replicon (C). (D-E) Corresponding representative fluorescent microscopy images and two-dimensional flow cytometry plots for plasmid (D) and replicon (E) transfection. When the parts are encoded on the alphaviral replicon bistability occurs, while in the case of DNA delivery, bistability is not observed, likely due to decoupled processes of mRNA production (transcription) and repression (post-transcriptional).

FIGS. 6A-6B. (A) TetR translational control in a eukaryotic cell (Adapted from Goldfless 2012 (20)). (B) Inducible RNA-protein interaction system as booster for vaccination.

FIGS. 19A-19F. pDNA time-lapse flow cytometry and qPCR. (a,b) pDNA-encoded EGFP or EGFP-PEST (41) were transfected into 293FT cells. EGFP fluorescence was measured by flow cytometry (a) and mRNA level was measured by qRT-PCR (b). qRT-PCR results were normalized to endogenous 18S rRNA level. Error bars indicate the average±standard deviation of triplicates. (c,d) Behavior of L7Ae:2×K-turn system encoded with pDNA. 293FT cells transfected with pDNA 2xKt-EGFP with or without L7Ae-expressing construct and analyzed by flow cytometry (c) and qRT-PCR (d). (e,f) Cascade circuit delivered with pDNA. Plasmids encoding the cascade circuit stages 0-3 (FIG. 8A) were transfected into 293FT cells and analyzed by flow cytometry (e) and qRT-PCR (f). Note that miR-FF4 expressed from a plasmid was used here (Table 1). EGFP fluorescence was measured at 3 h, 6 h, 12 h and days 1-8. qRT-PCR was performed for samples harvested at 6 h, 12 h and days 1-5. In the case of the cascade circuit, only the most crucial time points were followed with qRT-PCR: 6 h and days 1-4. Mean EGFP fluorescence was calculated for EGFP positive gate established based on non-transfected cells (all above the background fluorescence). FIGS. 20A-20F. modRNA time-lapse flow cytometry and qPCR. (a,b) modRNAs encoding EGFP or EGFP-PEST(41) were transfected into 293FT cells. EGFP fluorescence was measured by flow cytometry (a) and modRNA level was measured by qRT-PCR (b) at 3 h, 6 h, 12 h, day 1, day 2, day 3, day 4 and day 5. qRT-PCR results were normalized to endogenous 18S rRNA level, and relative levels of the modRNA to that at 3 h after transfection were shown. Insets show respective modRNA levels at the 3 h time point. Error bars indicate the average±standard deviation of triplicates. (c,d) Behavior of L7Ae:K-turn system delivered by modRNAs. 293FT cells were transfected with Kt-EGFP modRNA with or without L7Ae-expressing modRNA and analyzed by flow cytometry (c) and qRT-PCR (d). qRT-PCR was performed at following selected time points; 3 h, day 1, day 2, and day 3. (e,f) Cascade circuit delivered by modRNAs. Sets of modRNAs and siRNAs encoding the cascade circuit were transfected into 293FT cells and analyzed by flow cytometry (e) and qRT-PCR (f) at the same time points as in (c) and (d), respectively.

FIGS. 31A-31B. Theoretical model diagrams. Diagrams of the models for (a) pDNA and (b) replicon systems. The primary species, pL/pC and rL/rC, represent the transfected pDNA or replicons respectively. 1' pertains to L7Ae-related species and 'C' to MS2-CNOT7-related species (i.e. pL: pDNA L7Ae species). The pDNA system is inert until the plasmids enter the nucleus upon cell division, whereas for the replicon model, nonstructural proteins transport cytoplasmic replicon RNA strands to the plasma membrane (kTR) where they form spherules that act as replication factories ('RF') and become double-stranded. The pDNA in the nucleus and the double-stranded RNA in the spherules both serve as templates for mRNA (mL/mC) transcription (kTS). The mRNAs are translated (kTL) into their respective RBPs, L7Ae or MS2-CNOT7. MS2-CNOT7 binds the L7Ae transcript and increases its degradation rate while L7Ae binds the MS2-CNOT7 transcript and blocks translation. Within the first few hours of the replicon system, while transcribing mRNAs, the spherules also transcribe more of the original genomic RNAs (c). Also, the RBPs not only interact with mRNA but with the replicons themselves. MS2-CNOT7 binds the L7Ae replicon and increases its degradation rate (arrow). We also considered the possibility that binding of RBPs to the replicons can inhibit replication complex formation (dashed lines, (3).

FIGS. 32A-32B. Theoretical model: Mutual Exclusivity (MEx) metric. (a) The MEx score was calculated by fitting the log-transform of the data to a line. The distribution is more mutually exclusive if cells enter the extreme regions of the plot (high L7Ae, low MS2-CNOT7 or low L7Ae, high MS2-CNOT7) and therefore have a large variance along the line (V). Normalizing V by the distance from the origin (M)

gives higher scores to distributions with high variance that approach the x and y axes. The MEx score was thus calculated as V/M. Since cells with generally low expression (low transcription rate or low copy number) are close to the origin and receive artificially high scores, we normalized the data to the starting copy number (P0 or R0) and transcription rate (kTS) before performing this analysis. (b) Examples of cell distributions and their MEx scores. Insets show the same data on a linear scale.

Figure 33A:
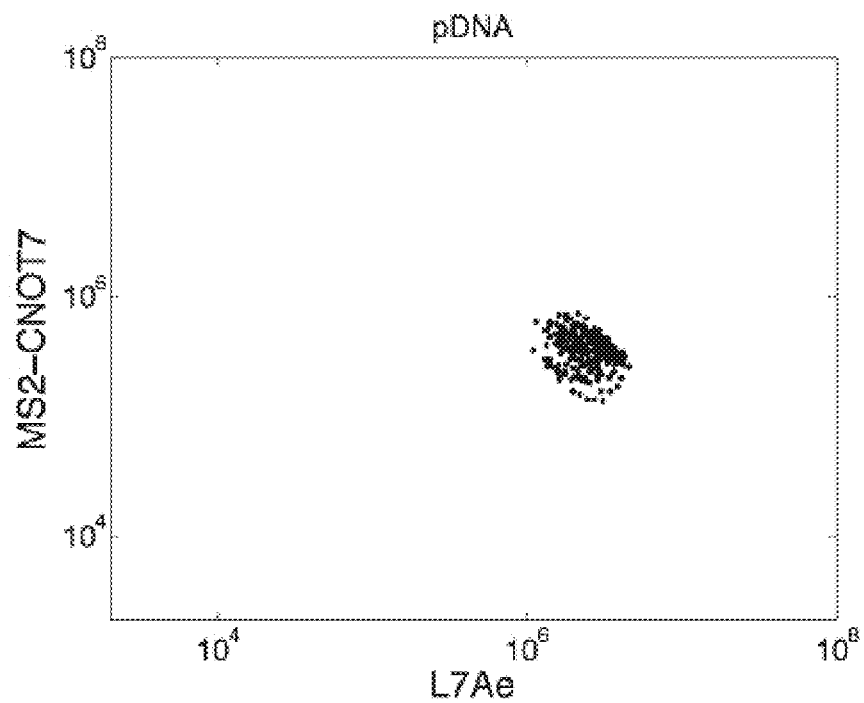
Figure 33B:
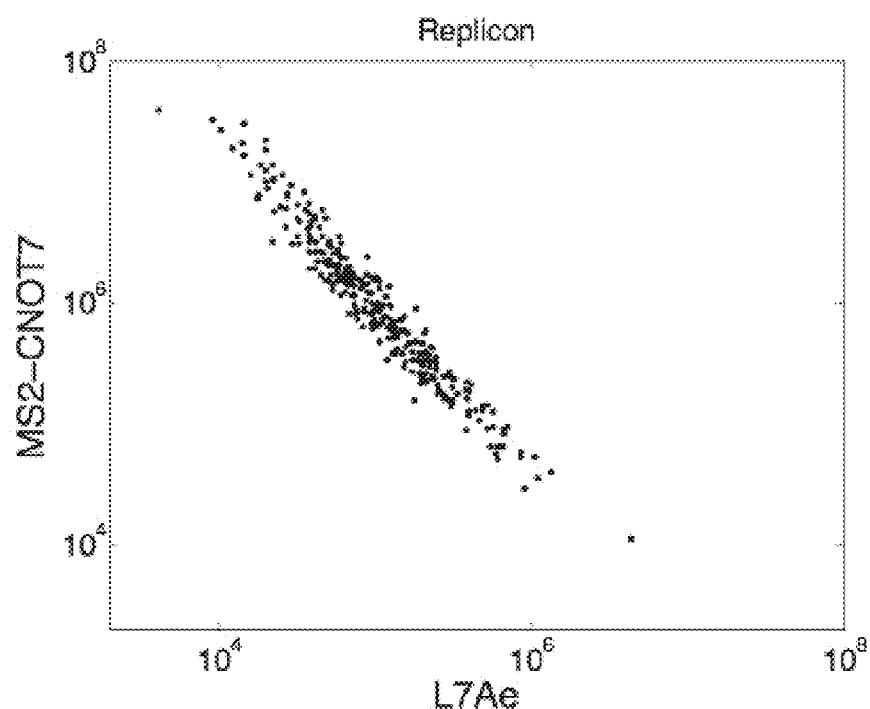

FIGS. 33A-33B. Theoretical model: comparison of long-term behavior. Simulations of the long-term effects for both the pDNA (a) system and replicon (b) system for the example parameters listed in Table 6. Both simulations involve 288 cells. The pDNA and replicon models were run for simulation times of 48 hours and 24 hours respectively to correspond to the experimental set-up of FIG. 8F (pDNA and replicon, siRNA Ctrl case).

Figure 34:
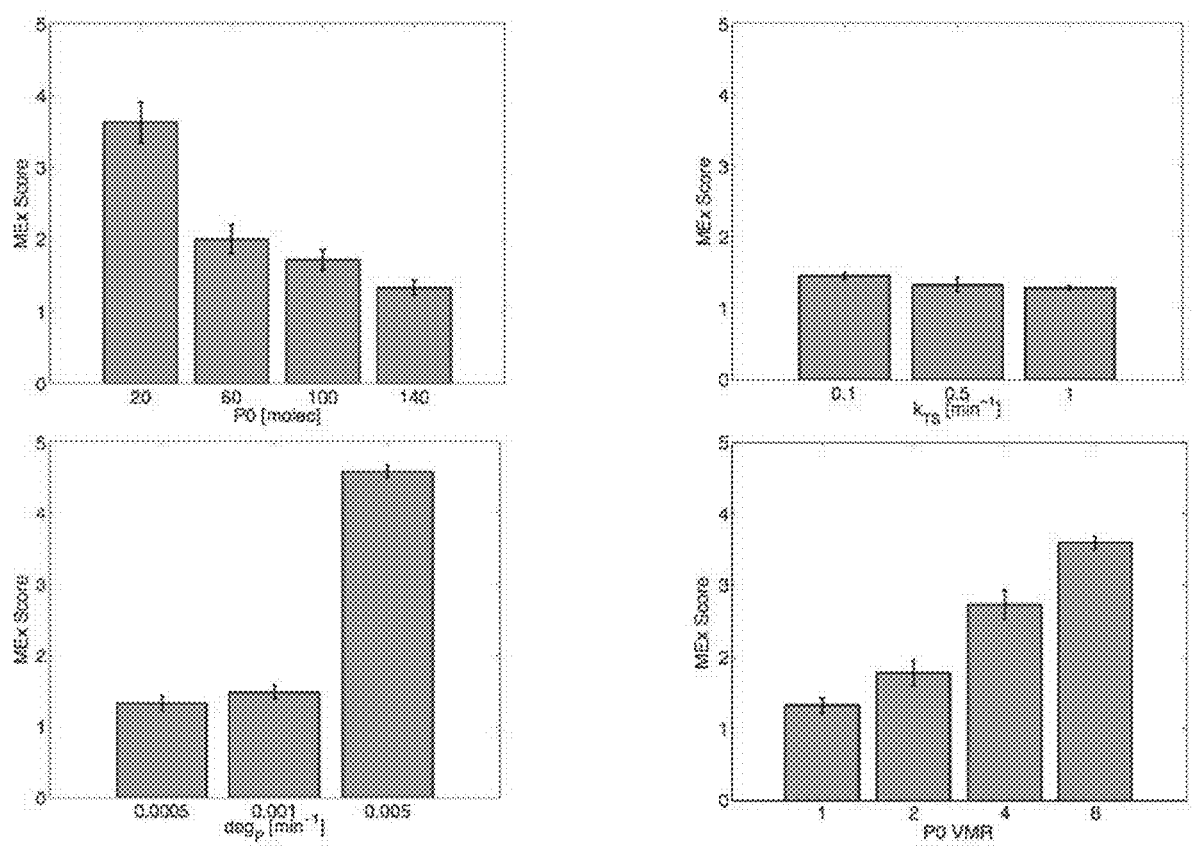

FIG. 34. Theoretical model: pDNA system analysis of mutual exclusivity. Parameter perturbations for starting copy number (P0), transcription rate (kTS), protein degradation rate (degP), and the starting copy number variance-to-mean ratio (P0 VMR). For each parameter set, 3 simulations were run with 96 cells each. Error bars are one standard deviation. Values from Table 6 were used for parameters that are unperturbed.

Figures 35A, 35B:
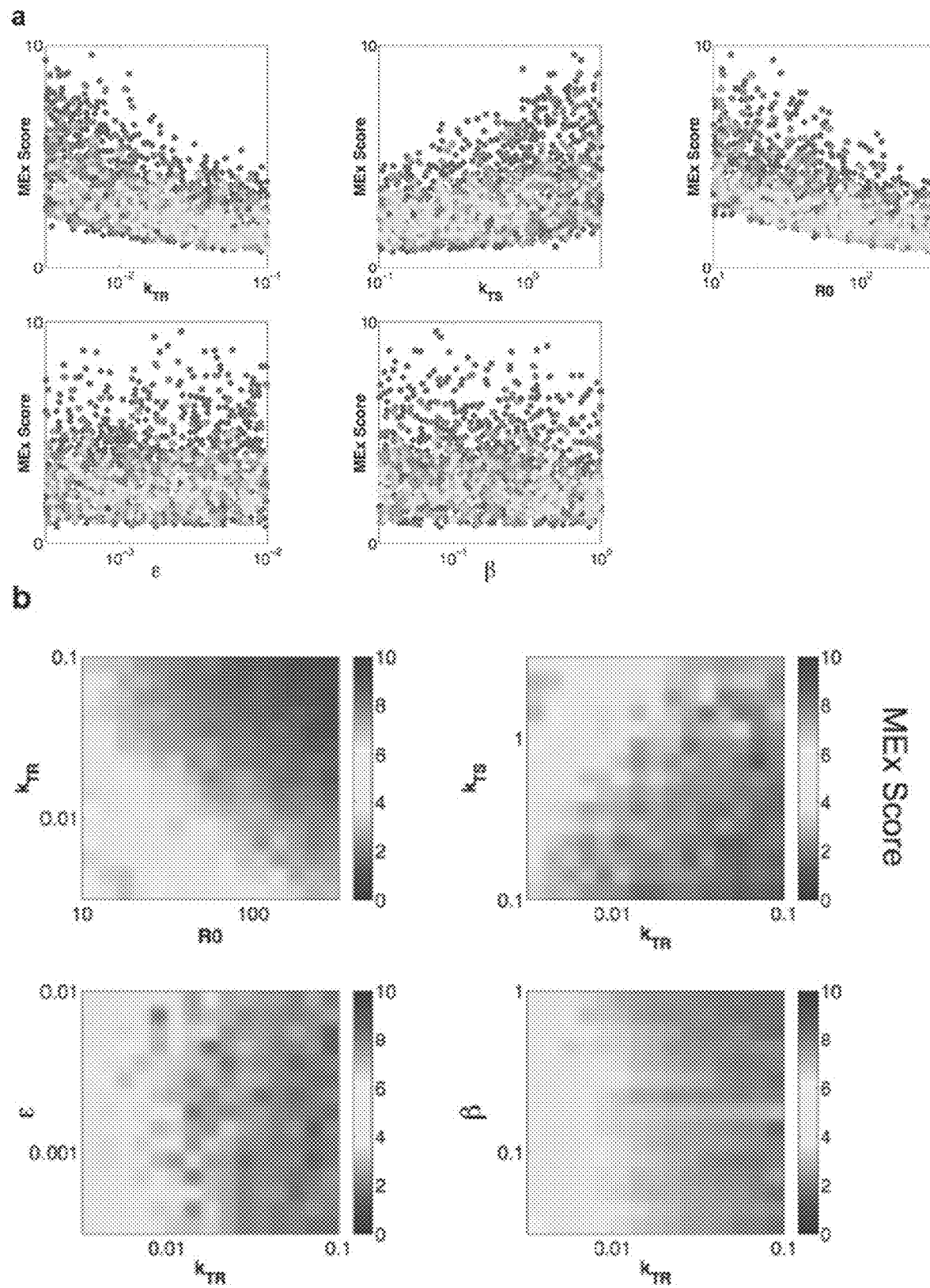

FIGS. 35A-35B. Theoretical model: replicon system analysis of mutual exclusivity. (a) MEx scores from distributions of 2000 simulated cell populations plotted for each parameter. Warmer colors indicate higher point density. (b) Heat maps for the identification of parameter interactions, with color intensity indicating MEx score. kTR: transport rate, kTS: transcription rate, R0: starting replicon copy number, c: positive feedback, (3: replication inhibition.

Figure 36A:
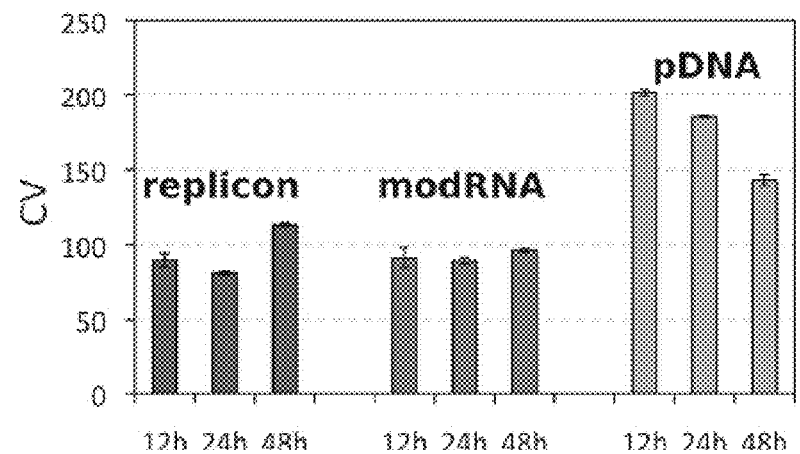
Figure 36B:
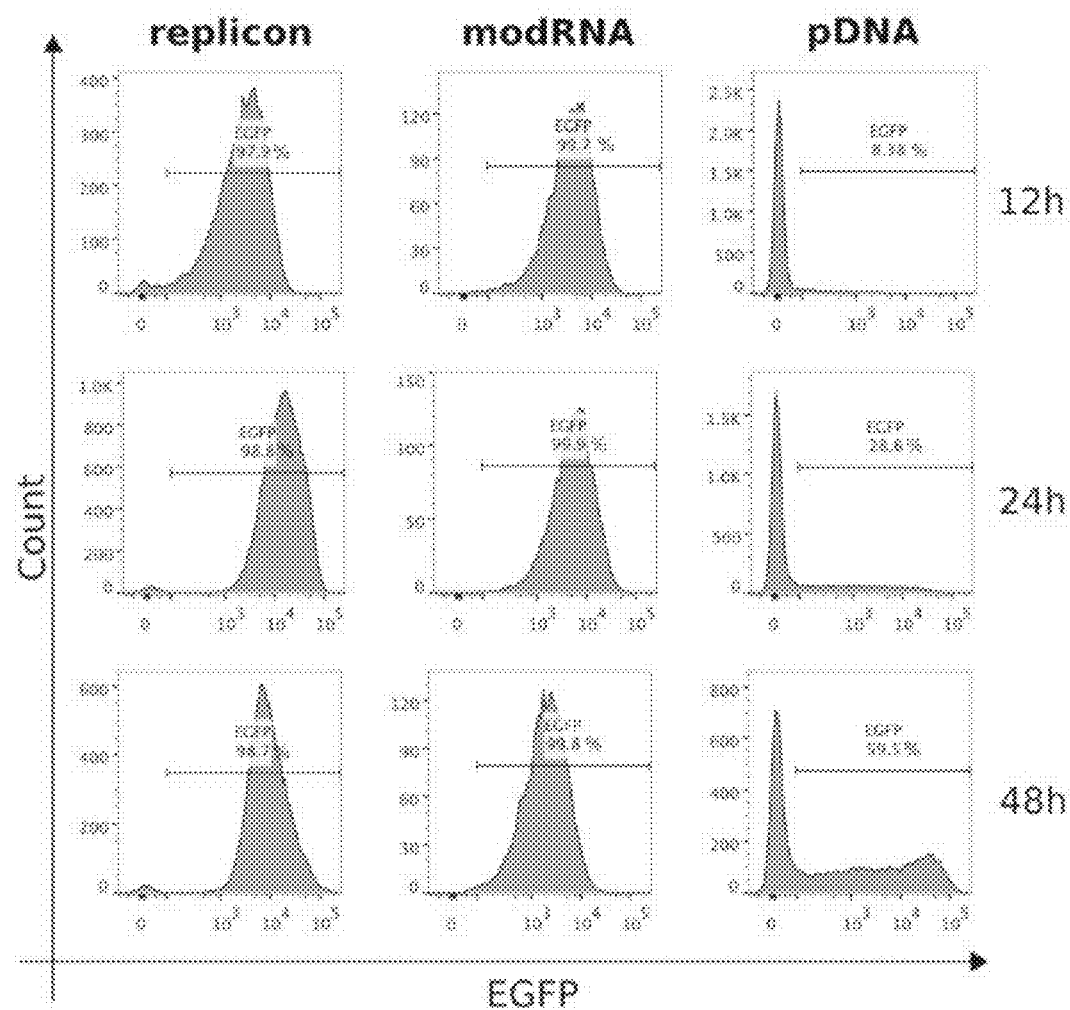

FIGS. 36A-36B. EGFP expression profiles after delivery with VEE replicon, modRNA or pDNA. (a) CV measured at 12, 24 and 48 h after transfection (CVs were computed using Flowjo software for EGFP positive cells), Flowjo: flowjo.com/v9/html/statdefinitions.html; (b) corresponding representative histograms of EGFP expression (indicated gate contains EGFP positive cells). Replicon experiments were performed using BHK21 cells and HEK 293FT cells were used in modRNA and pDNA transfections.

FIGS. 37A-37G. Programmable RNA replicon-based vaccination platform. (A) LNP-packaging of RNA replicons prolongs the duration of fluc reporter expression. (B) SIV gag long peptide immunogen encoded on LNP-packaged replicons elicits a potent immune response. (C) Exponential prime/boost dosing drastically increases antibody-titers. (D) Replicon toggle switch. (E) Replicon small molecule-regulated ON switch. (F) Replicon small molecule-regulated OFF switch. (G) Replicon small molecule-regulated cascade.

Figures 38A, 38B, 38C:
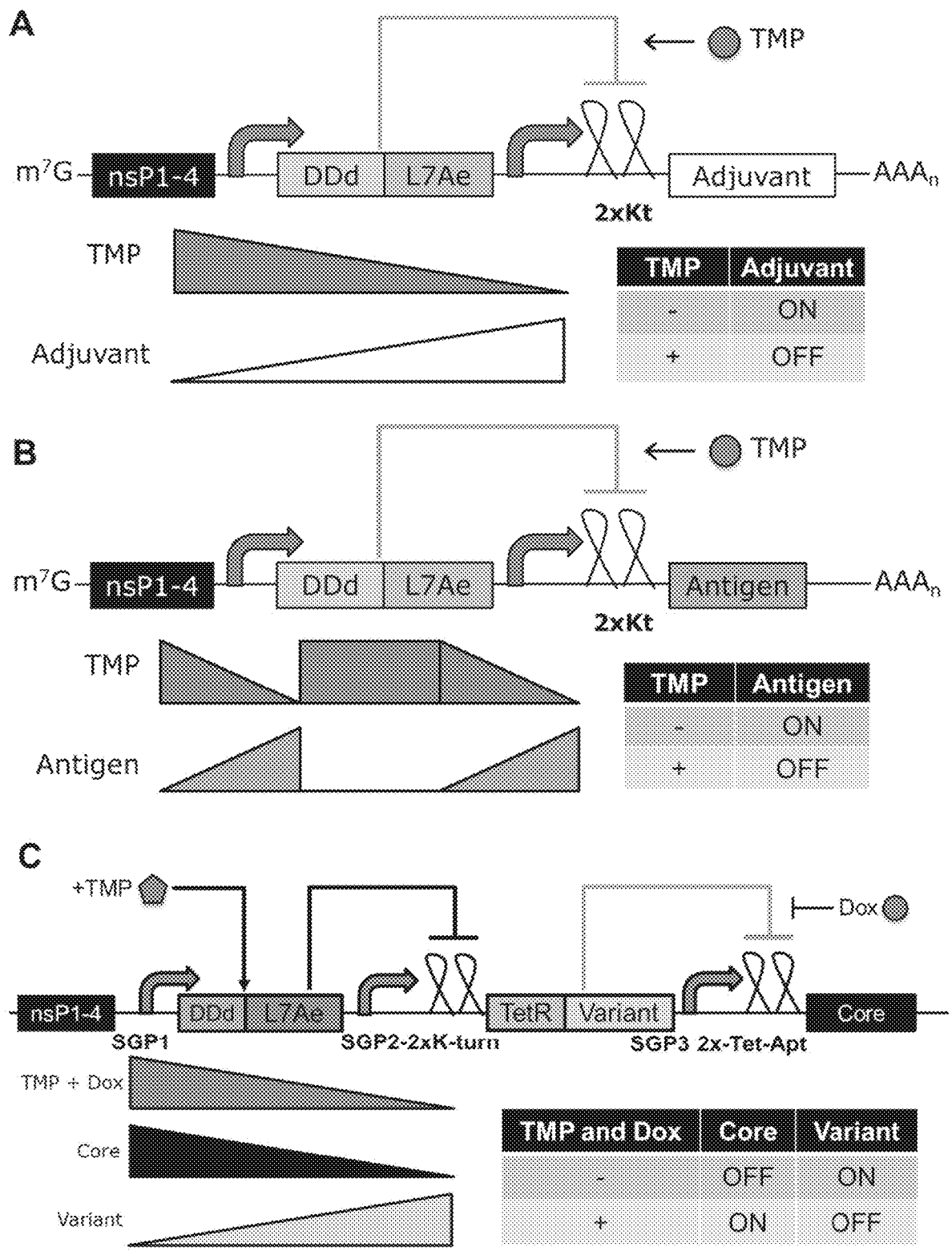

FIGS. 38A-38C. Engineering of optimal antigen/adjuvant expression kinetics using a programmable RNA replicon vaccine platform. (A) Delayed adjuvant expression using a replicon OFF switch and nanoparticle-based slow release of small molecules. (B) Exponential prime/boost expression of gag or gp120 using a replicon OFF switch. (C) Sequential expression of gp120 antigens for the induction of cross-reactive antibodies.

Figure 39:
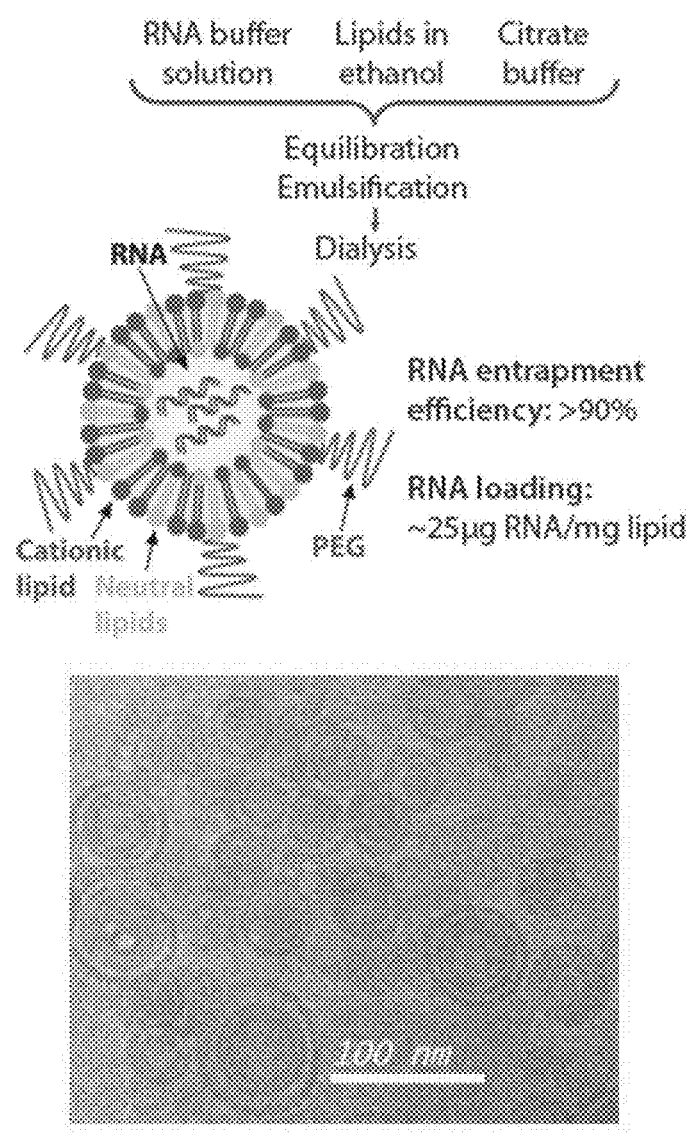
Figure 39:
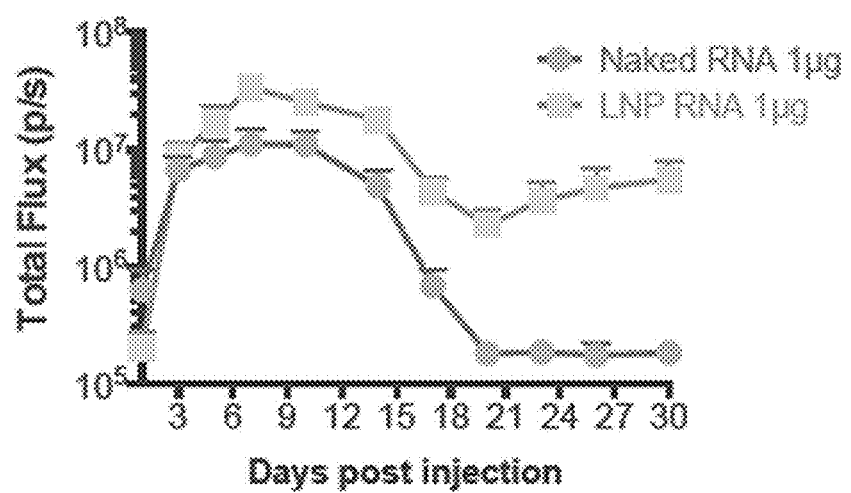

FIG. 39. LNP lipid nanoparticle delivery of replicons into muscle substantially augments in vivo gene expression. Schematic: Synthesis schematic of our custom PEGylated lipid nanoparticle formulation. Image: Cryoelectron microscopy image of LNPs. Graph: C57BL/6 mice were administered different doses of luciferase-encoding replicon RNA either as naked RNA or formulated in LNPs to opposite flanks of mice, and bioluminescence was recorded over 1 week post administration.

Figures 40A, 40B:
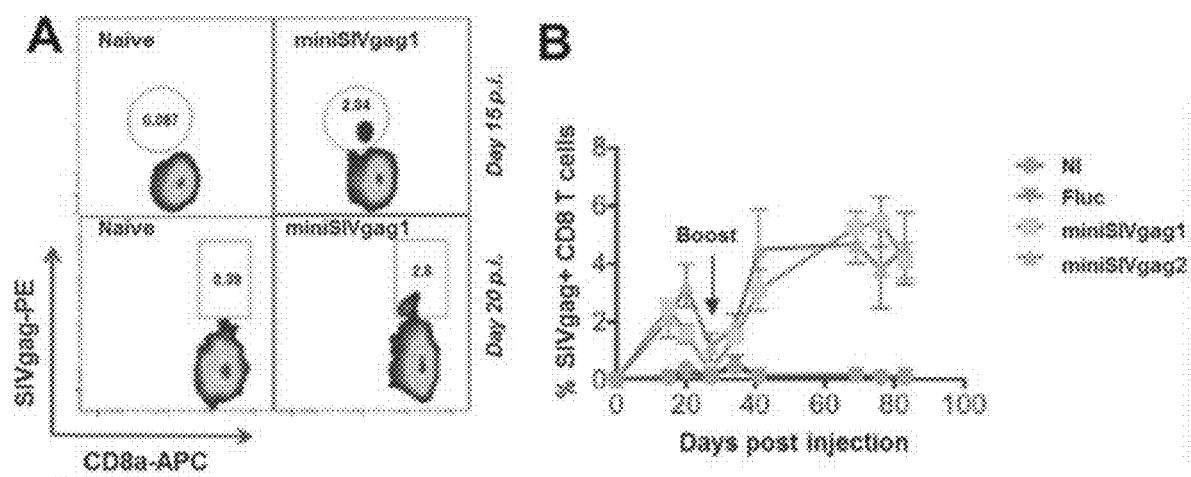
Figure 40C:
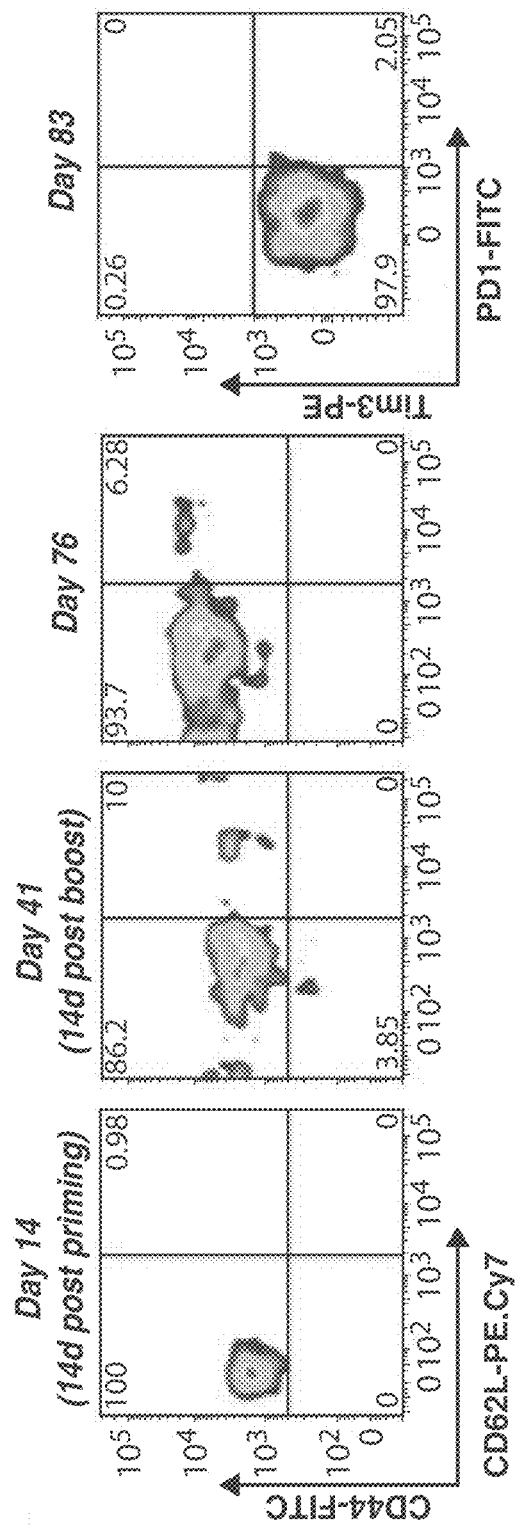

FIGS. 40A-40C. Long-lived antigen-specific T-cell responses elicited by prime-boost replicon vaccination. Groups of C57BL/6 mice were immunized with 6 μg replicon RNA encapsulated in lipid nanoparticles encoding two different variant gag peptides (miniSIVgag1, miniSIVgag2), luciferase (as a control), or were injected with PBS alone (not immunized, NI). Animals received a boost injection of the same formulations on day 28. Antigen-specific CD8+ T-cells in blood were traced over time by peptide-MHC tetramer staining. Shown are (A) representative tetramer staining flow cytometry plots, (B) mean tetramer+ cells over time, and (C) the phenotypes of the antigen-specific cells tracked by flow cytometry.

Figure 41:
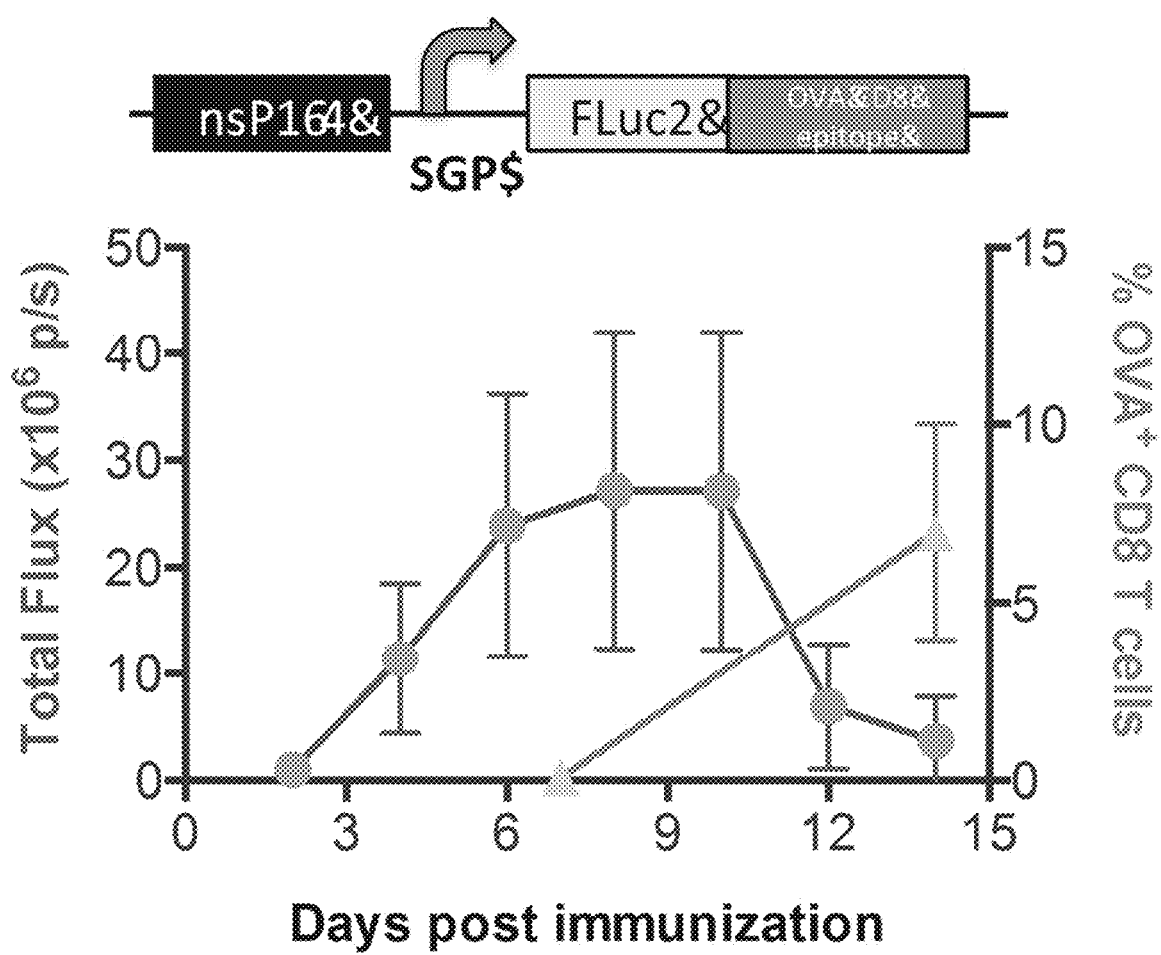

FIG. 41. Simultaneous visualization of replicon expression and tracking of immune response to a replicon-encoded antigen. (Top) Schematic structure of replicon encoding a luciferase (Fluc2)-ovalbumin peptide (SIINFEKL, SEQ ID NO: 25) fusion. (Bottom) C57Bl/6 mice (n=5/group) were immunized with 6 μg Fluc2-OVA replicons packaged in lipid nanoparticles i.m. Shown are parallel longitudinal IVIS imaging of luciferase expression (left axis) and tracking of OVA-specific T-cells by peptide-MHC tetramer staining on peripheral blood T-cells (right axis).

Figure 42:
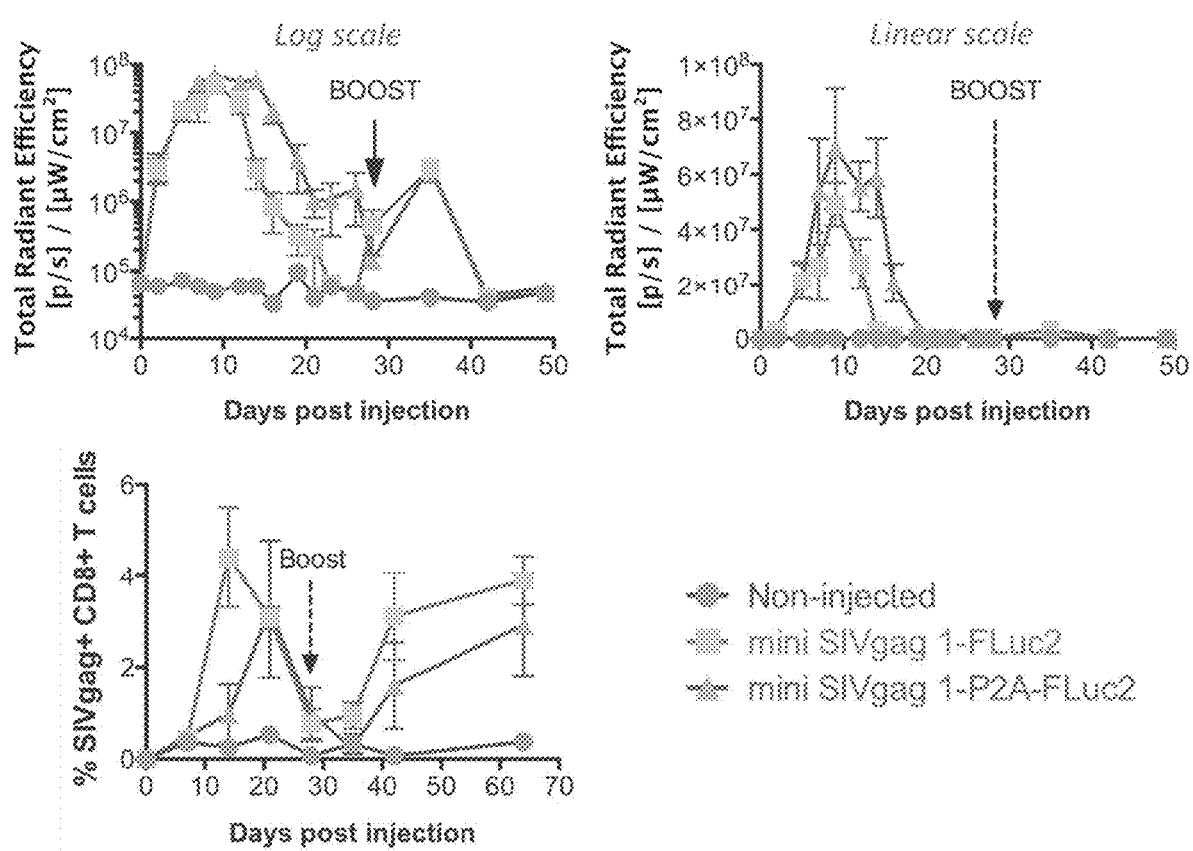

FIG. 42. SIVgag and luciferase co-expressing replicons for simultaneous tracking of antigen expression and immune response. C57Bl/6 mice were immunized i.m. with 6 μg of lipid NP-encapsulated VEE replicons encoding either a fusion of SIVgag antigen and luciferase (miniSIVgag1-Fluc2) or gag antigen expressed as a separate protein from Fluc via a 2A skip peptide (miniSIVgag1-P2A-Fluc2). Shown are luciferase expression over time (top graphs) and antigen-specific T-cell responses over time (lower graph).

Figure 43:
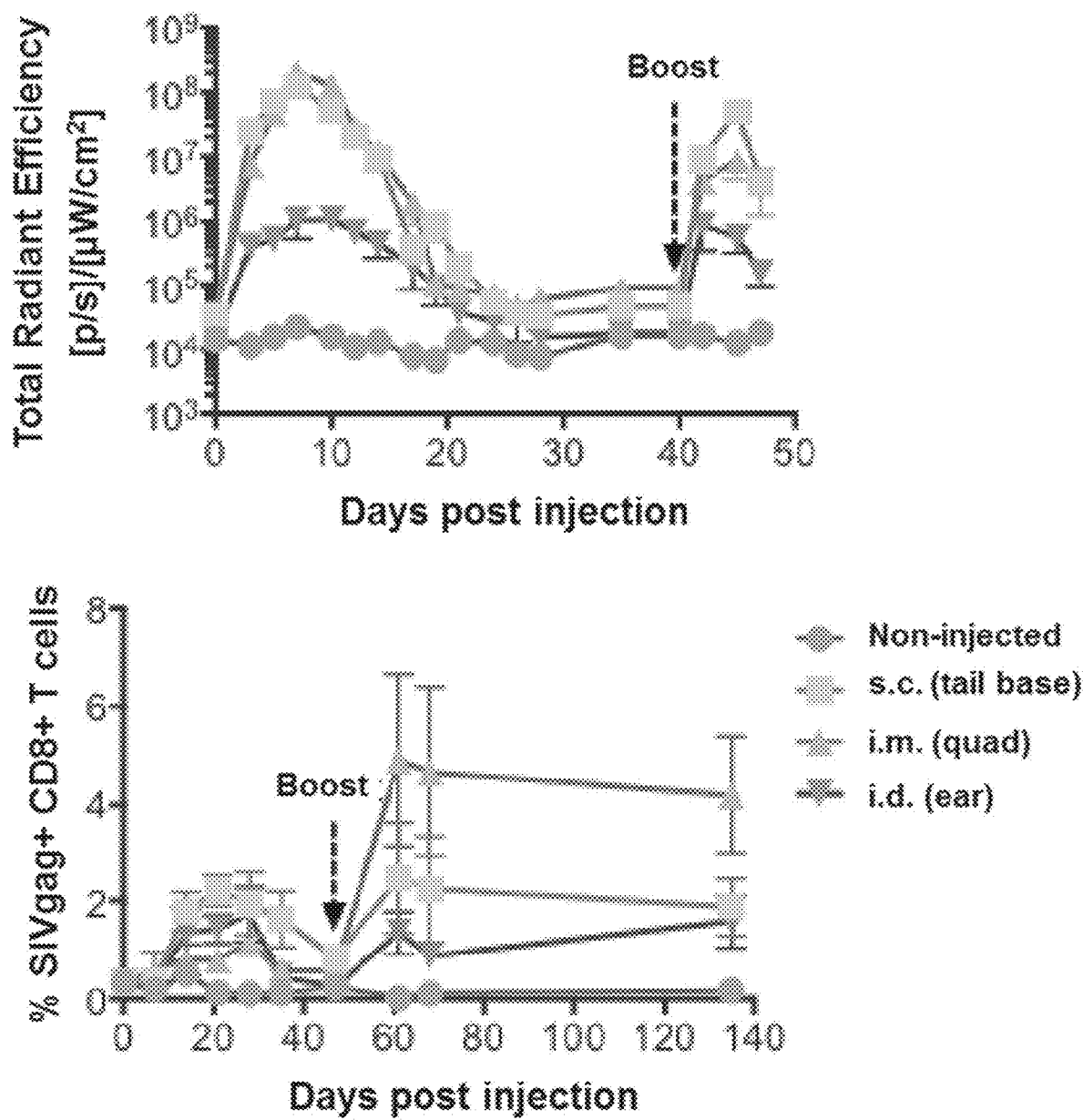

FIG. 43. Comparison of replicon expression and T-cell priming by 3 routes of injection. Groups of albino C57Bl/6 mice were immunized with lipid NP-encapsulated mini-SIVgag-Fluc2 replicons, and gene expression was followed by bioluminescence imaging in tandem with tracking of antigen-specific CD8 T-cells in blood by peptide-MHC tetramer staining.

Figures 44A, 44B, 44C, 44D:
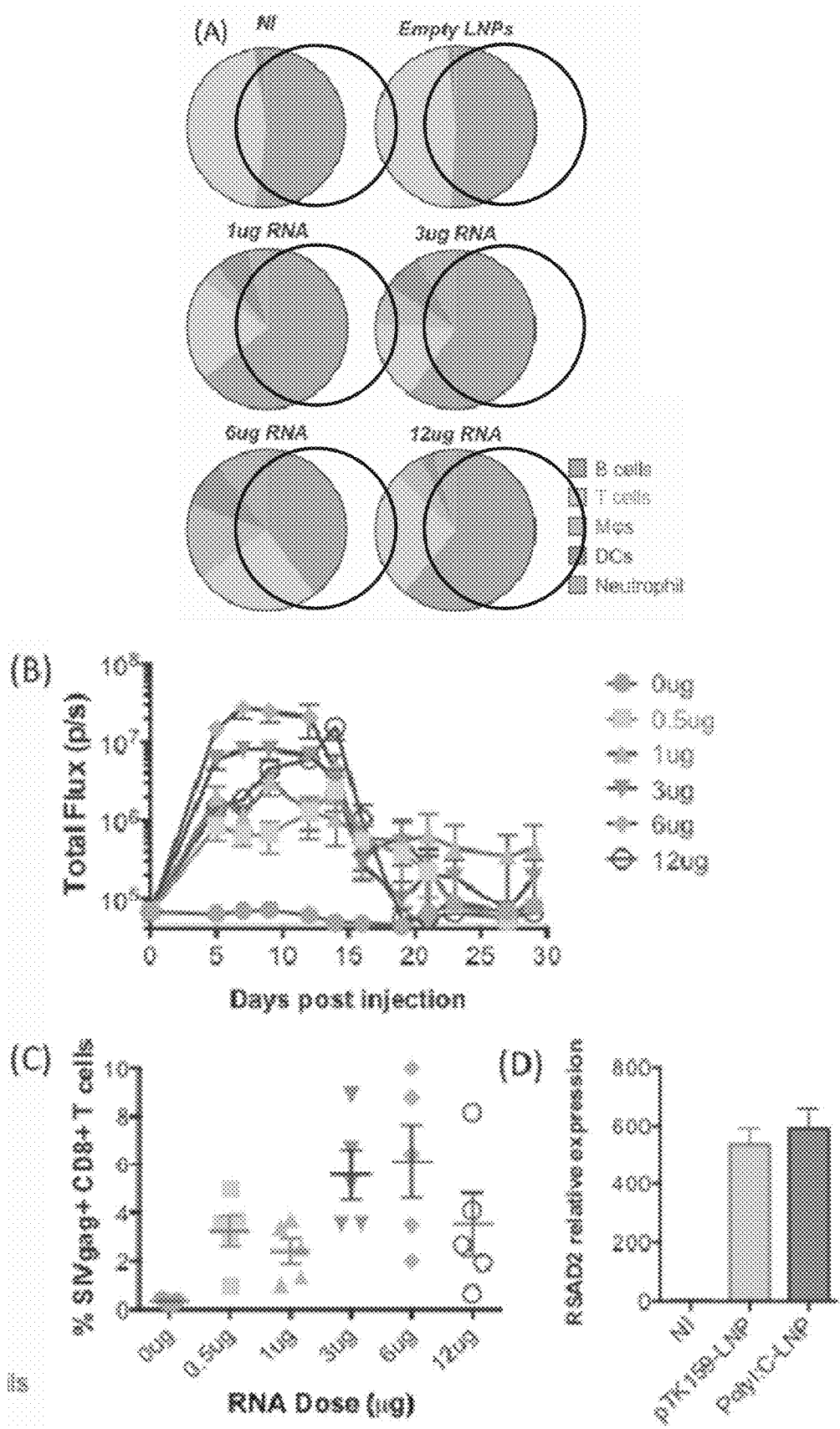

FIGS. 44A-44C. Albino C57BL/6 mice were injected with either empty or replicon-loaded LNPs at the indicated dose. Seven days post injection half of the animals were sacrificed, muscles digested and mononuclear cells isolated by enzymatic digestion. Cells were further analyzed by flow cytometry (A). Luciferase expression in vivo was measured every other day by IVIS (B), and percentage of SIVgag specific T CD8+ cells was evaluated at day 14 post injection by tetramer staining of blood cells (C). In a separate experiment animals were injected via intramuscular with 6 ug of either luciferase-expressing RNA replicon (pTK159)- or Poly (I:C)-loaded LNPs, and expression of viperin (rsad2), a gene downstream of type I interferon activation, was measured by quantitative PCR (D).

Figure 45A:
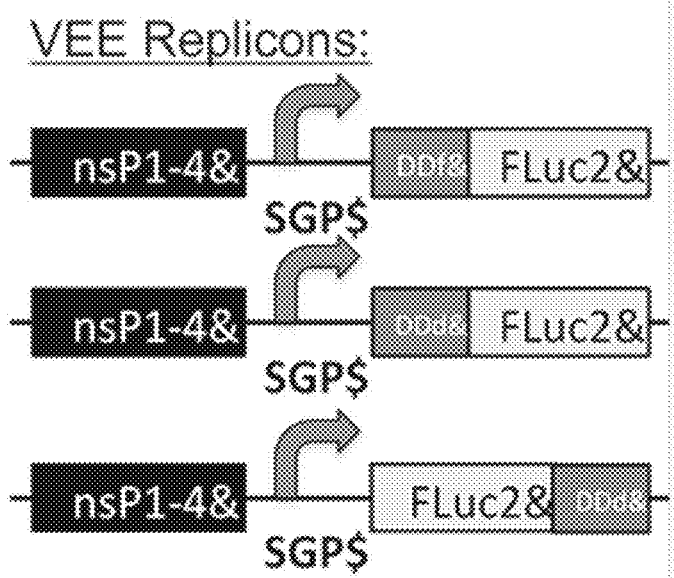
Figure 45B:
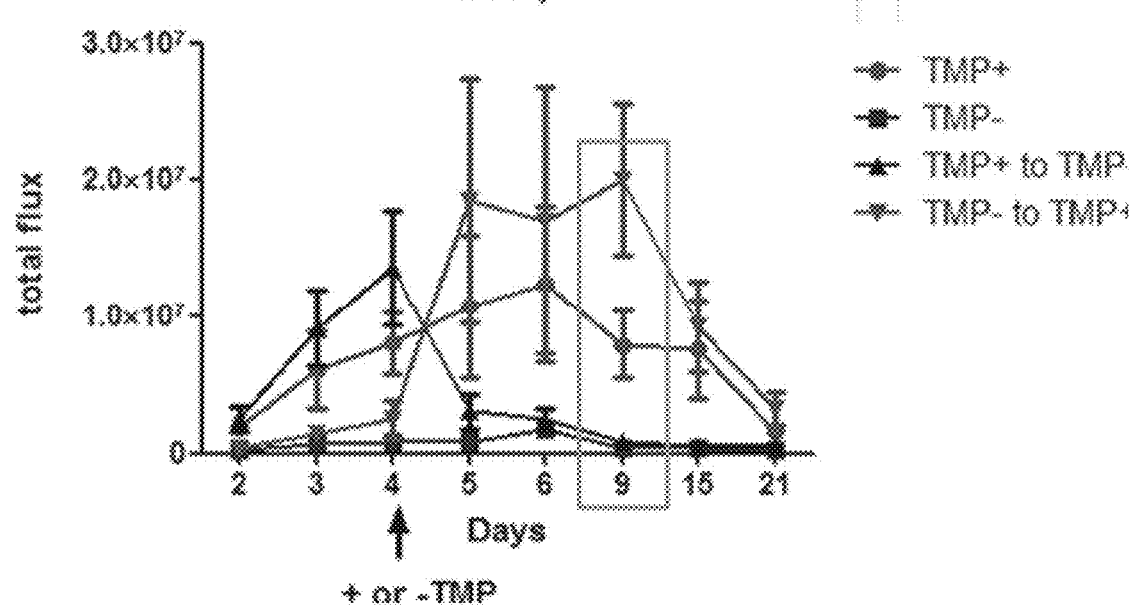

FIG. 45A-45B. Small-molecule-regulated gene expression from RNA replicons in vivo. (A) Schematic structure of several TMP-regulated "DD" replicon constructs generated. (B) In vivo bioluminescence signal (total flux) measured vs. time in C57Bl/6 mice (n=5/group) given 6 μg of DD-Fluc2 luciferase replicon RNA packaged in lipid nanoparticles on day 0, administered i.m. Animals either received no TMP at any time (TMP−), constant TMP exposure in drinking water (TMP+), or had TMP added (TMP− to TMP+) or withdrawn (TMP+ to TMP−) on day 4.

Figures 46A, 46B, 46C:
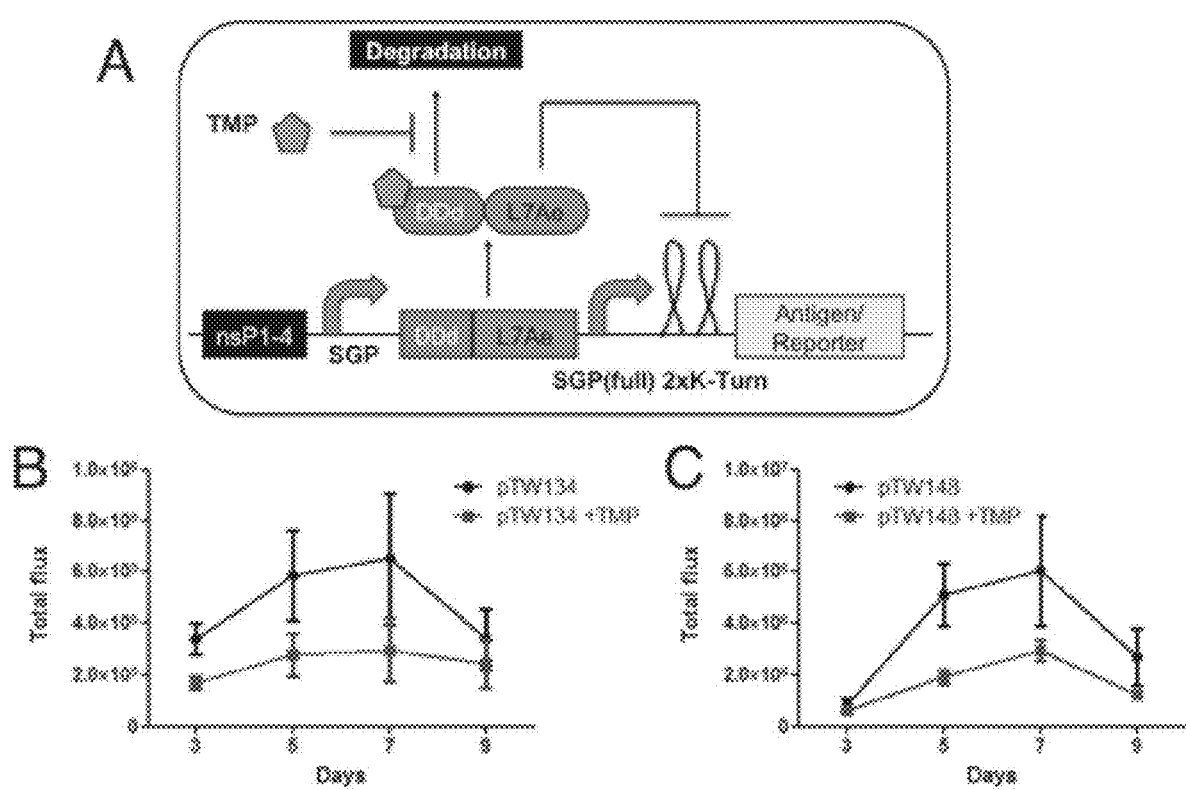

FIGS. 46A-46C. DD-L7Ae circuits for indirect regulation of antigen/reporter gene expression in vivo. (A) Schematic of L7Ae circuit which shuts off antigen/reporter gene expression in the presence of TMP. (B-C) C57Bl/6 mice were immunized i.m. with 6 µg of lipid NP-encapsulated L7Ae constructs encoding luciferase as the output gene downstream of the 2×K-turn. Shown are results for two different replicon promoter configurations in the presence (+TMP) or absence of TMP administered ad libitum orally, demonstrating reduced reporter gene expression in the presence of TMP.

Figures 47A, 47B:
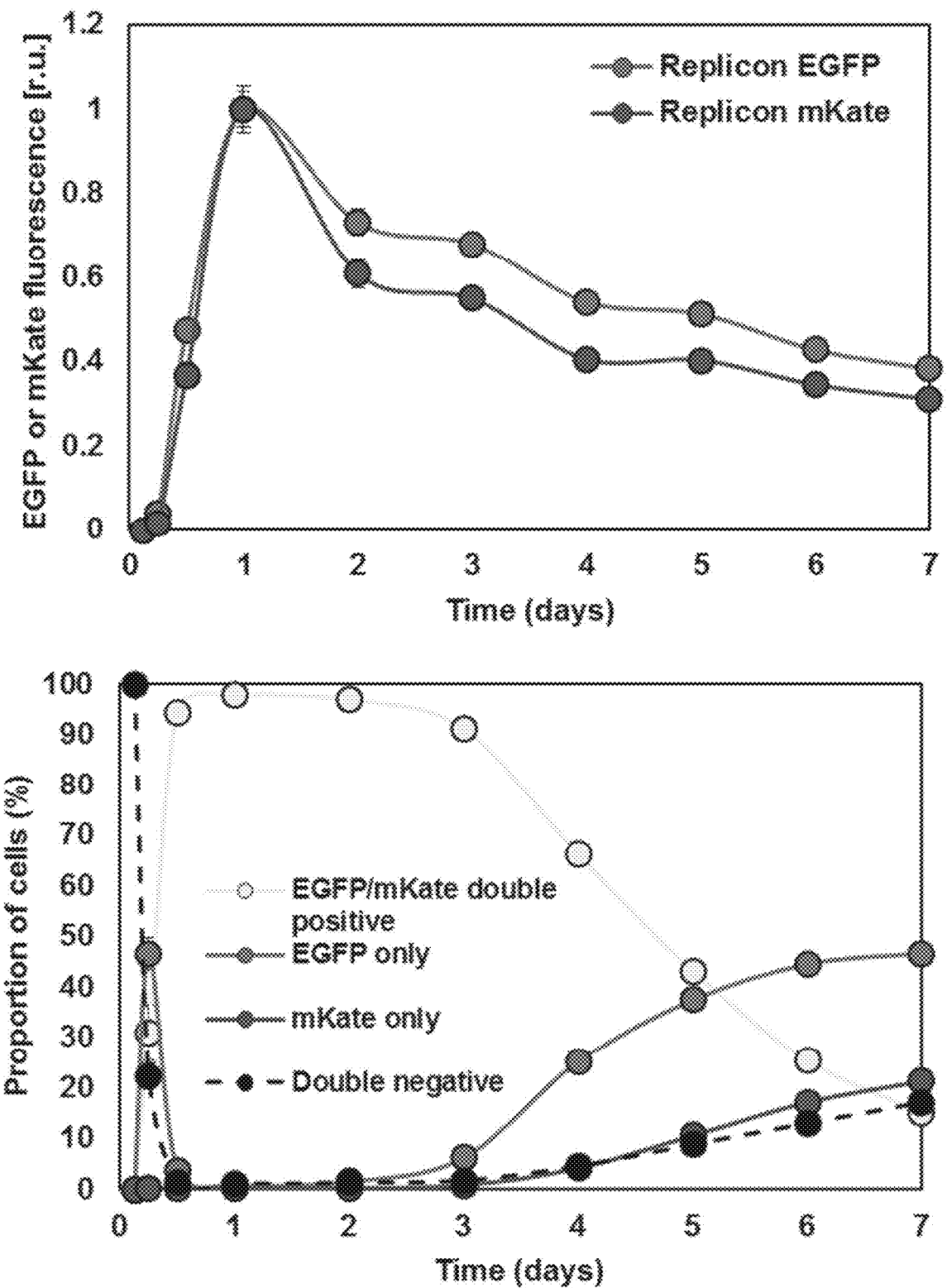

FIGS. 47A-47B. (A) Mean expression of EGFP and mKate of a co-transfected population. (B) Percent EGFP and mKate positive cells.

Figure 48:
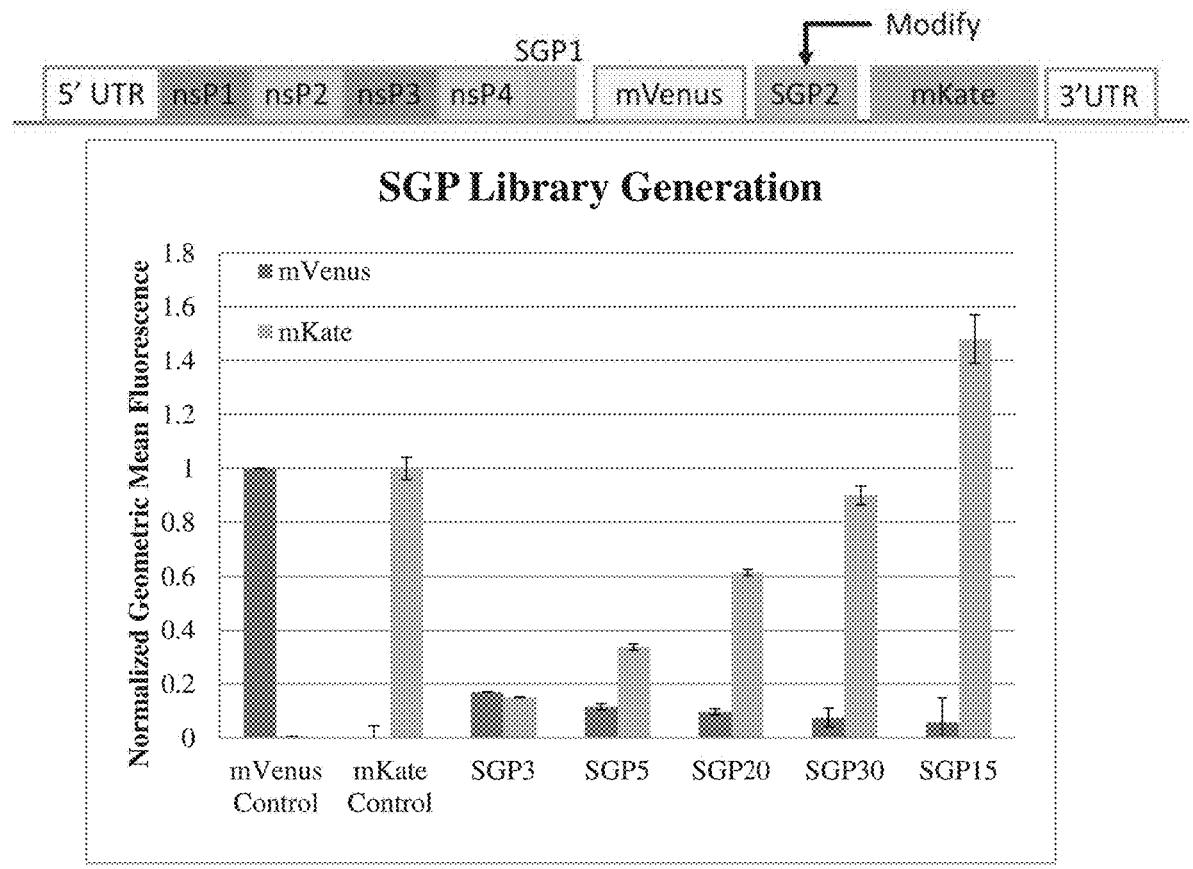

FIG. 48. Top: Schematic of tandem SGP construct. The SGP2 was used to test the SGP library to prevent deleterious mutations of nsP4. Bottom: Five SGPs representing the dynamic range of the SGP library.

Figure 49:
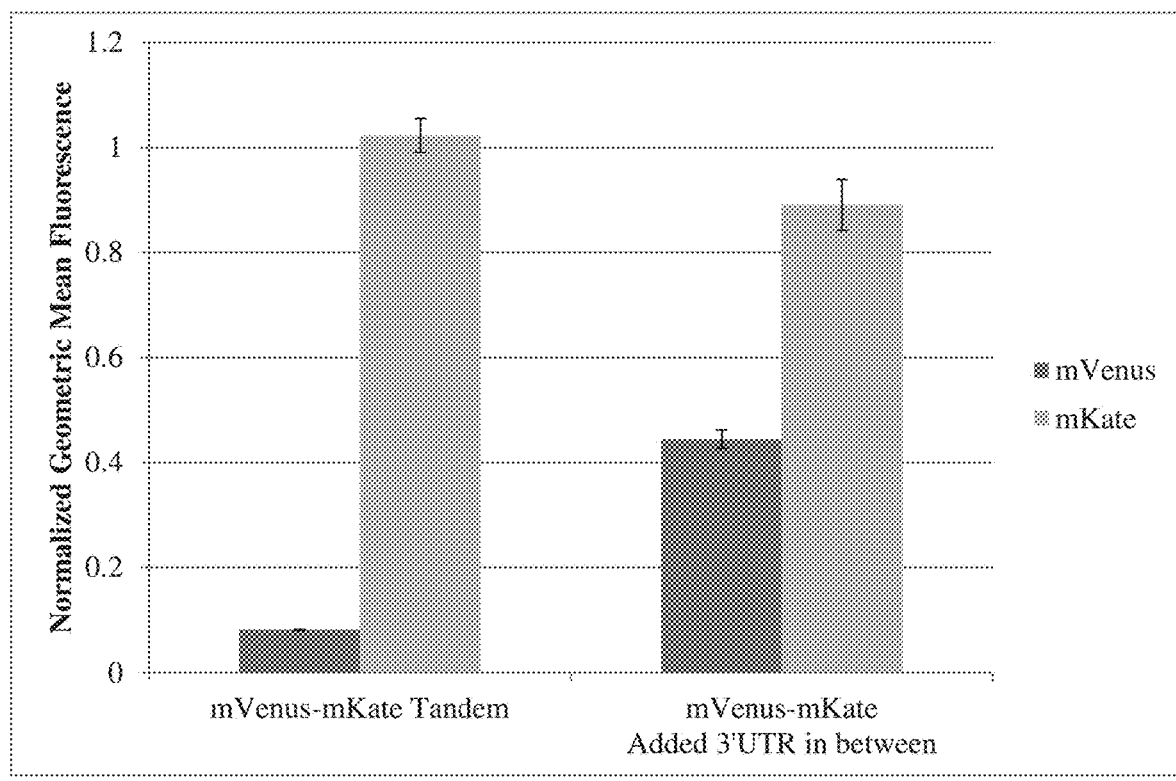

FIG. 49. Including additional 3'UTRs in between two translational units increases expression of the first gene, while only slightly decreasing expression from the second gene.

Figure 50:
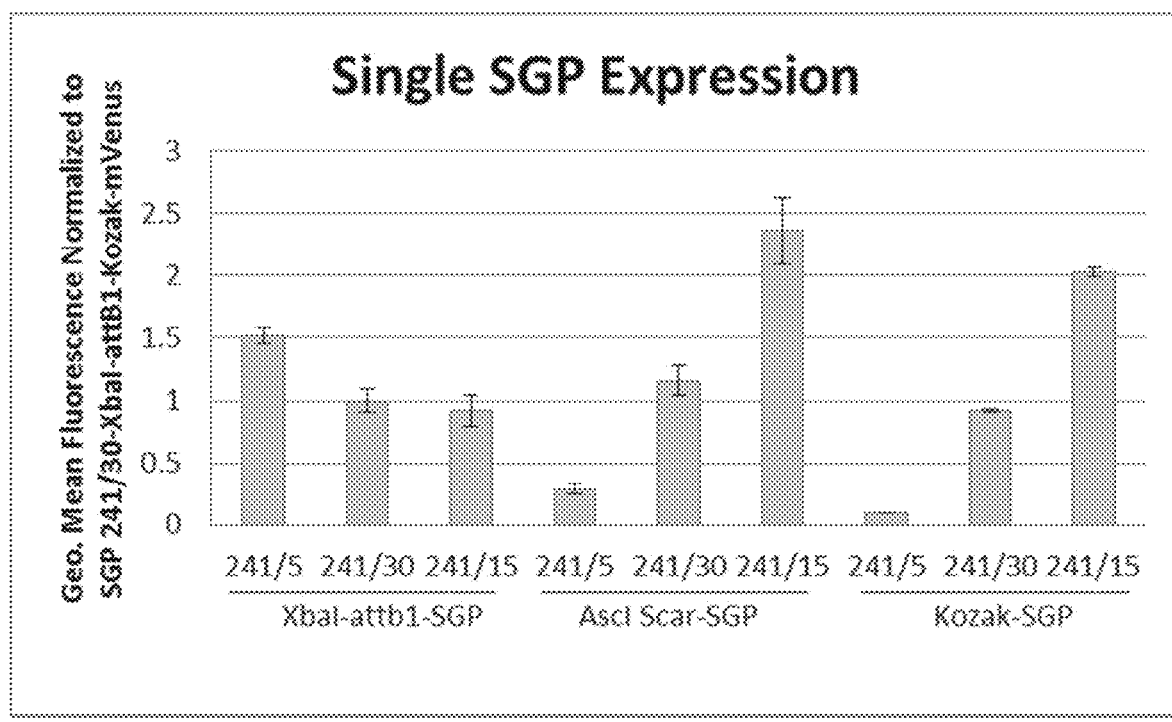

FIG. 50. Single SGP Optimization showed that the sequence between the SGP and Kozak directly affected replicon expression. In particular, the XbaI-attb1 sequence in our standard replicon decreased expression and prevented us from achieving the dynamic range observed in a tandem format.

Figure 51:
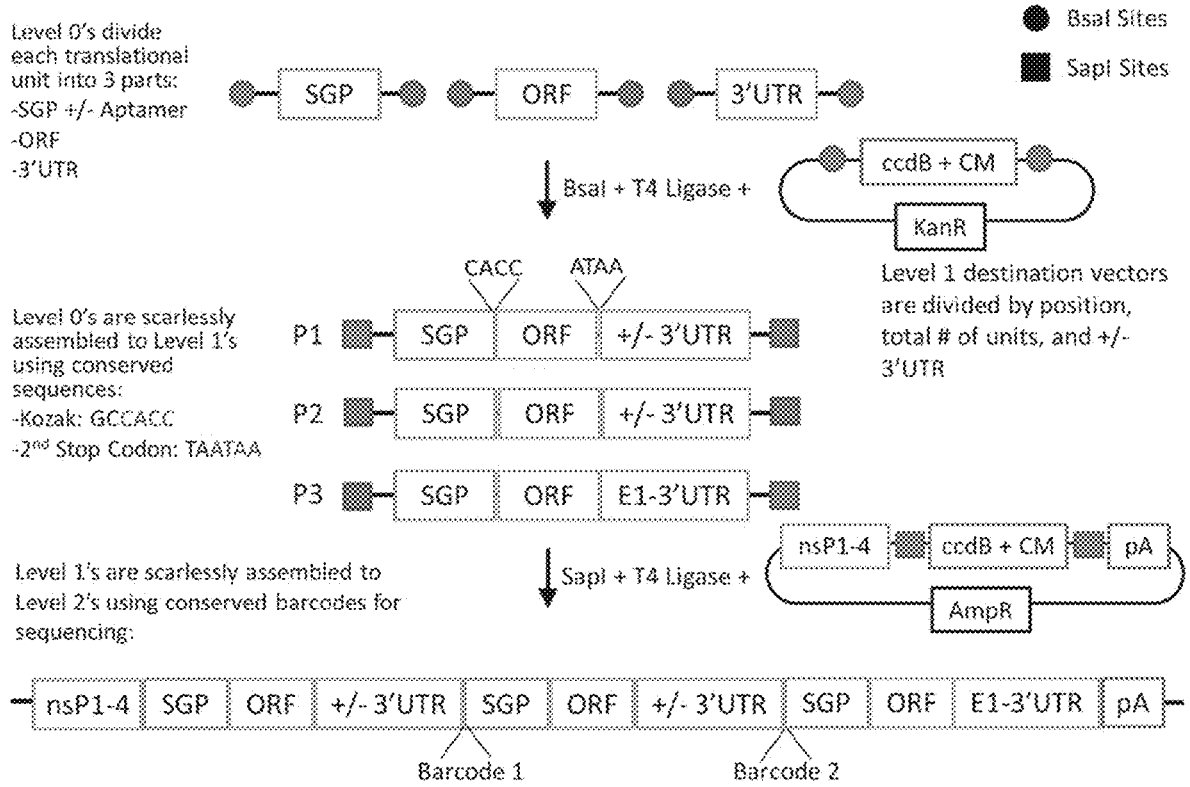

FIG. 51. Schematic of MoClo-based assembly strategy for multi-unit replicons.

Figure 52A:
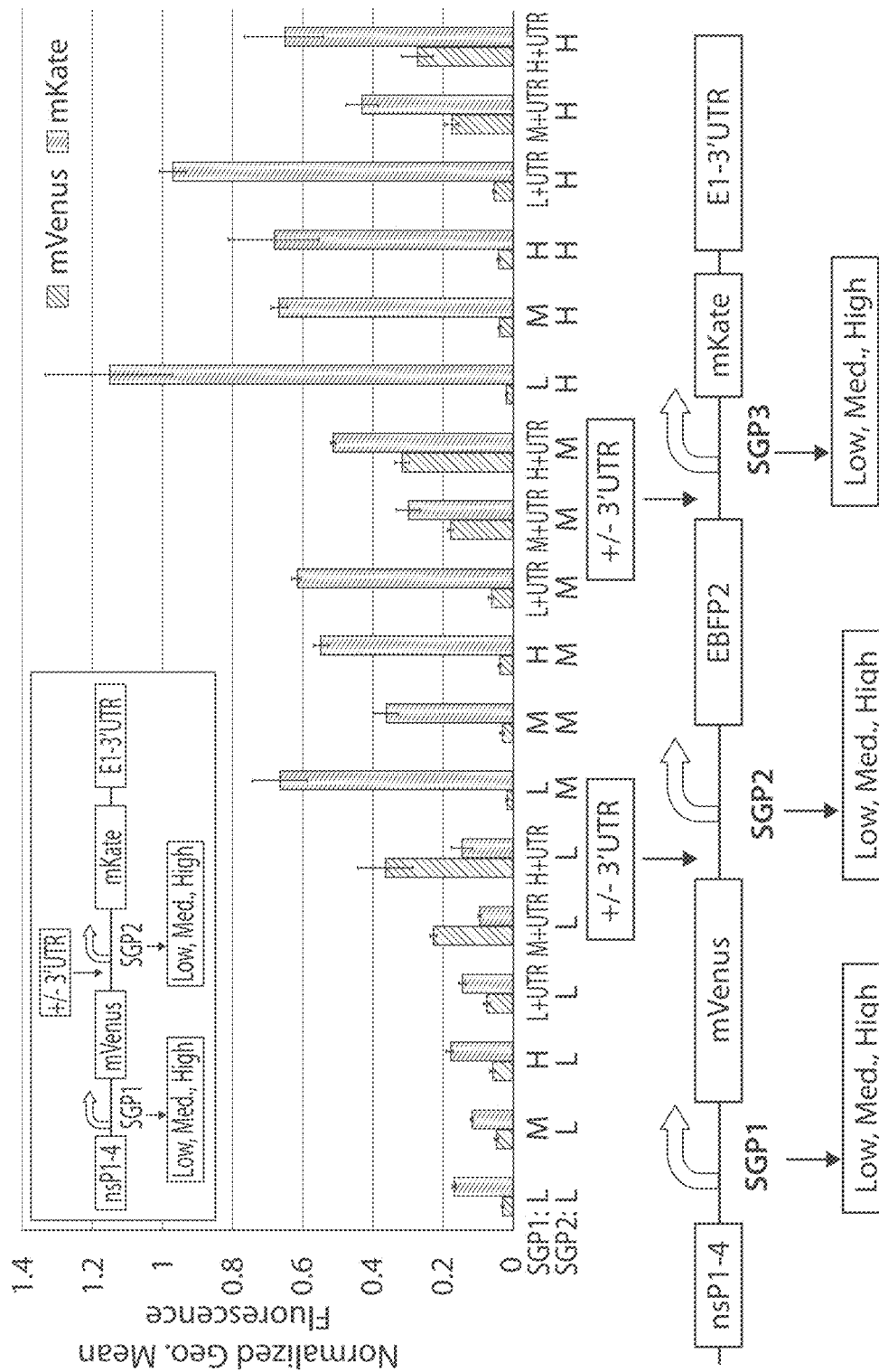

FIGS. 52A-52B. (A) Two SGP constructs with all combinations of SGP 5 (low (L)), 30 (midrange(M)), and 15 (high(H)) with and without an additional 3'UTR. (B) Three SGP constructs with all combinations of low, midrange, and high SGPs with and without additional 3'UTRs. All fluorescent values are normalized to the respective fluorescent positive controls.

Figure 53:
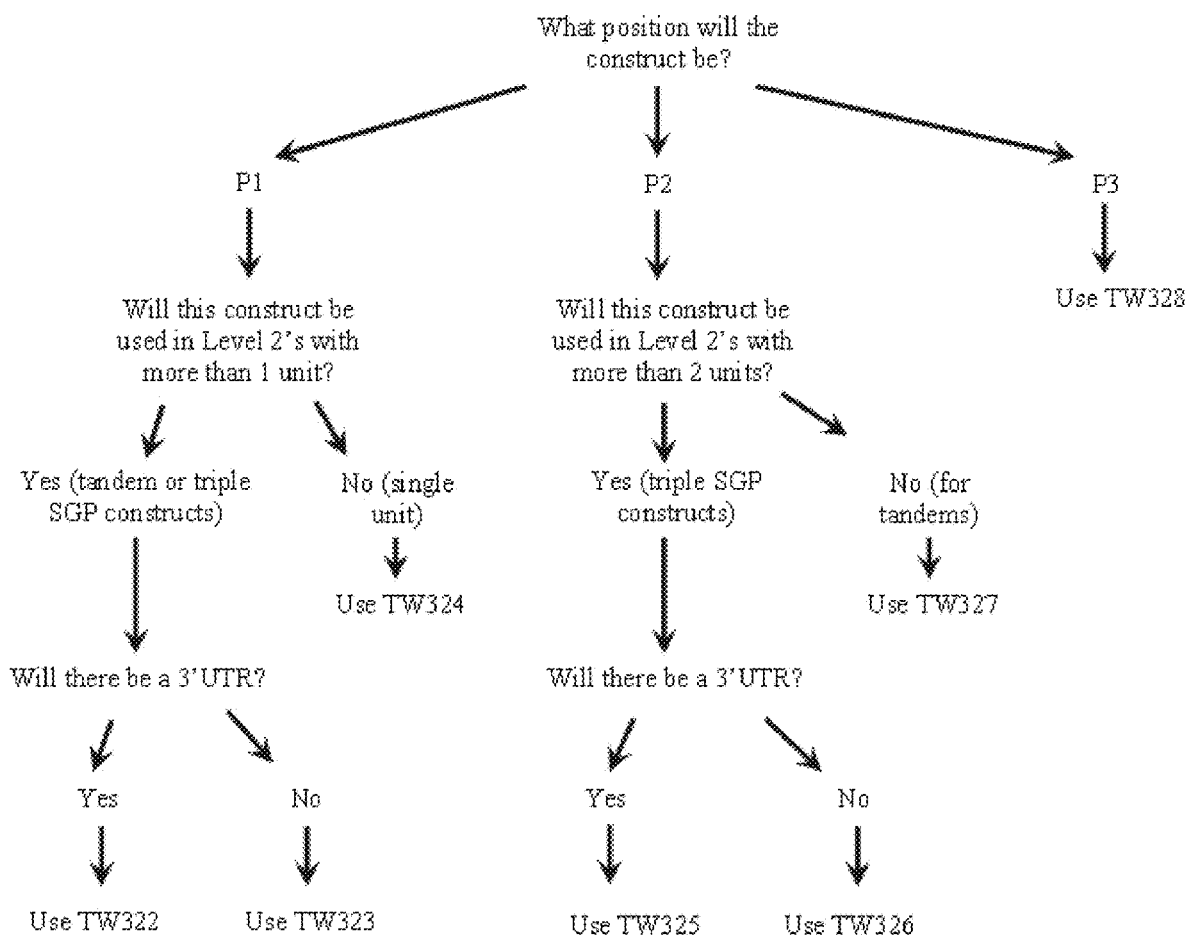

FIG. 53. Flow diagram of destination vectors (Table 8).

Figure 54:
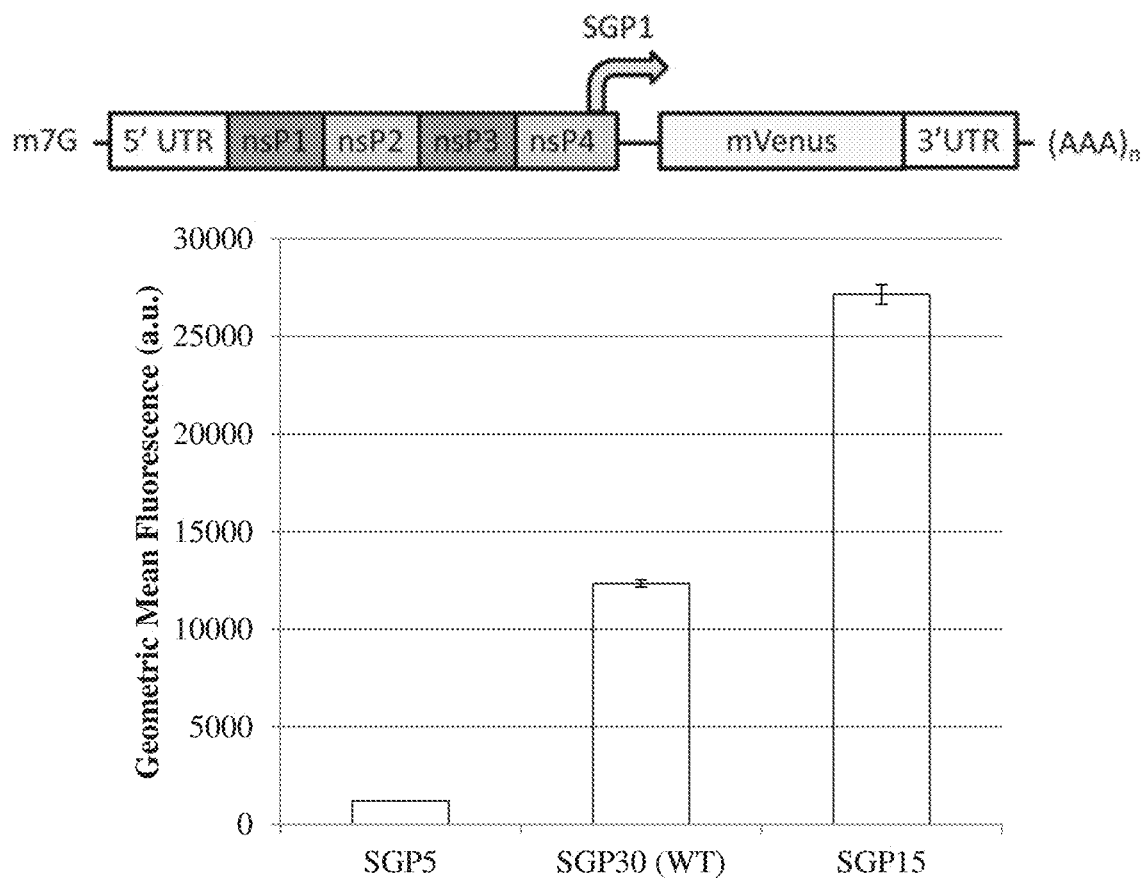

FIG. 54. The full dynamic range of the SGP library could be achieved using only plus side truncations, so the library was portable to single SGP systems. The same hierarchy between SGPs was observed, with an increased range of expression levels, reaching 22-fold.

Figure 55A:
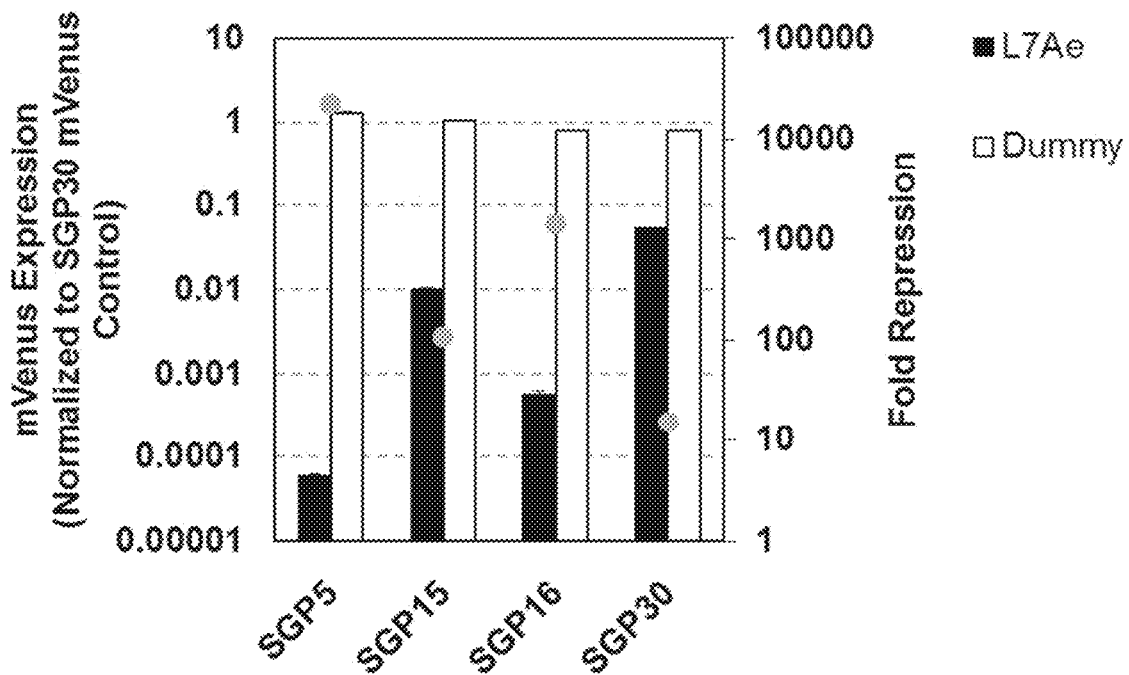
Figure 55B:
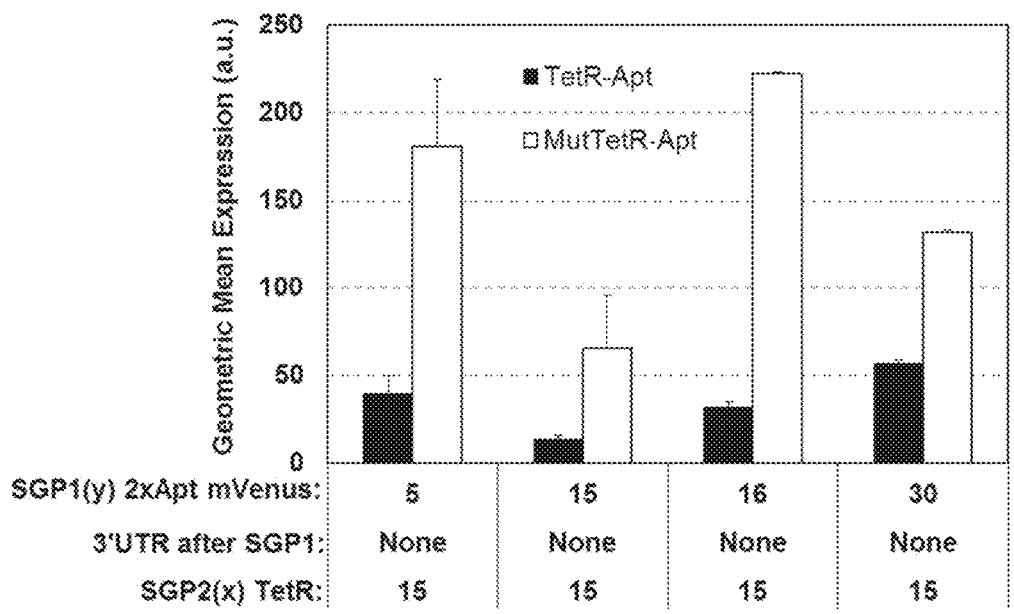

FIGS. 55A-55B. (FIG. 55A) L7Ae is expressed in the first position under SGP30, while the second SGP preceding a 2×K-turn mVenus is varied. L7Ae shows strong repression compared to the same construct with a dummy protein in place of L7Ae. The optimal construct represses to baseline, or the negative control. (FIG. 55B) TetR is expressed from the second position under the strongest SGP, with optimal repression of 7-fold compared to a mutant Tet-aptamer control.

Figure 56:
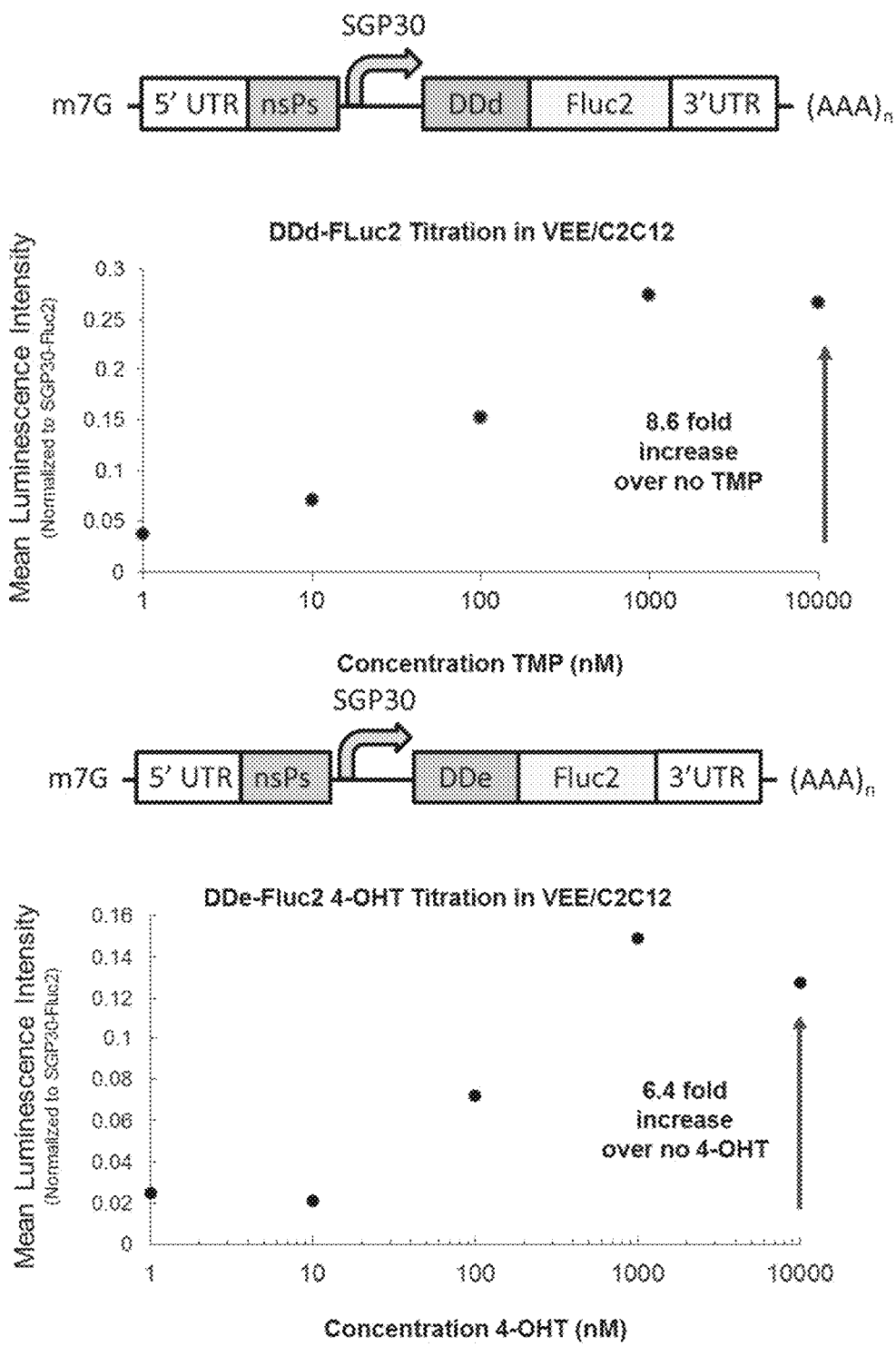

FIG. 56. Titration of DDd-Fluc2 with TMP and DDe-Fluc2 with 4-OHT resulted in 8.6- and 6.4-fold increases compared to expression when no small molecule is present. This data is normalized to Fluc2 constitutively expressed under the wild type SGP30, revealing that both DDd and DDe decrease expression of the protein to which they are fused.

Figures 57A, 57B, 57C:
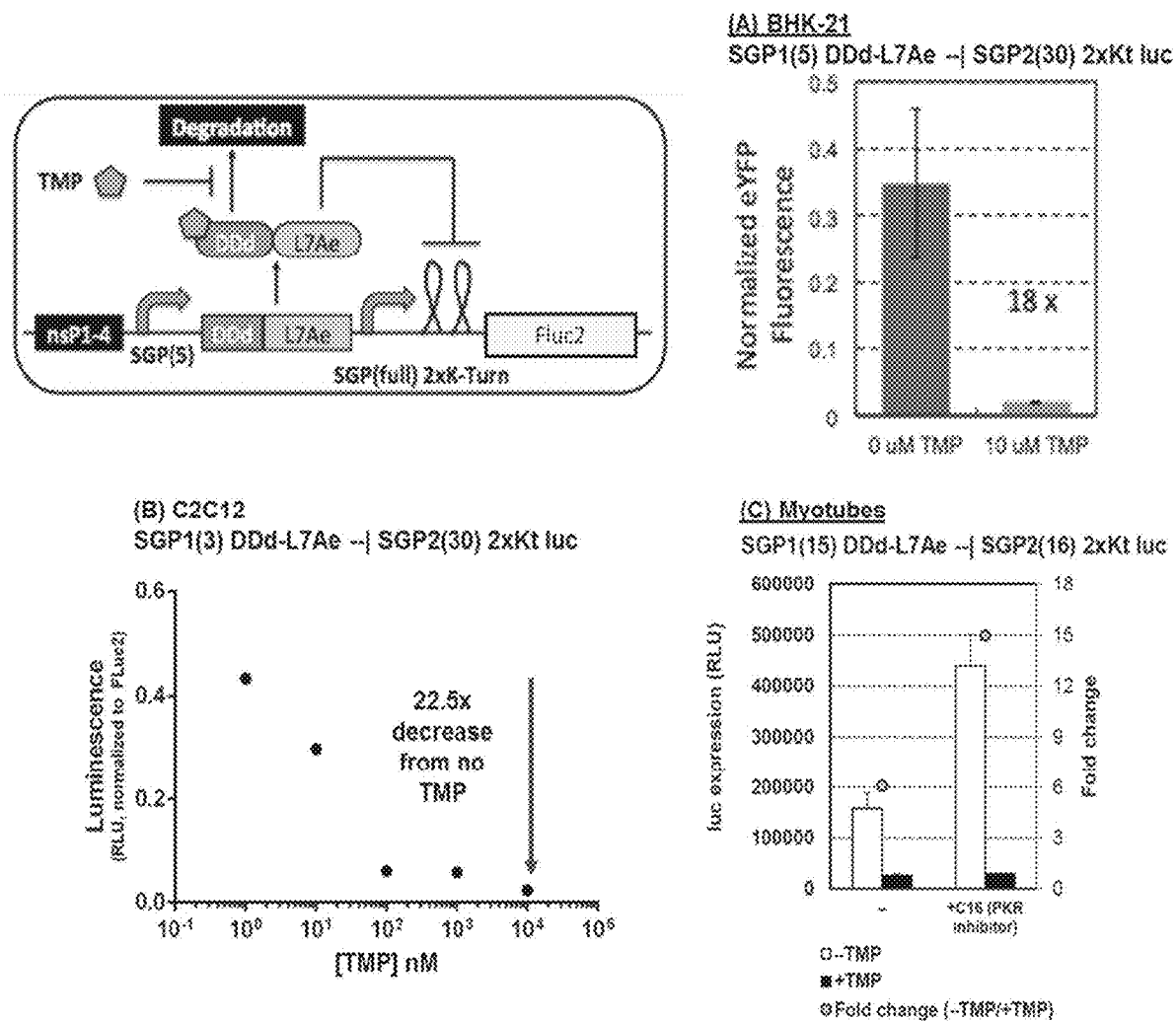

FIGS. 57A-57C. DDd-L7Ae was tested in (FIG. 57A) BHK-21, (FIG. 57B) C2C12, and (FIG. 57C) myotubes differentiated from C2C12 myoblasts. When TMP is present, L7Ae is stabilized and the output is repressed. An EYFP reporter was used in BHK-21 cells, while Fluc2 was used in C2C12 and myotubes. As shown, C16, a PKR inhibitor was used in myotubes to increase expression and overall fold change.

FIGS. 58A-58D. (FIG. 58A) Expression of mVenus over time for various doses of Sindbis replicon, showing a rapid increase to dose-independent level. Dose is indicated by hue, ranging geometrically from 21 ng/ul to 2055 ng/ul. (FIG. 58B) The same data shown for the first 11 hours. (FIG. 58C) Co-transfection of two replicons at varying ratios and a constant combined dose produces a linear relation between relative dose and fluorescence and (FIG. 58D) a constant total fluorescence. Expression units are MEFL: Molecules of Equivalent FLuorescein$^2$.

FIGS. 59A-59D. (FIG. 59A) DI RNA generation by deletion of the parts of the nsPs (FIG. 59B) Validation that DI RNA containing an A3 mutation results in higher DI RNA expression (FIG. 59C) Helper RNA can be optimized to slightly increase DI RNA expression by preventing subgenomic translation and increasing nsP production from the helper (FIG. 59D) An optimal helper:DI-RNA ratio exists for maximal DI RNA expression.

Figure 60A:
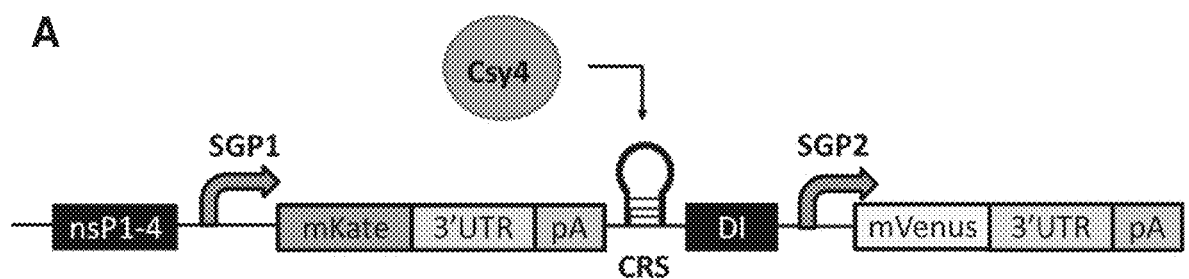
Figure 60B:
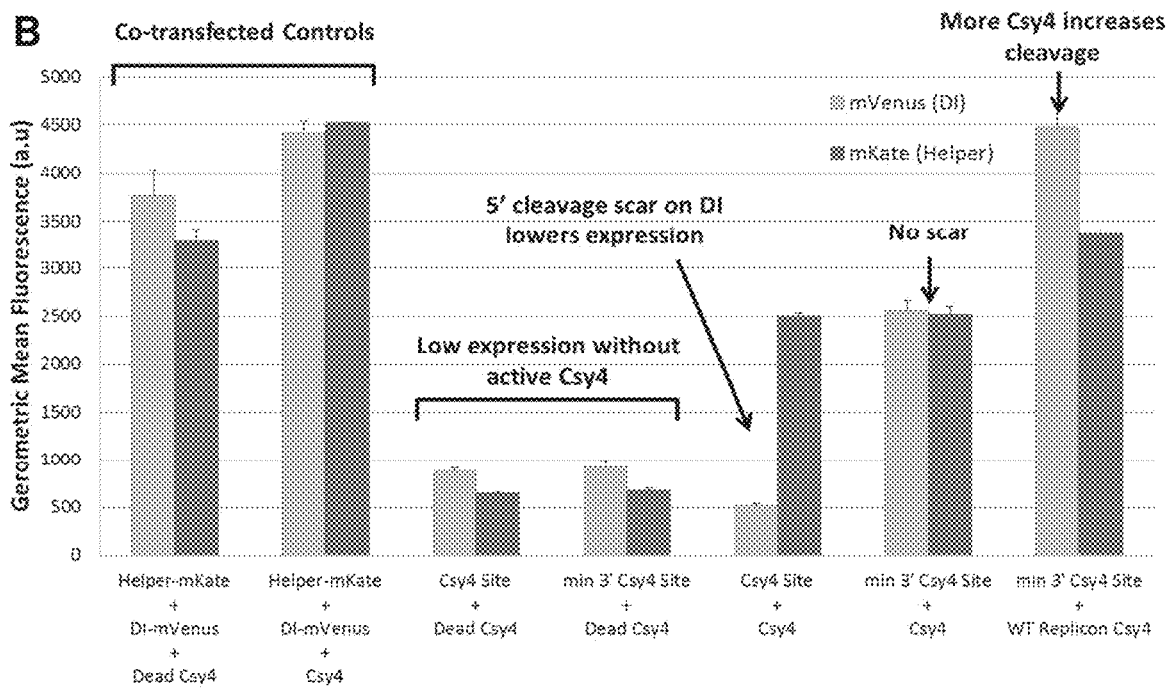

FIGS. 60A-60B. (FIG. 60A) Schematic of a helper-CRS-DI RNA system. In preliminary experiments, Csy4 was expressed on a co-transfected replicon, but in the future is expressed via an IRES on the same replicon. This should allow Csy4 to be expressed before or early during replication and result in higher cleavage efficiency. (FIG. 60B) A minimal Csy4 recognition site (CRS) is required to prevent a scar on the 5' of the DI RNA that dramatically reduces replication. When using this minimal CRS, increasing the amount of Csy4 has a positive effect on DI RNA expression, presumably due to enhanced cleavage.

Figure 61A:
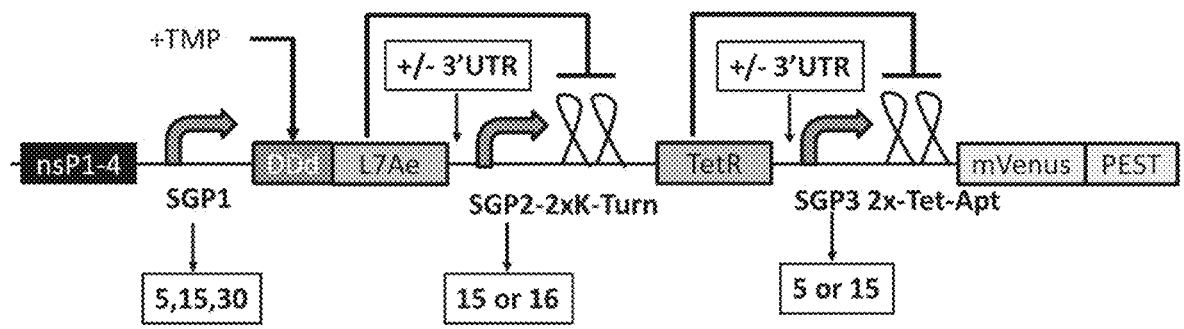
Figure 61A:
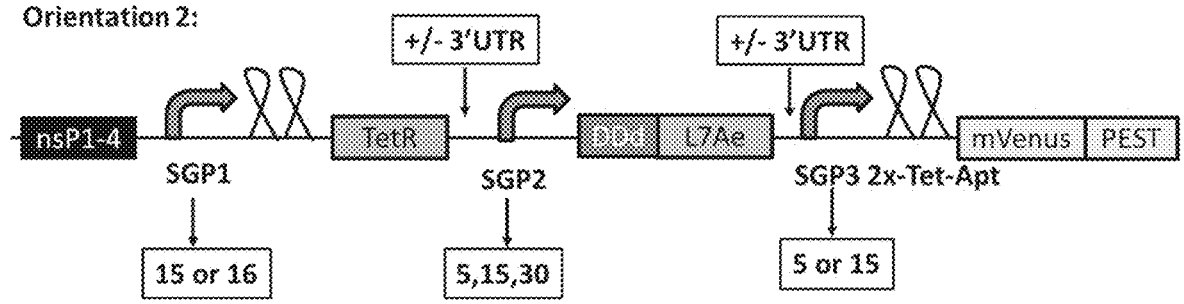
Figure 61B:
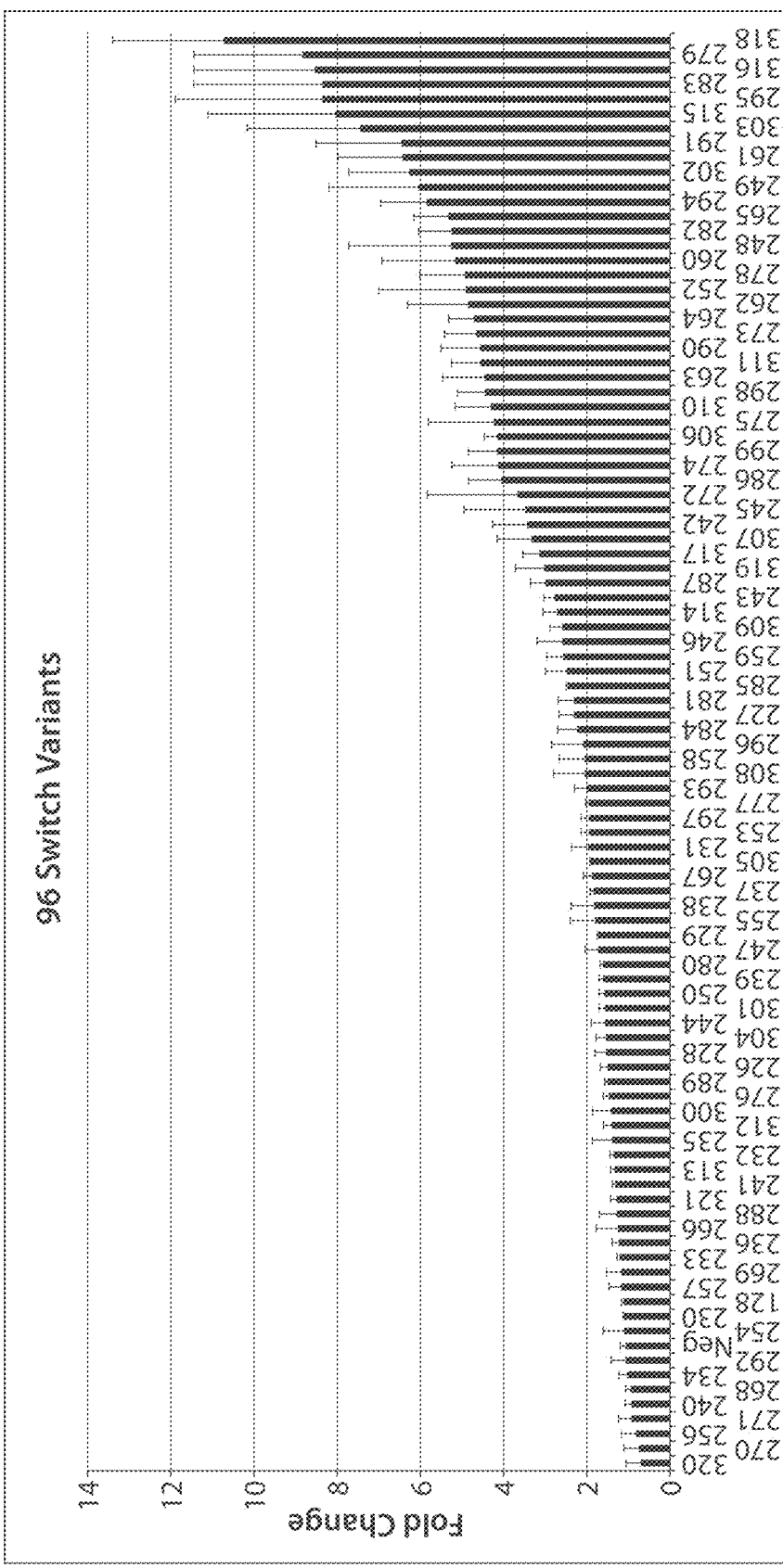

FIGS. 61A-61B. (FIG. 61A) Schematic of the 96 variants of a TMP inducible switch with cascade topology. In this switch, L7Ae is stabilized by TMP, represses TetR, allowing expression of the output. (FIG. 61B) Fold changes between the OFF state (−TMP/−Dox) and the ON state (+TMP/+Dox) in BHK-21 cells 48 hours post-transfection.

Figure 62:
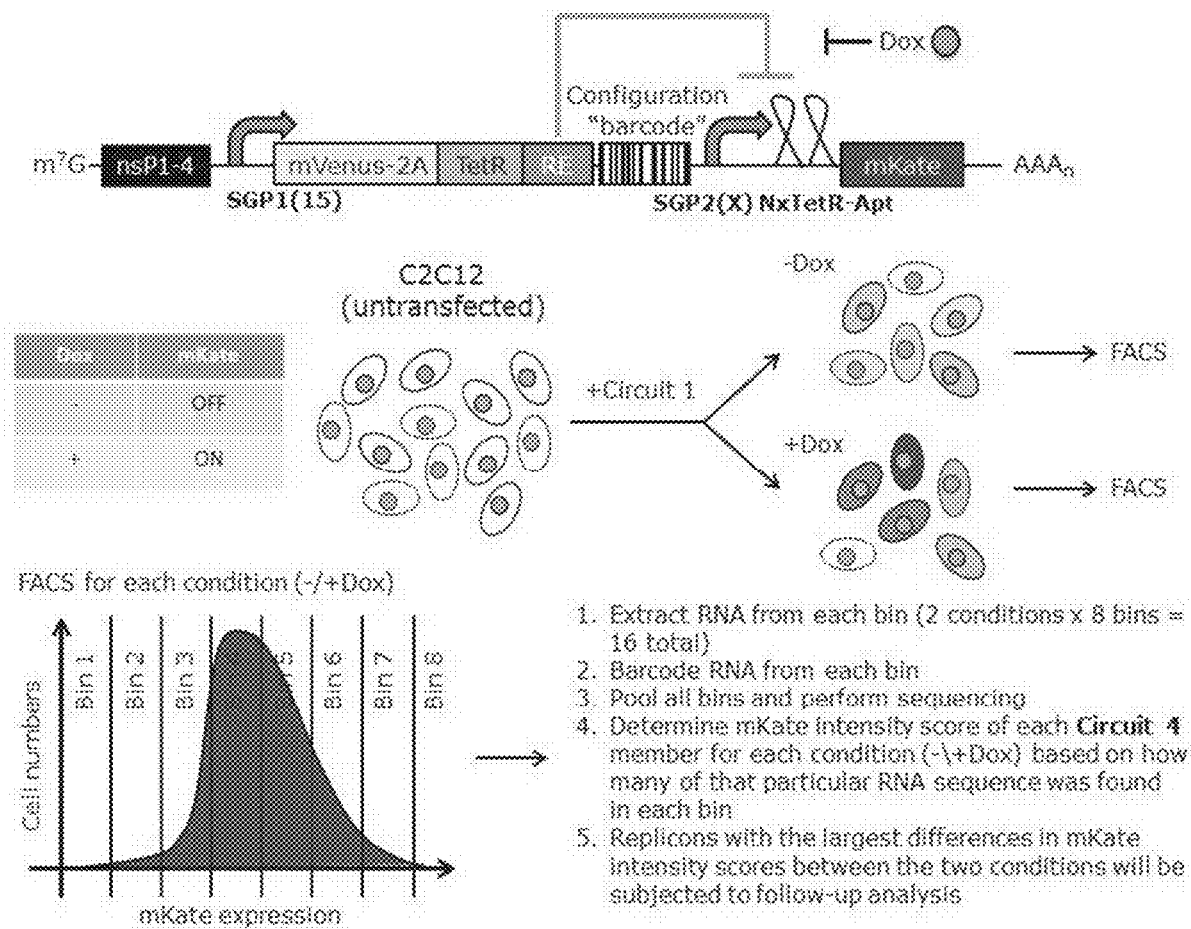

FIG. 62. Schematic for screen of TetR-repression enhancer fusions. Briefly, a library of Dox-inducible ON switches is screened using FACS and RNA-seq to find repression enhancers that promote higher ON/OFF fold changes when fused to TetR.

FIGS. 63A-63B. (FIG. 63A) Preliminary Csy4 cleavage-based irreversible switch. Before Csy4 cleavage, mKate is expressed slightly higher due to positional effect, while mVenus remains low. When Csy4 is co-transfected, the second translational unit is removed, allowing mVenus expression to increase. (FIG. 63B) To optimize this circuit, the mKate ON state is increased using stronger SGPs, include an inducible Csy4 on the replicon, and introduce DDd-L7Ae to decrease mVenus expression in its OFF state, as shown in the truth table.

Figure 64:
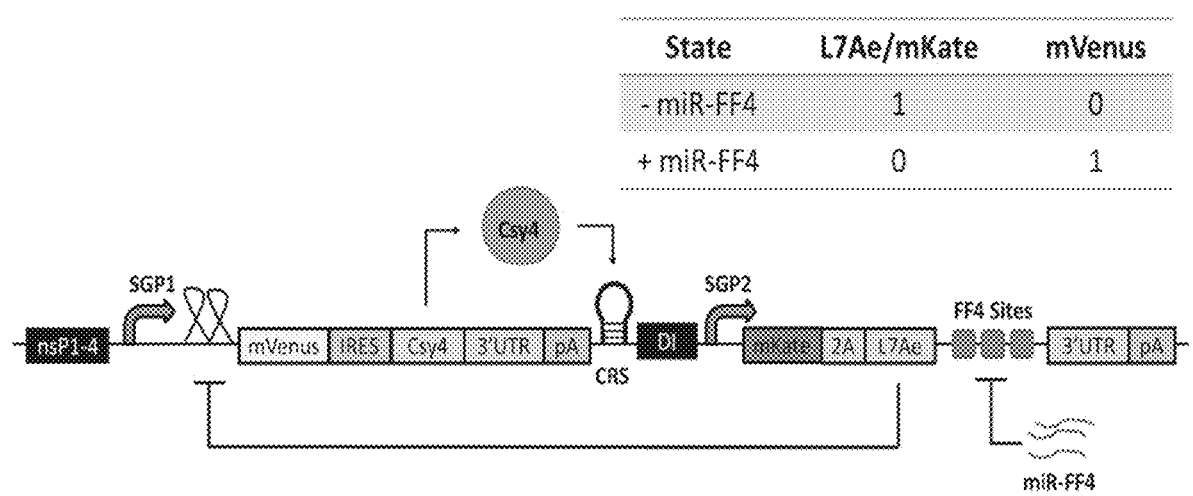

FIG. 64. Schematic of helper DI high sensor. Csy4 is expressed for an IRES and cleaves the helper-CRS-DI RNA. If miR-FF4 is absent, L7Ae from the DI RNA represses mVenus on the helper. If miR-FF4 is added to the system, the DI RNA is degraded, no L7Ae is present, and mVenus expresses.

Figure 65:
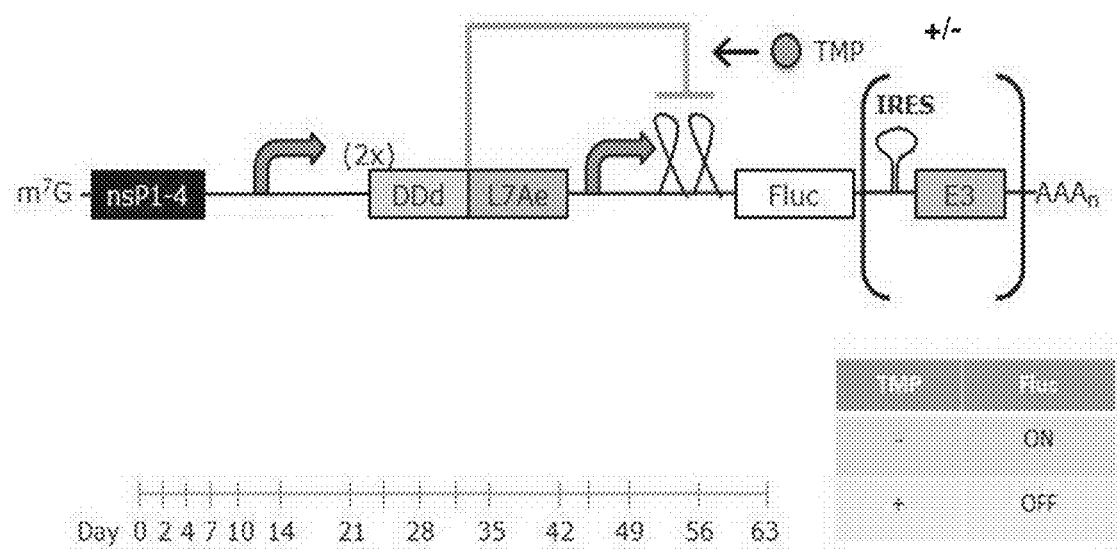

FIG. 65. TMP inducible OFF switch. When TMP is present, L7Ae is stabilized and the reporter is repressed. When TMP is removed, L7Ae is degraded and the reporter is expressed.

Figure 66:
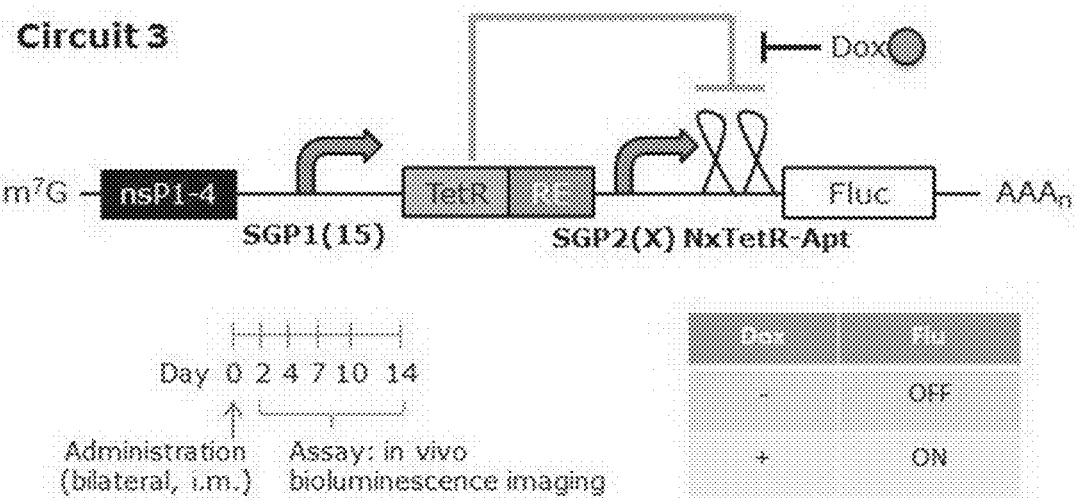

FIG. 66. In vivo testing of the optimized small molecule-inducible ON switch.

Figure 67:
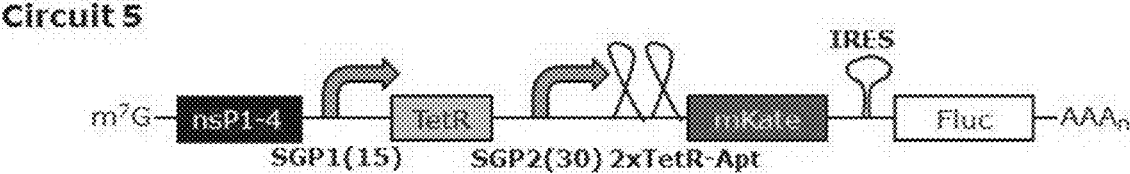
Figure 67:
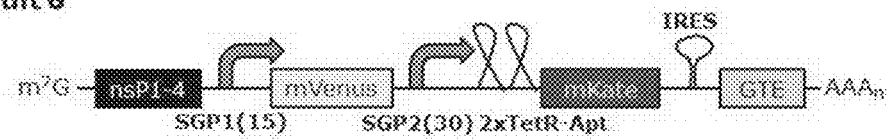

FIG. 67. Schematic of the circuit to identify the optimal IRES for protein expression from an RNA replicon.

Figure 68:
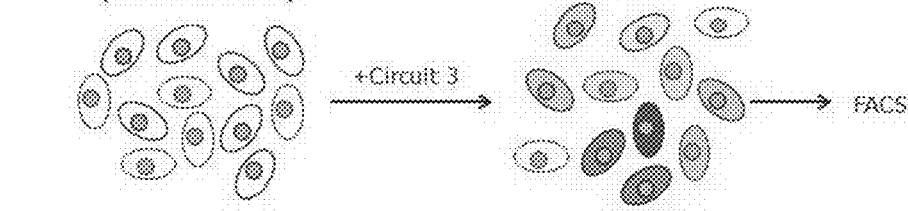
Figure 68:
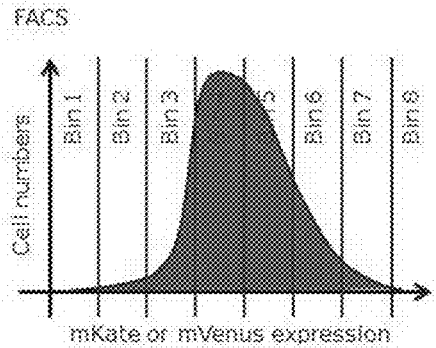

FIG. 68. Overview of the FACS/RNA-Seq-based in vitro screen to identify general enhancers of translation in myoblasts which may be used to improve circuit performance of the TetR-RE ON switch.

Figure 69:
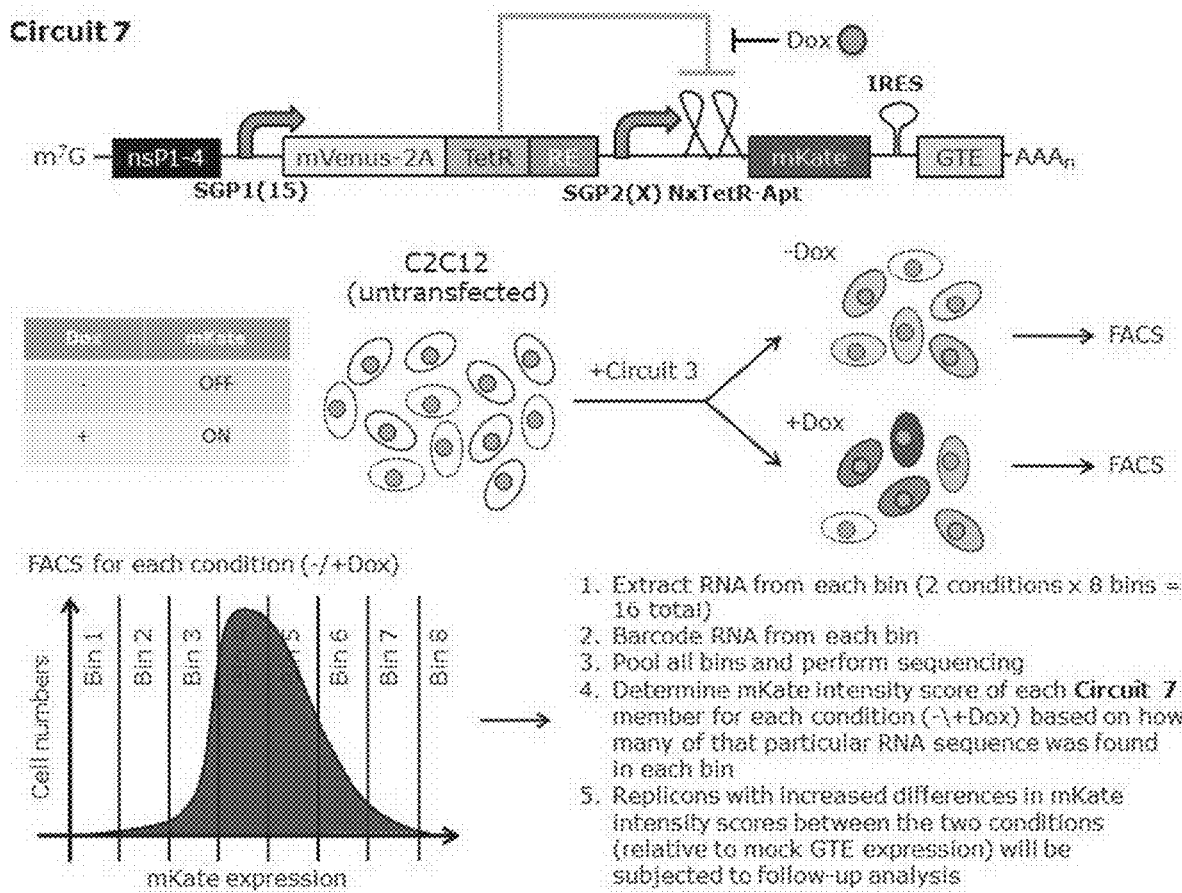

FIG. 69. Overview of the FACS/RNA-Seq-based in vitro screen to identify enhancers of TetR-RE-based replicon ON switch circuit performance.

Figure 70:
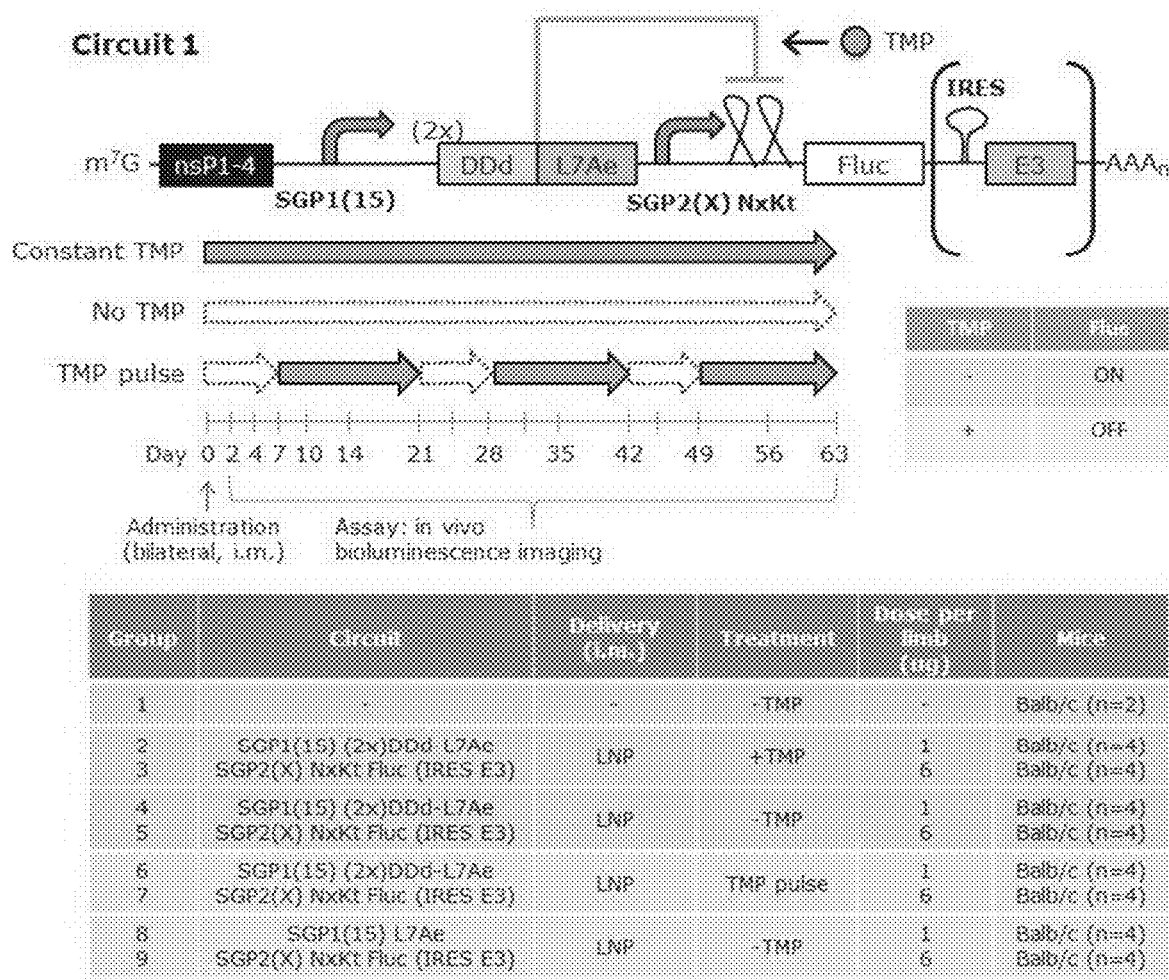

FIG. 70. Pulsing Fluc expression in vivo using the DDd-L7Ae-based replicon "OFF switch" in mice.

Figure 71:
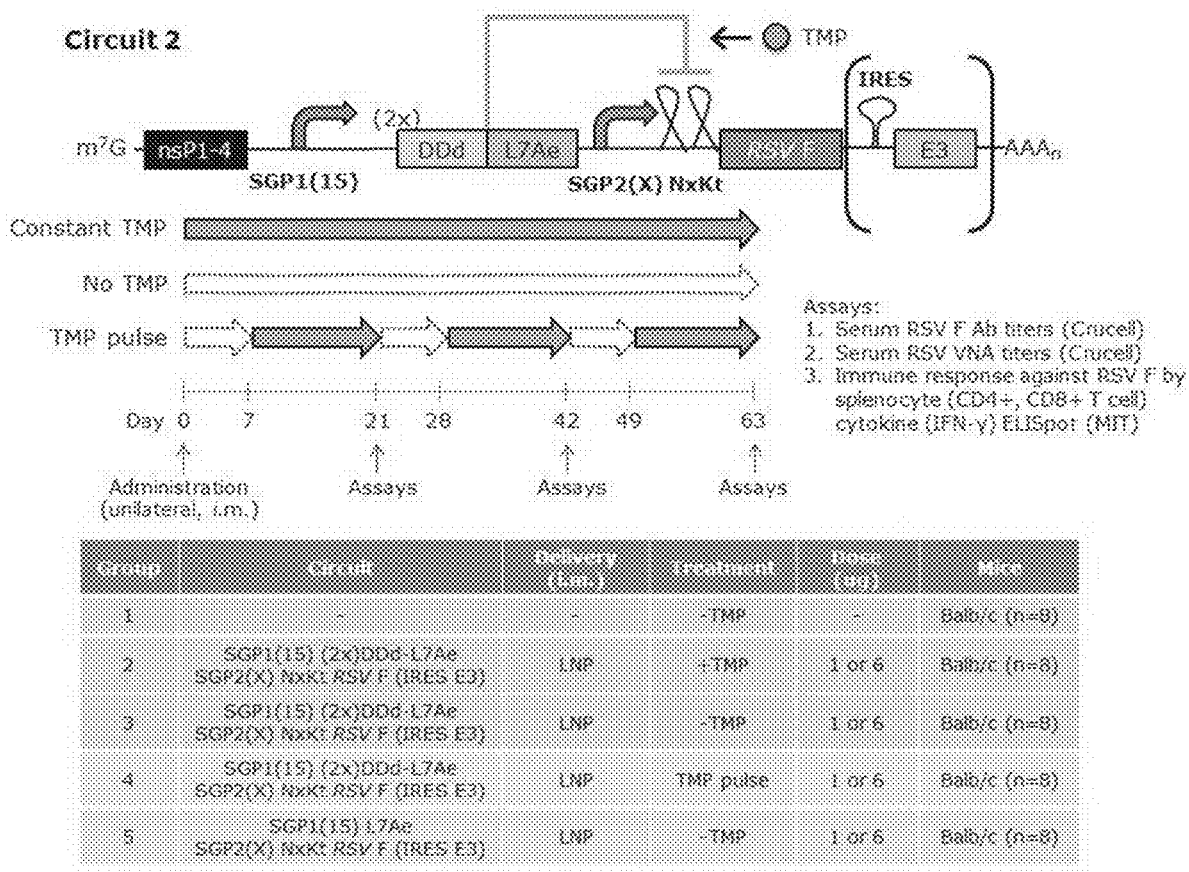

FIG. 71. Pulsing RSV F expression in vivo using the DDd-L7Ae-based replicon "OFF switch" in mice.

Figure 72:
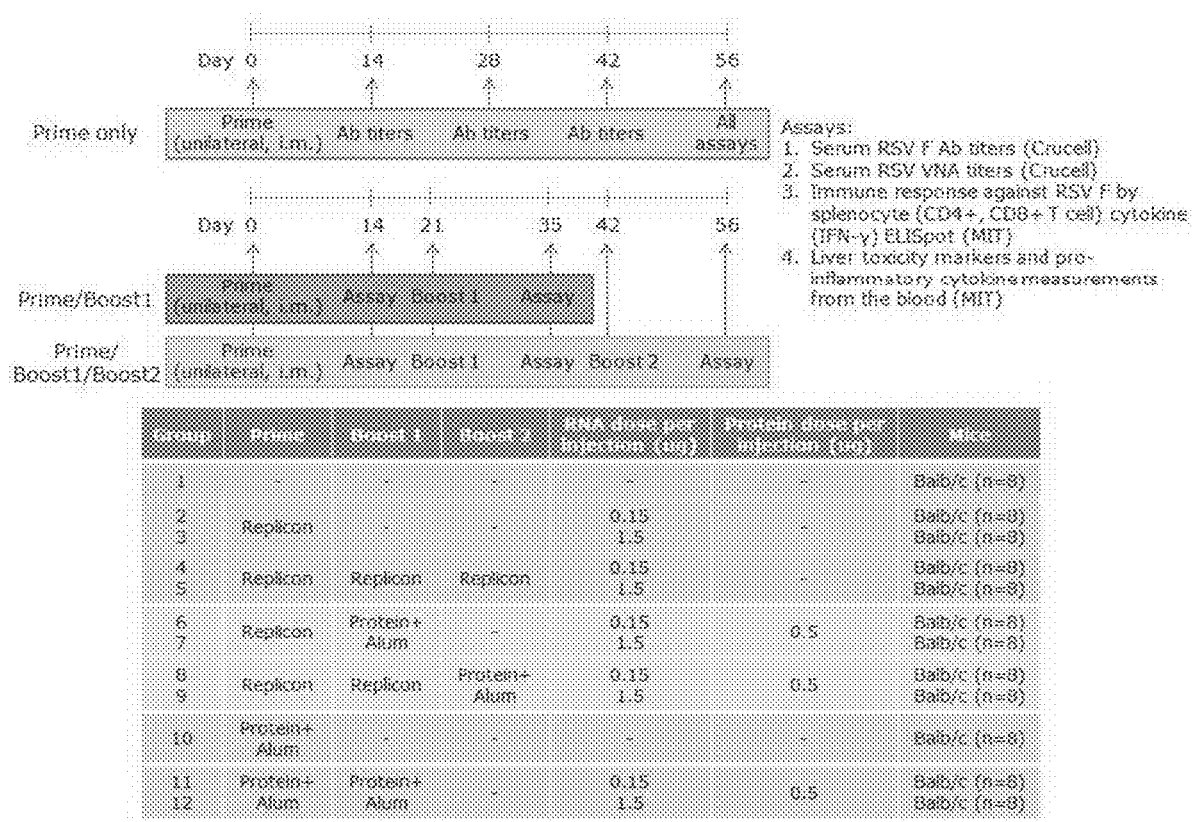

FIG. 72. Comparison of immune responses of homologous vs heterologous prime/boost.

Figure 73:
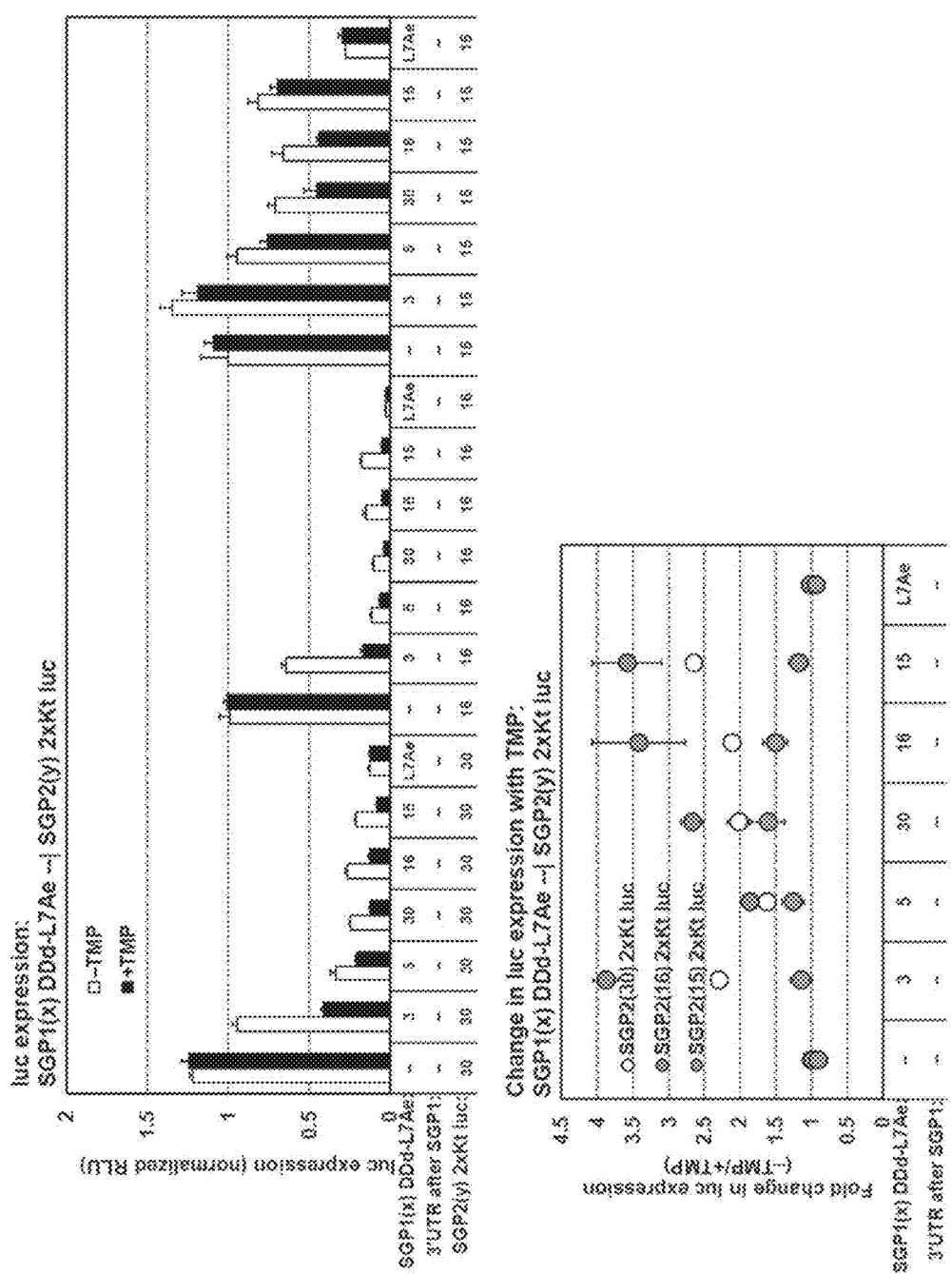
Figure 73:
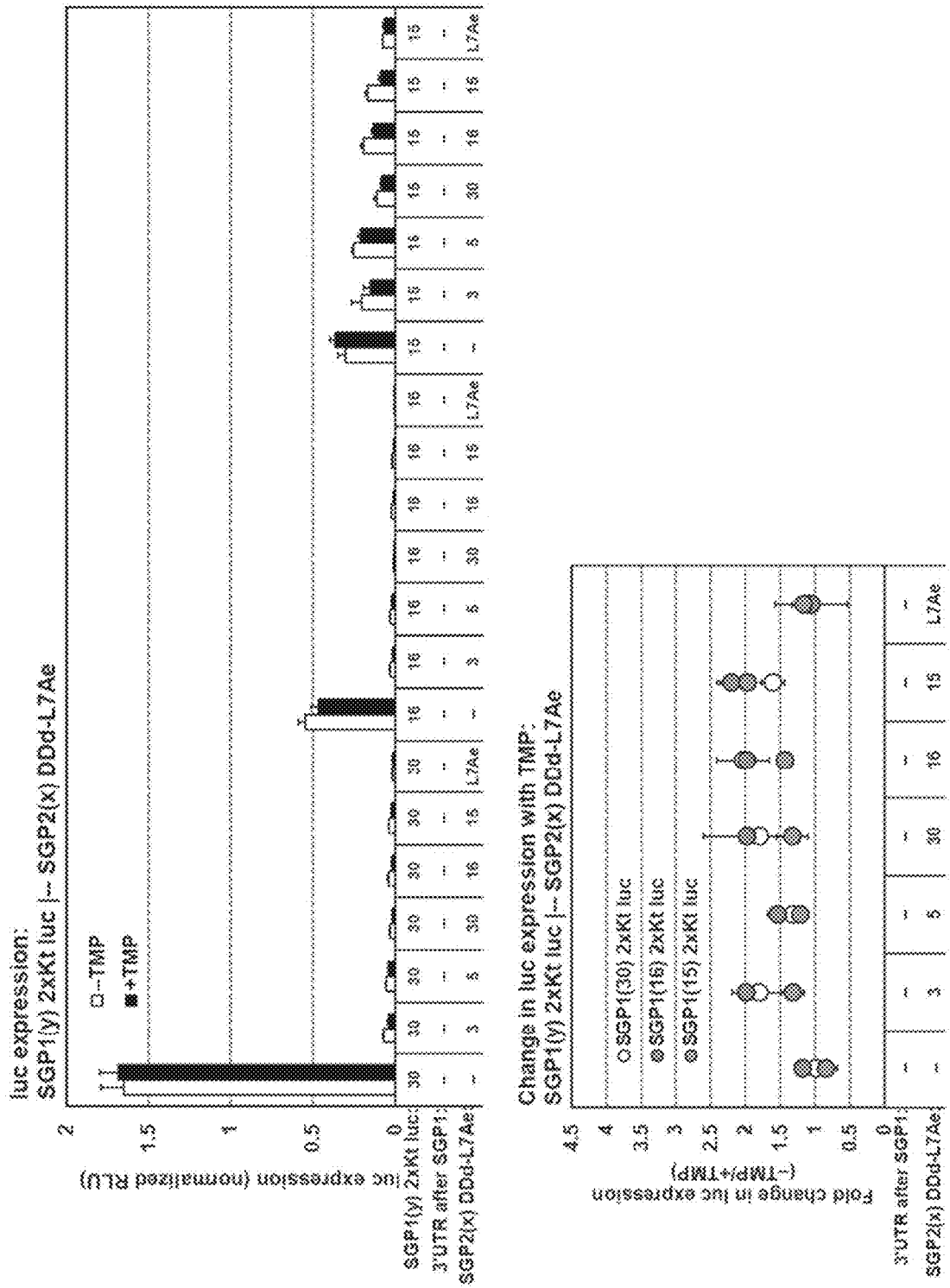
Figure 73:
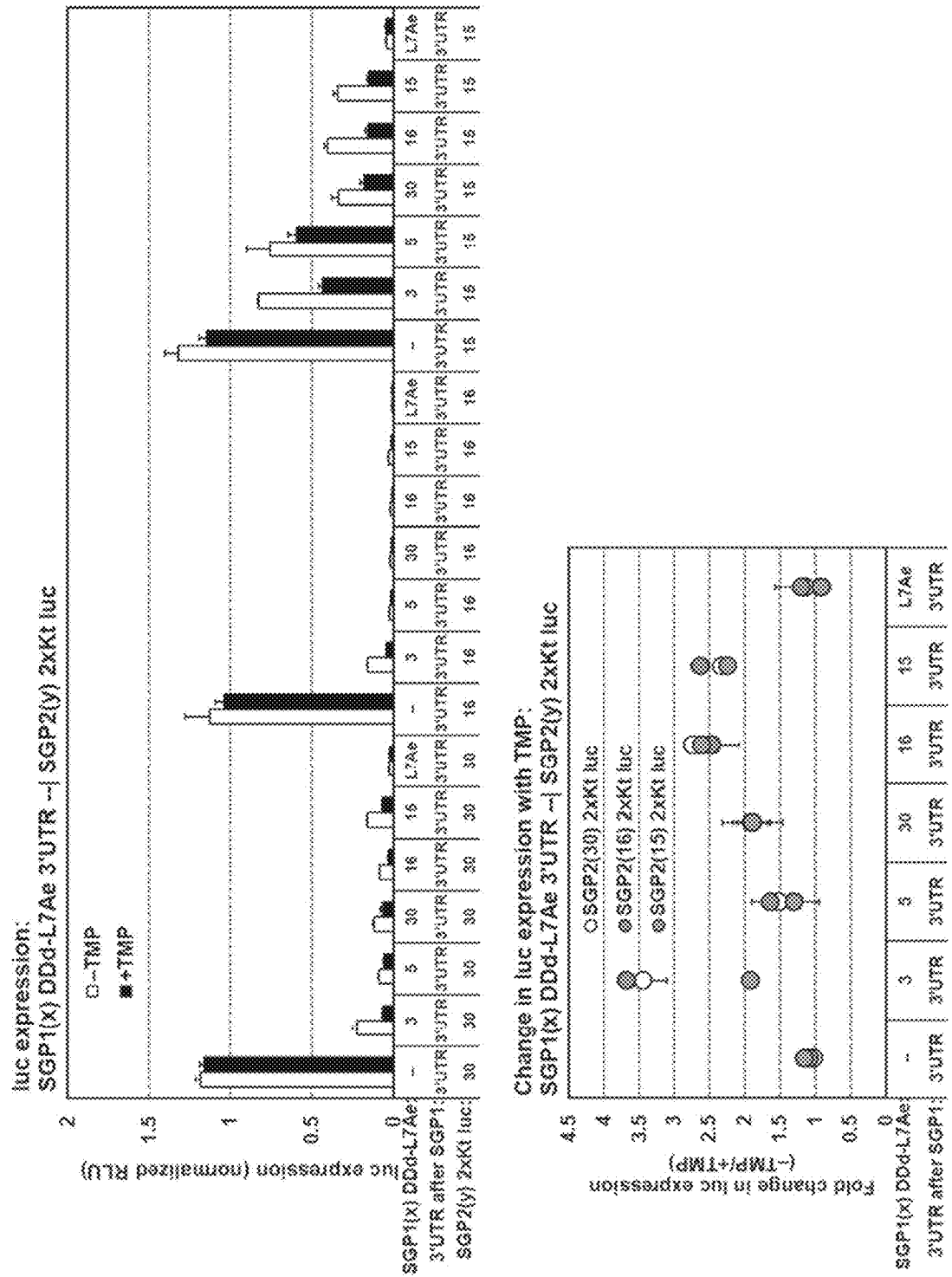
Figure 73:
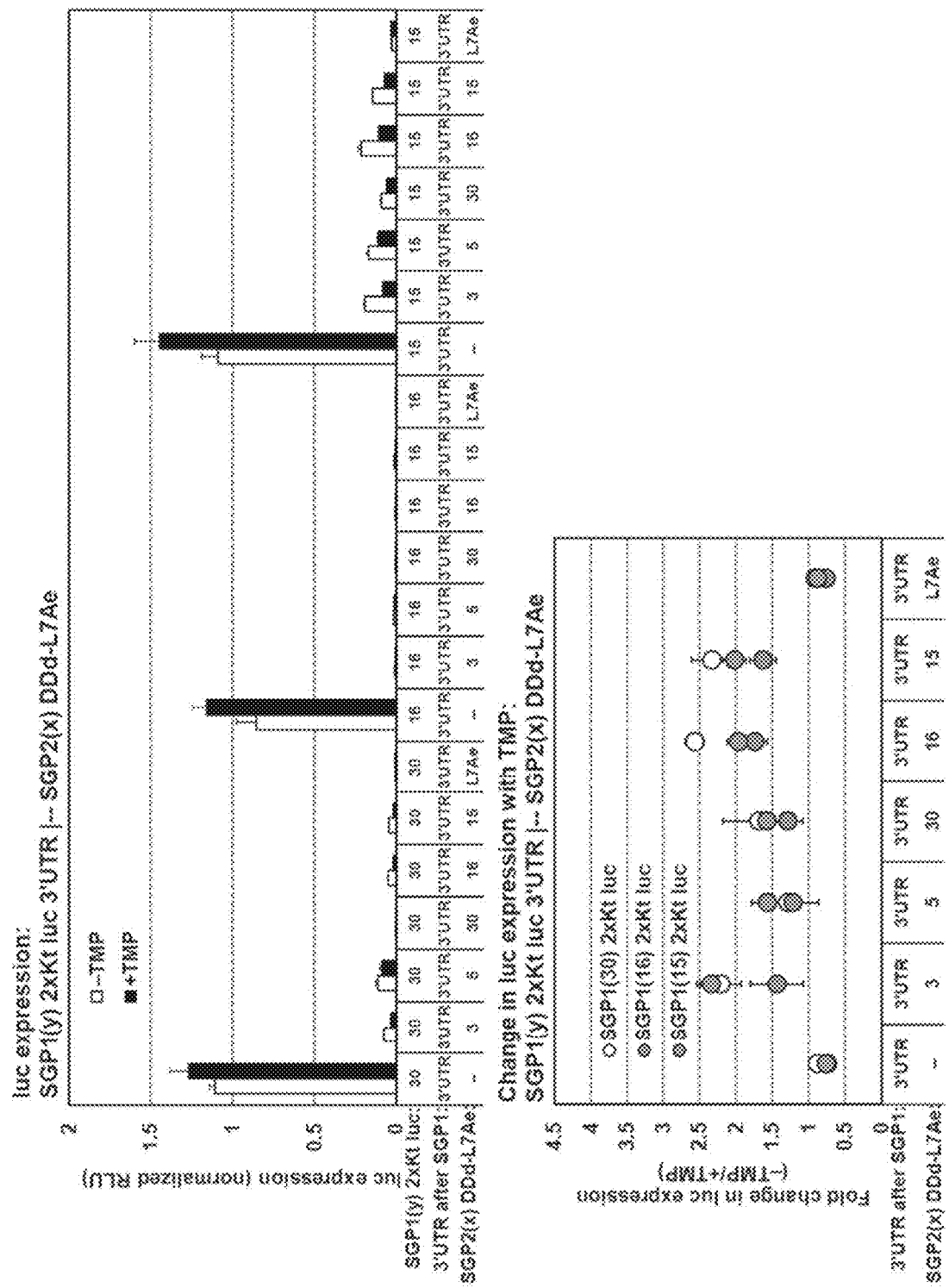

FIG. 73. Screen #1: SGP/UTR tuning (20140917 to 20141026) 500 ng RNA normalized to pXZ065.

Figure 74:
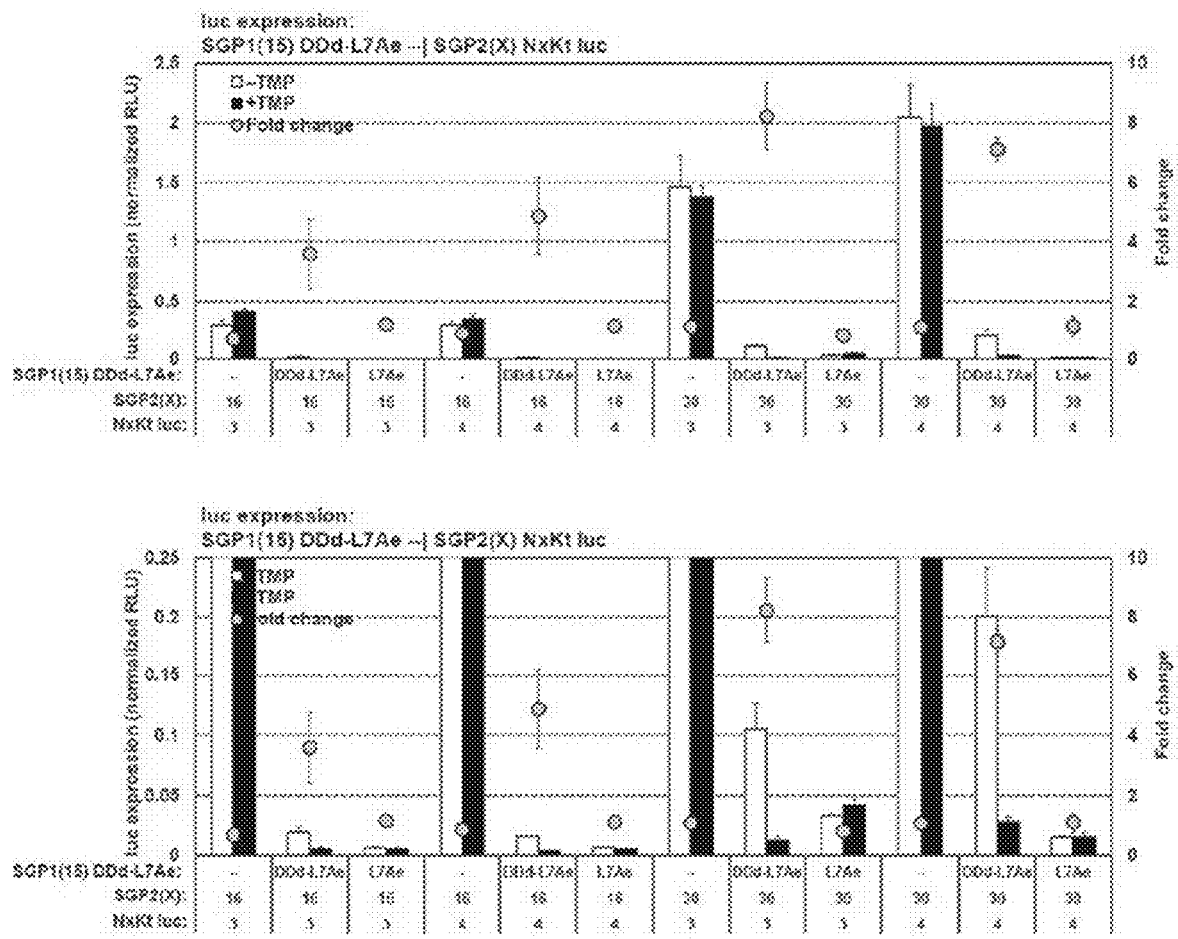

FIG. 74. Screen #2: NxKt tuning 100 ng RNA normalized to pXZ065.

Figure 75:
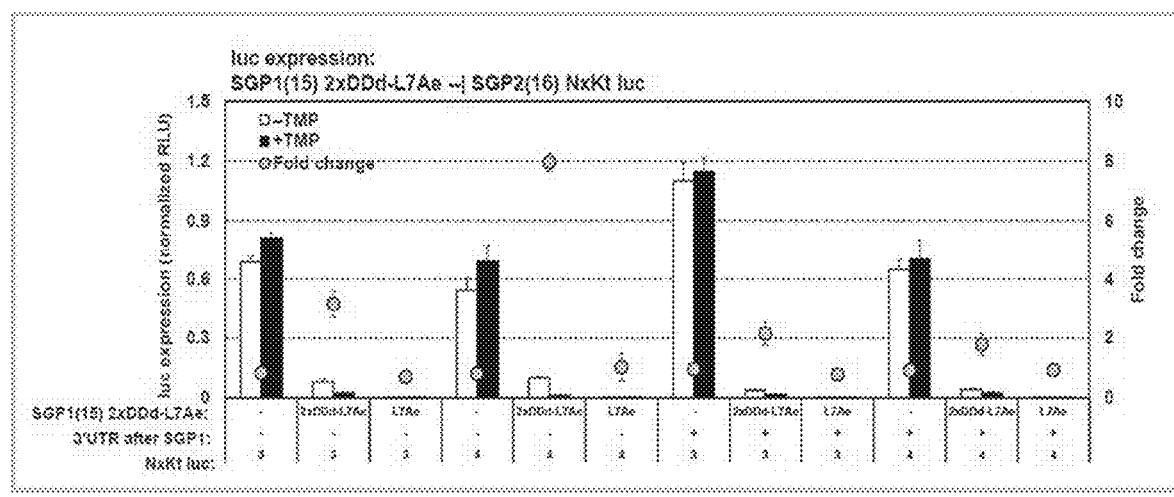

FIG. 75. Screen #3: 2×DDd tuning (20150506) 100 ng RNA normalized to pXZ065.

Figure 76:
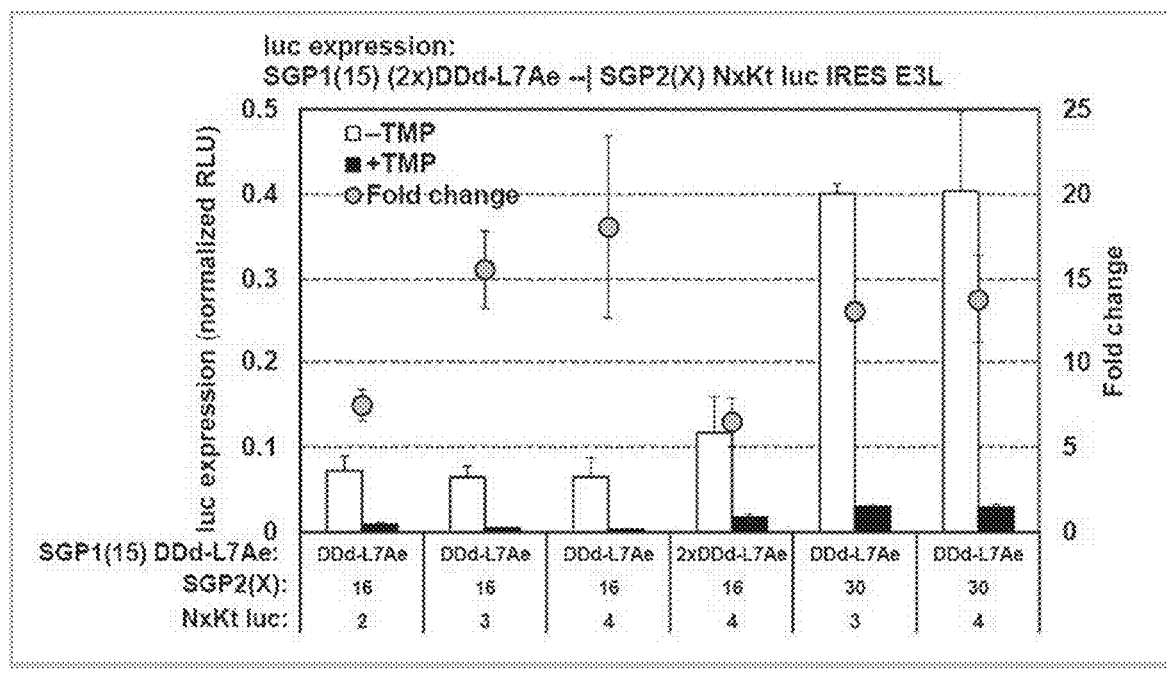

FIG. 76. Screen #4: sidebyside −/+IRES E3L 100 ng RNA normalized to pXZ065.

Figure 77:
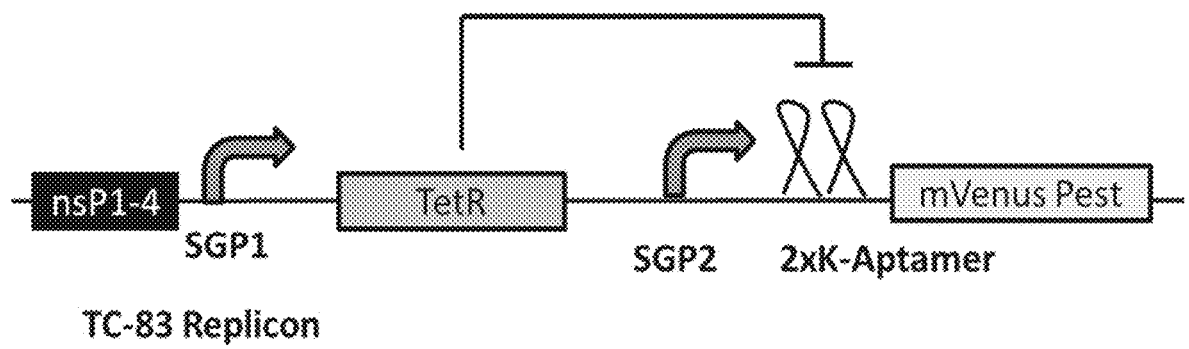
Figure 77:
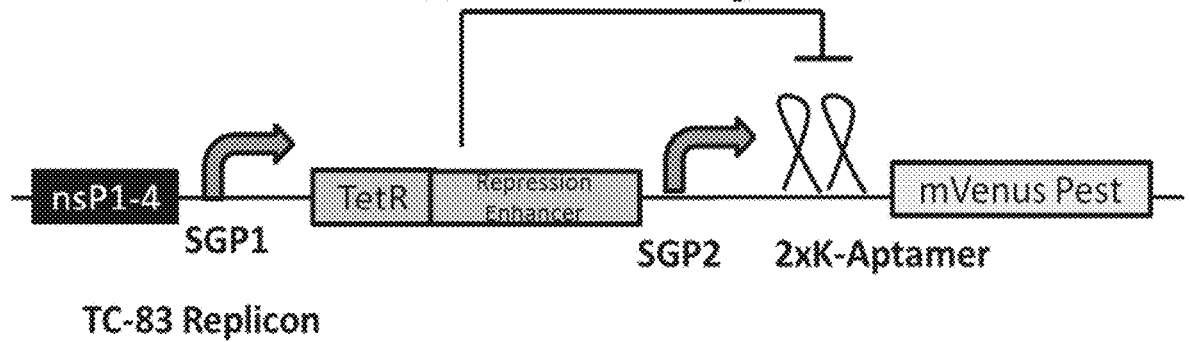

FIG. 77. TetR repression from tandem replicon. TetR-fusion multi SGP circuit diagram.

Figure 78:
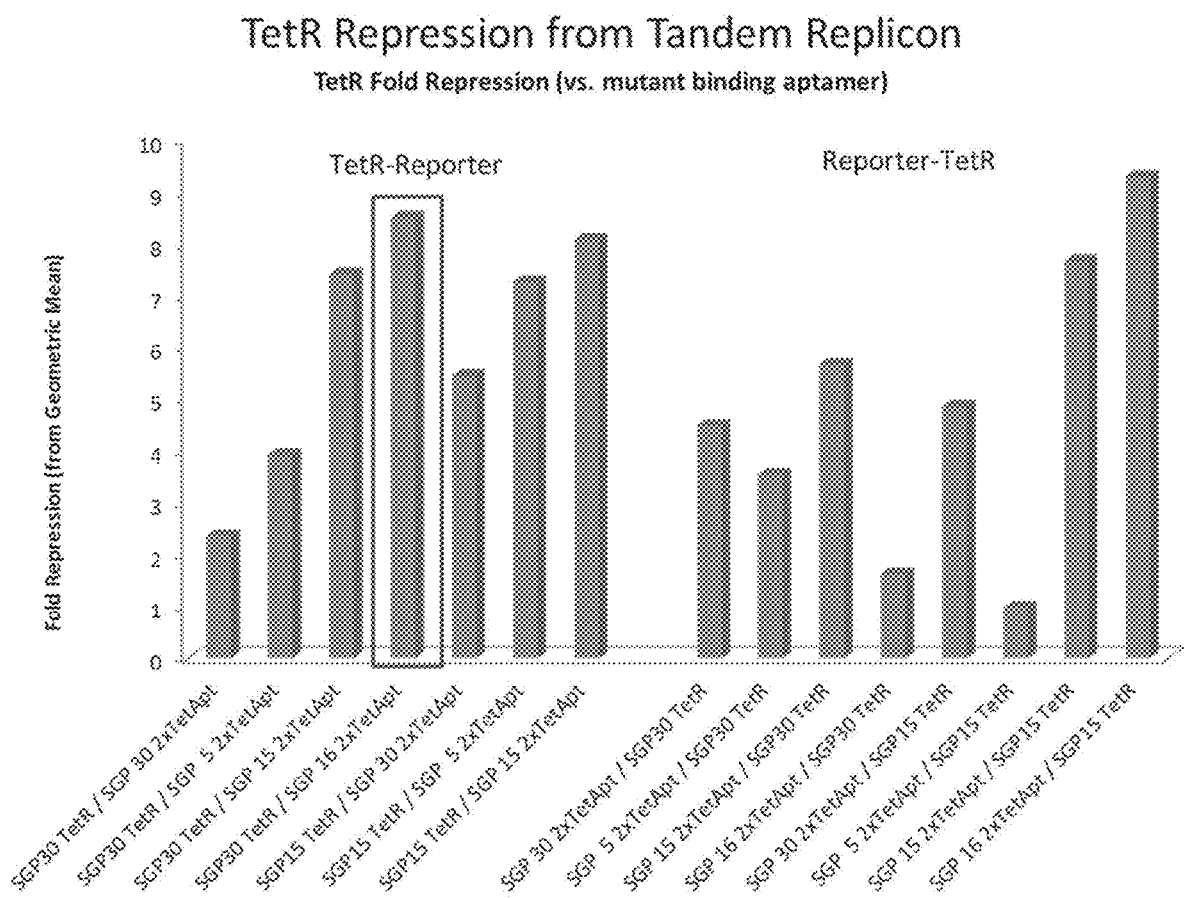

FIG. 78. TetR repression from tandem replicon. TetR fold repression vs. mutant binding aptamer.

Figure 79:
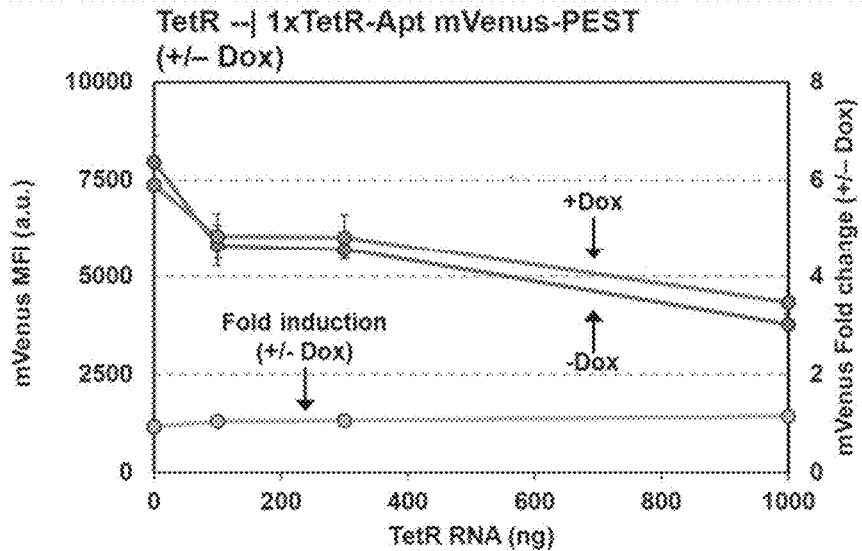
Figure 79:
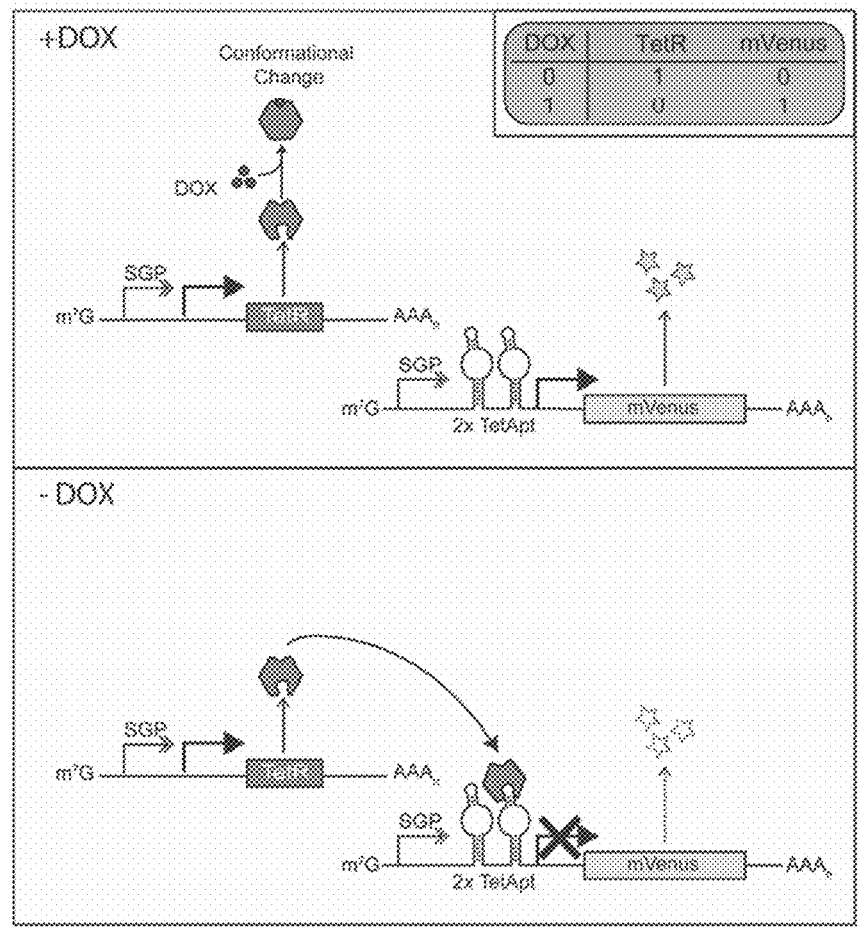

FIG. 79. Transferring TetR to modRNA presents some issues. TetR does not repress very well or respond to Dox from a modRNA platform.

Figure 80:
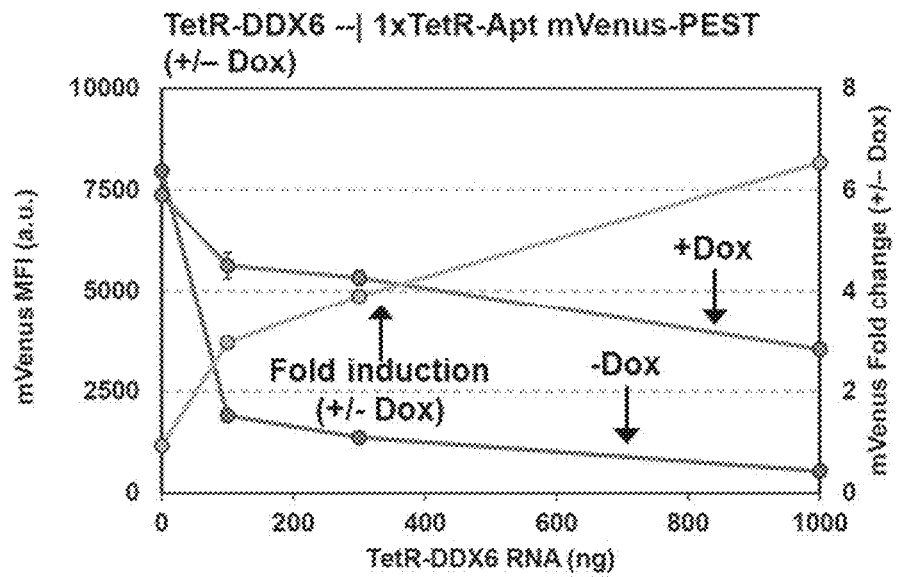
Figure 80:
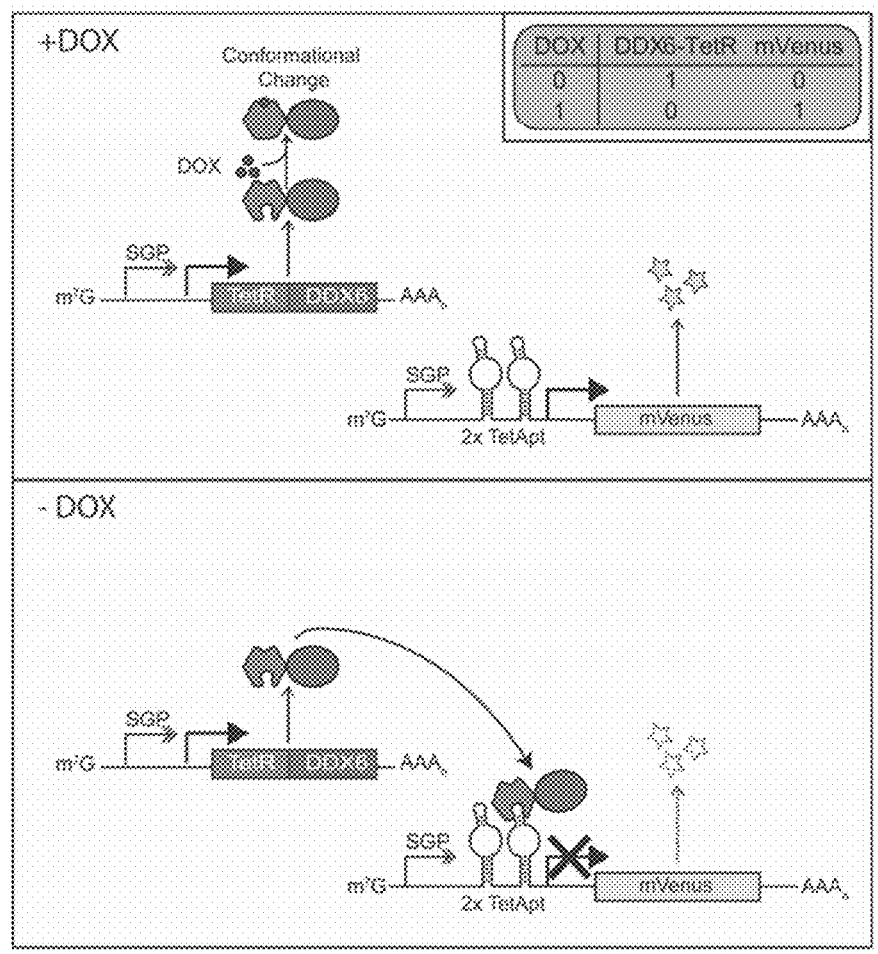

FIG. 80. TetR-DDX6 modRNA. Fusing TetR to DDX6 allows it to efficiently repress and respond to Dox induction.

Figure 81A:
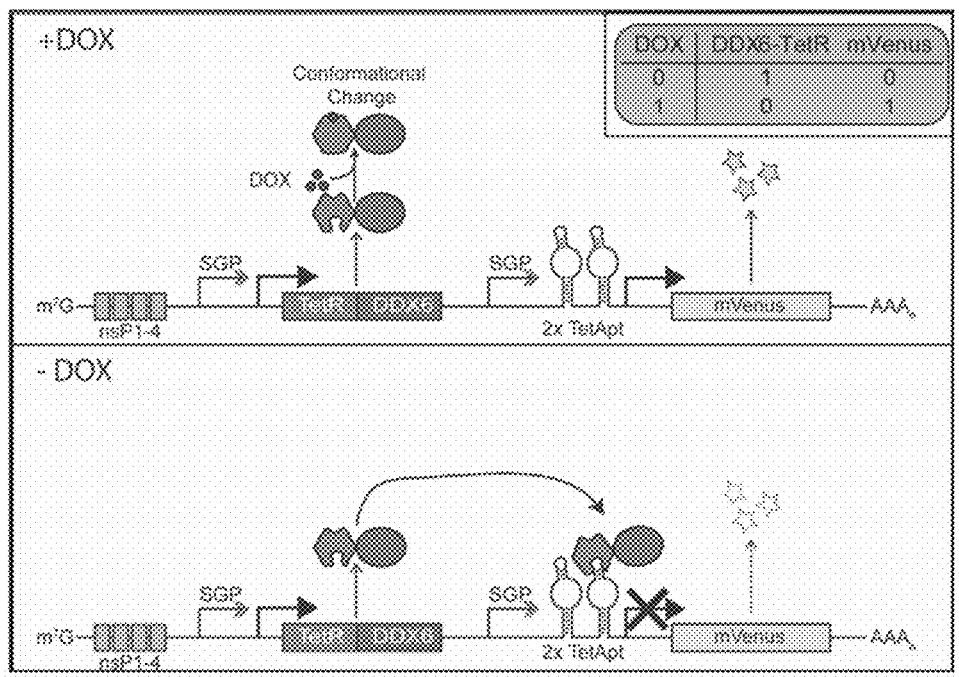
Figure 81B:
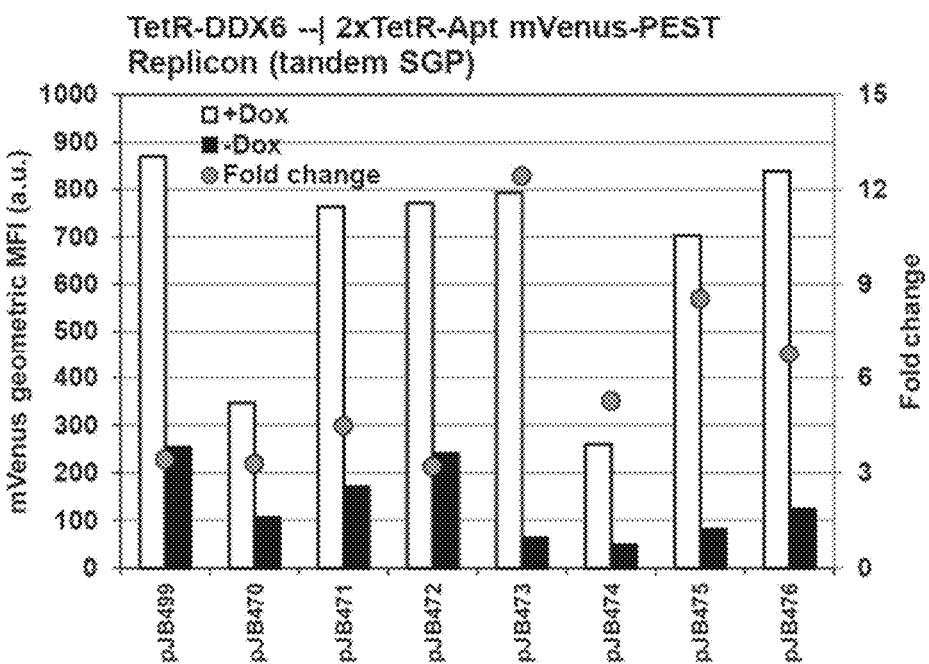
Figure 81C:
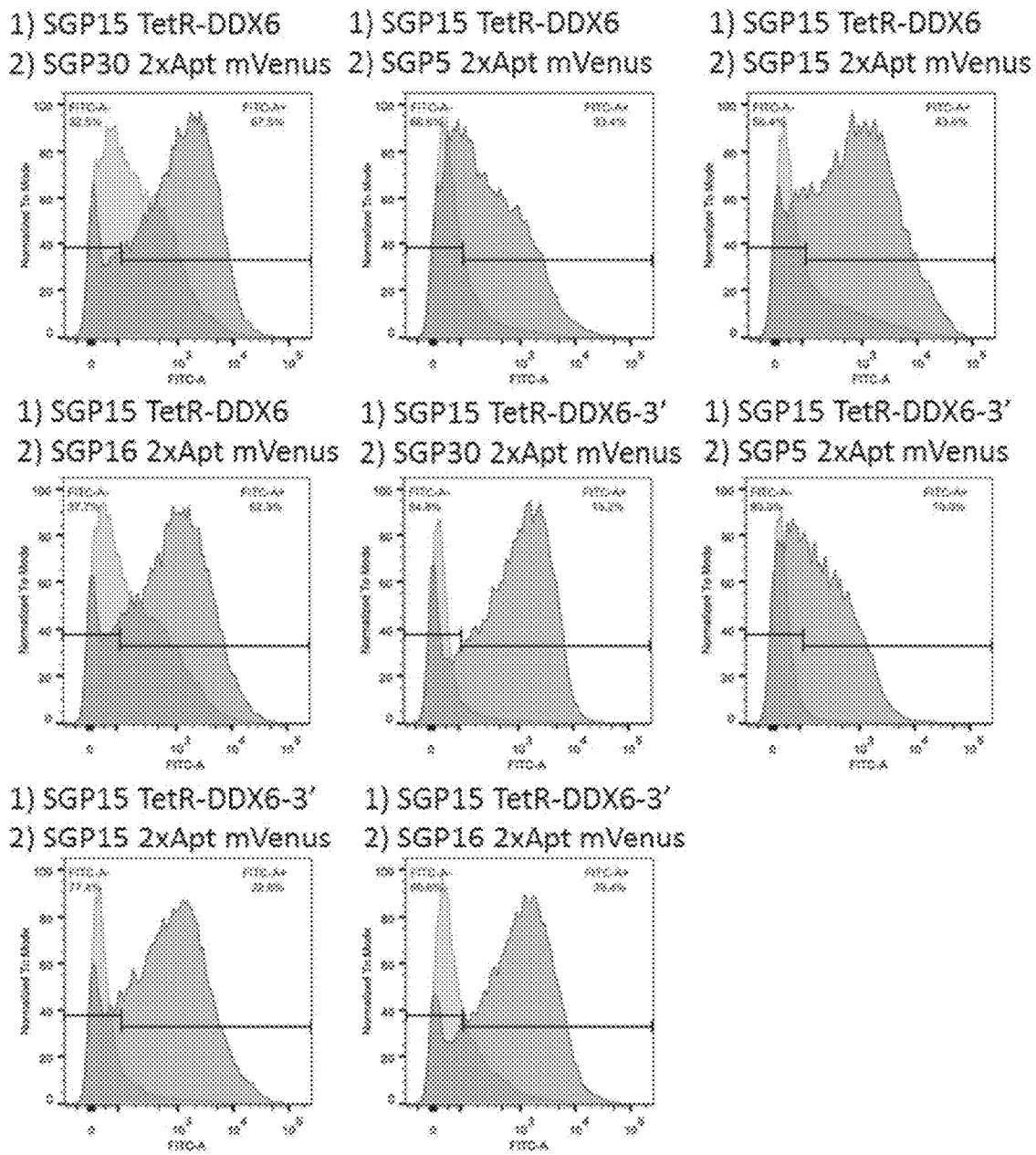

FIGS. 81A-81C. TetR-DDX6 in replicon can replace the cascade for small molecule "ON" switch (FIGS. 81A-81C).

DETAILED DESCRIPTION OF DISCLOSURE

Methods are described herein for safe, programmable control of cell behavior, with minimal risk of harmful genomic integration, through synthetic regulatory circuits encoded exclusively on RNA. Towards the goal of a plug-and-play platform for RNA-encoded regulation several post-transcriptional circuits were created by wiring regulatory devices based on RNA binding proteins. The circuit behavior can also be tuned/controlled via a small molecule dependent aptamer or degradation domain. As demonstrated herein, the circuits function when encoded on self-amplifying RNA replicon, providing means for long-term expression and a potential platform for future therapeutic applications.

Synthetic regulatory circuits encoded on RNA rather than DNA could provide a means to control cell behavior while avoiding potentially harmful genomic integration in therapeutic applications. Post-transcriptional circuits were created using RNA-binding proteins, which can be wired in a plug-and-play fashion to create networks of higher complexity. As demonstrated herein, the circuits function in mammalian cells when encoded on modified mRNA or self-replicating RNA.

In some embodiments, synthetic RNA circuits that are multi-input microRNA-based cell classifiers are provided. Such circuits can include a plurality of RNA molecules. A first RNA molecule includes at least one sequence recognized by at least one microRNA (first microRNA) that is/are specifically expressed in a first cell type, and a sequence encoding a protein that specifically binds to a RNA motif and inhibits protein production. A second RNA molecule includes at least one sequence recognized by at least one different (second) microRNA that is/are not expressed in the first cell type or is expressed at a low level relative to a second cell type, at least one RNA motif and a sequence encoding an output molecule. By sensing the presence and/or absence of the first and second microRNAs, each of which can be a single or a plurality of different microRNAs, the circuit expresses the output molecule only under specific conditions, which are indicative of a particular cell type(s). For example, in a cell that expresses the first microRNA(s) but not the second microRNA(s), the RNA molecule encoding the protein that specifically binds to a RNA motif and inhibits protein production is not translated or is degraded, which then permits expression of the output molecule. If the second microRNA(s) is present, then the RNA molecule that includes the sequence encoding an output molecule is not translated or is degraded. In the absence of the first microRNA(s), the first RNA molecule expresses the protein that specifically binds to a RNA motif and inhibits protein production, which binds to and represses translation of or degrades the second RNA molecule that encodes the output molecule. Thus, only in cells in which the first microRNA(s) is present and the second microRNA(s) is absent is the output molecule produced. This allows for specific control over the expression of the output molecule.

For example, in some embodiments, expression is controlled by the presence and absence of certain microRNAs in a cancer cell. In one embodiment, a microRNA that is expressed in the cancer cell is miR-21, and microRNAs that are not expressed in the cancer cell are miR-141, miR-142 and/or miR-146.

In some embodiments, synthetic RNA circuits that are post-transcriptional cascades are provided. Such circuits can include a plurality of RNA molecules. A first RNA molecule includes at least one sequence recognized by a protein that specifically binds to a RNA motif and inhibits protein production, and a sequence encoding an output molecule. A second RNA molecule includes at least one sequence recognized by a second protein that specifically binds to a RNA motif and inhibits protein production, and a sequence encoding the first protein that specifically binds to a RNA motif and inhibits protein production. A third RNA molecule includes at least one sequence recognized by an siRNA molecule or a microRNA molecule, and a sequence encoding the second protein that specifically binds to a RNA motif and inhibits protein production. The synthetic RNA circuit also can include the siRNA molecule or microRNA molecule that binds to the third RNA molecule. The siRNA molecule can be a synthetic siRNA molecule. The microRNA molecule can be an endogenously expressed microRNA molecule.

Without the siRNA or microRNA, the second protein that specifically binds to a RNA motif and inhibits protein production is translated, and it represses translation of or degrades the second RNA molecule. This means that the first protein that specifically binds to a RNA motif and inhibits protein production, which is encoded on the second RNA molecule, is not expressed. As a result, the first RNA molecule can be translated, and this permits production of the output molecule. If the siRNA or microRNA is present, the second protein that specifically binds to a RNA motif and inhibits protein production is not translated, and it cannot repress translation of or degrade the second RNA molecule. This means that the first protein that specifically binds to a RNA motif and inhibits protein production, which is encoded on the second RNA molecule, is expressed. As a result, translation of the first RNA molecule is repressed (or the RNA is degraded), and the output molecule is not translated.

In some embodiments, the synthetic RNA circuits include a first RNA molecule that includes at least one sequence recognized by a first protein that specifically binds to a RNA motif and inhibits protein production, and a sequence encoding an output molecule; and a second RNA molecule that includes at least one sequence recognized by an siRNA molecule or a microRNA molecule, and a sequence encoding the first protein that specifically binds to a RNA motif and inhibits protein production. The synthetic RNA circuit of can also include the siRNA molecule or microRNA molecule that binds to the second RNA molecule. The siRNA molecule can be a synthetic siRNA molecule. The microRNA molecule can be an endogenously expressed microRNA molecule. In the presence of the siRNA or microRNA, the first protein that specifically binds to a RNA motif and inhibits protein production is not produced and the output molecule is produced, whereas in the absence of the siRNA or microRNA, the first protein that specifically binds to a RNA motif and inhibits protein production is produced and the output molecule is not produced.

In some embodiments, synthetic RNA circuits that are two-state switches are provided. Such circuits can include a plurality of RNA molecules. A first RNA molecule includes at least one sequence recognized by a first protein that specifically binds to a RNA motif and inhibits protein production, a sequence encoding a second protein that specifically binds to a RNA motif and inhibits protein production, and at least one sequence recognized by a first siRNA molecule or microRNA molecule. A second RNA molecule includes at least one sequence recognized by the second protein that specifically binds to a RNA motif and inhibits protein production, a sequence encoding the first protein that specifically binds to a RNA motif and inhibits protein production, and at least one sequence recognized by a second siRNA molecule or microRNA molecule. The synthetic RNA circuit of can also include the siRNA molecule or microRNA molecule that binds to the second RNA molecule. The siRNA molecule can be a synthetic siRNA molecule. The microRNA molecule can be an endogenously expressed microRNA molecule.

In some embodiments, the the first RNA molecule and/or the second RNA molecule further comprise a sequence encoding one or more output molecules that are not a protein that specifically binds to a RNA motif and inhibits protein production. The presence of the first siRNA molecule or microRNA molecule determines whether the first or second protein that specifically binds to a RNA motif and inhibits protein production is produced, and in some embodiments, whether one or more output molecules are produced.

In some embodiments, synthetic RNA circuits that are ON or OFF switches are provided. In some embodiments, a synthetic RNA circuit is provided including an RNA molecule that includes a sequence encoding a destabilization domain fused to an output protein. The destabilization domain facilitates degradation of the output protein in the absence of a small molecule that binds to the destabilization domain. In some embodiments, the destabilization domain is, or is derived from, the E. coli DHFR protein (DDd).

In some embodiments, a synthetic RNA circuit is provided including a plurality of RNA molecules. A first RNA molecule includes a sequence encoding a destabilization domain fused to a protein that specifically binds to a RNA motif and inhibits protein production. A second RNA molecule includes at least one sequence recognized by the protein that specifically binds to a RNA motif and inhibits protein production, and a sequence encoding an output molecule. The destabilization domain facilitates degradation of the protein that specifically binds to a RNA motif and inhibits protein production in the absence of a small molecule that binds to the destabilization domain. In some additional embodiments, the output molecule is a fusion of a TetR protein and a second protein; and the RNA molecule(s) further include an aptamer sequence and a second output molecule. The aptamer sequence is bound by the TetR protein in the absence of tetracycline. The aptamer sequence is positioned relative to the second output molecule so that it inhibits production of the second output molecule in the absence of tetracycline.

In some embodiments, a synthetic RNA circuit is provided that includes an RNA molecule comprising a sequence encoding a TetR protein and a sequence encoding an output protein, and an aptamer sequence that is bound by the TetR protein in the absence of tetracycline. The aptamer sequence is positioned relative to the sequence encoding the output protein so that it inhibits production of the output protein in the absence of tetracycline. In some embodiments, the aptamer is positioned in the 5' untranslated region (UTR) of the sequence encoding an output protein. In other embodiments the TetR protein is a fusion protein.

The output molecule typically is a protein. However, the output molecule can be another type of molecule, such as a nucleic acid molecule, for example an RNA molecule that is an input for a strand displacement reaction. Protein output molecules include therapeutic proteins, cell death proteins, fluorescent proteins, antigen (and/or adjuvants), selection proteins, and immunomodulators.

Therapeutic proteins can be any protein that is used in therapy of disease. For example, a therapeutic protein can be a protein used for protein replacement therapy, such as for metabolic disorders; Myr-Akt for treating Duchenne muscular dystrophy; or follistatin for treating Becker muscular dystrophy, Duchenne muscular dystrophy, inclusion body myositis.

Selection proteins can be used for selection or purification of a cell in which the selection protein is expressed. For example, the selection protein can be a protein that confers drug resistance to a cell, or acts as a marker for the cell type for separation from other cells by separation techniques such as flow cytometry.

Fluorescent proteins include many different types of proteins known in the art, such as enhanced green fluorescent protein (EGFP), enhanced yellow fluorescent protein (EYFP), enhanced blue fluorescent protein (EBFP), cyan fluorescent proteins (e.g., AmCyan1), other green fluorescent proteins (e.g., AcGFP1, and ZsGreen1), other yellow fluorescent proteins (e.g., ZsYellow1 and mBananna), orange fluorescent proteins (e.g., mOrange and mOrange2), red fluorescent proteins (e.g., DsRed, tdTomato, mStrawberry and mCherry), and far-red fluorescent proteins (e.g., mKate, HcRed1, mRaspberry and mPlum).

Antigens include proteins of infectious agents or cancer antigens, of which many are known in the art. Protein adjuvants also can be expressed, alone or in conjunction with antigen output proteins.

Immunomodulator proteins include cytokines, for example, IL-12, IL-15 or IL-21, or immunosuppressant proteins.

Cell death proteins include hBax.

In some embodiments, the synthetic RNA circuits described herein include RNA molecules that encode more than one output molecule.

Proteins that specifically bind to an RNA motif and inhibit protein production by a variety of mechanisms including repression of translation or degradation of RNA are included in many of the embodiments of the synthetic RNA circuits described herein. Such proteins may be referred to herein as a "protein that specifically binds to an RNA motif and inhibits protein production" or an "RNA binding protein" or the like. Such RNA binding proteins bind to a specific RNA sequence (also referred to as a "RNA motif" herein) and inhibit protein production by repressing translation of the RNA molecule to which they bind. Repression of translation can occur any of the several mechanisms known in the art for repression of translation. Alternatively, such RNA binding proteins bind to a specific RNA sequence (also referred to as a "RNA motif" herein) and inhibit protein production by degradation of RNA.

One example of a protein that specifically binds to an RNA motif and inhibits protein production is L7Ae. The L7Ae protein binds to one or more Box C/D, K-turn and/or K-loop motifs in an RNA molecule. In some embodiments more than one Box C/D, K-turn and/or K-loop motifs (such as two K-turn motifs) are included in an RNA molecule to confer better binding to the RNA molecule and repression of RNA translation. In some embodiments, the one or more Box C/D, K-turn and/or K-loop motifs are placed in the 5' untranslated region (UTR) of the RNA molecule, i.e., upstream of a sequence encoding an output molecule. In addition, other proteins that bind specific RNA motifs and inhibit protein production can be used in the same manner as described herein for L7Ae.

Another example of a protein that specifically binds to an RNA motif and inhibits protein production is a fusion of MS2 protein and a protein degrades RNA. In some embodiments, MS2 protein can be fused to CNOT7 protein (to form MS2-CNOT7) or Dm-POP2 protein (to form MS2-Dm-POP2), each of which are deadenylases, but other proteins that degrade RNA also can be fused or linked to MS2. In addition, other proteins that bind specific RNA motifs but do not repress translation can be fused to a protein that degrades RNA, and used in the same manner as described herein for MS2-CNOT7.

MS2 protein binds to one or more MS2 coat protein binding sites. In some embodiments more than one MS2 coat protein binding sites (such as eight MS2 coat protein binding sites) are included in an RNA molecule to confer better binding to the RNA molecule and inhibition of protein production, e.g., by degradation of the RNA. In some embodiments, the one or more MS2 coat protein binding sites are placed in the 3' untranslated region (UTR) of the RNA molecule, i.e., downstream of a sequence encoding an output molecule.

In some embodiments, the RNA molecule(s) of the synthetic RNA circuit includes modified RNA. Such modified RNA molecules can include, for example, 5-methylcytosine-triphosphate and/or pseudouridine-triphosphate. Other modifications of RNA molecules are known in the art, and may be useful, for example, to increase stability or resistance to RNAses.

In some embodiments, the RNA molecule(s) of the synthetic RNA circuit are encoded on one or more RNA replicons. RNA replicons are known in the art and include alphavirus derived replicons, Venezuelan equine encephalitis virus derived replicons or Sindbis derived virus replicons. In such embodiments, the RNA molecule(s) can be expressed from one or more subgenomic promoters of the one or more replicons. In some embodiments, the one or more subgenomic promoters are regulated by a small molecule, such as trimethoprim (TMP).

In some embodiments, the RNA molecule(s) of the synthetic RNA circuit are encoded on one or more plasmids.

Also provided are methods for treating disease using the synthetic RNA circuits described herein. In some embodiments, methods of treating cancer in a mammal are provided, in which a synthetic RNA circuit is administered to a mammal. In some embodiments, the synthetic RNA circuit produces an output protein that treats the cancer, including but not limited to a cell death protein such as hBax, or an immunomodulatory protein.

Also provided are methods for inducing an immune response in a mammal using the synthetic RNA circuits described herein. In some embodiments, the methods include administering to a mammal a synthetic RNA circuit, which produces an output protein that induces the immune response, or augments an immune response. Such methods may be used in vaccination of a mammal, or for other uses in which inducing an immune response is beneficial to the mammal. The output protein produced typically is one or more antigens, but may also include one or more adjuvants, and/or other immunomodulatory proteins. In addition, the methods include controlling the expression of the output protein(s) by administering molecules that control destabilization domains (e.g., trimethoprim) or that control binding of TetR protein to aptamers (e.g., tetracycline). This enables administering the synthetic RNA circuits described herein at one time and administering molecules that control expression of the output protein(s) at a different time, including at several times after the administration of the synthetic RNA circuits. Such administration of the synthetic RNA circuits described herein and the molecules that control expression of the output protein(s) can be used to produce expression of antigens and/or adjuvants at certain times relative to one another in order to produce an improved immune response in the mammal. The molecules that control expression of the output protein(s) can be administered by any suitable method, including by oral administration, intramuscular injection of lipid nanoparticles, or or by implantation of a polymeric implant for sustained release.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teachings that are referenced herein.

EXAMPLES

Example 1

In our initial circuits, we use two translational repressors, L7Ae (12) and a fusion protein MS2-CNOT7 (13). L7Ae is an archeal protein that binds K-turn and K-loop motifs with high affinity. When the motif is placed in the 3'UTR of the target mRNA, L7Ae can strongly repress translation of the output gene by blocking ribosome scanning. As has been shown, using multiple repeats of the binding motif and placing the motif close to the transcription start result in enhanced repression (14). We used two repeats of the K-turn motif with an eighteen base pair spacer from the transcription start and such configuration resulted in a very strong repression even at low doses of L7Ae. MS2 is another RNA binding protein, a coat protein from bacteriophage MS2. CNOT7 is a human deadenylase that can efficiently repress translation of mRNA, if directed to its 3'UTR (13). In our system, the reporter mRNA contains eight repeats of the MS2 coat protein binding site in the 3'UTR and MS2 is fused with repression domain, CNOT7.

Towards the goal of creating a platform for future applications through a plug-and-play post-transcriptional regulation framework we engineered a set of diverse regulatory circuits including a multi-input cell type classifier, a cascade and a two-state switch. Additional capabilities, or further tuning of the synthetic regulatory pathways can be achieved with the use of small molecule dependent aptamers or degradation domains.

Regulation with RNA-Binding Proteins (RBP)

To demonstrate that the RBP-based repressors can be utilized to create variable functional circuits we engineered a multi-input microRNA sensor, a cascade and a two-input switch. The microRNA sensing circuit is a post-transcriptional only version of our previously designed (15) HeLa cell classifier. The circuit recognizes microRNA profile that is specific for HeLa cells (high miR-21, low miR-141, miR-142(3p) and miR-146a, FIG. 1) and triggers a response only if the profile is matched. As shown in FIG. 1, the L7Ae-based classifier is able to distinguish HeLa cells from HEK 293 and MCF7 in a fluorescence assay. Moreover, when a pro-apoptotic gene hBax is used as the output of the circuit, the classifier selectively induces apoptosis in HeLa cells while not affecting viability of HEK cells. The performance of our new classifier is comparable to the DNA-based version reported earlier, but the ability to deliver it purely with RNA provides means for utilizing it in much broader spectrum of applications, including selective stem cell reprogramming, or vaccination.

Our next circuit (FIG. 2), a three-layer cascade expresses fluorescent protein, EGFP as the final output (level 0). The 3'UTR of the EGFP contains eight repeats of the MS2 binding sites allowing repression by MS2-CNOT7 (level 1). We placed two repeats of the K-turn motif in the 5'UTR of the MS2-CNOT7 construct, which in turn allows for repression by L7Ae (level 2) and restoration of the output. Finally, L7Ae gene is followed by four repeats of target sites (Ts) for synthetic microRNA miR-FF4 (level 3), which permits further tuning of the cascade output. The synthetic microRNA regulation can be replaced with endogenous one, linking the cascade operation with cellular context. As shown in, the optimized version of our cascade exhibits nearly perfect behavior when tested with DNA transfection. The first layer repression results in 13-fold difference in EGFP expression, followed by 15-fold output restoration at level 2, and finally 12-fold repression at level 3, when all parts of the cascade are present. Therefore the system utilizes the full dynamic range of the MS2-CNOT7 repressor.

Figure 1A:
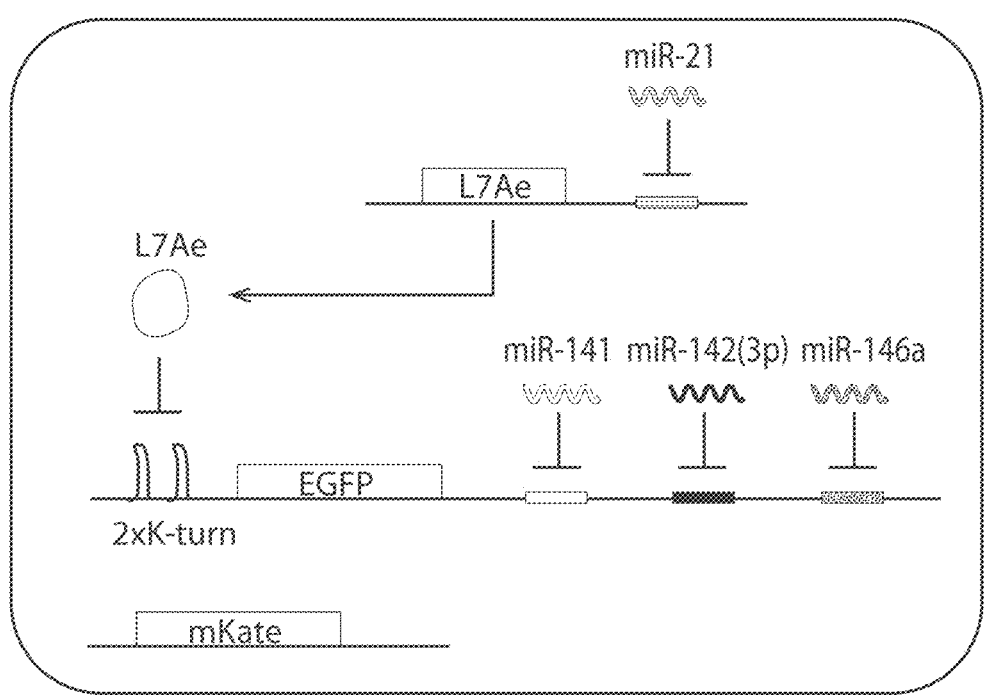
FIGS. 1A-1D. RNA-only multi-input microRNA sensor is able to differentiate between HeLa, HEK 293 and MCF7 cell lines as demonstrated with transient DNA transfection. (A) Implementation of the L7Ae-based miRNA sensor that specifically recognizes HeLa cells based on specific miRNA profile (highly expressed miR21 and low levels of 141, 142(3p) and 146a). (B) Expression scheme of the sensor inputs, operator and output in HeLa cells. Operation of the circuit results in high expression of the output only in HeLa cells, but not other cell types. (C) Differential expression of the output protein, EGFP, in HEK, MCF7 and HeLa cells. When output is not regulated by endogenous microRNA the EGFP fluorescence is high in all three cell types (set to 1, not shown). Control of the EGFP expression by the sensor circuit results in over 9-fold higher output in HeLa cells with respect to HEK cells and almost 11-fold higher output as compared with MCF7 cells. (D) Specific induction of apoptosis in HeLa cells by expression of circuit-controlled hBax protein as determined with Annexin V staining and pDNA transfection.
Figure 1B:
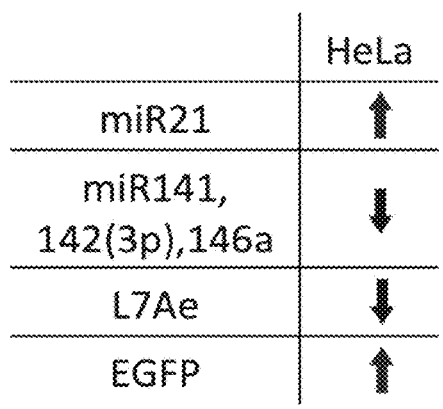
Figure 1C:
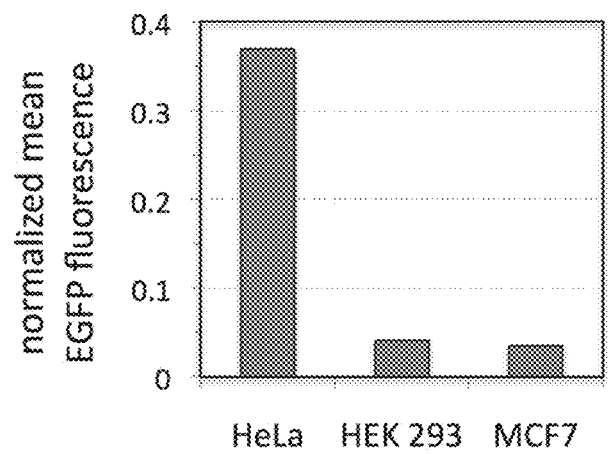
Figure 1D:
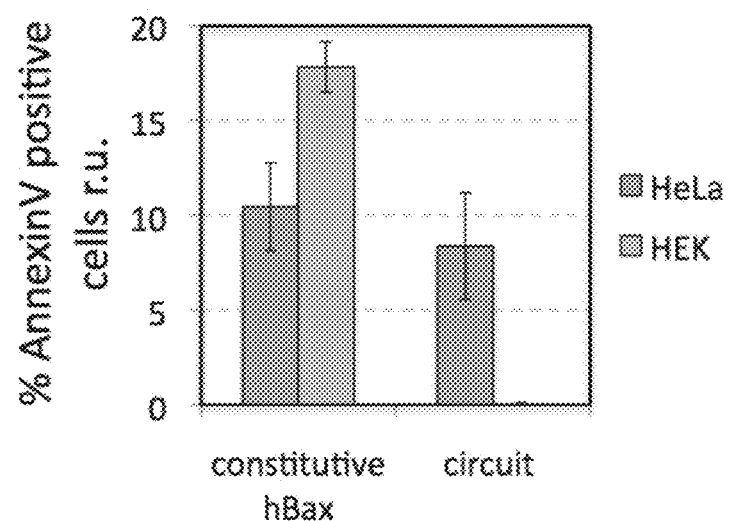
Figure 2A:
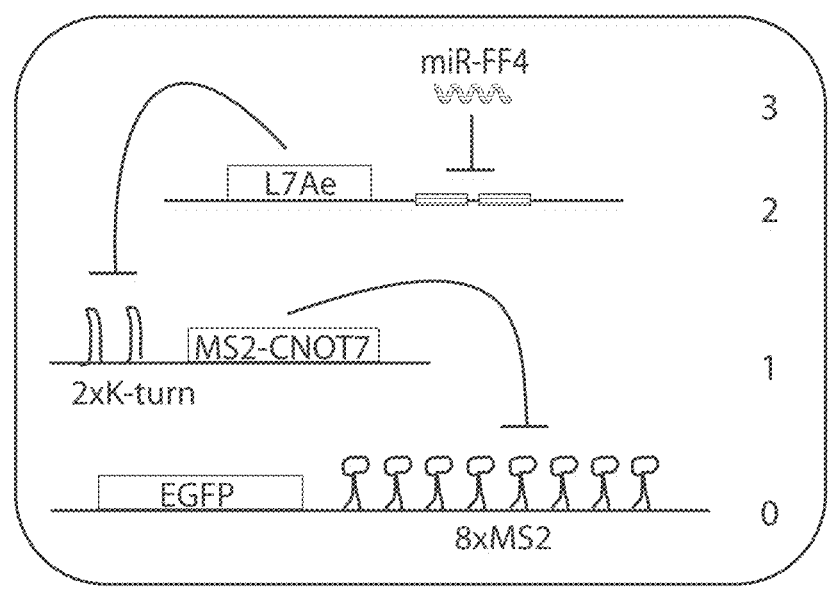
FIGS. 2A-2D. Experimental operation of the post-transcriptional cascade demonstrated with transient transfection of DNA (A-B) and the replicon RNA (C-D). (A) Design of the plasmid encoded cascade with the output, EGFP, at level 0 being repressed by MS2-CNOT7 (level 1), that in turn is repressed by L7Ae (level 2) relieving EGFP production. At the last, level 3, translation of L7Ae is repressed by a synthetic microRNA miRFF4 causing in effect repression of the final output. Red fluorescent protein, mKate, was used as a transfection control. (C) Replicon encoded two-stage cascade with the output, EYFP, at level 0 being repressed by L7Ae (level 1), that in turn is repressed by a synthetic siRNA-FF4 (level 2). siRNA knockdown results in expression of the output EYFP. L7Ae was fused to red fluorescent protein mKate, and both, EYFP and mKate-L7Ae were fused with a degradation tag, PEST. (B,D) Normalized mean EGFP fluorescence for the different layers of cascade encoded on plasmid DNA (B) or alphaviral replicon (D).
Figure 2B:
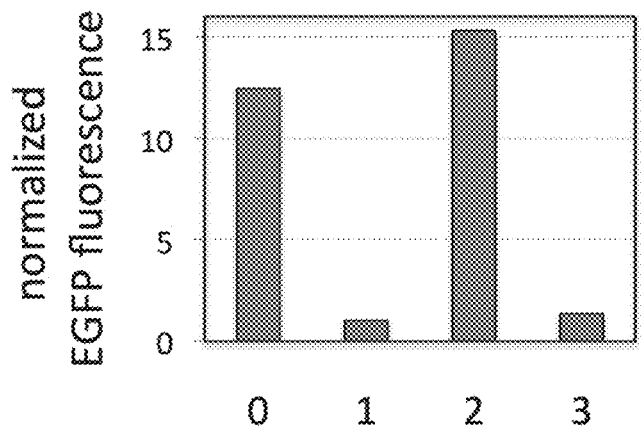
Figure 2C:
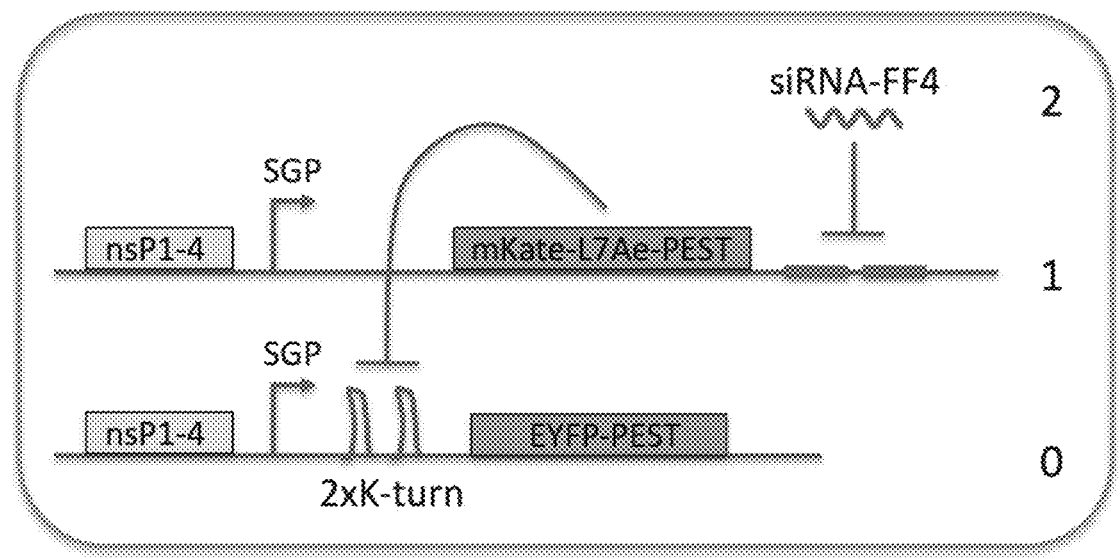
Figure 2D:
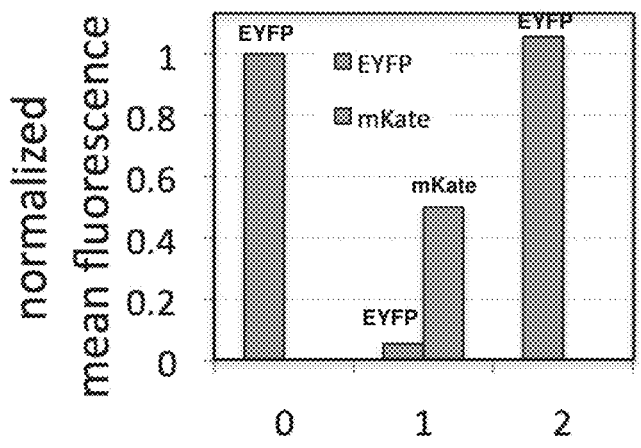

We next tested a two-layer version of the cascade encoded on self-amplifying viral replicon for RNA-only delivery (FIGS. 2C-2D). In this minimal circuit, that is also an essential component of the microRNA sensor and the switch, the output gene (EYFP) was placed under the subgenomic promoter with two repeats of the K-turn motif in the 3'UTR. L7Ae expressed from a separate replicon was also followed by four repeats of the FF4 target site. To allow tracking of the L7Ae production, we fused it to a red fluorescent protein, mKate. Both genes, EYFP and mKate-L7Ae contained degradation tags for faster turnover. As shown in FIG. 2D, L7Ae repression results in 20-fold repression of EYFP (level 1), and knockdown by the synthetic siRNA-FF4 fully restores the output production (level 2).

Our third circuit is a two-state switch where two repressors mutually regulate their expression (FIG. 3A). The state of the system can be set with the use of a synthetic siRNA, synthetic or endogenous miRNA, or other endogenous repressors. The components of the switch include MS2-CNOT7 with two K-turn motifs in the 5'UTR and L7Ae with eight repeats of the MS2 binding site in the 3'UTR. For monitoring the behavior of the switch we additionally co-expressed a blue fluorescent protein (EBFP) together with MS2-CNOT7 and EYFP with L7Ae via 2A tags (from the same mRNA). To set the states of the switch we used two artificial and orthogonal siRNA (FF4 and FF5). When no specific siRNA is present, both repressors and associated reporters remain at low levels (FIGS. 3B and 3D), with pDNA transfection. siRNA FF4 sets the state to high MS2-CNOT7 (as measured by EBFP fluorescence) resulting with over 4-fold higher expressions of the genes and complete silencing of L7Ae (as measured by EYFP fluorescence). Conversely, siFFSS causes over 3-fold upregulation of L7Ae/EYFP. Since most potential applications of the switch would require longer-term expression, we encoded the circuit on self-replicating RNA. Interestingly, in the absence of specific siRNA, the circuit exhibits bi-stability: cells randomly fall into one of the available states. Similarly as with pDNA transfections, siRNA FF4 and FF5 set the state specifically and permanently.

Small Molecule Regulation

Another form of regulation of RNA circuits, especially useful in a clinical setting would be with the use of a small molecule switch. Here, we have engineered an ON/OFF switch to regulate expression from self-replicating RNA using an FDA-approved small molecule and have achieved more than 20-fold induction. A potential application of this method may include the regulated delivery of antigens for safer programmable vaccines.

Figures 4A, 4B, 4C:
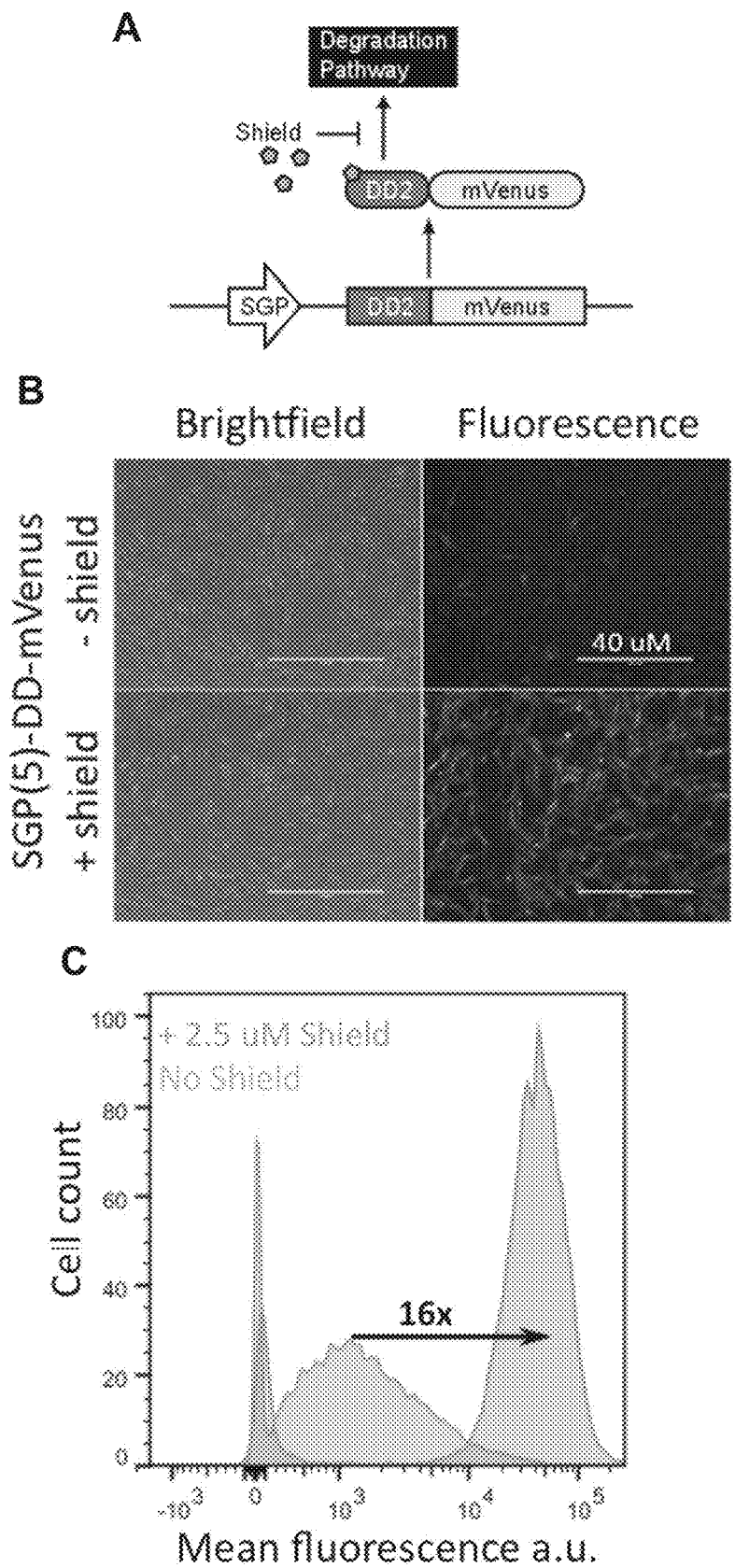
FIGS. 4A-4C. Induction of expression from self-replicating RNA using destabilization domains, DD. (A) The Sindbis replicon consists of a DD-tagged mVenus in place of the Sindbis structural proteins. The Shield protects mVenus from degradation by binding to the destabilization domain (B) Microscopy images taken 24 hours post-electroporation of BHK-21 cells with the replicon, +/−2.5 uM Shield. (C) Corresponding flow cytometry data showing over 16-fold increase in fluorescence upon addition of shield.

To build the ON/OFF switch, we used destabilization domains, which mark proteins for degradation. Upon addition of a small molecule ligand, the ligand binds the domain, and the protein is stabilized and no longer degraded. To test destabilization domains (DDs) as a control mechanism for the replicon, we fused the domain, FKBP12 (16), to the N-terminus of a yellow fluorescent protein, mVenus, electroporated into BHK-21 cells and induced with Shield (17) to test the ON switch. See FIGS. 4A-4C.

Figure 5A:
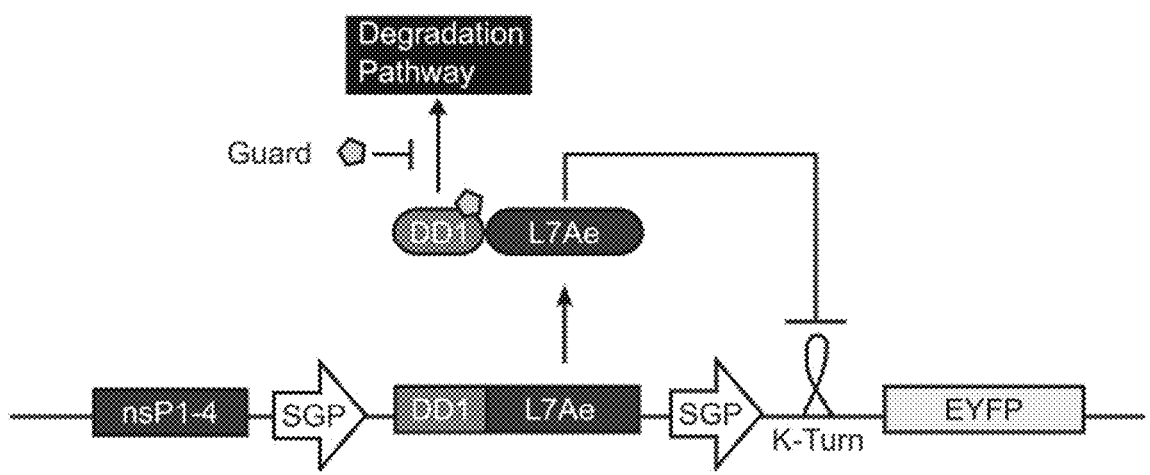
FIGS. 5A-5C. OFF switch with Destabilization Domains. (A) A simple replicon circuit is modulated by an inducer, Guard, which binds to the fusion protein. DD-L7Ae. Guard stabilizes the repressor, which binds to a 2×K-turn motif and represses EYFP expression. (B) Flow cytometry data collected 24 hours post-electroporation of the replicon SGP-DD-L7Ae-SGP-2×K-Turn-EYFP-PEST into BHK-21 cells. Addition of 10 uM Guard (19) results in a 24-fold decrease in mean fluorescence. (C) Controls: cells electroporated without substrate (negative control) and cells electroporated with only SGP-2×K-Turn-EYFP-PEST (positive control).
Figure 5B:
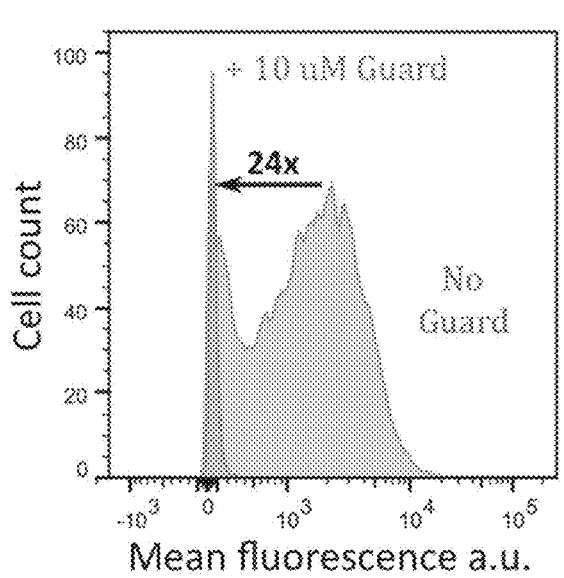
Figure 5C:
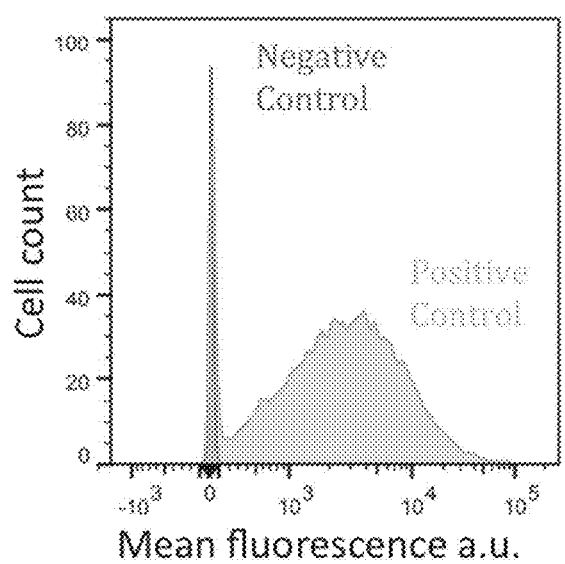

Next, we created the OFF switch by fusing a destabilization domain, ecDHFR (18), to the L7Ae repressor as shown in FIGS. 5A-5C.

Aptamer-Based Regulation

Tunable expression can also be achieved with an RNA based circuit whose dynamics are governed by TetR/Dox, and by TetR-homolog/small-molecule. Tet Repressor protein (TetR)-binding RNA elements is placed in the 5'-untranslated region (5'-UTR) of mRNA, such that translation of a downstream antigen coding sequence is directly controlled by TetR and tetracycline analogs (20); see FIGS. 6A-6B.

Advantages and Improvements Over Existing Methods, Devices or Materials

Proteins vary in solubility, are difficult to purify and expensive to store. DNA vaccinations and therapy present potential risks such as integration into the host genome or induction of pathogenic anti-DNA antibodies.

Recently, RNA-based vaccines employing alphavirus replicons, which undergo sustained self-replication of RNA sequences encoding protein antigens within infected cells, have gained attention as a potential strategy for safe and effective vaccination. Such RNA-based vaccines are expected to be safer than DNA-based vectors (lacking the potential for integration into the host genome), and because their function requires delivery only to the cytosol (but not the nucleus) of target cells, synthetic materials may be capable of delivering RNA vaccines without the manufacturing and safety issues of viral vectors. Self-replicating RNA and modified RNA have gained much interest as potential therapeutic agents and in stem cell reprogramming.

No control mechanisms have been developed/used for self-replicating or modified RNA. We propose multiple ways of such control that would allow for e.g. tunable or delayed expression of a therapeutic agent and switching between two different agents.

Example 2. Mammalian Synthetic Circuits with RNA Binding Proteins Delivered by RNA Materials and Methods
Cell Culture HEK293FT and HEK293 (293-H) cell lines were purchased from Invitrogen. HeLa (CCL.2) and MCF7 (HTB-22) cell lines were originally obtained from ATCC. The performance of DNA-encoded miRNA sensors in these cell lines had been characterized previously (15). HEK293FT were freshly purchased from the supplier. HeLa, MCF7 and BHK21, although not recently authenticated, were tested for mycoplasma. All cell lines used in this study were maintained in Dulbecco's modified Eagle medium (DMEM, Cellgro) supplemented with 10% FBS (Atlanta BIO), 1% penicillin/streptomycin/L-Glutamine (Sigma-Aldrich) and 1% non-essential amino acids (HyClone) at 37° C. and 5% $CO_2$. In the case of MCF7 cells, DMEM without phenol red was used. BHK21 cells were maintained in Eagle's Minimum Essential Medium (EMEM, ATCC) supplemented with 10% FBS.

DNA Preparation and Transfection

All transfections were carried out in 24-well format. Parallel transfections in HEK293, HeLa and MCF7 cells (4-input sensor, FIGS. 7B and 7C, FIGS. 11, 12A-12C, FIGS. 13 and 14) were performed with Lipofectamine LTX (Life Technologies) according to manufacturer's protocol. Lipofectamine LTX was used as it provides the best transfection efficiencies across the 3 cell lines among tested reagents. Total of 400 ng DNA was mixed with Opti-MEM I reduced serum medium (Life Technologies) to a final volume of 100 ul followed by addition of 0.5 ul PLUS reagent. After 5 minutes 1.5 ul Lipofectamine LTX was added, the samples were briefly vortexed and incubated for 30 min at room temperature. During the incubation time, cells were harvested by trypsinization and seeded in 500 ul of complete culture medium in 24-well plate (HEK: $2 \times 10^5$, HeLa: $1.2 \times 10^5$ and MCF7: $1.5 \times 10^5$ cells per well). Transfection complexes were added dropwise to the freshly seeded cells followed by gentle mixing. Cells were supplemented with 1 ml of fresh growth medium 5 hours post transfection and analyzed by flow cytometry after 48 hours (after 24 hours for apoptosis assay). Plasmid DNA and siRNA co-transfections (cascade and switch circuits, FIGS. 8B and 8G, FIGS. 17A, 18A-18C, 27, and 28) were carried out with Lipofectamine 2000 according to the manufacturer's protocol. Lipofectamine 2000 was used as it provides the best DNA/siRNA co-transfection efficiencies among tested reagents. A total of up to 300 ng DNA and 1-5 pmol siRNA were mixed with Opti-MEM I reduced serum medium (Life Technologies) to a final volume of 50 ul. Separately, 2 ul of Lipofectamine 2000 was mixed with 50 ul of Opti-MEM. After 5 min incubation, lipofectamine and DNA/siRNA dilutions were combined and briefly vortexed. Cells were prepared, transfected and analyzed as described above. All the remaining transfections (repressor optimization in FIGS. 10A-10E and time lapse in FIGS. 19A-19F) were carried out with Attractene (Qiagen). Up to 300 ng total DNA was mixed with DMEM base medium (Cellgro) without supplements to a final volume of 60 ul. 1.5 ul Attractene was added to the dilutions and the samples were promptly vortexed to mix. The complexes were incubated for 10-15 min and subsequently added to cells prepared as described above. 500 ul of fresh medium was added to each well the next day (media change was not necessary in the case of Attractene transfections). Transfection details for each experiment are shown in Table 1. The list of all plasmids used in this study is shown in Table 2.

TABLE 1

| FIG. 7B, FIGS. 12A-12C | | | | | |
|---|---|---|---|---|---|
| | untreated | Constitutive output | Low sensors | High sensor | Circuit | Efficiency |
| pL-S3 | | | | 200 ng | 200 ng | |
| PL-S2 | | | 100 ng | | 100 ng | |
| pL-S1 | | 100 ng | | 100 ng | | |
| pL-A1 | | 100 ng | 100 ng | 100 ng | 100 ng | |
| PL-A2 | 400 ng | 200 ng | 200 ng | 0 ng | 0 ng | |
| reagent/cells | | | | | | |
| Opti-MEM | 96 ul | 96 ul | 96 ul | 96 ul | 96 ul | |
| Plus-reagent | 0.5 ul | 0.5 ul | 0.5 ul | 0.5 ul | 0.5 ul | |
| Lipofectamine-LTX | 1.5 ul | 1.5 ul | 1.5 ul | 1.5 ul | 1.5 ul | |
| Hela | 120,000 cells | 120,000 cells | 120,000 cells | 120,000 cells | 120,000 cells | 45-60% |
| HEK293 | 200,000 cells | 200,000 cells | 200,000 cells | 200,000 cells | 200,000 cells | 35-50% |
| MCF7 | 150,000 cells | 150,000 cells | 150,000 cells | 150,000 cells | 150,000 cells | 12-20% |

Figures 7A, 7B, 7C, 7D, 7E:
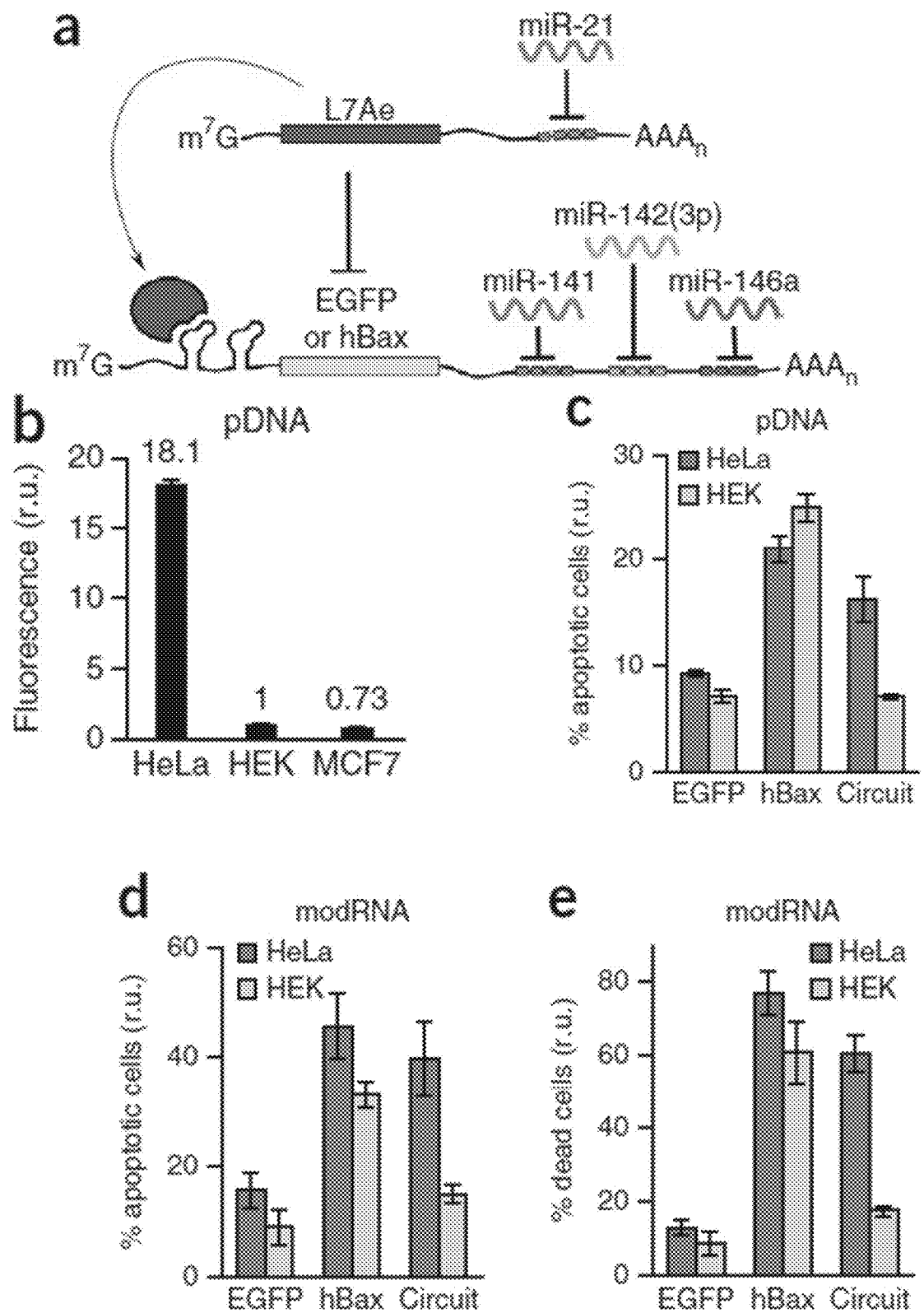
FIGS. 7A-7E. RNA-only multi-input microRNA classifier circuit differentiates between HeLa, HEK 293 and MCF7 cells. (a) An L7Ae-based multi-input microRNA classifier specifically recognizes HeLa cells based on a unique microRNA profile (highly expressed miR21 and low levels of miR141, 142(3p) and 146a). (b) Differential expression of output protein EGFP in HeLa, HEK and MCF7 cells with transient pDNA transfection. EGFP expression from the classifier circuit results in 18-fold and 25-fold higher output in HeLa cells in comparison to HEK and MCF7 cells, respectively (HEK fluorescence was normalized to 1 and circuit-regulated EGFP fluorescence was normalized to mKate expressed constitutively from the same promoter, to account for different expression levels across cell types). (c-d) Specific induction of apoptosis in HeLa cells by expression of circuit-controlled hBax protein compared with constitutive hBax expression: Annexin V positive cells in pDNA (c) and modRNA (d) transfected cells. (e) Cell death assay in a mixed HEK/HeLa-EBFP2 culture with modRNA delivery. The graphs indicate percent of dead cells as measured with AADvanced staining, with HEK and HeLa cells distinguished by EBFP fluorescence. EGFP-only transfection was used as a control in all apoptotic/cell death assays.
Figure 14:
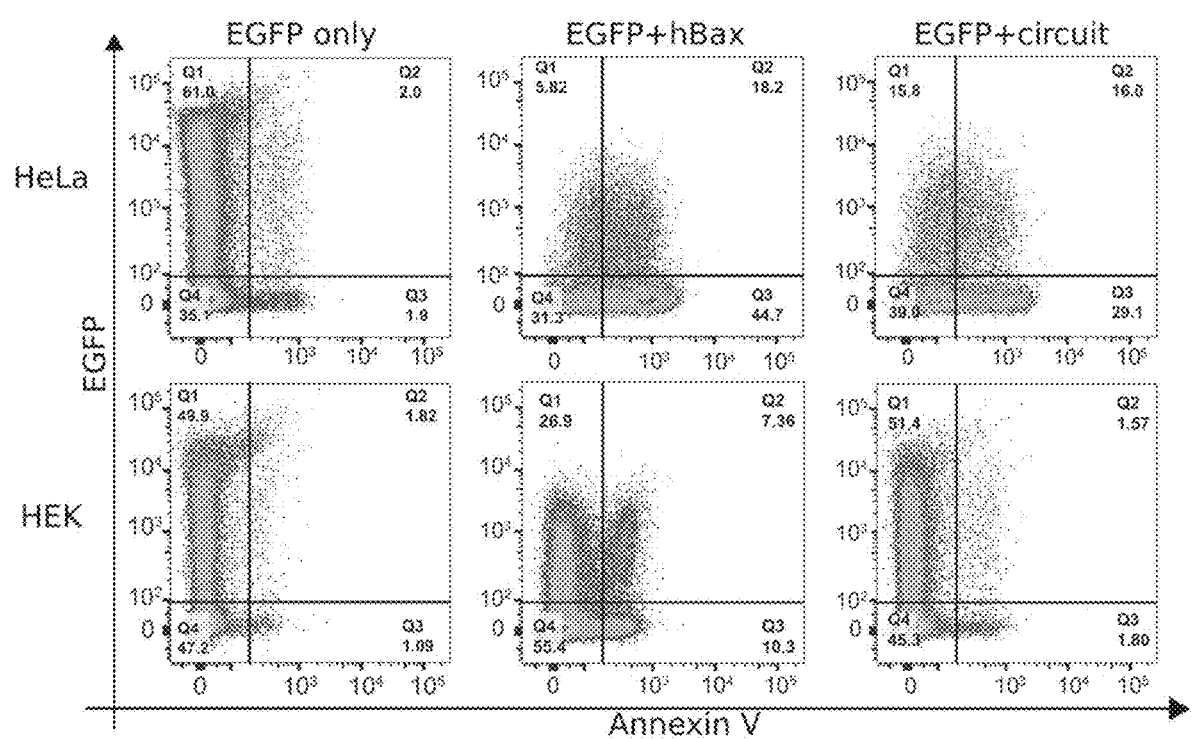
FIG. 14. Representative two-dimensional flow cytometry plots for apoptotic assay in separate cultures of HEK 293 and HeLa cells (pDNA as circuit carrier). HeLa classifier circuit, apoptotic assay (FIG. 7C) additional data. AnnexinV staining and flow cytometry were performed 24 h post-transfection. EGFP was used as a transfection marker, as it has faster maturation time than mKate and can be detected even in hBax expressing cells that undergo apoptosis. The percentage of apoptotic cells in pDNA experiment is much lower than in modified RNA experiments (FIGS. 7D-7E and FIGS. 15 and 16), most likely because of a delay in hBax production related to transcription (crossing of nuclear envelope by pDNA, transcription and transport to the cytoplasm.
Figure 15:
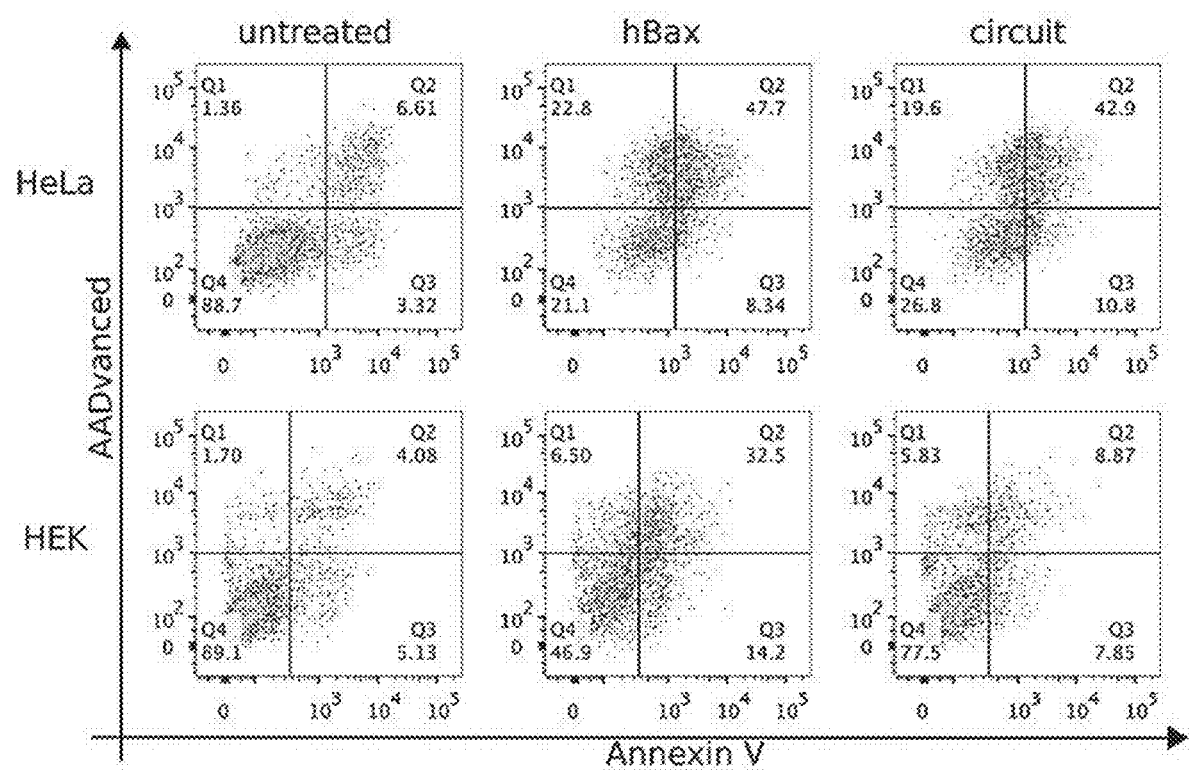
FIG. 15. Representative two-dimensional flow cytometry plots for apoptotic and cell death assay in separate cultures of HEK 293 and HeLa cells (modRNA as circuit carrier). HeLa classifier circuit, apoptotic and cell death assays (FIG. 7D) additional data: AnnexinV (apoptosis marker) vs. AADvanced (cell death stain) dotplots. HEK 293 or HeLa cells were cultured and transfected separately. AnnexinV positive cells were counted as apoptotic cells. In all modRNA cell classifier experiments (including FIGS. 7D-7E) L7Ae was additionally fused with Bcl-2 (L7Ae-Bcl-2) to further inhibit apoptosis.

| FIG. 7C, FIG. 14 | | | | |
|---|---|---|---|---|
| | EGFP | hBax | Circuit | Efficiency |
| pL-S3 | | | 50 ng | |
| pL-C3 | | | | |
| pL-K3 | | | 50 ng | |
| pL-K4 | | 50 ng | | |
| pL-S4 | 50 ng | 50 ng | 50 ng | |
| pL-A2 | 350 ng | 300 ng | 250 ng | |

TABLE 1-continued

| reagent/cells | | | | |
|---|---|---|---|---|
| Opti-MEM | 96 ul | 96 ul | 96 ul | |
| Plus-reagent | 0.5 ul | 0.5 ul | 0.5 ul | |
| Lipofectamine-LTX | 1.5 ul | 1.5 ul | 1.5 ul | |
| HeLa | 150,000 cells | 150,000 cells | 150,000 cells | 35-40% |
| HEK293 | 200,000 cells | 200,000 cells | 200,000 cells | 35-40% |

Figures 8A, 8B, 8C, 8D, 8E, 8F, 8G, 8H:
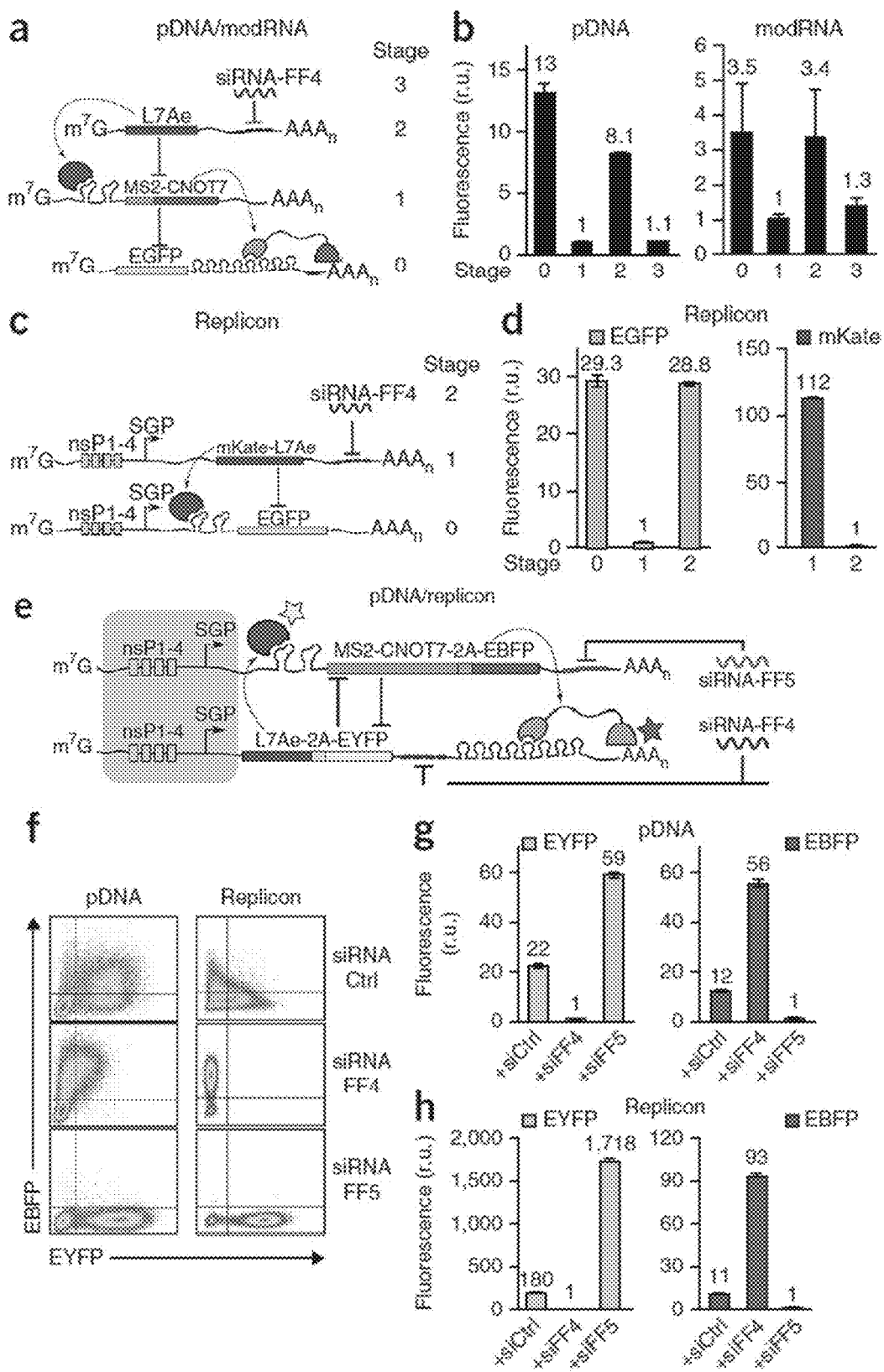
FIGS. 8A-8H. Post-transcriptional cascades and two-state switch. (a) Cascade design for the pDNA and modRNA experiments. (b) Normalized mean EGFP fluorescence for the indicated cascade stages encoded either on pDNA or modRNA. Each stage n involves co-transfection of constructs 0 to n. (c) Replicon encoded two-stage cascade. L7Ae was fused to red fluorescent protein mKate. Each replicon additionally encodes four non-structural proteins (nsP1-4) and a subgenomic promoter (SGP) driving expression of circuit components. (d) Normalized mean EGFP and mKate fluorescence for cascade encoded on self-replicating RNA. (e) Switch design; shaded: replicon components that include nsP1-4 and SGP. (f) Corresponding representative two-dimensional flow cytometry plots for pDNA and replicon transfections. (g,h) Normalized mean fluorescence of the two reporters in the different states of the switch encoded on pDNA (g) or replicon (h). Fluorescence was normalized to the lowest level in each chart.
Figures 17A, 17B, 17C, 17D:
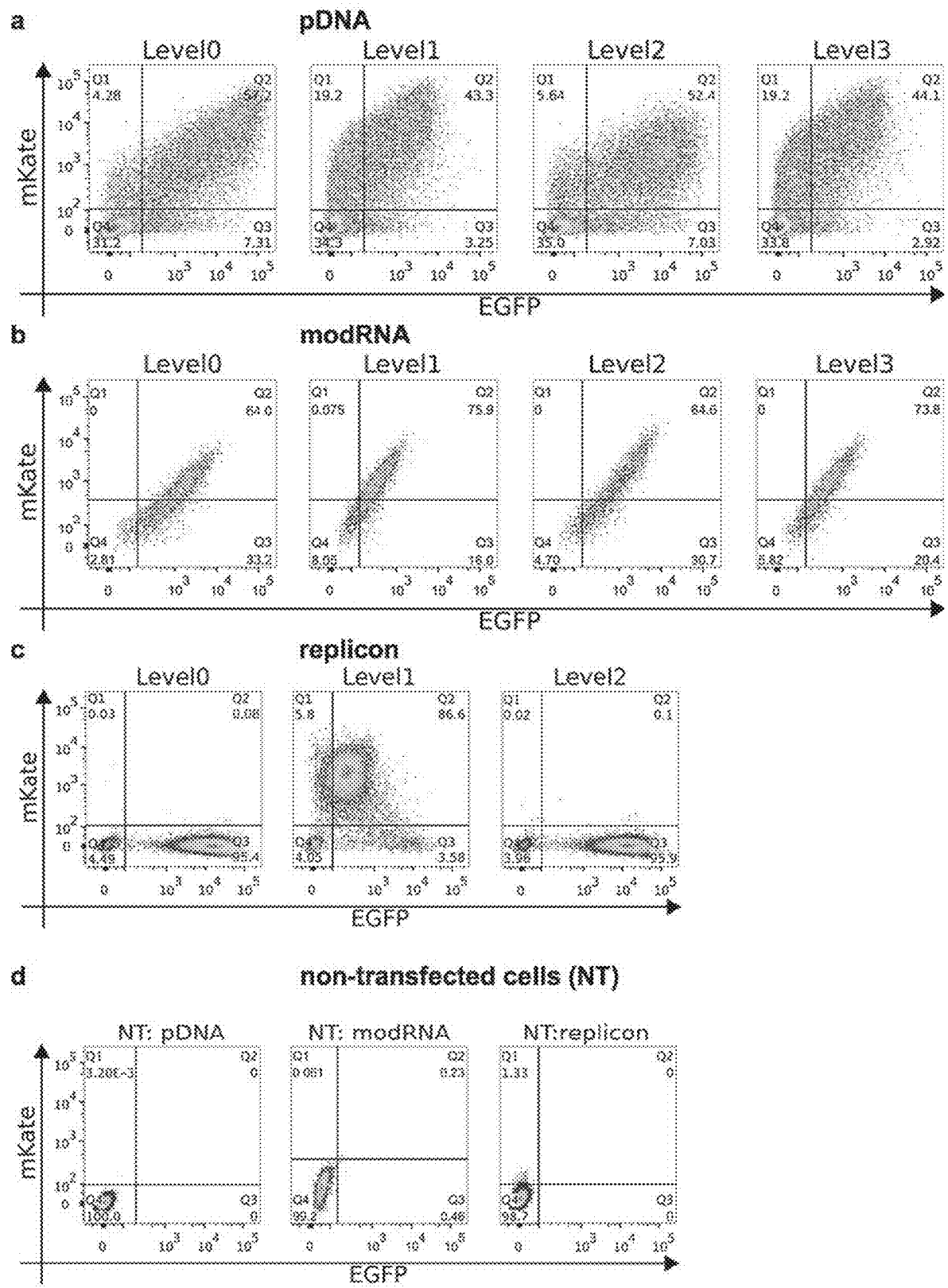
FIGS. 17A-17D. Representative flow cytometry data for cascade circuit. Raw flow cytometry data for cascade circuit (FIGS. 8A-8D) with all three modalities tested: pDNA (a), modRNA (b) and replicon (c). Populations of live, single cell were first determined based on forward and side scatter. Gates shown on the plots were established based on negative control (non-transfected, NT) cells (d) and cells transfected with EGFP or mKate only (not shown). In the case of pDNA transfections, the transfection efficiency, as determined by % of mKate transfection control cells, was 60-65%. Before calculating average EGFP fluorescence, we gated the populations on mKate positive cells (reported EGFP fluorescence was calculated for cells from Q1 and Q2 gates). In the case of modRNA and replicon transfections, the transfection efficiency was very high (>90%), and therefore all live cells were used to calculate average output (EGFP) fluorescence (cells from gates Q1-Q4). Replicon experiments were performed using BHK21 cells, and HEK 293FT cells were used in modRNA and pDNA transfections. The NT populations (d) differ between pDNA and modRNA experiments, as the two data sets were collected and analyzed with different flow cytometers (see Methods for details).
Figures 18A, 18B, 18C:
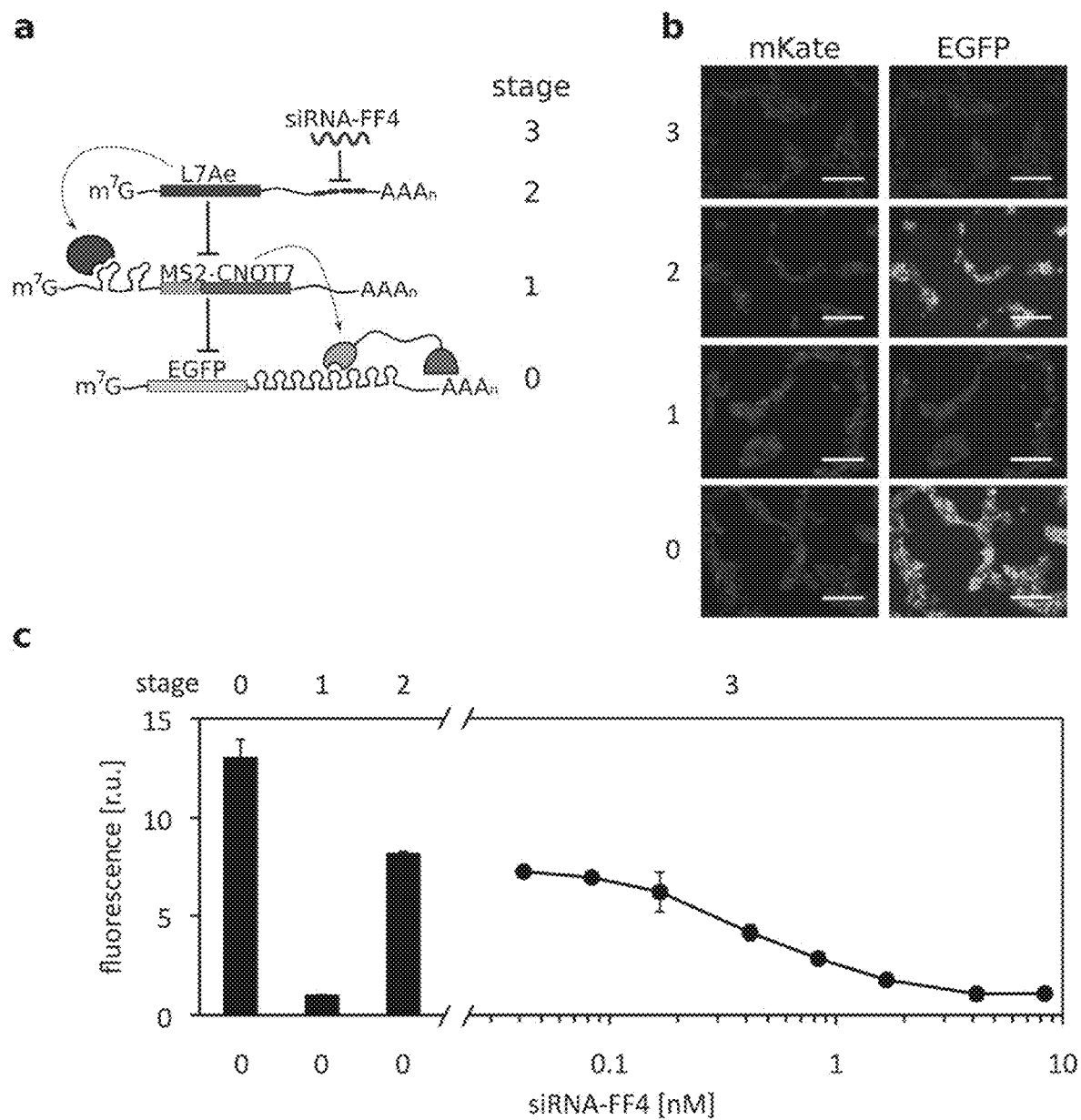
FIGS. 18A-18C. Post-transcriptional cascade optimization and additional data (pDNA as circuit carrier). (a) Cascade scheme. mKate transfection marker is not shown. (b) Microscopy images for pDNA experiment (optimized cascade) using 4.2 nM siRNA-FF4 input. Scale bars indicate 200 μm. (c) Cascade dosage response with various concentrations of the input (siRNA-FF4, from 0.04 to 8.33 nM).

FIG. 8B, FIG. 17A (Level 3 siRNA conditions shown in bold), FIGS. 18A-18C

| | Level0 | Level1 | Level2 | Level3 | Efficiency |
|---|---|---|---|---|---|
| pL-C1 | 50 ng | 50 ng | 50 ng | 50 ng | |
| pL-C2 | | 12.5 ng | 12.5 ng | 12.5 ng | |
| pL-C3 | | | 75 ng | 75 ng | |
| pL-A1 | 50 ng | 50 ng | 50 ng | 50 ng | |
| pL-A2 | 87.5 ng | 75 ng | | | |
| siRNA FF4 | 0 | 0 | 0 | 0.025, 0.05, 0.1, 0.25, 0.5, 1, 2.5, 5 pmol | |
| siRNA NS | 5 pmol | 5 pmol | 5 pmol | 49.75, 4.95, 4.9, 4.75, 4.5, 4, 2.5, 0 pmol | |
| reagent/cells | | | | | |
| Opti-MEM | 96 ul | 96 ul | 96 ul | 96 ul | |
| Lipofectamine-2000 | 2 ul | 2 ul | 2 ul | 2 ul | |
| HEK293FT | 200,000 cells | 200,000 cells | 200,000 cells | 200,000 cells | 65-75% |

FIGS. 8F-8G, FIG. 27, and FIG. 28

| | siRNA FF55 | siRNA FF4 | siRNA Ctrl | Efficiency |
|---|---|---|---|---|
| pL-T1 | 100 ng | 100 ng | 100 ng | |
| pL-T2 | 100 ng | 100 ng | 100 ng | |
| pL-A3 | 100 ng | 100 ng | 100 ng | |
| siRNA | 1 pmol, FF5 | 1 pmol, FF4 | 1 pmol, NS | |
| reagent/cells | | | | |
| Opti-MEM | 96 ul | 96 ul | 96 ul | |
| Lipofectamine-2000 | 2 ul | 2 ul | 2 ul | |
| HEK 293FT | 200,000 cells | 200,000 cells | 200,000 cells | 65-75% |

FIG. 10C

| | 1xK-turn | | 2xK-turn | | 1xK-turnMUT | | |
|---|---|---|---|---|---|---|---|
| | −L7AE | +L7Ae | −L7AE | +L7Ae | −L7AE | +L7Ae | Efficiency |
| pL7Ae | | 100 ng | | 100 ng | | 100 ng | |
| P1xKt | 50 ng | 50 ng | | | | | |
| pL-S1 | | | 50 ng | 50 ng | | | |
| pL-A6 | | | | | | | |
| pL-A1 | 50 ng | 50 ng | 50 ng | 50 ng | 50 ng | 50 ng | |
| pL-A2 | 100 ng | | 100 ng | | 100 ng | | |
| reagent/cells | | | | | | | |
| DMEM | 98 ul | 98 ul | 98 ul | 98 ul | 98 ul | 98 ul | |
| Attractene | 1.5 ul | 1.5 ul | 1.5 ul | 1.5 ul | 1.5 ul | 1.5 ul | |
| HEK 293FT | 200,000 | 200,000 | 200,000 | 200,000 | 200,000 | 200,000 | 55-60% |

FIG. 10D

| | No Repressor | MS2-CNOT7 | MS2-Dm-Pum-RD2 | MS2-Dm-POP2 | MS2-Hs-PUM1-3 | MS2-Hs-PUM1-N | Efficiency |
|---|---|---|---|---|---|---|---|
| pL-R1 | | 100 ng | | | | | |
| pL-R2 | | | 100 ng | | | | |
| pL-R3 | | | | 100 ng | | | |
| pL-R4 | | | | | 100 ng | | |
| pL-R5 | | | | | | 100 ng | |
| pL-C1 | 50 ng | 50 ng | 50 ng | 50 ng | 50 ng | 50 ng | |
| pL-A1 | 50 ng | 50 ng | 50 ng | 50 ng | 50 ng | 50 ng | |
| pL-A2 | 100 ng | | | | | | |
| | | | reagent/cells | | | | |
| DMEM | 98 ul | 98 ul | 98 ul | 98 ul | 98 ul | 98 ul | |
| Attractene | 1.5 ul | 1.5 ul | 1.5 ul | 1.5 ul | 1.5 ul | 1.5 ul | |
| HEK 293FT | 200,000 | 200,000 | 200,000 | 200,000 | 200,000 | 200,000 | 55-62% |

TABLE 1-continued

Figures 10A, 10B, 10C, 10D, 10E:
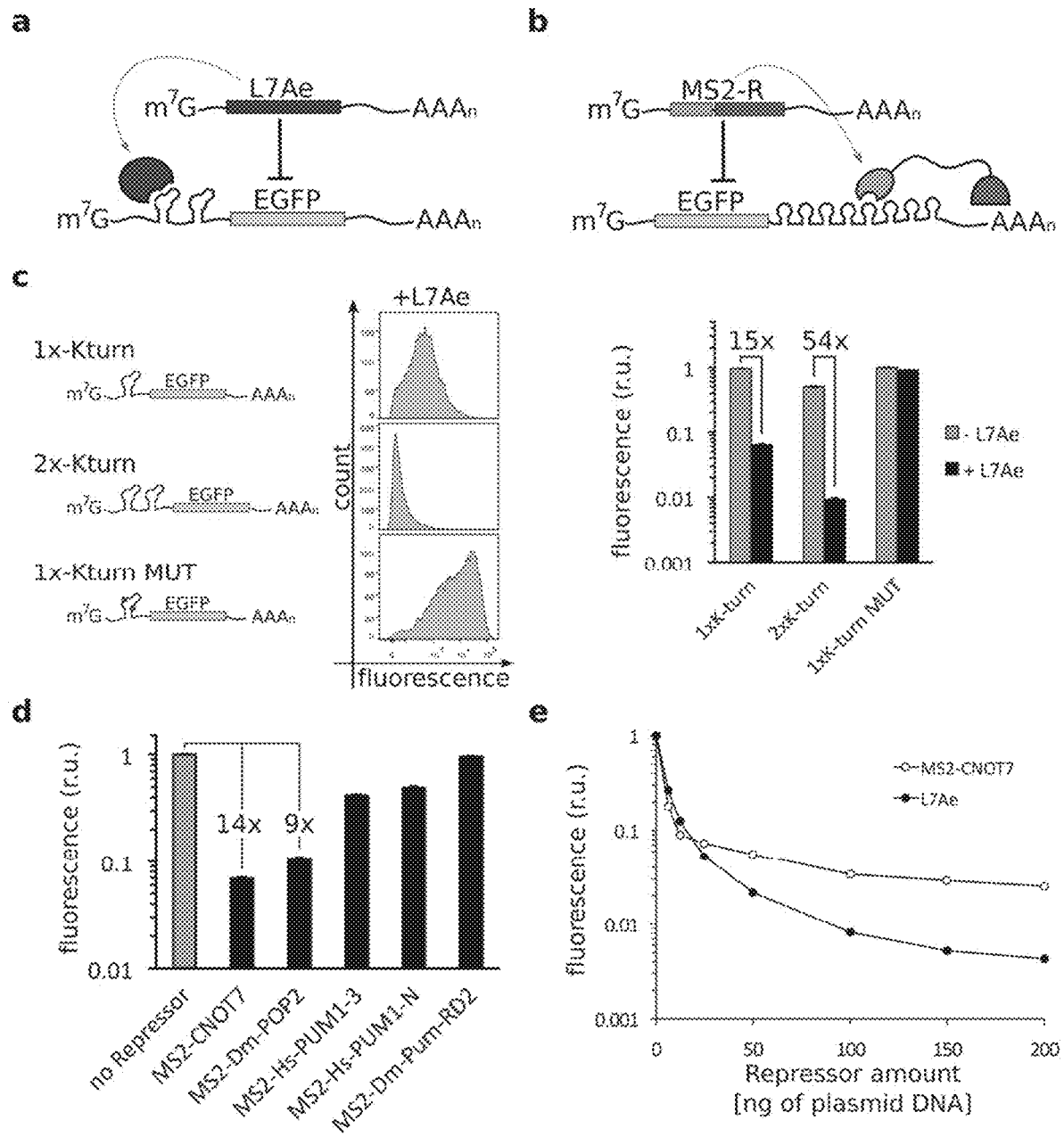
FIGS. 10A-10E. Engineering and characterization of RNA binding protein (RBP) regulatory parts. (a) L7Ae:K-turn system. (b) MS2-tethered repressors (MS2-R). (c) Optimization of L7Ae:K-turn repression: using two repeats of the L7Ae binding motif, K-turn, in the 5'UTR of the reporter mRNA provides strong repression of the reporter as shown in the representative flow cytometry histograms (left) and by mean reporter fluorescence (right). K-turn MUT motif contains two base pair mutations that inhibit L7Ae binding (36). (d) Characterization of MS2-fusion repressors. Fold change for best repressors indicated. (e) Dose response curves of the two best repressors (with 50 ng of reporter pDNA). Optimization of parts was performed with pDNA and results are calculated/shown only for transfected cells (cells expressing transfection marker, mKate). Fluorescence was normalized to the highest level per series in each graph.

| FIG. 10E, L7Ae | | |
|---|---|---|
| | | Efficiency |
| pL7Ae | 0, 6.25, 12.5, 25, 50, 100, 150, 200 ng | |
| pL-S1 | 50 ng | |
| pL-A1 | 50 ng | |
| pL-A2 | 200, 193.75, 187.5, 175, 150, 100, 50, 0 ng | |
| reagent/cells | | |
| DMEM | 97 ul | |
| Attractene | 1.5 ul | |
| HEK 293FT | 200,000 | 55-60% |

| FIG. 10E, MS2-CNOT7 | | |
|---|---|---|
| | | Efficiency |
| pL-R1 | 0, 6.25, 12.5, 25, 50, 100, 150, 200 ng | |
| pL-C1 | 50 ng | |
| pL-A1 | 50 ng | |
| pL-A2 | 200, 193.75, 187.5, 175, 150, 100, 50, 0 ng | |
| reagent/cells | | |
| DMEM | 97 ul | |
| Attractene | 1.5 ul | |
| HEK293FT | 200,000 | 55-60% |

Figure 11:
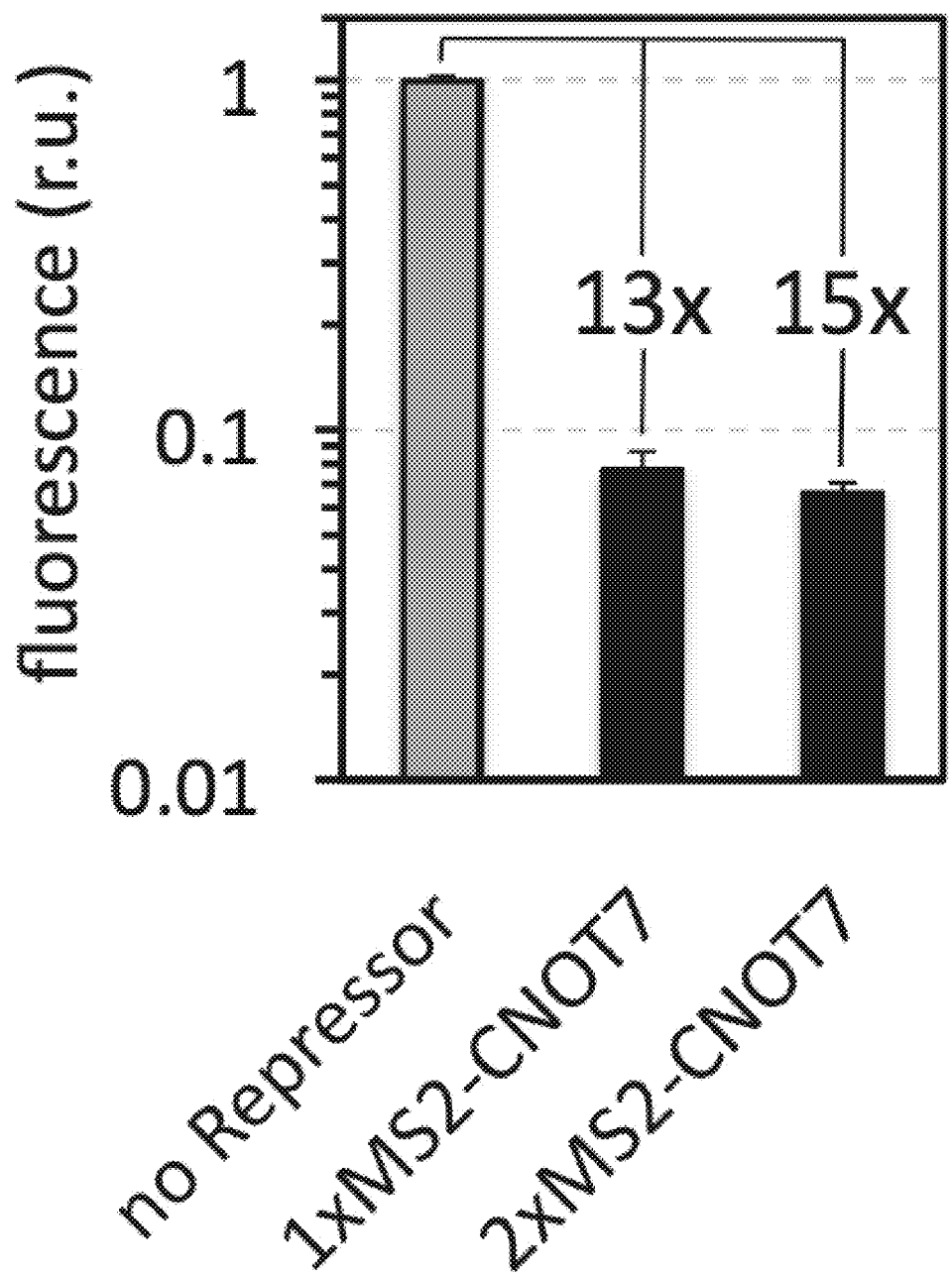
FIG. 11. MS2-CNOT7 repressor is also effective in HeLa cells. The observed dynamic range was comparable to that observed in HEK293 cells (pDNA as delivery method). Both reporter and repressor were driven by pCMV promoters. 1× and 2×MS2-CNOT7 indicate 1:1 and 2:1 repressor (MS2-CNOT7) to reporter ratios, respectively.
Figures 12A, 12B, 12C:
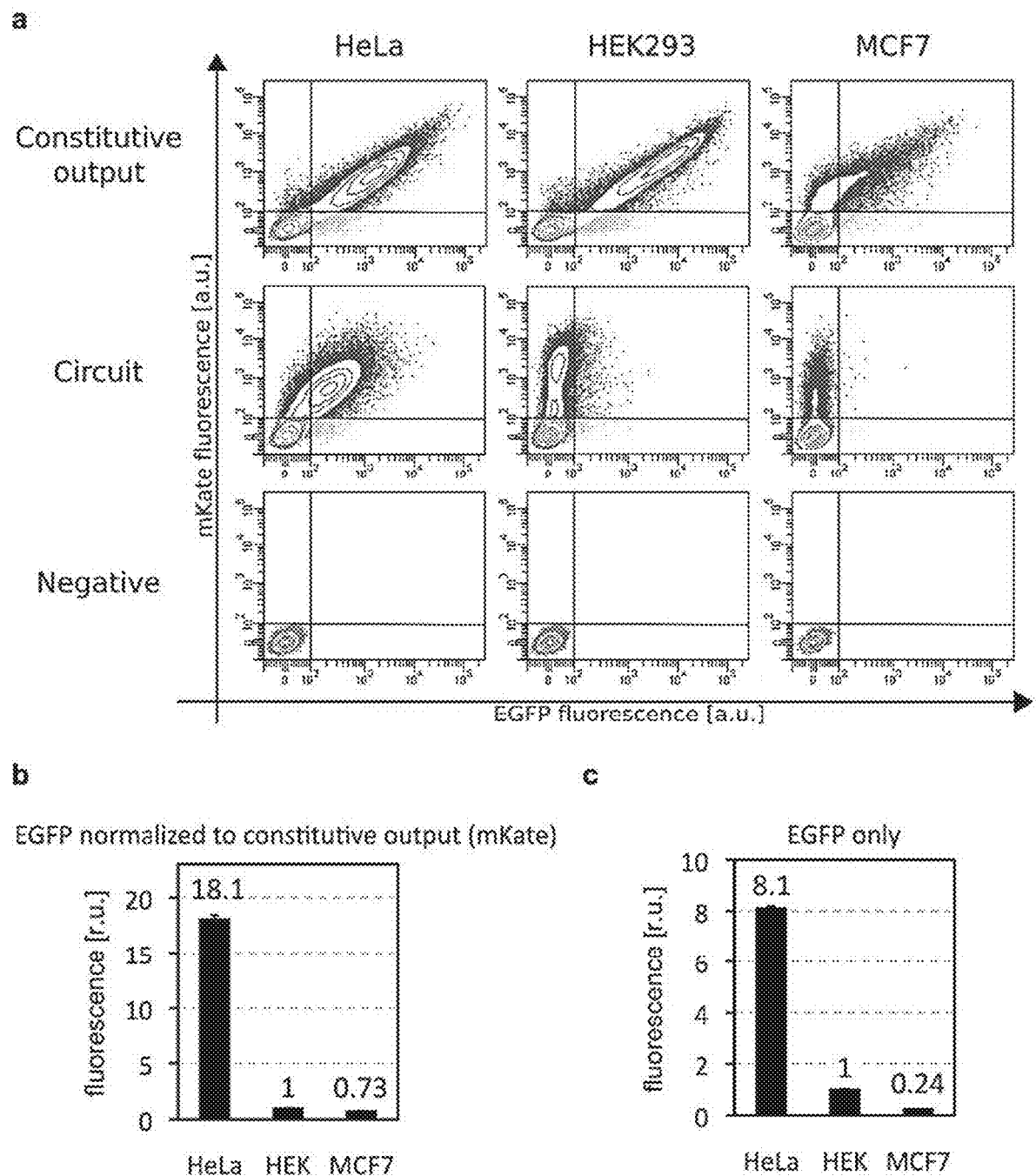
FIGS. 12A-12C. HeLa classifier circuit (pDNA as circuit carrier), fluorescent assay (FIG. 7B) additional data. (a) two dimensional flow cytometry plots; EGFP—circuit output, mKate—transfection marker. "Negative" denotes non-transfected cells (Hela, HEK293 and MCF7 as indicated). The negative population was used to set gates for transfected cells. All mKate positive cells (above horizontal bars) were used to calculate mean fluorescence. (b,c): Differential expression of output protein EGFP in HeLa, HEK293 and MCF7 cells with transient pDNA transfection. (b) As in FIG. 7B, circuit-regulated EGFP fluorescence was normalized to mKate expressed constitutively from the same promoter, to account for different expression levels across cell types. Additionally, HEK fluorescence was normalized to 1 (normalized EGFP expression from the classifier circuit results in 18-fold and 25-fold higher output in HeLa cells in comparison to HEK and MCF7 cells, respectively). (c) Circuit-regulated EGFP fluorescence without normalization to mKate (HEK fluorescence was normalized to 1). EGFP expression from the classifier circuit results in 8-fold and 34-fold higher output in HeLa cells in comparison to HEK and MCF7 cells, respectively.

| FIG. 11 | | | | |
|---|---|---|---|---|
| | No Repressor | 1x MS2-CNOT7 | 2x MS2-CNOT7 | Efficiency |
| pL-C5 | | 100 ng | 200 ng | |
| pL-C1 | 100 ng | 100 ng | 100 ng | |
| pL-A1 | 100 ng | 100 ng | 100 ng | |
| pL-A2 | 200 ng | 100 ng | | |
| reagent/cells | | | | |
| Opti-MEM | 96 ul | 96 ul | 96 ul | |
| Plus-reagent | 0.5 ul | 0.5 ul | 0.5 ul | |
| Lipofectamine-LTX | 1.5 ul | 1.5 ul | 1.5 ul | |
| HeLa | 150,000 cells | 150,000 cells | 150,000 cells | 50% |

Figure 13:
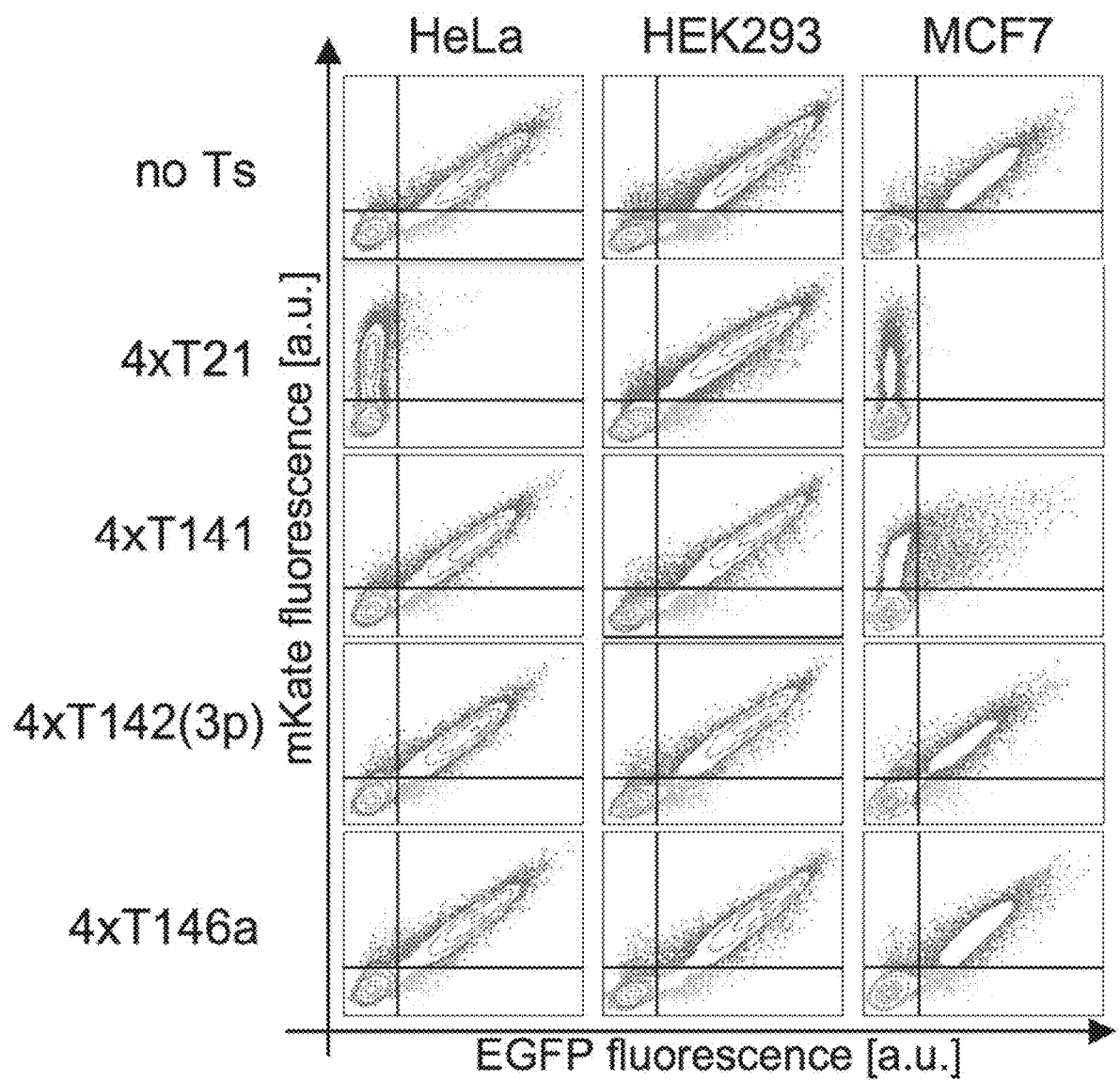
FIG. 13. HeLa classifier circuit (pDNA as circuit carrier), fluorescent assay, single microRNA marker data. Reporter constructs containing EGFP (circuit output) followed by four repeats of target sites for the particular single marker microRNA were co-transfected into HeLa, HEK293 and MCF7 cells together with mKate (transfection marker) expressing constructs. The same pCMV promoter was used to drive expression of both EGFP and mKate. Two dimensional flow cytometry plots are shown and top row contains data for EGFP without target sites (no Ts).

| FIG. 13 | | | | | |
|---|---|---|---|---|---|
| | No Ts | 4xT21 | 4xT141 | 4xT1423-3p | 4xT146a | Efficiency |
| pL-A6 | 100 ng | | | | | |
| pL-S28 | | 100 ng | | | | |
| pL-S29 | | | 100 ng | | | |
| pL-S30 | | | | 100 ng | | |
| pL-S31 | | | | | 100 ng | |
| pL-A1 | 100 ng | 100 ng | 100 ng | 100 ng | 100 ng | |
| pL-A2 | 200 ng | 200 ng | 200 ng | 200 ng | 200 ng | |
| reagent/cells | | | | | | |
| Opti-MEM | 96 ul | 96 ul | 96 ul | 96 ul | 96 ul | |
| Plus-reagent | 0.5 ul | 0.5 ul | 0.5 ul | 0.5 ul | 0.5 ul | |
| Lipofectamine-LTX | 1.5 ul | 1.5 ul | 1.5 ul | 1.5 ul | 1.5 ul | |
| HeLa | 120,000 cells | 120,000 cells | 120,000 cells | 120,000 cells | 120,000 cells | 40-52% |
| HEK293 | 200,000 cells | 200,000 cells | 200,000 cells | 200,000 cells | 200,000 cells | 45-55% |
| MCF7 | 150,000 cells | 150,000 cells | 150,000 cells | 150,000 cells | 150,000 cells | 20-28% |

Figures 19A, 19B, 19C, 19D, 19E, 19F:
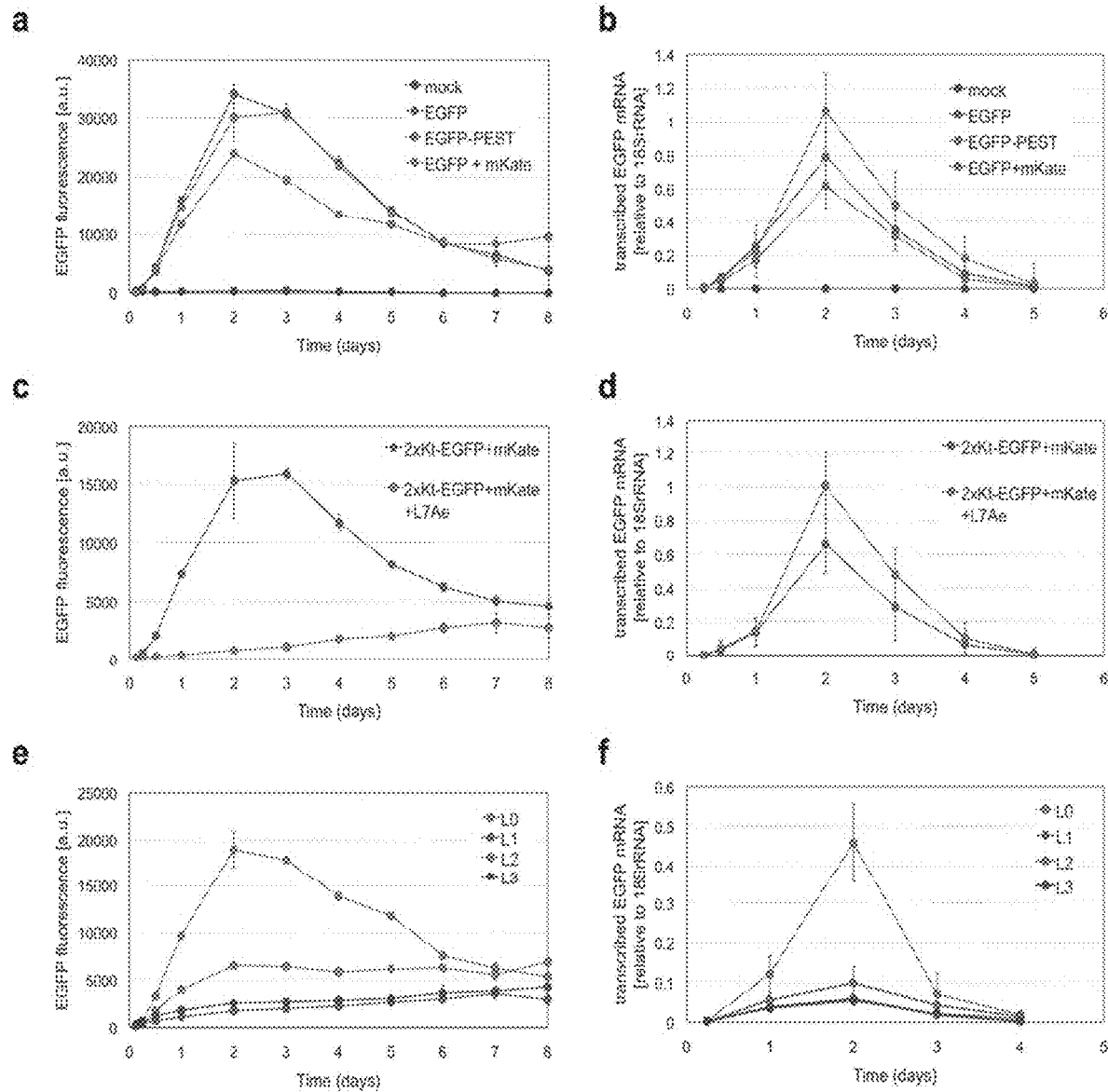
FIGS. 19A-19F and 20A-20F).
Figure 20A:
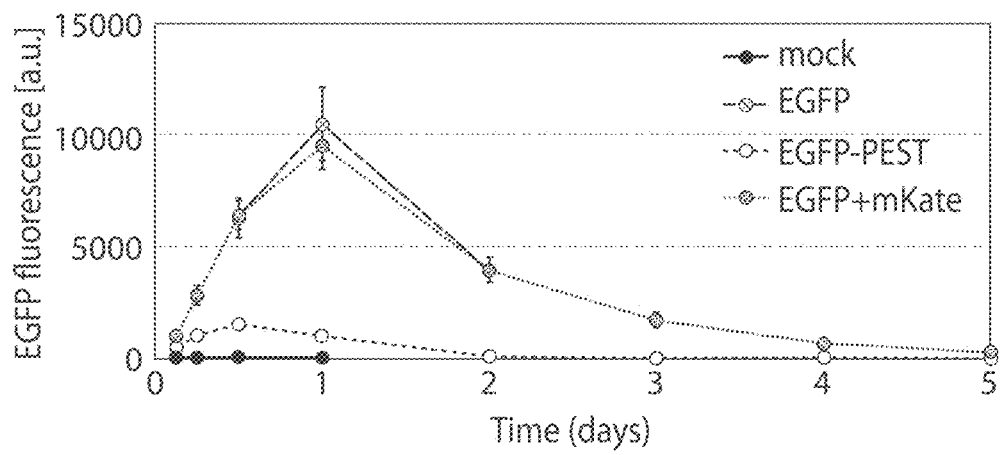
Figure 20B:
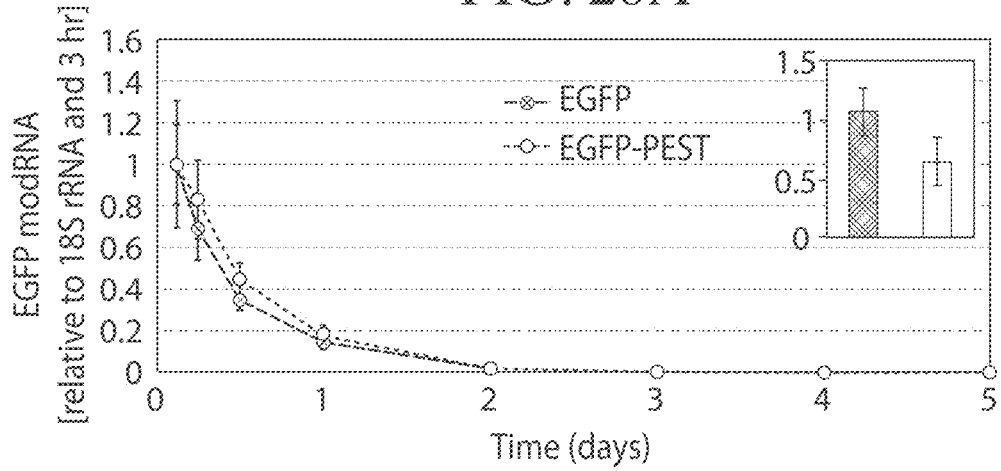
Figure 20C:
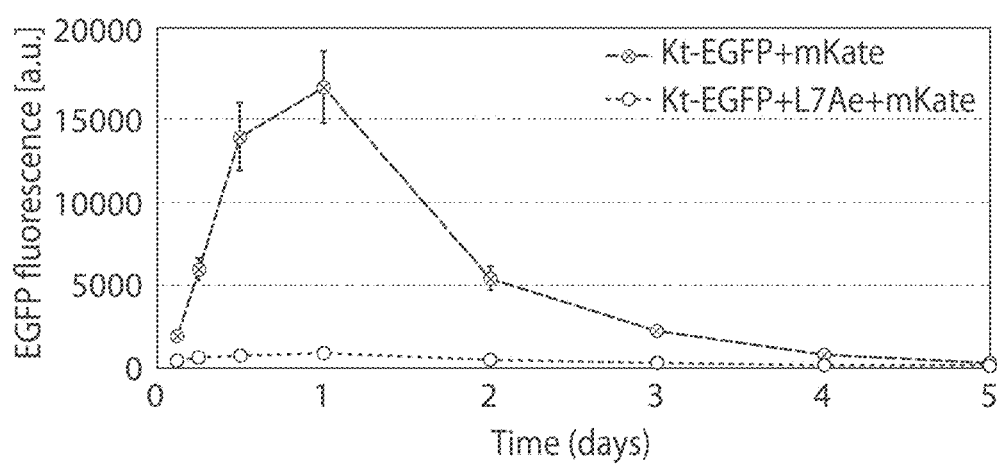
Figure 20D:
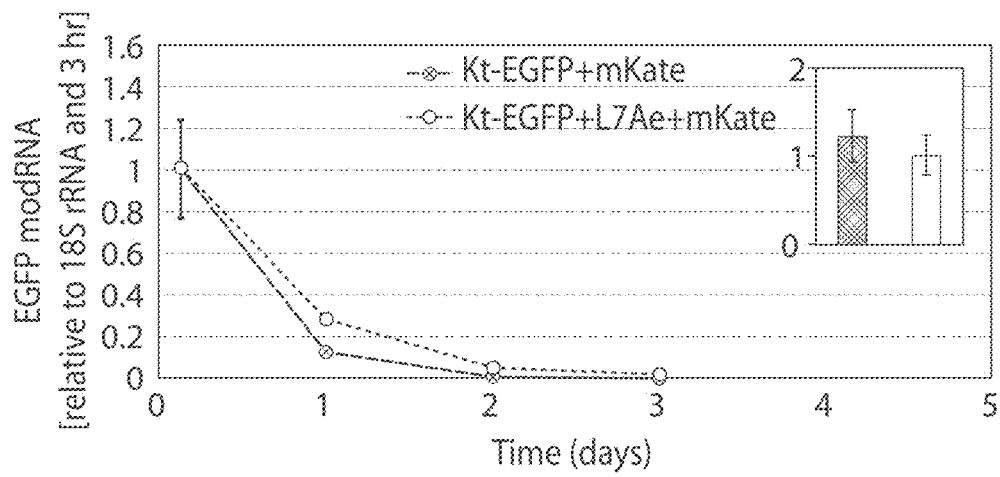
Figure 20E:
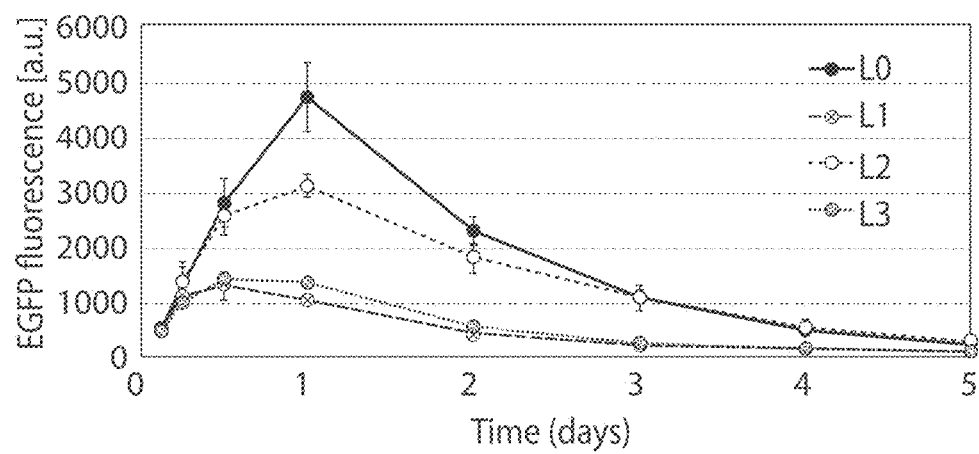
Figure 20F:
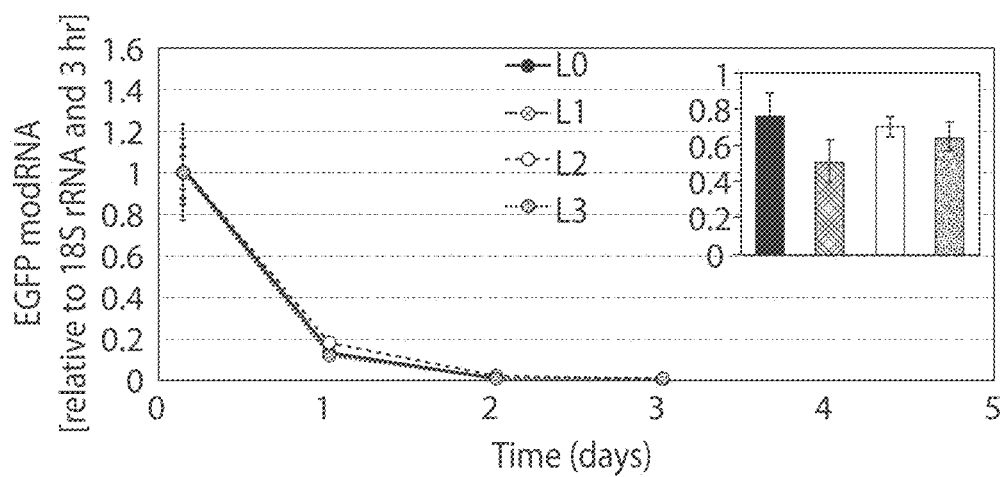

| FIGS. 19A-19B | | | | |
|---|---|---|---|---|
| | mock | EGFP | EGFP-PEST | EGFP + mKate | Efficiency |
| pL-A6 | | 50 ng | | 50 ng | |
| pL-A7 | | | 50 ng | | |
| pL-A1 | | | | 50 ng | |
| pL-A2 | 50 ng | | | | |
| reagent/cells | | | | | |
| DMEM | 59.5 ul | 59.5 ul | 59.5 ul | 59 ul | |
| Attractene | 1.5 ul | 1.5 ul | 1.5 ul | 1.5 ul | |
| HEK 293FT | 200,000 cells | 200,000 cells | 2000,000 cells | 200,000 cells | 65-75% |

TABLE 1-continued

FIGS. 19C-19D

|  | 2xKt-EGFP + mKate | 2xKt-EGFP + mKate + L7AE | Efficiency |
|---|---|---|---|
| pL-S1 | 50 ng | 50 ng | |
| pL-A1 | 50 ng | 50 ng | |
| pL7Ae | | 100 ng | |
| pL-A2 | 100 ng | | |
| reagent/cells | | | |
| DMEM | 58 ul | 58 ul | |
| Attractene | 1.5 ul | 1.5 ul | |
| HEK 293FT | 200,000 cells | 200,000 cells | 70% |

FIGS. 19C-19D

|  | Level0 | Level1 | Level2 | Level3 | Efficiency |
|---|---|---|---|---|---|
| pL-C1 | 50 ng | 50 ng | 50 ng | 50 ng | |
| pL-C2 | | 25 ng | 25 ng | 25 ng | |
| pL-C3 | | | 75 ng | 75 ng | |
| pL-A1 | 50 ng | 50 ng | 50 ng | 50 ng | |
| pL-A5 | | | | 100 ng | |
| pL-A4 | | | 100 ng | | |
| pL-A2 | 200 ng | 175 ng | | | |
| reagent/cells | | | | | |
| DMEM | 57 ul | 57 ul | 57 ul | 57 ul | |
| Attractene | 1.5 ul | 1.5 ul | 1.5 ul | 1.5 ul | |
| HEK 293FT | 200,000 cells | 200,000 cells | 200,000 cells | 200,000 cells | 45-60% |

FIGS. 7D-7E, FIG. 15, and FIG. 16

|  | hBax | Circuit | -L7AeBcl2 | -4xT21 | Efficiency |
|---|---|---|---|---|---|
| hBax | 350 ng | | | | |
| Kt-hBax-4xT141-L7Ae-2A-Bcl2-4xT21 | | 350 ng | 350 ng | 350 ng | |
| L7Ae-2A-Bcl2 | | 17.5 ng | | 17.5 ng | |
| TransIT-mRNA | 1 uL | 1 uL | 1 uL | 1 uL | |
| HeLa | 50,000 | 50,000 | 50,000 | 50,000 | 97% |
| HEK 293 | 100,000 | 100,000 | 100,000 | 100.000 | 86% |
| HeLa-BFP cells + | 50,000 | 50,000 | 50,000 | 50,000 | |
| HEK 293 cells | 50,000 | 50,000 | 50,000 | 50,000 | Mixed: 85% |

FIGS. 8B, FIG. 17B, and FIGS. 20E-20F

|  | level 0 | level 1 | level 2 | level 3 | Efficiency |
|---|---|---|---|---|---|
| mKate | 100 ng | 100 ng | 100 ng | 100 ng | |
| EGFP-8xM2S | 100 ng | 100 ng | 100 ng | 100 ng | |
| MS2 | 100 ng | | | | |
| Kt-MS2-CNOT7 | | 100 ng | 100 ng | 100 ng | |
| L7Ae-4xFF4 | | | 30 ng | 30 ng | |
| siRNA-control | 1 pmol | 1 pmol | 1 pmol | | |
| siRNA-FF4 | | | | 1 pmol | |
| StemFect | 1 uL | 1 uL | 1 uL | 1 uL | |
| 293FT cells | 100,000 | 100,000 | 100,00 | 100,000 | 94% |

FIGS. 20A-20D

|  | EGFP | EGFP-PEST | EGFP + mKate | Kt-EGFP | Kt-EGFP + L7Ae | Efficiency |
|---|---|---|---|---|---|---|
| EGFP | 100 ng | | 100 ng | | | |
| EGFP-PEST | | 100 ng | | | | |
| Kt-EGFP | | | | 100 ng | 100 ng | |
| mKate | | | 100 ng | 100 ng | 100 ng | |
| L7Ae | | | | | 30 ng | |
| StemFect | 1 uL | 1 uL | 1 uL | 1 uL | 1 uL | |
| 293FT cells | 100,000 | 100,000 | 100,000 | 100,000 | 100,000 | 94% |

TABLE 1-continued

Replicon
For replicon delivery, electroporation was used instead of lipid-based transfection (no transfection reagent) and all electroporations were carried out using 100,000 BHK21 cells per sample (as described in the Methods section). Transfection efficiency reported after 24 h.
FIG. 8D, FIG. 17C (no PEST domain), and FIG. 25

|  | EGFP | | | EGFP-PEST | | | | |
|---|---|---|---|---|---|---|---|---|
|  | — | L7Ae | | L7Ae-PEST | — | L7Ae | | LTAePEST | |
|  | — | Ctrl | FF4 | Ctrl | FF4 | — | Ctrl | FF4 | Ctrl | FF4 | Efficiency |
| PTK295 | 2100 ng | | | | | | | | | | 96% (EGFP --) |
| pTK296 | | | | | | 2100 ng | | | | | |
| PTK297 | 700 ng | | | | | | | | | | |
| pTK298 | | | | 700 ng | | | | | 700 ng | | |
| siRNA-Ctrl | | 5 pmol | | 5 pmol | | | 5 pmol | | 5 pmol | | |
| siRNA-FF4 | | | 5 pmol | | 5 pmol | | | 5 pmol | | 5 pmol | |

FIG. 8F-8H, FIG. 28

|  | siRNA-Ctrl | sIRNA-FF4 | siRNA-FF5 | Efficiency |
|---|---|---|---|---|
| pTK095 | 2000 ng | 2000 ng | 2000 ng | 89% (siRNA-FF5) |
| pTK332 | 2000 ng | 2000 ng | 2000 ng | |
| siRNA-Ctrl | 5 pmol | | | |
| siRNA-FF4 | | 5 pmol | | |
| siRNA-FF5 | | | 5 pmol | |

FIGS. 22A-22E

|  | EGFP | EGFP-PEST | Efficiency |
|---|---|---|---|
| pTK312 | 1000 ng | | 99% (EGFP) |
| pTK313 | | 1000 ng | |

FIGS. 23A-23C

|  | EGFP | EGFP + L7Ae + siRNA-Ctrl | EGFP + L7Ae + siRNA-FF4 | Efficiency |
|---|---|---|---|---|
| pTK317 | 1000 ng | 1000 ng | 1000 ng | 98% (EGFP) |
| pTK331 | | 1000 ng | 1000 ng | |
| siRNA-Ctrl | | 5 pmol | | |
| siRNA-FF4 | | | 5 pmol | |

FIGS. 24A-24B

|  | EGFP + mKate | Efficiency |
|---|---|---|
| pTK312 | 2000 ng | 99% |
| pTK194 | 2000 ng | |

FIGS. 26A-26C

|  | KtMUT (1000 ng) panel a | Kt (1000 ng) panel a | KtMUT (250 ng) panel a | Kt (250 ng) panel a | Kt (1000 ng) panel b, c | Kt (250 ng) panel b, c | Efficiency |
|---|---|---|---|---|---|---|---|
| pTK297 | 2500 ng | 2500 ng | 2500 ng | 2500 ng | | | |
| pL-S4 | 1000 ng | | 250 ng | | | | |
| pL-S1 | | 1000 ng | | 250 ng | 1000 ng | 250 ng | 91% (Kt (1000 ng) panel b, c) |

FIGS. 29A-29D

|  | EBFP2 siRNA-Ctrl | EBFP2 siRNA-FF5 | EYFP siRNA-Ctrl | EYFP siRNA-FF4 | Efficiency |
|---|---|---|---|---|---|
| pTK095 | | | 1500 ng | 1500 | 94% (EYFP siRNA-Ctrl 0 pmol) |
| pTk332 | 1500 ng | 1500 ng | | | |
| siRNA-Ctrl | 0, 0.00005, 0.00016, 0.0005, 0.0016, 0.005, 0.016, 0.05, 0.16, 0.5, 1.6, 5 pmol | | 0, 0.00005, 0.00016, 0.0005, 0.0016, 0.005, 0.016, 0.05, 0.16, 0.5, 1.6, 5 pmol | | |

TABLE 1-continued

| | | |
|---|---|---|
| siRNA-FF4 | | 0, 0.00005, 0.00016, 0.0005, 0.0016, 0.005, 0.016, 0.05, 0.16, 0.5, 1.6, 5 pmol |
| siRNA-FF5 | 0, 0.00005, 0.00016, 0.0005, 0.0016, 0.005, 0.016, 0.05, 0.16, 0.5, 1.6, 5 pmol | |

FIGS. 30A-30C

| | Control | Switch | Efficiency |
|---|---|---|---|
| pTK299 | 2000 ng | | 80% (Control) |
| pTK333 | 2000 ng | | |
| pTK095 | | 2000 ng | |
| pTK332 | | 2000 ng | |
| siRNA-Ctrl | 5 pmol | 5 pmol | |

TABLE 2

Plasmids used in this study: DNA and sequence files for the main circuit components can be obtained from Addgene (deposit number 71270).

| FIG. | Short plasmid name | Full plasmid name | Parts from |
|---|---|---|---|
| | | pDNA | |
| 1 | pL-R1 | pT-GTW6-CMV-MS2-CNOT7 | A. C. Goldstrohm and C. Weidmann |
| 1 | pL-R2 | pT-GTW6-CMV-MS2-Dm-Pum-RD2 | A. C. G. and C. W. |
| 1 | pL-R3 | pT-GTW6-CMV-MS2-Dm-POP2 | A. C. G. and C. W. |
| 1 | pL-R4 | pT-GTW6-CMV-MS2-Hs-PUM1-3 | C. Weidman et al.[13] |
| 1 | pL-R5 | pT-GTW6-CMV-MS2-Hs-PUM1-N | C. Weidman et al.[13] |
| 1&3 | pL-C1 | pBoxCDGCmut_KMet-EGFP-8xMS2-pA | pL-A3 and C. Weidman et al.[13] |
| 1 | pL7Ae | pcDNA3_1_L7Ae_myc-His6 | H. Saito et al.[12] |
| 1 | pL-R6 | pT-GTW6-CMV-L7Ae | pL7Ae |
| 1 | | pBoxCDGC_KMet_EGFP | H. Saito et al.[12] |
| 1&2 | pL-S1 | pBoxCDGC_2xKMet_EGFP | pBoxCDGC_KMet_EGFP |
| ctrl | pL-A3 | pBoxCDGCmut_KMet_EGFP | H. Saito et al.[12] |
| 2 | pL-S2 | pBoxCDGC_2xKMet_EGFP-4xT141-4xT142-3p-4xT146a | pL-S1 and Xie et al.[15] |
| 2 | pL-S3 | pT-GTW6-CMV-L7Ae-4xT21 | pL7Ae and Xie et al.[15] |
| ctrl | pL-S4 | pBoxCDGCmut_2xKMet_EGFP | pBoxCDGCmut_KMet_EGFP |
| 2 | pZ238 | TRE-LacI-2A-Bcl2-T21x4-miR-FF4 | Xie et al.[15] (Bcl2: NM_000633.2) |
| 2 | pZ241 | CAGOP-hBax-T141x4-T142-3px4-T146ax4-FF4x3 | Xie et al.[15] (hBax: Addgene #19741)[44] |
| 2 | pL-K1 | pT-GTW6-CMV-L7Ae-P2A-Bcl-2-4xT21 | pL-S3 and pZ238 |
| 2 | pL-K2 | pT-GTW6-CMV-L7Ae-P2A-Bcl-2-4xFF4 | pL-S3 and pZ238 |
| 2 | pL-K3 | pBoxCDGC_2xKMet_hBax-4xT141-4xT142-3p-4xT146a | pL-S1 and pZ241 |
| 2 | pL-K4 | pBoxCDGC_2xKMet_hBax | pL-S1 and pZ241 |
| 3 | pL-C2 | pBoxCDGC-2xKMet-MS2-CNOT7 | pL-S1 and pL-R1 |
| 3 | pL-C3 | pT-GTW6-CMV-L7Ae-4xFF4 | pL7Ae |
| 3 | pL-C4 | pT-GTW6-hEF1a-mKateExI-miRFF4-mKateExII | pZ238, intron design: courtesy of H. Chung |
| 1 | pL-C5 | pT-GTW6-CMV-MS2-CNOT7-4xFF4 | pL-R1 |
| 4 | pL-T1 | pT-GTW6-hEF1a-L7Ae-P2A-EYFP-4xFF4-8xMS2pA | EYFP: Addgene #18722[45] |
| 4 | pL-T2 | pBoxCDGC-2xKMet-MS2-CNOT7-P2A-EBFP2-4xFF5 | EBFP2: Addgene #14893[45] |
| S4 | pL-A6 | pCMV-EGFP | pBoxCDGCmut_KMet_EGFP |
| S10 | pL-A7 | pCMV-EGFP-PEST | pCMV-EGFP, PEST[41] |
| S4 | pL-S28 | pCMV-EGFP-4xT21 | pCMV-EGFP |
| S4 | pL-S29 | pCMV-EGFP-4xT141 | pCMV-EGFP |
| S4 | pL-S30 | pCMV-EGFP-4xT142-3p | pCMV-EGFP |
| S4 | pL-S31 | pCMV-EGFP-4x146a | pCMV-EGFP |
| ctrl | pL-A1 | pT-GTW6-CMV-mKate | mKate: Evrogen[47] |
| ctrl | pL-A2 | pDT007 | Xie et al.[15] |

TABLE 2-continued

Plasmids used in this study: DNA and sequence files for the main circuit components can be obtained from Addgene (deposit number 71270).

| FIG. | Short plasmid name | Full plasmid name | Parts from |
|---|---|---|---|
| ctrl | pL-A3 | pT-GTW6-hEF1a-mKate | pL-A1 |
| ctrl | pL-A4 | pT-GTW6-hEF1a-Bla | |
| ctrl | pL-A5 | pT-GTW6-hEF1a-Bla-miRFF4 | |

Modified RNA Preparation and mRNA Transfection

A template DNA for in vitro transcription was generated via PCR, using a forward primer containing T7 promoter and a reverse primer containing 120-nucleotide-long Poly (T) tract transcribed into a Poly(A) tail. PCR products amplified from plasmids were subjected to digestion by Dpn I restriction enzyme and purified. Reactions of in vitro transcription were performed using MegaScript T7 kit (Life Technologies) under a modified condition, in which GTP, CTP and UTP was replaced by GTP mixed with Anti Reverse Cap Analog (New England Biolabs) at the ratio of 1 to 4, 5-methylcytosine-triphosphate and pseudouridine-triphosphate (TriLink BioTechnologies), respectively. Transcripts were treated with Turbo DNase (Life Technologies) for 30 min at 37° C. and purified using RNeasy MiniElute Cleanup Kit (QIAGEN). Resulting mRNAs were incubated with Antarctic Phosphatase (New England Biolabs) for 30 min at 37° C. and purified again. Modified mRNAs were transfected into the cells using TransIT-mRNA transfection kit (Mirus Bio) according to manufacturer's protocol. Stem-Fect (Stemgent) was used to perform co-transfections of modified mRNAs with siRNAs, according to manufacturer's instruction. The medium was exchanged 4 hours after the transfection, and transfected cells were subjected to the analysis after 24 hours. Transfection details for each experiment are shown in Table 1. Detailed configurations for modified mRNA and sequences of mRNA used in this study are shown in Tables 3 and 4.

TABLE 3

Preparation of modified mRNA by PCR and IVT.

| Name | Type | templates | Forward Primer | Reverse Primer | additional oligos |
|---|---|---|---|---|---|
| hBax | IVT template | hBax_ORF, 5'UTR, 3'UTR | T7pro1 | A120 | |
| Kt-hBax-4xT141-4xT142(3p)-4xT146a | IVT template | hBax-4xT141-4xT142(3p)-4xT146a | T7pro2 | A120 | T7-Kt, 5'spacer |
| L7Ae-2A-Bcl2-4xT21 | IVT template | L7Ae-2A-Bcl2_ORF, 5'UTR, 4xT21 | T7pro1 | A120 | |
| L7Ae-2A-Bcl2 | IVT template | L7Ae-2A-Bcl2_ORF, 5'UTR, 3'UTR | T7pro1 | A120 | |
| mKate | IVT template | mKate_ORF, 5'UTR, 3'UTR | T7pro1 | A120 | |
| EGFP-8xMS2 | IVT template | EGFP-8xMS2_ORF, 5'UTR | T7pro1 | A120 | |
| MS2 | IVT template | MS2_ORF, 5'UTR, 3'UTR | T7pro1 | A120 | |
| Kt-MS2-CNOT7 | IVT template | MS2-CNOT7_ORF, 3'UTR | T7pro2 | A120 | T7-Kt, 5'spacer |
| L7Ae-4xFF4 | IVT template | L7Ae-4xFF4_ORF, 5'UTR | T7pro1 | A120 | |
| EGFP | IVT template | EGFP_ORF, 5'UTR, 3'UTR | T7pro1 | A120 | |
| EGFP-PEST | IVT template | d2EGFP_ORF, 5'UTR, 3'UTR | T7pro1 | A120 | |
| Kt-EGFP | IVT template | EGFP2_ORF, 3'UTR | T7pro2 | A120 | T7-Kt, 5'spacer |
| L7Ae | IVT template | L7Ae_ORF, 5'UTR, 3'UTR | T7pro1 | A120 | |
| hBax_ORF | ORF | pZ241 | hBax-F | hBax-R | |
| hBax-4xT141-4xT142(3p)-4xT146a | ORF + UTR | pZ241 | hBax-F | T141-UR | |
| L7Ae-2A-Bcl2_ORF | ORF | pL-K1 | L7Ae-F | Bcl2-R | |
| mKate_ORF | ORF | pL-A1 | mKate-F | mKate-R | |
| EGFP-8xMS2_ORF | ORF + UTR | pL-C1 | ORF-F | MS2-UR | |
| MS2_ORF | ORF | pMS2CP | MS2-F | MS2-R | |
| MS2-CNOT7_ORF | ORF | pL-C5 | ORF-F | CNOT7-R | |
| L7Ae-4xFF4_ORF | ORF + UTR | pL-C3 | L7Ae-F | FF4-UR | |
| EGFP_ORF | ORF | p413M-d2EGFP | ORF-F | EGFP-R | |
| d2EGFP_ORF | ORF | p413M-d2EGFP | ORF-F | d2EGFP-R | d2EGFP-rev1, d2EGFP-rev2 |
| EGFP_ORF2 | ORF | pEGFP | EGFP-F | ORF-R | |
| L7Ae_ORF | ORF | pL7Ae | L7Ae-F2 | ORF-R | |
| 5'UTR | UTR | 5UTR_temp | T7pro1 | 5UTR-R | |
| 3'UTR | UTR | 3UTR_temp | 3UTR-F | 3UTR-R | |
| 4xT21 | UTR | p4xT21 | 3UTRmi-F | 3UTRmi-R | |

TABLE 4 mRNA sequences used in this study.

>hBax (SEQ ID NO: 12)
GGGCGAAUUAAGAGAGAAAAGAAGAGUAAGAAGAAAUAUAAGACACCGGUCG
CCACCAUGGACGGGUCCGGGGAGCAGCCCAGAGGCGG
GGGGCCCACCAGCUCUGAGCAGAUCAUGAAGACAGGGGCCCUUUUGCUUC
AGGGUUUCAUCCAGGAUCGAGCAGGGCGAAUGGGGGGGG
AGGCACCCGAGCUGGCCCUGGACCCGGUGCCUCAGGAUGCGUCCACCAAG
AAGCUGAGCGAGUGUCUCAAGCGCAUCGGGGACGAACUG
GACAGUAACAUGGAGCUGCAGAGGAUGAUUGCCGCCGUGGACACAGACUC
CCCCCGAGAGGUCUUUUUCCGAGUGGCAGCUGACAUGUU
UUCUGACGGCAACUUCAACUGGGGCCGGGUUGUCGCCCUUUUCUACUUUGC
CAGCAAAGUGGYGCUCAAGGCCCUGUGCACCAAGGUGC
CGGAACUGAUCAGAACCAUCAUGGGCUGGACAUUGGACUUCCUCCGGGAG
CGGCUGUUGGGCUGGAUCCAAGACCAGGGUGGUUGGGAC
GGCCUCCUCUCCUACUUUGGGACGCCCACGUGGCAGACCGUGACCAUCUUU
GUGGCGGGAGUGGUCACCGCCUCGCUCACCAUCUGGAA
GAAGAUGCGCUGACUCUAGACCUUCUGCGGGGCUUGCCUUCUGGCCAUGCCC
UUCUUCUCUCCCUUGCACCUGUACCUCUUGGUCUUUG
AAUAAAGCCUGAGUAGGAAAAAAAAAAAAAAAAAAAAAAAAAAAAAAAAAA
AAAAAAAAAAAAAAAAAAAAAAAAAAAAAAAAAAA
AAAAAAAAAAAAAAAAAAAAAAAAAAAAAAAAAAAAAAAAAAAA

>Kt hBax-4xT141-4xT142(3p)-4xT146a (SEQ ID NO: 13)
*GGAUCCGUGAUCGGAAACGUGAGAUCCACCUCAGAUCCGCUAGGACACCCGCAG
AUCGAGAAGAAGGCGAAUUAAGAGAGAAAAGAAGA
GUAAGAAGAAAUAUAAGACACCGGUCGCCACC*AUGGACGGGUCCGGGGAGC
AGCCCAGAGGCGGGGGGCCCACCAGCUCUGAGCAGAUC
AUGAAGACAGGGGCCCUUUUGCUUCAGGGUUUCAUCCAGGAUCGAGCAGG
GCGAAUGGGGGGGAGGCACCCGAGCUGGCCCUGGACCC
GGUGCCUCAGGAUGCGUCCACCAAGAAGCUGAGCGAGUGUCUCAAGCGCA
UCGCGGACGAACUGGACAGUAACAUGGAGCUGCAGAGGA
UGAUUGCCGCCGUGGACACAGACUCCCCCCGAGAGGUCUUUUUCCGAGUG
GCAGCUGACAUGUUUUCUGACGGCAACUUCAACUGGGGC
CGGGUUGUCGCCCGUUUCUACUUUGCCAGCAAACUGGUGCUCAAGGCCCUG
UGCACCAAGGUGCCGGAACUGAUCAGAACCAUCAUGGG
CUGGACAUUGGACUUCCUCCGGGAGCGGCUGUUGGGCUGGAUCCAAGACC
AGGGUGGUUGGGACGGCCUCCUCUCCUACUUUGGGACGC
CCACGUGGCAGACCGUGACCAUCUUUGUGGCGGGAGUGCUCACCGCCUCG
CUCACCAUCUGGAAGAAGAUGGGCUGAGCGGCCGCUAAA
*CCAUCUUUACCAGACAGUGUUACCAUCUUUACCAGACAGUGUUACCAUCUUUAC*
*CAGACAGUGUUACCAUCUUUACCAGACAGUGUUA**A
UCGAUGCCAUAAAGUAGGAAACACUACAUCCAUAAAGUAGGAAACACUACAUC
CAUAAAGUAGGAAACACUACAUCCAUAAAGUAGGAA
ACACUACAAAGCUU*AACCCAUGGAAUUCAGUUCUCAAACCCAUGGAAUUCAGUUC*
*UCAAACCCAUGGAAUUCAGUUCUCAAACCCAUCG*
*AAUUCAGUUCUCAGUCGAAGCUUCGAAUUCUGCAGUCGACUGAAUAAAGCCUG*
AGUAGGAAAAAAAAAAAAAAAAAAAAAAAAAAAA
AAAAAAAAAAAAAAAAAAAAAAAAAAAAAAAAAAAAAAAAAAAAAAAAAA
AAAAAAAAAAAAAAAAAAAAAAAAAAAAAAAAAA

>L7Ae-2A-Bcl2-4xT21 (SEQ ID NO: 14)
GGGCGAAUUAAGAGAGAAAAGAAGAGUAAGAAGAAAUAUAAGACACCGGUCG
CCACCAUGUACGUGAGAUUUGAGGUUCCUGAGGACAU
GCAGAACGAAGCUCUGAGUCUGCUGGAGAAGGUUAGGGAGAGCGGUAAGG
UAAAGAAAGGUACCAACGAGACGACAAAGGCUGUGGAGA
GGGGACUGGCAAAGCUCGUUUACAUCGCAGAGGAUGUUGACCCGCCUGAG
AUCGUUGCUCAUCUGCCCCUCCUCUGCGAGGAGAAGAAU
GUGCCGUACAUUUACGUUAAAAAGCAAGAACGACCUUGGAAGGGCUGUGGG
CAUUGAGGUGCAUGCGCUUCGGCAGCGAUAAUCAACGA
GGGAGAGCUGAGAAAGGAGCUUGGAAGCCUUGUGGAGAAGAUUAAAGGCC
UUCAGAAGGGAUCUGGCGCCACCAACUUCUCUCUGCUGA
*AGCAGGCCGGCGACGUGGAGGAGAACCCAGGCCCAAAUGGCGCACGCUGGGAGA
ACGGGGUACGAUAACCGGGAGAUAGUGAUGAAGUAC
AUCCAUUAUAAGCUGUCGCAGAGGGGCUACGAGUGGGAUGCGGGAGAUGU
GGGCGCCGCGCCCCGGGGCCGCCCCCGCACCGGGCAU
CUUCUCCUCCCAGCCCGGGCACACGCCCCAUCCAGCCGCAUCCCGGGACCC
GGUCGCCAGGACCUCGCCGCUGCAGACCCCGGCUGCCC
CCGGCGCCGCCGCGGGGCCUGCGCUCAGCCCGGUGCCACCUGUGGUCCAC
CUGACCCUCCGCCAGGCCGGCGACGACUUCUCCCGCCGC
UACCGCCGCGACUUCGCCGAGAUGUCCAGCCAGCUGCACCUGACGCCCUUC
ACCGCGCGGGGACGCUUUGCCACGGUGGUGGAGGAGCU
CUUCAGGGACGGGGUGAACUGGGGGAGGAUUGUGGCCUUCUUUGAGUUCG
GUGGGGUCAUGUGUGUGGAGAGCGUCAACCGGGAGAUGU
CGCCCCUGGUGGACAACAUCGCCCUGUGGAUGACUGAGUACCUGAACCGG
CACCUGCACACCUGGAUCCAGGAUAACGGAGGCUGGGAU
GCCUUUGUGGAACUGUACGGCCCCAGCAUGCGGCCUCUGUUUGAUUCUCC
UGGCUGUCUCUGAAGACUCUGCUCAGUUUGGCCCUGGU
GGGAGCUUGCAUCACCUGGGUGCCUAUCGGGCCACAAGUGAGUCUAGAC
CUUCUGCGGGGCGACGAGCUGUACAAGUAAUUCUAGAA

TABLE 4-continued mRNA sequences used in this study.

GAUCCCAAAUCAACAUCAGUCUGAUAAGCUAUCAACAUCAGUCUGAUAAGCUAUC
AACAUCAGUCUGAUAAGCUAUCAACAUCAGUCUG
AUAAGCUAAGAUCUCCCGGGCGUACAAGUAAAGCGUGAAUAAAGCCUGAGUAG
GAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAA

>L7Ae-24-Bcl2 (SEQ ID NO: 15)
GGGCGAAUUAAGAGAGAAAAGAAGAGUAAGAAGAAAUAUAAGACACCGGUCG
CCACCAUGUACGUGAGAUUUGAGGUUCCUGAGGACAU
GCAGAACGAAGCUCUGAGUCUGCUGGAGAAGGUUAGGGAGAGCGGUAAGG
UAAAGAAAGGUACCAACGAGACGACAAAGGCUGUGGAGA
GGGGACUGGCAAAGCUCGUUUACAUCGCAGAGGAUGUUGACCCGCCUGAG
AUCGUUGCUCAUCUGCCCCUCCUCUGCGAGGAGAAGAAU
GUGCCGUACAUUUACGUUAAAAGCAAGAACGACCUUGGAAGGGCUGUGGG
CAUUGAGGUGCCAUGCGCUUCGGCAGCGAUAAUCAACGA
GGGAGAGCUGAGAAAGGAGCUUGGAAGCCUUGUGGAGAAGAUUAAAGGCC
UUCAGAAGGGAUCU*GGCGCCACCAACUUCUCUCUGCUGA*
*AGCAGGCCGGCGACGUGGAGGAGAACCCA*GGCCCAAUGGCGCACGCUGGGAG
AACGGGUACGAUAACCGGGAGAUAGUGAUGAAGUAC
AUCCAUUAUAAGCUGUCGCAGAGGGGCUACGAGUGGGAUGCGGGAGAUGU
GGGCGCCGCGCCCCGGGGCCGCCCCCGCACCGGGCAU
CUUCUCCUCCCAGCCCGGGCACACGCCCCAUCCAGCCGCAUCCCGGGACCC
GGUCGCCAGGACCUCGCCGCUGCAGACCCCGGCUGCCC
CCGGCGCCGCCGCGGGGCCUGCGCUCAGCCCGGUGCCACCUGUGGUCCAC
CUGACCCUCCGCCAGGCCGGCGACGACUUCUCCCGCCGC
UACCGCCGCGACUUCGCCGAGAUGUCCAGCCAGCUGCACCUGACGCCCUUC
ACCGCGCGGGGACGCUUUGCCACGGUGGUGGAGGAGCU
CUUCAGGGACGGGGUGAACUGGGGGAGGAUUGUGGCCUUCUUUGAGUUCG
GUGGGGUCAUGUGUGUGGAGAGCGUCAACCGGGAGAUGU
CGCCCCUGGUGACAACAUCGCCCUGUGGAUGACUGAGUACCUGAACCGG
CACCUGCACACCUGGAUCCAGGAUAACGGAGGCUGGGAU
GCCUUUGUGGAACUGUACGGCCCCAGCAUGCGGCCUCUGUUUGAUUUCUCC
UGGCUGUCUCUGAAGACUCUGGUCAGUUUGGCCCUGGU
GGGAGCUUGCAUCACCCUGGGUGCCUAUCUGGGCCACAAGUGAGUCUAGAC
CUUCUGCGGGGCUUGCCUUCUGGCCCAUGCCCUUCUUCU
CUCCCUUGCACCUGUACCUCUUGGUCUUUGAAUAAAGCCUGAGUAGGAAAAA
AAAAAAAAAAAAAAAAAAAAAAAAAAAAAAAAAA
AAAAAAAAAAAAAAAAAAAAAAAAAAAAAAAAAAAAAAAAAAAAAAAAAA
AAAAAAAAAAAAAAAAAAAAAAAAAAAA

>mKate (SEQ ID NO: 16)
GGGCGAAUUAAGAGAGAAAAGAAGAGUAAGAAGAAAUAUAAGACACCGGUCCl
CCACCAUGGUGUCUAAGGGCGAAGAGCUGAUUAAGGA
GAACAUGCACAUGAAGCUGUACAUGGAGGGCACCGUGAACAACCACCACUU
CAAGUGCACAUCCGAGGGCGAAGGCAAGCCGUACGAGG
GCACCCAGACCAUGAGAAUCAAGGUGGUCGAGGGCGGCCCUCUCCCCUUC
GCCUUCGACAUCCUGGCUACCAGCUUCAUGUACGGCAGC
AAAACCUUCAUCAACCACACCCAGGGCAUCCCCGACUUCUUUAAGCAGUCC
UUCCCUGAGGGCUUCACAUGGGAGAGAGUCACCACAUA
CGAAGACGGGGGCGUGCUGACCGCUACCCAGGACACCAGCCUCCAGGACG
GCUGCCUCAUCUACAACGUCAAGAUCAGAGGGGUGAACU
UCCCAUCCAACGGCCCUGUGAUGCAGAAGAAAACACUCGGCUGGGAGGCCU
CCACCGAGAUGCUGUACCCCGCUGACGGCGGCCUGGAA
GGCAGAAGCGACAUGGCCCUGAAGCUCGUGGGCGGGGCCACCUGAUCUG
CAACUUGAAGACCACAUACAGAUCCAAGAAACCCGCUAA
GAACCUCAAGAUGCCCGGCGUCUACUAUGUGGACAGAAGACUGGAAAGAAU
CAAGGAGGCCGACAAAGAGACCUACGUCGAGCAGCACG
AGGUGGCUGUGGCCAGAUACUGCGACCUCCCUAGCAAACUGGGGCACAAA
CUUAAUUUGAUUCUAGACCUUCUGCGGGGCUUGCCUUCUG
GCCAUGCCCUUCUUCUCUCCCUUGCACCUGUACCUCUUGGUCUUUGAAUAAAG
CCUGAGUAGGAAAAAAAAAAAAAAAAAAAAAAAAAA
AAAAAAAAAAAAAAAAAAAAAAAAAAAAAAAAAAAAAAAAAAAAAAAAAA
AAAAAAAAAAAAAAAAAAAAAAAAAAAAAAA
AAAAA >EGFP-8xMS2 (SEQ ID NO: 17)
GGGCGAAUUAAGAGAGAAAAGAAGAGUAAGAAGAANAUAUAAGACACCGGUCG
CCACCAUGGUGAGCAAGGGCGAGGAGCUGUCCACCGG
GGUGGUGCCCAUCCUGGUCGAGCUGGACGGCGACGUAAACGCCACAAGU
UCAGCGUGUCCGGCGAGGGCGAGGGCGAUGCCACCUACG
GCAAGCUGACCCUGAAGUUCAUCUGCACCACCGGCAAGCUGCCCGUGCCCU
GGCCCACCCUCGUGACCACCCUGACCUACGGCGUGCAG
UGCUUCAGCCGCUACCCCGACCACAUGAAGCAGCACGACUUCUUCAAGUCC
GCCAUGCCCGAAGGCUACGUCCAGGAGCGCACCAUCUUU
CUUCAAGGACGACGGCAACUACAAGACCCGCGCCGAGGUGAAGUUCGAGG
GCGACACCCUGGUGAACCGCAUCGAGCUGAAGGGCAUCG TABLE 4-continued mRNA sequences used in this study.

ACUUCAAGGAGGACGGCAACAUCCUGGGGCACAAGCUGGAGUACAACUACA
ACAGCCACAACGUCUAUAUCAUGGCCGACAAGCAGAAG
AACGGCAUCAAGGUGAACCUCAAGAUCCGCCACAACAUCGAGGACGGAGC
GUGCAGCUCGCCGACCACUACCAGGAGAACACCCCCAU
CGGCGACGGCCCCGUGCUGCUGCCCGACAACCACUACCUGAGCACCCAGUC
CGCCCUGAGCAAAGACCCCAACGAGAAGCGCGAUCACA
UGGUCCUGCUGGAGUUCGUGACCGCCGCCGGGAUCACUCUCGGCAUGGAC
GAGCUGUACAAGUAAUUCUAGGCGAUCGCUCGAAAAACA
*UGAGGAUCACCCAUGUCUGCAGGUCGACUCUAGAAAACAUGAGGAUCACCCAUGU*
*CCUGCAGGUCGACUCUAGAUAAACAUGAGGAUCAC*
*CCAUGUCUGCAGGUCGACUCUAGAAAACAUGAGGAUCACCCAUGUCCUCGAAAAA*
*CAUGAGGAUCACCCAUGUCUGCAGGUCGACUGUA*
*GAAAACAUGAGGAUCACCCAUGUCCUGCAGGUCGACUCUAGAAAACAUGAGGAUC*
*ACCCAUGUCUGCAGGUCGACUCUAGAAAACAUGA*
*GGAUCACCCAUGUCCUCGAGGUGUGCGGCCGCUGAAUAAAGCCUGAGUAGGAA*
AAAAAAAAAAAAAAAAAAAAAAAAAAAAAAAAAAA
AAAAAAAAAAAAAAAAAAAAAAAAAAAAAAAAAAAAAAAAAAAAA
AAAAAAAAAAAAAAAAAAAAAAAAAAAA

>MS2 (SEQ ID NO: 18)
GGGCGAAUGAAGAGAGAAAAGAAGAGUAAGAAGAAAUAUAAGACACCGOUCO
CCACCAUGGGAUCCGCUUCUAACCUUACUCAGUUCGU
UCUCGUCGACAAUGGCGGAACUGGCGACGUGACUGUCGCCCCAAGCAACUU
CGCUAACGGGGUCGCUGAAUGGAUCAGCUCUAACUCGC
GAUCACAGGCUUACAAAGUAACCUGUAGCGUUCGUCAGAGCUCUGCGCAGA
AUCGCAAAUACACCAUCAAAGUCGAGGUGCCUAAAGGC
GCAUGGAGGUCUUACUUAAAUAUGGAACUAACCAUUCCAAUUUUCGCCACG
AAUUCCGACUGCGAGCUUAUUGUUAAGGCAAUGCAAGG
UCUCCUAAAAGAUGGAAACCCGAUUCCCUCGGCCAUCGCGGCCAACUCCGG
CAUCUACAGAUCUCAUAUGCAUCUCGAGUGAUAGUCUA
GACCUUCUGCGGGGCUUGCCUUCUGGCCAUGCCCUUCUUCUCUCCCUUGCACC
UGUACCUCUUGGUCUUGAAUAAAGCCUGAGUAGGA
AAAAAAAAAAAAAAAAAAAAAAAAAAAAAAAAAAAAAAAAAAAAAAAA
AAAAAAAAAAAAAAAAAAAAAAAAAAAAAAAAAAA
AAAAAAAAAAAAAAAAAAAAAAAAAAAA

>Kt-MS2-CNOT7 (SEQ ID NO: 19)
*GGAUCCGUGAUCGGAAACGUGAGAUCCACCUCAGAUCCGCUAGGACACCCGCAG*
AUCGAGAAGAAGGCGAAUUAAGAGAGAAAAGAAGA
GUAAGAAGAAAUAUAAGACACCGGUCGCCACCAUGGCUUCUAACUUUACUCA
GUUCGUUCUCGUCGACAAUGGCGGAACUGGCGACGUG
ACUGUCGCCCCAAGCAACUUCGCUAACGGGGUCGCUGAAUGGAUCAGCUCU
AACUCGCGUUCACAGGCUUACAAAGUAACCUGUAGCGU
UCGUCAGAGCUCUGCGCAGAAGCGCAAAUACACCAUCAAAGUCGAGGUGCC
UAAAGUGGCAACCCAGACUGUUGGUGGUGUAGAGCUUC
CUGUAGCCGCAUGGCGUUCGUACUUAAAUAUGGAACUAACCAUUCCAAUUU
UCGCCACGAAUUCCGACUGCGAGCUUAUUGUUAAGGCA
AUGCAAGGUCUCCUAAAAGAUGGAAACCCGAUUCCCUCGGCCAUCGCAGCA
AACUCCGGCAUCUACUCGAUCGCCAUGCCAGCGGCAAC
UGUAGAUCAUAGCCAAAGAAUUUGUGAAGUUUGGGCUUGCAACUUGGAUGA
AGAGAUGAAGAAAAUUCGUCAAGULAUCCGAAAAUAUA
AUUACGUUGCUAUGGACACCGAGUUUCCAGGUGUGGUUGCAAGACCCAUUG
GAGAAUUCAGGAGCAAUGCUGACUAUCAAUACCAACUA
UUGCGGUGUAAUGUAGCUUGUUAAAGAUAAUUCAGCUAGGACUGACAUUU
AUGAAUGAGCAAGGAGAAUACCCUCCCAGGAACUUCAAC
UUGGCAGUUUAAUUUUAAAUUUAAUUUGACGGAGGACAUGUAUGCCCAGGA
CUCUAUAGAGCUACUAACAACAUCUGGUAUCCAGUUUA
AAAAACAUGAGGAGGAAGGAAUUGAAACCCAGUACUUUGCAGAACUUCUUA
UGACUUCUGGAGUGGUCCUCUGUGAAGGGGUCAAAUGG
UUGUCAUUUCAUAGCGGUUACGACUUUGGCUACUUAAUCAAAAUCCUAACC
AACUCUAACUUGCCUGAAGAAGAACUUGACUUCUUUGA
GAUCCUUCGAUUGUUUUUUCCUGUCAUUUAUGAUGUGAAGUACCUCAUGAA
GAGCUCCAAAAAUCUCAAAGGUGGAUUACAGGAGGUGG
CAGAACAGUUAGAGCUGGAACGGAUAGGACCACAACAUCAGGCAGGAUCU
GAUUCAUUGCUCACAGGAAUGGCCUUUUCAAAAUGAGA
GAAAUGUUCUUUGAAGAUCAUAUUGAUGAUGCCAAAUAUUGUGGUCAUUUG
UAUGGCCUUGGUUCUGGUUCAUCCUAUGUACAGAAUGG
CACAGGGAAUGCAUAUGAAGAGGAAGCCAACAAGCAGUCAGUUUUAAAUCUA
GACCUUCUGCGGGGCUUGCCUUCUGGCCAUGCCCUUCU
UCUCUCCCUUGCACCUGUACCUCUUGGUCUUUGAAUAAAGCCUGAGUAGGAAA
AAAAAAAAAAAAAAAAAAAAAAAAAAAAAAAAAAA
AAAAAAAAAAAAAAAAAAAAAAAAAAAAAAAAAAAAAAAAAAAAA
AAAAAAAAAAAAAAAAAAAAAAAAAAAA

TABLE 4-continued mRNA sequences used in this study.

>L7Ae-4xFF4 (SEQ ID NO: 20)
GGGCGAAUUAAGAGAGAAAAGAAGAGUAAGAAGAAAUAUAAGACACCGGUCG
CCACCAUGUACGUGAGAUUUGAGGUUCCUGAGGACAU
GCAGAACGAAGCUCUGAGUCUGCUGGAGAAGGUUAGGGAGAGCGGUAAGG
UAAAGAAAGGUACCAACGAGACGACAAAGGCUGUGGAGA
GGGGACUGGCAAAGCUCGUUUACAUCGCAGAGGAUGUUGACCCGCCUGAG
AUCGUUGCUCAUCUGCCCCUCCUCUGCGAGGAGAAGAAU
GUGCCGUACAUUUACGUUAAAAGCAAGAACGACCUUGGAAGGGCUGUGGG
CAUUGAGGUGCCAUGCGCUUCGGCAGCGAUAAUCAACGA
GGGAGAGCUGAGAAAGGAGCUUGGAAGCCUUGUGGAGAAGAUUAAAGGCC
UUCAGAAGUAAGGCGCGCC*CCGCUUGAAGUCUUUAAUUA*
*AACCGCUUGAAGUCUUUAAUUAAACCGCUUGAAGUCUUUAAUUAAACCGCUUGAA*
*GUCUUUAAUUAAAGCUAGUUACCCAGCUUUCUUG*
UACAAAGUGAAUAAAGCCUGAGUAGGAAAAAAAAAAAAAAAAAAAAAAAAAA
AAAAAAAAAAAAAAAAAAAAAAAAAAAAAAAAAAAA
AAAAAAAAAAAAAAAAAAAAAAAAAAAAAAAAAAAAAAAAAAAAAAAAA
AAAAA

>EGFP (SEQ ID NO: 21)
GGGCGAAUUAAGAGAGAAAAGAAGAGUAAGAAGAAAUAUAAGACACCGGUCG
CCACCAUGGUGAGCAAGGGCGAGGAGCUGUUCACCGG
GGUGGUGCCCAUCCUGGUCGAGCUGGACGGCGACGUAAACGGCCACAAGU
UCAGCGUGUCCGGCGAGGGCGAGGGCGAUGCCACCUACG
GCAAGCUGACCCUGAAGUUCAUCUGCACCACCGGCAAGCUGCCCGUGCCCU
GGCCCACCCUCGUGACCACCCUGACCUACGGCGUGCAG
UGCUUCAGCCGCUACCCCGACCACAUGAAGCAGCACGACUUCUUCAAGUCC
GCCAUGCCCGAAGGCUACGUCCAGGAGCGCACCAUCUU
CUUCAAGGACGACGGCAACUACAAGACCCGCGCCGAGGUGAAGUUCGAGG
GCGACACCCUGGUGAACCGCAUCGAGCUGAAGGGCAUCG
ACUUCAAGGAGGACGGCAACAUCCUGGGGCACAAGCUGGAGUACAACUACA
ACAGCCACAACGUCUAUAUCAUGGCCGACAAGCAGAAG
AACGGCAUCAAGGUGAACUUCAAGAUCCGCCACAACAUCGAGGACGGCAGC
GUGCAGCUCGCCGACCACUACCAGCAGAACACCCCCAU
CGGCGACGGCCCCGUGCUGCUGCCCGACAACCACUACCUGAGCACCCAGUC
CGCCCUGAGCAAAGACCCCAACGAGAAGCGCGAUCACA
UGGUCCUGCUGGAGUUCGUGACCGCCGCCGGGAUCACUCUCGGCAUGGAC
GAGCUGUACAAGUAGGUCUAGACCUUCUGCGGGGCUUGC
CUUCUGGCCAUGCCCUUCUUCUCUCCCUUGCACCUGUACCUCUUGGUCUUUGA
AUAAAGCCUGAGUAGGAAAAAAAAAAAAAAAAAAAAA
AAAAAAAAAAAAAAAAAAAAAAAAAAAAAAAAAAA
AAAAAAAAAAA

>EGFP-PEST (SEQ ID NO: 22)
GGOCGAAULAAGAGAGAAAAGAAGAGUAAGAAGAAAUAUAAGACACCGGUCG
CCACCAUGGUGAGCAAGGGCGAGGAGCUGUUCACCGG
GGUGGUGCCCAUCCUGGUCGAGCUGGACGGCGACGUAAACGGCCACAAGU
UCAGCGUGUCCGGCGAGGGCGAGGGCGAUGCCACCUACG
GCAAGCUGACCCUGAAGUUCAUCUGCACCACCGGCAAGCUGCCCGUGCCCU
GGCCCACCCUCGUGACCACCCUGACCUACGGCGUGCAG
UGCUUCAGCCGCUACCCCGACCACAUGAAGCAGCACGACUUUCUU
CUUCAAGGACGACGGCAACUACAAGACCCGCGCCGAGGUGAAGUUCGAGG
GCGACACCCUGGUGAACCGCAUCGAGCUGAAGGGCAUCG
ACUUCAAGGAGGACGGCAACAUCCUGGGGCACAAGCUGGAGUACAACUACA
ACAGCCACAACGUCUAUAUCAUGGCCGACAAGCAGAAG
AACGGCAUCAAGGUGAACUUCAAGAUCCGCCACAACAUCGAGGACGGCAGC
GUGCAGCUCGCCGACCACUACCAGCAGAACACCCCCAU
CGGCGACGGCCCCGUGCUGCUGCCCGACAACCACUACCUGAGCACCCAGUC
CGCCCUGAGCAAAGACCCCAACGAGAAGCGCGAUCACA
UGGUCCUGCUGGAGUUCGUGACCGCCGCCGGGAUCACUCUCGGCAUGGAC
GAGCUGUACAAG*AAGCUUAGCCAUGGCUUCCCGCCGGAG*
*GUGGAGGAGCAGGAUGAUGGCACGCUGCCCAUGUCUUGUGCCCAGGAGAGCGG*
*GAUGGACCGUCACCCUGCAGCCUGUGCUUCUGCUAG*
*GAUCAAUGUG*9UAGCUCUAGACCUUCUGCGGGGCUUGCCUUCUGGCCAUGCCCU
UCUUCUCUCCCUUGCACCUGUACCUCUUGGUCUUUG
AAUAAAGCCUGAGUAGGAAAAAAAAAAAAAAAAAAAAAAAAAAA
AAAAAAAAAAAAAAAAAAAAAAAAAAAAAAA
AAAAAAAAAAAAAAAAAAAAAAAAAAAAAAAAAAAAAAAAA

>Kt-EGFP (SEQ ID NO: 23)
*GGAUCCGUGAUCGGAAACGUGAGAUCCACCCUCAGAUCCGCUAGGACACCCGCAG*
*AUCGAGAAGAAGGCGAAUUAAGAGAGAAAAGAAGA*
GUAAGAAGAAAUAUAAGACACCGGUCGCCACCAUGGGAUCCGUGAGCAAGGG
CGAGGAGCUGUUCACCGGGGUGGUGCCCAUCCUGGUC
GAGCUGGACGGCGACGUAAACGGCCACAAGUUCAGCGUGUCCGGCGAGGG
CGAGGGCGAUGCCACCUACGGCAAGCUGACCCUGAAGUU

TABLE 4-continued mRNA sequences used in this study.

```
CAUCUGCACCACCGGCAAGCUGCCCGUGCCCUGGCCCACCCUCGUGACCAC
CCUGACCUACGGCGUGCAGUGCUUCAGCCGCUACCCG
ACCACAUGAAGCAGCACGACUUCUUCAAGUCCGCCAUGCCCGAAGGCUACG
UCCAGGAGCGCACCAUCUUCUUCAAGGACGACGGCAAC
UACAAGACCCGCGCCGAGGUGAAGUUCGAGGGCGACACCCUGGUGAACCG
CAUCGAGCUGAAGGGCAUCGACUUCAAGGAGGACGGCAA
CAUCCUGGGGCACAAGCUGGAGUACAACUACAACAGCCACAACGUCUAUAU
CAUGGCCGACAAGCAGAAGAACGGCAUCAAGGUGAACU
UCAAGAUCCGCCACAACAUCGAGGACGGCAGCGUGCAGCUCGCCGACCACU
ACCAGCAGAACACCCCCAUCGGCGACGGCCCCGUGCUG
CUGCCCGACAACCACUACCUGAGCACCCAGUCCGCCCUGAGCAAAGACCCC
AACGAGAAGCGCGAUCACAUGGUCCUGCUGGAGUUCGU
GACCGCCGCCGGGAUCACUCUCGGCAUGGACGAGCUGUACAAGAGAUCUC
AUAUGCAUCUCGAGUGAUAGUCUAGACCUUCUGCGGGGC
UUGCCUUCUGGCCAUGCCCUUCUUCUCUCCCUUGCCCUGUACCUCUUGGUCU
UUGAAUAAAGCCUGAGUAGGAAAAAAAAAAAAAAAAA
AAAAAAAAAAAAAAAAAAAAAAAAAAAAAAAAAAAAAAAAAAAAAAAAAA
AAAAAAAAAAAAAAAAAAAAAAAAAAAAAAAAAAAAAA
AAAAAAAAAAAAAAAA

>L7Ae (SEQ ID NO: 24)
GGGCGAAUUAAGAGAGAAAAGAAGAGUAAGAAGAAAUAUAAGACACCGGUCG
CCACCAUGUACGUGAGAUUUGAGGUUCCUGAGGACAU
GCAGAACGAAGCUCUGAGUCUGCUGGAGAAGGUUAGGGAGAGCGGUAAGG
UAAAGAAAGGUACCAACGAGACGACAAAGGCUGUGGAGA
GGGGACUGGCAAAGCUCGUUUACAUCGCAGAGGAUGUUGACCCGCCUGAG
AUCGUUGCUCAUCUGCCCCUCCUCUGCGAGGAGAAGAAU
GUGCCGUACAUUUACGUUAAAAGCAAGAACGACCUUGGAAGGGCUGUGGG
CAUUGAGGUGCCAUGCGCUUCGGCAGCGAUAAUCAACGA
GGGAGAGCUGAGAAAGGAGCUUGGAAGCCUUGUGGAGAAGAUUAAAGGCC
UUCGAAGAGAUCUCAUAUGCAUCUCGAGUGAUAGUCUA
GACCUUCUGCGGGGCUUGCCUUCUGGCCAUGCCCUUCUUCUCUCCCUUGCACC
UGUACCUCUUGGUCUUUGAAUAAAGCCUGAGUAGGA
AAAAAAAAAAAAAAAAAAAAAAAAAAAAAAAAAAAAAAAAAAAAAAAAAA
AAAAAAAAAAAAAAAAAAAAAAAAAAAAAAAAAAAAAA
AAAAAAAAAAAAAAAAAAAAAAAAAAAAA
```

1. The 5' terminus of the mRNA is capped with 3'-O-Me-m'G
2. The protein coding regions are shown in bold.
3. The start and the stop codons are underlined.
4. RNA motifs, peptide tags and miRNA target sites are colored as indicated above each sequence.

Self-Replicating RNA Preparation and Electroporation

All replicon experiments were performed in BHK21 cells (a kind gift from Dr. Odisse Azizgolshan(34)) using an alphaviral replicon derived from the genome of the Sindbis virus TE12 strain (35) containing a P726S mutation in nsP2 (36) as described previously (37) or an alphaviral replicon derived from the Venezuelan equine encephalitis (VEE) TC-83 strain containing a A3G mutation in the 5'UTR and a Q739L mutation in nsP2 (38) constructed in this study. Briefly, BHK21 cells cultured at 37 degrees C. and 5% CO2 in EMEM (ATCC) medium containing 10% FBS (PAA) were electroporated using the Neon® Transfection System (Life Technologies) per the manufacturer's instructions with ~1-6 ug of replicon RNA per ~100,000 cells and plated in 24 well plates (Corning). Transfection details for all experiments are provided in Table 1. Sindbis replicon RNA was produced by run-off in vitro transcription (IVT) of SacI-HF (NEB)-digested replicon plasmid DNA using the mMES-SAGE mMACHINE® SP6 Kit (Life Technologies) and purified using the RNeasy® Mini Kit (Qiagen). VEE replicon RNA was produced by run-off in vitro transcription (IVT) of I-SceI (NEB)-digested replicon plasmid DNA using the MEGAscript® T7 Transcription Kit, followed by purification using the RNeasy® Mini Kit (Qiagen), denaturation of the RNA at 65 degrees C., enzymatic (cap1) capping of the RNA using the ScriptCap™ 2'-O-Methyltransferase Kit (Cellscript) and ScriptCap™ m7G Capping System (Cellscript), and a final purification using the RNeasy® Mini Kit (Qiagen) following the manufacturers' protocols. siRNAs (IDT) were co-electroporated (0-10 nM final concentration) along with replicon RNA. Cells were analyzed by flow cytometry 24 h post electroporation. Replicon encoding plasmids used as templates for IVT are listed in Table 5.

TABLE 5

Replicon constructs used in this study: sequences, GenBank files, and E. coli glycerol stocks for plasmids used for replicon RNA synthesis can be obtained from Addgene (deposit number 71270).

| | Replicon |
|---|---|
| pTK095 | SIN SP6 P1234 (nsP2 P726S) SGP(14) Kozak L7Ae-P2A-EYFP 4xFF4 8xMS2 |
| pTK101 | SIN SP6 P1234 (nsP2 P726S) SGP(14) mKate-G8-L7Ae-PEST 4xFF4 |
| pTK105 | SIN SP6 P1234 (nsP2 P726S) SGP(14) 2xK-turn EYFP-PEST |
| pTK194 | TC-83 I-SceI T7 5'UTR (A3G) P1234 (nsP2 Q739L) SGP XbaI attB1 Kozak mKate opal attB2 AscI (truncated E1) 3'UTR Poly A I-SceI |

TABLE 5-continued

Replicon constructs used in this study: sequences, GenBank files, and E. coli glycerol stocks for plasmids used for replicon RNA synthesis can be obtained from Addgene (deposit number 71270).

| | Replicon |
|---|---|
| pTK295 | SIN SP6 P1234 (nsP2 P726S) SGP(14) 2xK-turn Kozak EGFP |
| pTK296 | SIN SP6 P1234 (nsP2 P726S) SGP(14) 2xK-turn Kozak EGFP-PEST |
| pTK297 | SIN SP6 P1234 (nsP2 P726S) SGP(14) Kozak mKate-G8-L7Ae 4xFF4 |
| pTK298 | SIN SP6 P1234 (nsP2 P726S) SGP(14) Kozak mKate-G8-L7Ae-PEST 4xFF4 |
| pTK299 | SIN SP6 P1234 (nsP2 P726S) SGP(14) Kozak L7Ae-P2A-EYFP 4xFF4 |
| pTK312 | TC-83 I-SceI T7 5'UTR (A3G) P1234 (nsP2 Q739L) SGP XbaI attB1 Kozak EGFP ochre attB2 AscI (truncated E1) 3'UTR Poly A I-SceI |
| pTK313 | TC-83 I-SceI T7 5'UTR (A3G) P1234 (nsP2 Q739L) SGP XbaI attB1 Kozak EGFP-PEST ochre attB2 AscI (truncated E1) 3'UTR Poly A I-SceI |
| pTK317 | TC-83 I-SceI T7 5'UTR (A3G) P1234 (nsP2 Q739L) SGP(16) 2xK-turn Kozak EGFP attB2 AscI (truncated E1) 3'UTR Poly A I-SceI |
| pTK331 | TC-83 I-SceI T7 5'UTR (A3G) P1234 (nsP2 Q739L) SGP(14) Kozak mKate-G8-L7Ae-PEST 4xFF4 attB2 SGP2(98/30) XbaI attB1 EBFP2 ochre attB2 (insert) AscI (truncated E1) 3'UTR Poly A I-SceI |
| pTK332 | SIN SP6 P1234 (nsP2 P726S) SGP(14) 2xK-turn Kozak MS2-CNOT7 (SacI mutated)-P2A-EBFP2-4xFF5 |
| pTK333 | SIN SP6 P1234 (nsP2 P726S) SGP(14) Kozak MS2-CNOT7 (SacI mutated)-P2A-EBFP2 4xFF5 | qRT-PCR

In the case of pDNA and modRNA, total RNA was reverse transcribed with High-Capacity cDNA Reverse Transcription Kit (Life Technologies). Resulting cDNA was subjected to qPCR on StepOnePlus (Life Technologies) for modRNA using Power SYBR Green PCR Master Mix (Life Technologies). Same Master Mix and Mastercycler ep Realplex (Eppendorf) was used for pDNA experiments. For qRT-PCR of RNA replicons, total RNA was purified from BHK21 cells using the RNeasy® Mini Kit (Qiagen). RNA was reverse transcribed using the QuantiTect Reverse Transcription Kit (Qiagen) and qPCR was performed on a Mastercycler ep Realplex (Eppendorf) using the KAPA SYBR® FAST Universal 2xqPCR Master Mix (Kapa Biosystems) or the KAPA PROBE FAST Universal 2x qPCR Master Mix (Kapa Biosystems) following the manufacturer's recommended protocol. Primers unique to the genomic RNA regions were used to calculate the absolute copy number of genomic and antigenomic RNA using a standard curve of synthetic DNA. Subgenomic RNA copy numbers were calculated by subtracting the copy numbers of genomic and antigenomic RNA from the absolute copy numbers of all replicon RNA (i.e. genomic, antigenomic, and subgenomic RNA) using primers spanning the regions downstream of the SGP. Genomic and subgenomic RNA quantities were then normalized to 18S rRNA (internal control) levels quantified using QuantumRNA™ Universal 18S Internal Standard (Life Technologies) or Eukaryotic 18S rRNA Endogenous Control (FAM™/MGB probe, non-primer limited; Life Technologies).

Primer Sequences:

```
EGFP-qPCR-F
                                        (SEQ ID NO: 1)
AAGGGCATCGACTTCAAGG

EGFP-qPCR-R
                                        (SEQ ID NO: 2)
TGCTTGTCGGCCATGATATAG

VEE-nsP1-qPCR-F
                                        (SEQ ID NO: 3)
CTGACCTGGAAACTGAGACTATG

VEE-nsP1-qPCR-R
                                        (SEQ ID NO: 4)
GGCGACTCTAACTCCCTTATTG

VEE-nsP4-EGFP-qPCR-F
                                        (SEQ ID NO: 5)
CCCTATAACTCTCTACGGCTAAC

VEE-nsP4-EGFP-qPCR-R
                                        (SEQ ID NO: 6)
AGAAGTCGTGCTGCTTCA

SIN-nsP4-L7Ae-qPCR-F
                                        (SEQ ID NO: 7)
GGCGTGGTTTAGAGTAGGTATAA

SIN-nsP4-L7Ae-qPCR-R
                                        (SEQ ID NO: 8)
TCGTCTCGTTGGTACCTTTC

MS2-Taqman-F1
                                        (SEQ ID NO: 9)
GCTGAATGGATCAGCTCTAACT MS2-Taqman-R1
                                        (SEQ ID NO: 10)
CAGTCTGGGTTGCCACTTTA MS2-Taqman-P1-2
                                        (SEQ ID NO: 11)
ACCTGTAGCGTTCGTCAGTCCTCT
```

Flow Cytometry and Data Analysis

Cells were analyzed with LSR Fortessa or FACSAria flow cytometer, equipped with 405, 488 and 561 nm lasers (BD Biosciences). We collected 30,000-100,000 events per sample and fluorescence data were acquired with the following cytometer settings: 488 nm laser and 530/30 nm bandpass filter for EYFP/EGFP, 561 nm laser and 610/20 nm filter for mKate, and 405 nm laser, 450/50 filter for EBFP. In detecting mKate by FACSAria, a 780/60 nm bandpass filter was used. Data analysis was performed with FACSDiva software (BD Biosciences) and FlowJo (flowjo.com). For all fluorescence assays, populations containing live, single cells were first determined based on forward and side scatter. Red fluorescent protein (mKate) was used in all pDNA experiments as a transfection marker. Reported fluorescence values of pDNA experiments present normalized mean output fluorescence (EYFP, EGFP or EBFP) for all mKate positive cells. Non-transfected cells were used to set the gate determining mKate positive cells. For replicon electroporations and modRNA transfections the efficiency of nucleic acid delivery usually exceeds 90% and therefore all live, single cells were taken into account for calculating mean output fluorescence.

In FIG. 7B, output (EGFP) fluorescence level may depend both on circuit function and overall expression in a particular cell line (different promoter activities and transfection efficiencies). To account for cell type specific expression we therefore applied here normalization to mKate. Mean EGFP fluorescence for each sample was divided by mean mKate fluorescence and the ratio was normalized to the HEK293 level (HEK293 relative fluorescence set to 1).

Microscope Measurements and Image Processing

Fluorescence microscopy images of live cells were taken in 24-well plates using Zeiss Axiovert 200 microscope and Plan-Neofluar 10×/0.30 Ph1 objective. The filters used were 390/22 (excitation) and 460/50 (emission) for EBFP2, 500/20 (excitation) and 535/50 (emission) for EYFP and 565/30 (excitation) and 620/60 (emission) for mKate. Data collection and processing were performed using AxioVision software (Zeiss).

Apoptosis and Cell Death Assays

Sample cells including those in supernatant were collected 24 h post-transfection, washed with PBS and stained with Pacific Blue conjugated 1 µL of Annexin V (Life Technologies) or 0.5 µL of SYTOX AADvanced (Life Technologies) in 50 µL of binding buffer for 30 min at room temperature. The cells were analyzed by flow cytometry. Percentage of apoptosis induction was defined as the percentage of Annexin V positive cells. In the case of HEK/HeLa co-culture assay, HeLa cells were labeled with stable expression of EBFP2 fluorescent protein (excitation/emission maxima of 383 nm and 448 nm) and therefore SYTOX AADvanced (excitation/emission maxima of 546 nm and 647 nm) was used instead Pacific Blue Annexin V (excitation/emission maxima of 415 nm and 455 nm). HEK293 and HeLa-EBFP2 cells were mixed in 1:1 ratio, cultured together and the cell mixture was transfected with modRNA-encoded circuit or controls. Cells were stained with SYTOX AADvanced and analyzed by flow cytometry 24 h post-transfection. % of cell death was calculated as follows: (number of HEK (or HeLa) AAdvanced positive cells/total number of HEK (or HeLa) cells)*100%.

Generation of HeLa-EBFP2 Cells for Co-Culture Cell Death Assay

HeLa-EBFP2 cells were generated through lentiviral infection and antibiotic selection. First, HEK293FT packaging cells (Invitrogen) were used for virus production. $2\times10^6$ cells were seeded in a 60 mm dish (to ~80% confluency), approximately 3 h later supplemented with 3 ml of fresh complete medium and co-transfected with the following plasmids:

- 0.5 µg pLV-hEF1a-EBFP2-P2A-Bla (hEF1a—human elongation factor 1alpha promoter, P2A—ribosomal skipping 2A sequence from porcine teschovirus-1(39), Bla—blasticidin resistance gene)
- 1.1 µg pCMV-dR8.2 dvpr helper plasmid (40) (Addgene plasmid 8455)
- 0.55 µg pCMV-VSV-G helper plasmid (40) (Addgene plasmid 8454)

Transfections were performed using attractene (Qiagen) and standard manufacturer's protocol. Transfection complexes were added dropwise to the adhered cells without additional media change. 2 days later, media from virus producing cells were collected into 3 ml syringe, and pressed through a low protein binding 0.45 µm sterile filter. 1 ml of the filtered virus containing media was mixed with $4\times10^3$ HeLa cells in 0.5 ml fresh culture media and placed in a 12-well dish. Cells were supplemented with fresh media the next day and 10 µg/ml blasticidin (Invivogen) was added to the media on days 3-8 post-infection. Selected cells were over 99% BFP positive throughout the course of experiments as determined by flow cytometry. We additionally performed a fluorescent assay using our classifier circuit (as described in FIG. 8B) with HEK293, HeLa and HeLa-EBFP2 cells and we verified that the HeLa-EBFP2 cells behave as the parent cell line.

Computational Model

I. pDNA Model

Species:

| | |
|---|---|
| pC | nuclear MS2-CNOT7 plasmid |
| pL | nuclear L7Ae plasmid |
| mC | MS2-CNOT7 mRNA |
| mL | L7Ae mRNA |
| LmC | L7Ae protein bound to cytoplasmic MS2-CNOT7 mRNA |
| CmL | MS2-CNOT7 protein bound to cytoplasmic L7Ae mRNA |
| $L_2mC$ | L7Ae protein doubly bound to cytoplasmic MS2-CNOT7 mRNA |
| $C_2mL$ | MS2-CNOT7 protein doubly bound to cytoplasmic L7Ae mRNA |
| C | MS2-CNOT7 protein |
| L | L7Ae protein |

Reactions:

Transcription

Transcription is assumed to be first-order upon cell division when the pDNA enters the cell nucleus.

$$pC \rightarrow pC + mC \quad k_{TS} \quad [1]$$

$$pL \rightarrow pL + mL \quad k_{TS} \quad [2]$$

Translation

Translation is assumed to be first-order. While MS2-CNOT7 binding does not have any steric effect on L7Ae translation, bound L7Ae greatly inhibits translation. When one L7Ae protein is bound to the RNA it inhibits translation by a factor, σ, and when two copies of L7Ae are RNA-bound translation is inhibited twice as much.

$$mC \rightarrow mC + C \quad k_{TL} \quad [3]$$

$$LmC \rightarrow LmC + C \quad k_{TL} \cdot \sigma \quad [4]$$

$$L2mC \rightarrow L2mC + C \quad k_{TL} \cdot \sigma/2 \quad [5]$$

$$mL \rightarrow mL + L \quad k_{TL} \quad [6]$$

$$CmL \rightarrow CmL + L \quad k_{TL} \quad [7]$$

$$C2mL \rightarrow C2mL + L \quad k_{TL} \quad [8]$$

Repressor Binding/Unbinding

For simplicity, two binding sites were assumed for both MS2-CNOT7 and L7Ae RNA. A second-order association rate is used and first-order dissociation rate.

$$L + mC \leftrightarrow LmC \quad 2 \cdot k_{ON,L}, k_{OFF,L} \quad [9]$$

$$C + mL \leftrightarrow CmL \quad 2 \cdot k_{ON,C}, k_{OFF,C} \quad [10]$$

$$L + LmC \leftrightarrow L2mC \quad k_{ON,L}, 2 \cdot k_{OFF,L} \quad [11]$$

$$C + CmL \leftrightarrow C2mL \quad k_{ON,C}, 2 \cdot k_{OFF,C} \quad [12]$$

Degradation

First-order degradation rates were assumed. When the deadenylase MS2-CNOT7 is bound to L7Ae RNA it increases the RNA's degradation rate by a factor, α: In addition to these reactions, all species (including plasmids) are diluted by cell division.

$$mC \to 0 \quad \deg_R \quad [13]$$

$$mL \to 0 \quad \deg_R \quad [14]$$

$$LmC \to L \quad \deg_R \quad [15]$$

$$CmL \to C \quad \deg_R \cdot \alpha \quad [16]$$

$$LmC \to mC \quad \deg_P \quad [17]$$

$$CmL \to mL \quad \deg_P \quad [18]$$

$$L2mC \to 2 \cdot L \quad \deg_R \quad [19]$$

$$C2mL \to 2 \cdot C \quad \deg_R \cdot 2 \cdot \alpha \quad [20]$$

$$L2mC \to LmC \quad \deg_P \quad [21]$$

$$C2mL \to CmL \quad \deg_P \quad [22]$$

$$C \to 0 \quad \deg_P \quad [23]$$

$$L \to 0 \quad \deg_P \quad [24]$$

II. Replicon Model
Species:
rC cytoplasmic MS2-CNOT7 replicon (genomic)
rL cytoplasmic L7Ae replicon (genomic)
rfC MS2-CNOT7 replicon in spherule (replication factory)
rfL L7Ae replicon in spherule
LrC L7Ae protein bound to cytoplasmic MS2-CNOT7 replicon
CrL MS2-CNOT7 protein bound to cytoplasmic L7Ae replicon
L2rC L7Ae protein doubly bound to cytoplasmic MS2-CNOT7 replicon
C2rL MS2-CNOT7 protein doubly bound to cytoplasmic L7Ae replicon
mC MS2-CNOT7 mRNA (subgenomic)
mL L7Ae mRNA (subgenomic)
LmC L7Ae protein bound to cytoplasmic MS2-CNOT7 mRNA
CmL MS2-CNOT7 protein bound to cytoplasmic L7Ae mRNA
L2mC L7Ae protein doubly bound to cytoplasmic MS2-CNOT7 mRNA
C2mL MS2-CNOT7 protein doubly bound to cytoplasmic L7Ae mRNA
C MS2-CNOT7 protein
L L7Ae protein
Reactions:
Transport
In this simplified model, the transport of replicons to the plasma membrane and the creation of spherules is assumed to be a first-order process. The transport of replicons into spherules depends on nonstructural proteins and other cellular factors and occurs independently for each replicon. In the replicon case, we also consider the inhibition of replicon transport through RBP binding, where β is a fraction (1=no inhibition, 0=complete inhibition).

$$rC \to rC + rfC \quad k_{TR} \quad [1]$$

$$rL \to rL + rfL \quad k_{TR} \quad [2]$$

$$LrC \to LrC + rfC \quad k_{TR} \cdot \beta \quad [3]$$

$$CrL \to CrL + rfL \quad k_{TR} \cdot \beta \quad [4]$$

$$L2rC \to L2rC + rfC \quad k_{TR} \cdot \beta \quad [5]$$

$$C2rL \to C2rL + rfL \quad k_{TR} \cdot \beta \quad [6]$$

Transcription
Transcription is assumed to be first-order upon the formation of spherules (replication factories). Spherules can also transcribe more genomic RNA (Equations 9 and 10). This positive feedback is tuned by the fraction e.

$$rfC \to rfC + mC \quad k_{TS} \quad [7]$$

$$rfL \to rfL + mL \quad k_{TS} \quad [8]$$

$$rfC \to rfC + rC \quad k_{TS} \cdot \varepsilon \quad [9]$$

$$rfL \to rfL + rL \quad k_{TS} \cdot \varepsilon \quad [10]$$

Translation
Translation is assumed to be first-order as in the pDNA case.

$$mC \to mC + C \quad k_{TL} \quad [11]$$

$$LmC \to LmC + C \quad k_{TL} \cdot \sigma \quad [12]$$

$$L2mC \to L2mC + C \quad k_{TL} \cdot \sigma/2 \quad [13]$$

$$mL \to mL + L \quad k_{TL} \quad [14]$$

$$CmL \to CmL + L \quad k_{TL} \quad [15]$$

$$C2mL \to C2mL + L \quad k_{TL} \quad [16]$$

Repressor Binding/Unbinding
Second-order association rates and first-order dissociation rates were used as above. In the replicon system we assume RBPs can also bind the genomic RNA with the same efficacy (Equations 17-20).

$$L + rC \leftrightarrow LrC \quad 2 \cdot k_{ON,L}, k_{OFF,L} \quad [17]$$

$$C + rL \leftrightarrow CrL \quad 2 \cdot k_{ON,C}, k_{OFF,C} \quad [18]$$

$$L + LrC \leftrightarrow L2rC \quad k_{ON,L}, 2 \cdot k_{OFF,L} \quad [19]$$

$$C + CrL \leftrightarrow C2rL \quad k_{ON,C}, 2 \cdot k_{OFF,C} \quad [20]$$

$$L + mC \leftrightarrow LmC \quad 2 \cdot k_{ON,L}, k_{OFF,L} \quad [21]$$

$$C + mL \leftrightarrow CmL \quad 2 \cdot k_{ON,C}, k_{OFF,C} \quad [22]$$

$$L + LmC \leftrightarrow L2mC \quad k_{ON,L}, 2 \cdot k_{OFF,L} \quad [23]$$

$$C + CmL \leftrightarrow C2mL \quad k_{ON,C}, 2 \cdot k_{OFF,C} \quad [24]$$

Degradation
First-order degradation rates were assumed as above. We assume that the degradation factor for mRNAs bound by MS2-CNOT7 also applies to genomic replicon RNAs bound by MS2-CNOT7. Spherules are assumed to be stable for the 4 hours simulated here and are only diluted through cell division.

$$rC \to 0 \quad \deg_R \quad [25]$$

$$rL \to 0 \quad \deg_R \quad [26]$$

$$LrC \to L \quad \deg_R \quad [27]$$

$$CrL \to C \quad \deg_R \cdot \alpha \quad [28]$$

$$LrC \to rC \quad \deg_P \quad [29]$$

$$CrL \to rL \quad \deg_P \quad [30]$$

$$L2rC \to 2 \cdot L \ \deg_R \quad [31]$$

$$C2rL \to 2 \cdot C \ \deg_R \cdot 2 \cdot \alpha \quad [32]$$

$$L2rC \to LrC \ \deg_P \quad [33]$$

$$C2rL \to CrL \ \deg_P \quad [34]$$

$$mC \to 0 \ \deg_R \quad [35]$$

$$mL \to 0 \ \deg_R \quad [36]$$

$$LmC \to L \ \deg_R \quad [37]$$

$$CmL \to C \ \deg_R \cdot \alpha \quad [38]$$

$$LmC \to mC \ \deg_P \quad [39]$$

$$CmL \to mL \ \deg_P \quad [40]$$

$$L2mC \to 2 \cdot L \ \deg_R \quad [41]$$

$$C2mL \to 2 \cdot C \ \deg_R \cdot 2 \cdot \alpha \quad [42]$$

$$L2mC \to LmC \ \deg_P \quad [43]$$

$$C2mL \to CmL \ \deg_P \quad [44]$$

$$C \to 0 \ \deg_P \quad [45]$$

$$L \to 0 \ \deg_P \quad [46]$$

Introduction

Figure 9A:
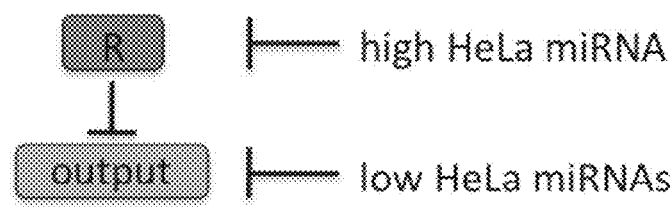
FIGS. 9A-9C. Schematic representation of the engineered post-transcriptional logic circuits. (a) multi-input microRNA sensor (cell type classifier), (b) post-transcriptional cascade (information transmission), and (c) switch (feedback regulation). R denotes post-transcriptional repressor.
Figure 9B:
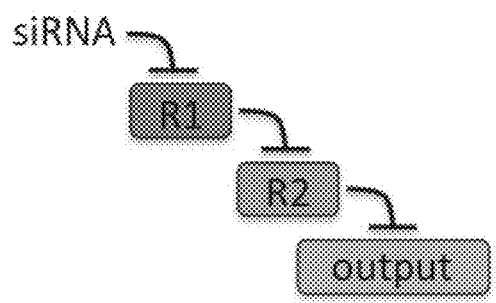
Figure 9C:
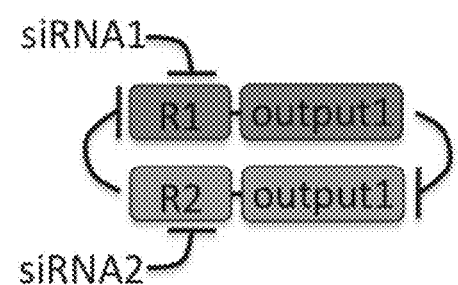

Gene delivery using messenger RNA (mRNA) rather than plasmid DNA (pDNA) may be safer owing to a reduced risk of genomic integration (2). Advances in chemical mRNA modification technology have made it possible to use stable in vitro synthesized mRNA with low immunogenicity for gene therapy (21). Self-replicating RNAs that couple RNA-only delivery with prolonged gene expression are of interest for biomedical applications including vaccination and stem cell reprogramming (21). Synthetic biology, however, has so far relied exclusively or partially on transcriptional regulation, which requires introduction of foreign DNA (9, 10). RNA-based regulatory parts, such as aptamers or riboswitches (22-24) cannot currently be interconnected to build complex RNA-encoded circuits. RNA strand displacement reactions, used to date only in bacteria (25, 26) could be combined into logic circuits (27). However, such multi-layered RNA circuits have not yet been successfully implemented. We propose that RNA-binding proteins (RBPs) (12) can function as both the input and the output of RNA regulatory devices and be wired to regulate production of each other towards the construction of complex circuits. The synthetic circuits containing RBPs reported to date have not shown that one RBP can regulate another and have depended on both translational and transcriptional regulation, requiring the use of pDNA for circuit delivery (24). Additionally, general mechanisms to regulate expression from synthetic mRNA or RNA replicons have not yet been implemented. In this article we report that RBP regulatory devices can be wired together and interconnected with cellular and synthetic signaling pathways to build complex circuits that can be delivered to mammalian cells as RNA. We characterize and optimize of a set of RBP devices and then use them to engineer diverse regulatory circuits including a multi-input cell type classifier, a cascade and a switch (FIGS. 9A-9C). These circuits carry out signal processing operations that detect intracellular biomarker levels, transmit information between cascaded regulatory devices and conserve circuit state through feedback regulation. We also show that the classifier can be used for selective induction of apoptosis in a targeted cell type (HeLa cancer cells) using RNA-only delivery.

As a first step toward creating RNA-encoded circuits, we optimized and characterized a set of RNA repressor devices comprising RBPs and their binding motifs (FIGS. 10A-10E and FIG. 11). Of the tested devices, L7Ae:K-turn system (12) and MS2-CNOT7:MS2 binding motif (29) were the most potent and used for further circuit construction.

As a first step toward creating RNA-encoded circuits, we improved the L7Ae:K-turn system (12). L7Ae is an archaeal protein that binds a K-turn motif with high affinity. When the K-turn motif is placed in the 5'UTR of target mRNA, L7Ae represses translation of the output gene. We increased repression of this system by using two repeats of the K-turn motif with a short 5'UTR (FIGS. 10A, 10C, and 10E). In the optimized system the repressed sub-population cannot be easily distinguished from the untransfected sub-population, thus creating an overall apparent unimodal response. Next, we characterized in mammalian cells the efficacy of MS2 coat protein fusions with various repression domains 4 (FIG. 10B), including N-terminal repression domains of PUF proteins as well as human and *Drosophila* deadenylases CNOT7 and POP2 (FIG. 10D-10E, FIG. 11). The target/reporter mRNA contains eight repeats of the MS2 binding site in the 3'UTR. MS2 RNA binding domain localizes the fused repression domain to the reporter mRNA. The repression mechanism of PUF proteins is not fully understood but they cause degradation of the targeted mRNA by recruiting deadenylases and also act in deadenylation-independent manner (29). Of the tested set of repressors, MS2-CNOT7 and MS2-POP2 were the most potent and MS2-CNOT7 was selected for further circuit construction.

Figure 16:
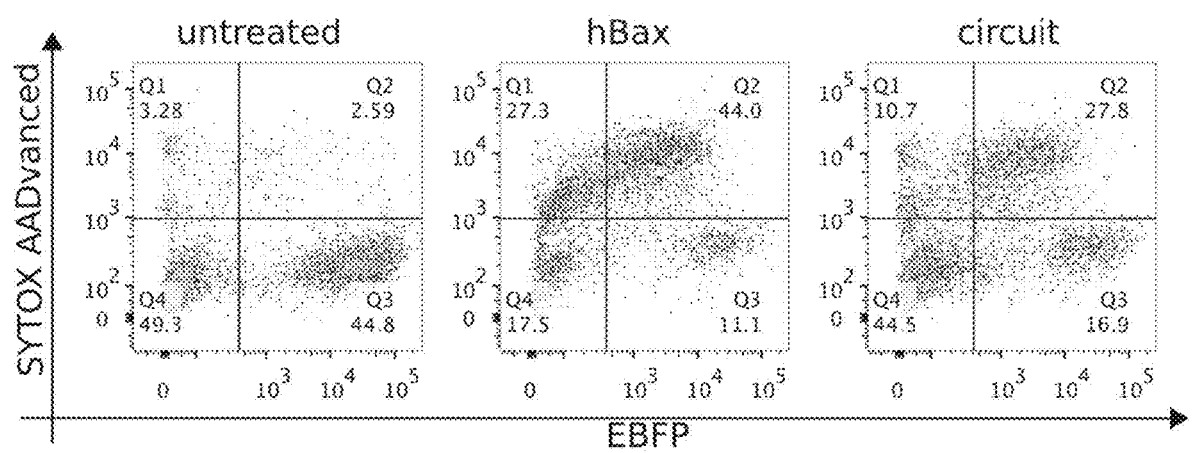
FIG. 16. Representative two-dimensional flow cytometry plots for cell death assay with modRNA as circuit carrier in mixed cell culture (HEK 293+HeLa-EBFP2 cells). HeLa classifier circuit cell death assay (FIG. 7E) additional data. Q4: live HEK 293, Q3: live HeLa-EBFP2, Q1: dead HEK 293, Q2: dead HeLa-EBFP2. AADvanced staining and flow cytometry were performed 24 h post-transfection. AnnexinV-Pacific Blue conjugate was not used in this case, as its excitation/emission spectra (Ex: 410 nm, Em: 455 nm) overlap with those of EBFP2 (Ex: 383 nm, Em: 448 nm).

To show that these RBP-based repressors can be used as a platform for composite RNA-encoded circuits, we engineered a multi-input microRNA sensing circuit that is a simplified post-transcriptional only version of our previously reported HeLa cell classifier (15). The circuit recognizes whether the cell has a microRNA expression profile indicative of HeLa cells (high miR-21, low miR141, 142(3p) and 146a) and triggers a response only if the profile is matched (FIG. 7, FIG. 9A). The circuit topology consists of two basic sensory modules, one for specific microRNAs that are highly expressed in the cancer phenotype (HeLa-high) and one for the microRNAs that are expressed at low levels (HeLa-low). HeLa-high microRNAs affect circuit output via double inversion by repressing L7Ae, which allows expression of an output protein. HeLa-low microRNAs directly repress translation of the output. As shown in FIG. 7B and FIG. 12A-12C, the L7Ae-based classifier is able to distinguish HeLa cells from HEK 293 and MCF7 in a fluorescence assay. While single microRNAs are often sufficient to differentiate between pairs of cell types (FIG. 13) a multi-input circuit is needed to distinguish HeLa cells from many other cell types simultaneously (15). When a pro-apoptotic gene hBax is incorporated as circuit output, the classifier selectively kills HeLa cells and does not strongly affect viability of HEK cells (FIGS. 7C-7D, FIGS. 14 and 15). Specific induction of apoptosis was achieved using both pDNA and modified mRNA (modRNA) to deliver circuits. Furthermore, the modRNA circuit specifically killed HeLa cells in a mixed HeLa/HEK cell population (FIG. 8E, FIG. 16). The performance of our new classifier coupled with the RNA-only delivery provides a safer means for using such classifier synthetic network for a range of applications, including selective stem cell reprogramming or vaccination.

We next connected RBP devices to produce a scalable RNA-only circuit design platform. To generate a one-way information transmitter, we designed a post-transcriptional cascade with three repression stages (FIG. 8A-8D, FIG. 9B). The input to the cascade (FIG. 8A) is a synthetic siRNA-FF4 which modulates expression of L7Ae through four repeats of the 1-1.4 target site in the 3'UTR. L7Ae then binds the K-turn motifs in the 5'UTR of RNA that encodes a second repressor, MS2-CNOT7, which regulates expression of output EGFP containing eight repeats of the MS2 binding site in its 3'UTR. We tested the behavior of the circuit with pDNA and modRNA transfections (FIG. 8B, FIGS. 17A-17D) and quantified cascade operation for a range of input concentrations and times (FIGS. 18A-C, 19A-19F, and 20A-20F).

Figure 25:
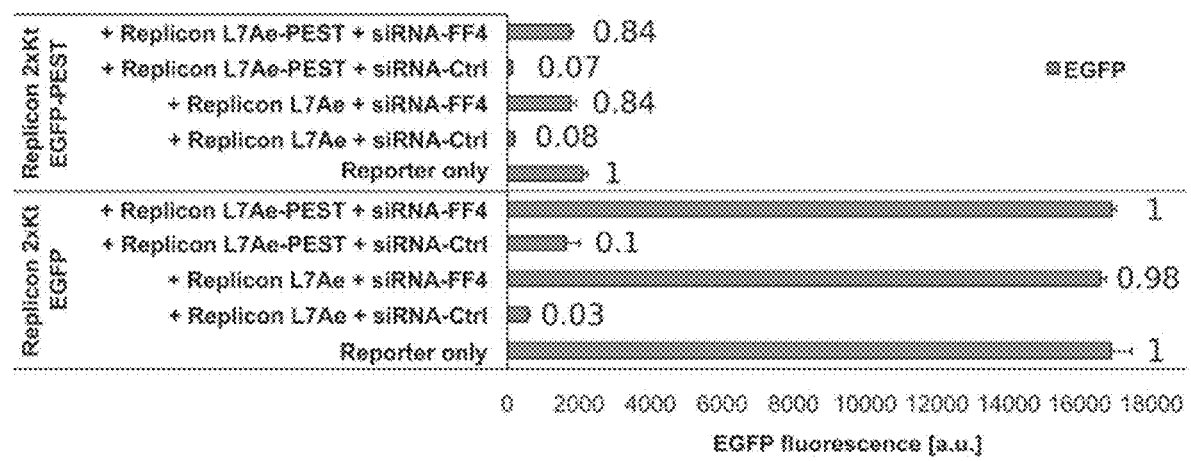
FIG. 25. Operation of the Sindbis replicon two-stage cascade with or without a degradation domain (PEST) fused to the reporter or repressor. PEST domains (41) reduce the half-life of a protein by targeting the protein for ubiquitin and proteasome-mediated degradation, providing means for additional tuning of the circuit and potentially faster dynamics. Design of the Sindbis replicon encoded two-stage cascade is as depicted in FIG. 8C. Variations of the original construct in which the EGFP reporter and/or the mKate-L7Ae repressor contained a C-terminal PEST domain fusion were tested. Experiments were performed in BHK-21 cells. Arbitrary units of EGFP fluorescence are plotted. Numbers inside or by the individual bars within the chart indicate EGFP expression level relative to each "Reporter only" construct (i.e. "Replicon 2×Kt EGFP" or "Replicon 2×Kt EGFP-PEST").
Figure 26A:
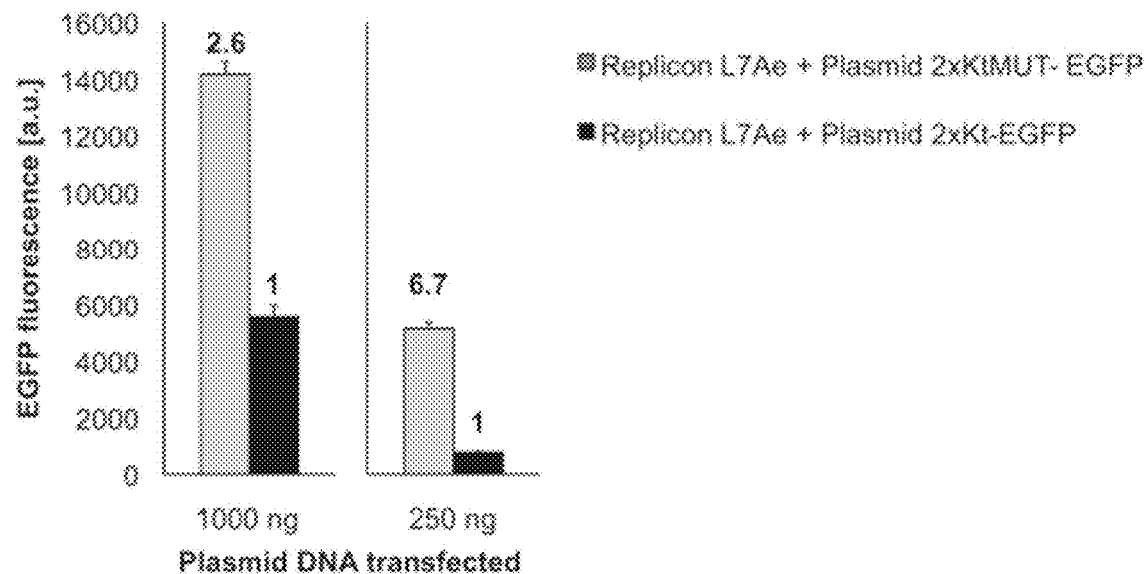
FIGS. 26A-26C. Repression of plasmid DNA (pDNA) 2×K-turn reporter by Sindbis replicon L7Ae and expression kinetics of the electroporated pDNA reporter (mixed pDNA/replicon delivery). (a) Replicon L7Ae was co-electroporated with pDNA 2×K-turn EGFP or pDNA mutant 2×K-turn EGFP into BHK21 cells and fluorescence levels were measured by flow cytometry. Arbitrary units of EGFP fluorescence are plotted. Numbers inside the chart indicate EGFP expression level relative to the "repressed state" (i.e. Replicon L7Ae+pDNA 2×K-turn EGFP). (b,c) Kinetics of EGFP expression from the electorporated pDNA 2×K-turn reporter. Expression was measured 3 h, 6 h, 12 h, and 24 h after electroporation. Arbitrary units of EGFP fluorescence are plotted using linear or log scales. L7Ae expressed from a replicon can repress a reporter gene with K-turn motifs expressed from pDNA upon replicon/pDNA co-electroporation (a), however, the repression efficiency is lower than when both the repressor and reporter are expressed from replicons (FIG. 8D, FIG. 25). This can be explained by the observation that a protein regulated by an SGP is expressed only after a lag due to dynamics of RNA replication, whereas a protein encoded on a plasmid is expressed much more quickly following electroporation (b,c). Note, that all other pDNA experiments in this study were carried out with lipid-based transfection, which also results in a lag in expression (FIGS. 19A-19F).
Figure 26B:
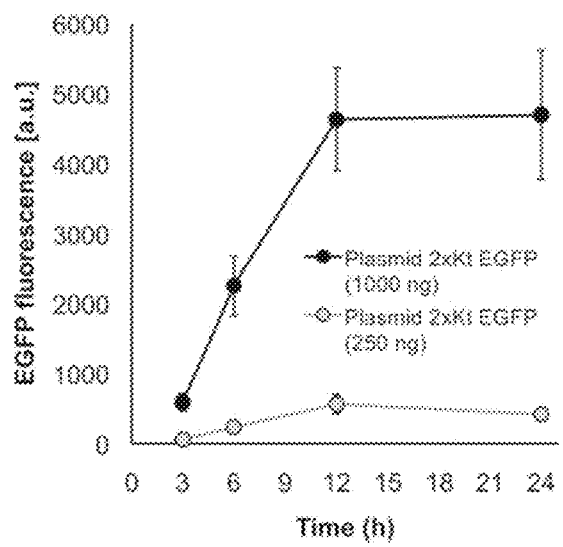
Figure 26C:
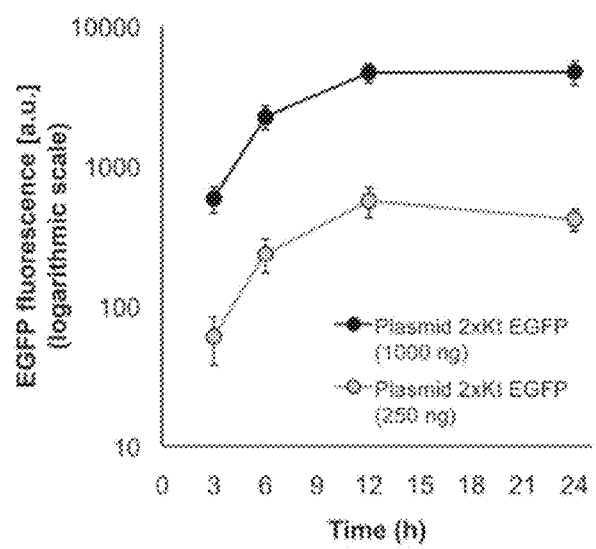
Figure 27:
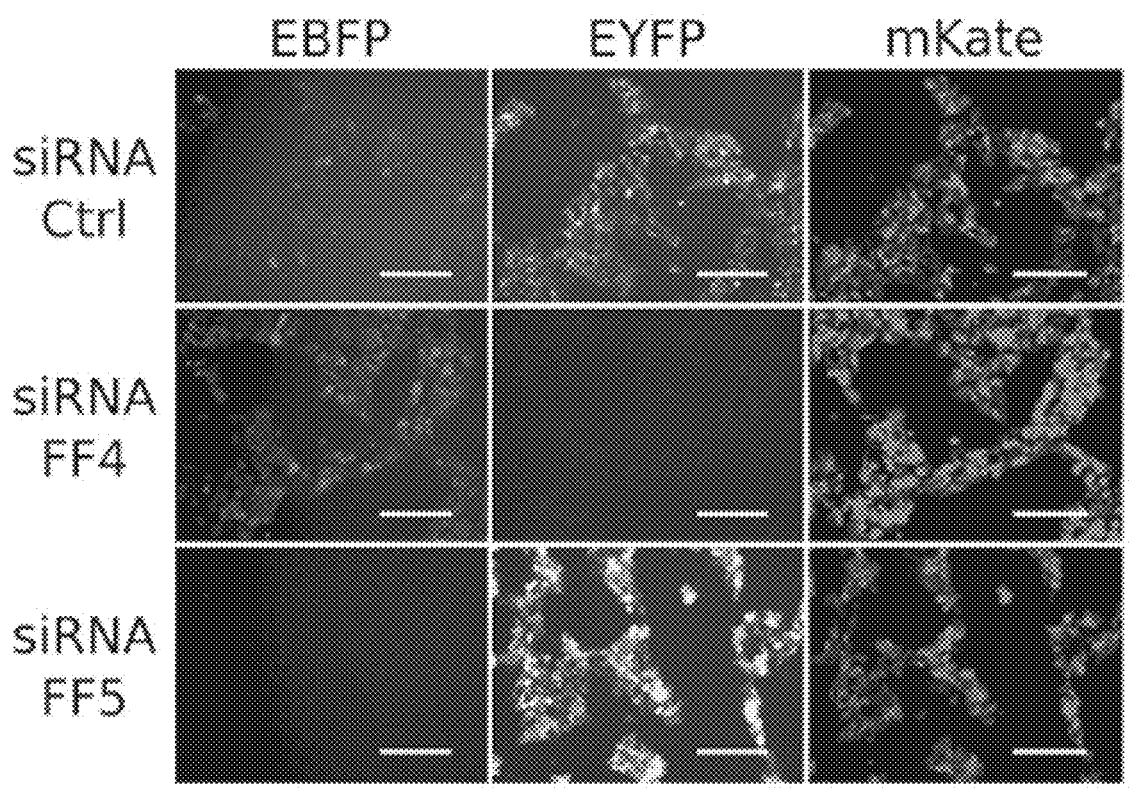
FIG. 27. Representative fluorescent microscopy images for switch circuit (pDNA as the circuit carrier). Images correspond to FIGS. 8E-8G (pDNA). Scale bars indicate 200 μm.
Figure 28:
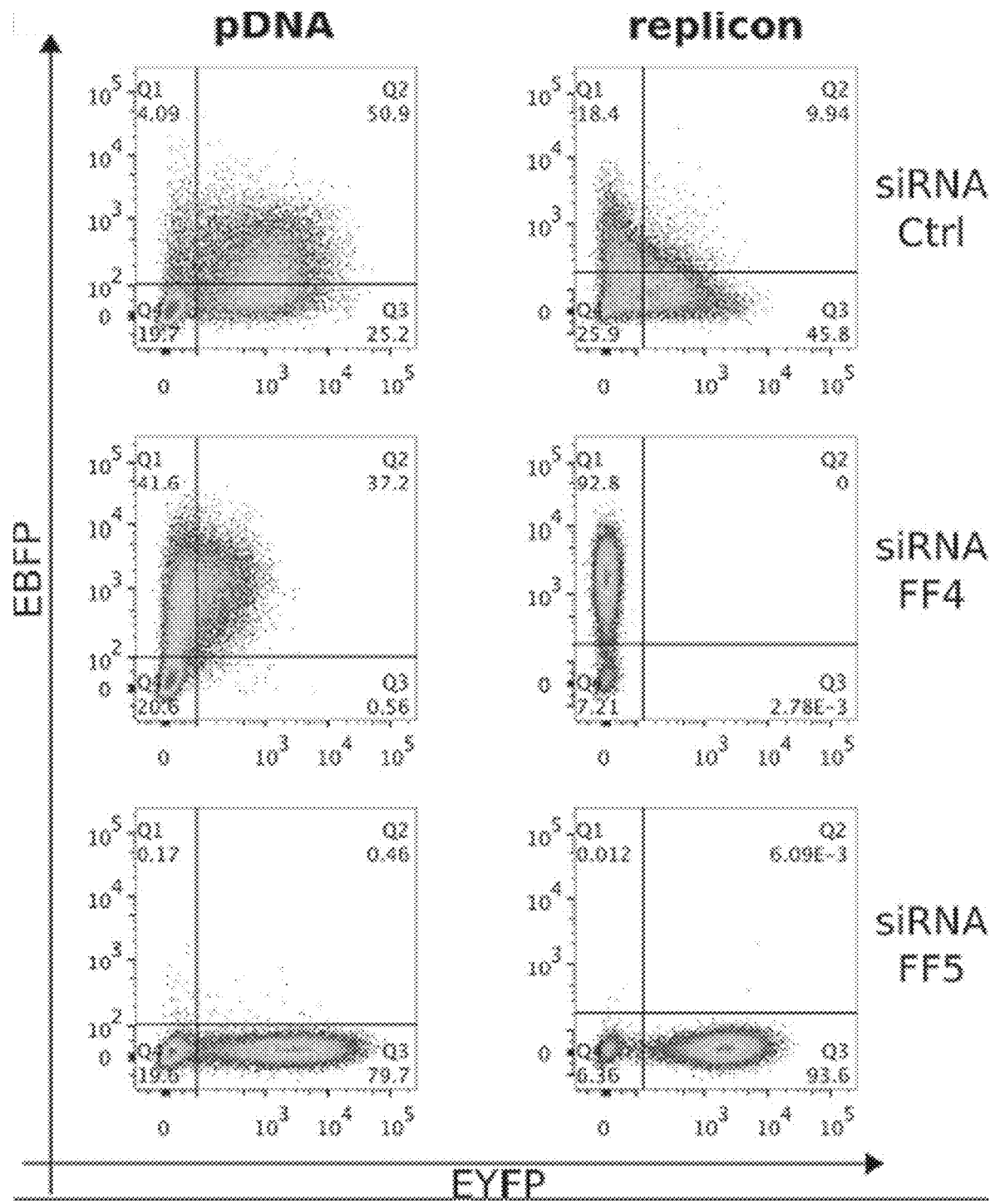
FIG. 28. Representative flow cytometry data for switch circuit. The graphs correspond to FIG. 8F, but additionally include axes labels and sub-population statistics. Gates shown on the plots were established based on negative (non-transfected) cells and cells transfected with EYFP or EBFP only. In the case of pDNA, only transfected cells (based on mKate transfection marker) were used to calculate output mean fluorescence (for EYFP or EBFP2). Replicon electroporations result in very high transfection efficiencies (Table 1), and therefore all live cells were used for calculation of the means in the replicon case and the grid lines are only included for visual guidance.
Figures 29A, 29B, 29C, 29D:
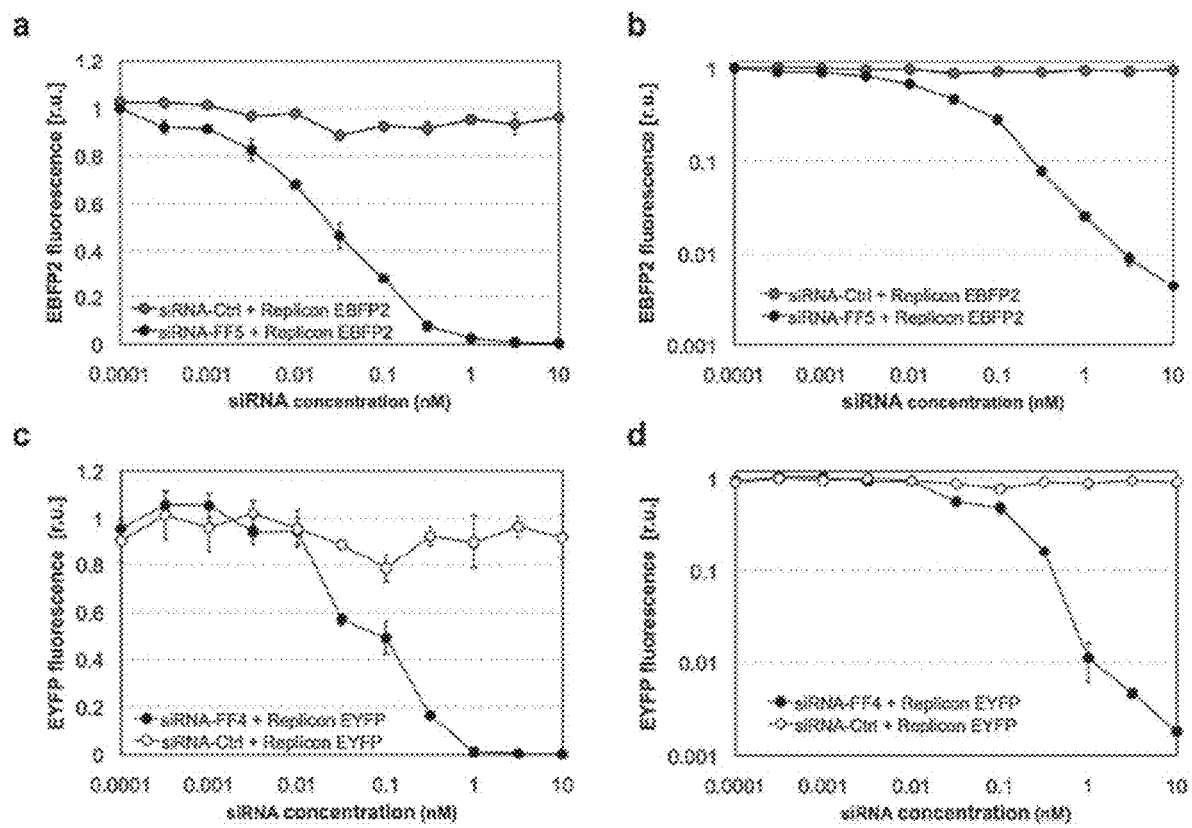
FIGS. 29A-29D. Characterization of siRNA knock-down efficiency of Sindbis replicons comprising the post-transcriptional switch. Increasing concentrations of siRNA targeting the MS2-CNOT7 EBFP2 replicon (a [linear scale y-axis], b [log scale y-axis]: siRNA-FF5) or replicon L7Ae EYFP (c [linear scale y-axis], d [log scale y-axis]: siRNA-FF4) were co-electroporated with corresponding target replicon into BHK21 cells. Fluorescence levels were measured by flow cytometry and normalized to a replicon-only control transfection without siRNA. Non-specific siRNA was used as a negative control (siRNA-Ctrl).

A two-stage version of the cascade was encoded on self-replicating RNA derived from Sindbis virus (30) (FIGS. 8C-8D, FIG. 17C). Replication is mediated by the viral RNA-dependent RNA polymerase (RdRp; comprised of nonstructural proteins nsP1-nsP4) and enables long-term gene expression (FIGS. 21, 22A-22E, 23A-23C, and 24A-24B). Production of exogenous genes is driven by a subgenomic promoter (SGP) of the replicon. In our replicon-encoded cascade circuit, siRNA-FF4 (input) regulates expression of L7Ae. The repressor is under the control of the replicon SGP and additionally contains four repeats of the F1-4 target site in its 3'UTR. A separate co-transfected replicon encodes output EGFP with two repeats of the K-turn motif in the 5'UTR. As shown in FIG. 8D and FIG. 25, L7Ae expression results in 29-fold repression of EGFP (stage 1), and knockdown of L7Ae by synthetic siRNA-FF4 fully restores the output (stage 2). The cascade also functions with combined replicon/pDNA co-electroporation, albeit with reduced repression efficiency (FIGS. 26A-26C).

Plasmid DNA (pDNA). Plasmids have been widely used for delivery and expression of foreign genes in mammalian cells. The ease and cost efficiency of sequence modification and pDNA handling make plasmids a popular modality for delivery in many types of experiments. pDNA constructs are also relatively stable and less prone to folding than RNA. While pDNA delivery leads mostly to transient expression, the DNA can still randomly integrate into the host genome, posing serious safety concerns. Additionally, the many steps required between transiently transfected pDNA cell entry and gene expression (nuclear transport of pDNA, transcription, mRNA transport to the cytoplasm and translation) as well as cell-to-cell variability in transfection amount make it a relatively noisy method, which may be not desirable for certain applications.

Modified mRNA (modRNA). Instead of being produced from delivered DNA, mRNAs synthesized in vitro have also been transferred directly into target cells. The use of mRNAs is gaining interest particularly in therapeutic applications due to its safety profile (53). The 5' end of endogenous mRNAs in eukaryotic cells is modified with a 7-methylguanosine cap structure, and their 3' ends are polyadenylated. These end structures play an essential role in post-transcriptional processes and facilitate protein production (54). Modification of pyrimidine residues is also known to enhance transgene expression from delivered mRNAs mostly because these modifications to the RNA molecules result in lower stimulation of the innate immune system of host cells (55). modRNAs used in this study contain anti-reverse cap analog and 120-nt poly(A) tail. In addition, all cytosine and uridine residues are replaced with 5-methylcytosine and pseudouridine.

Figure 21:
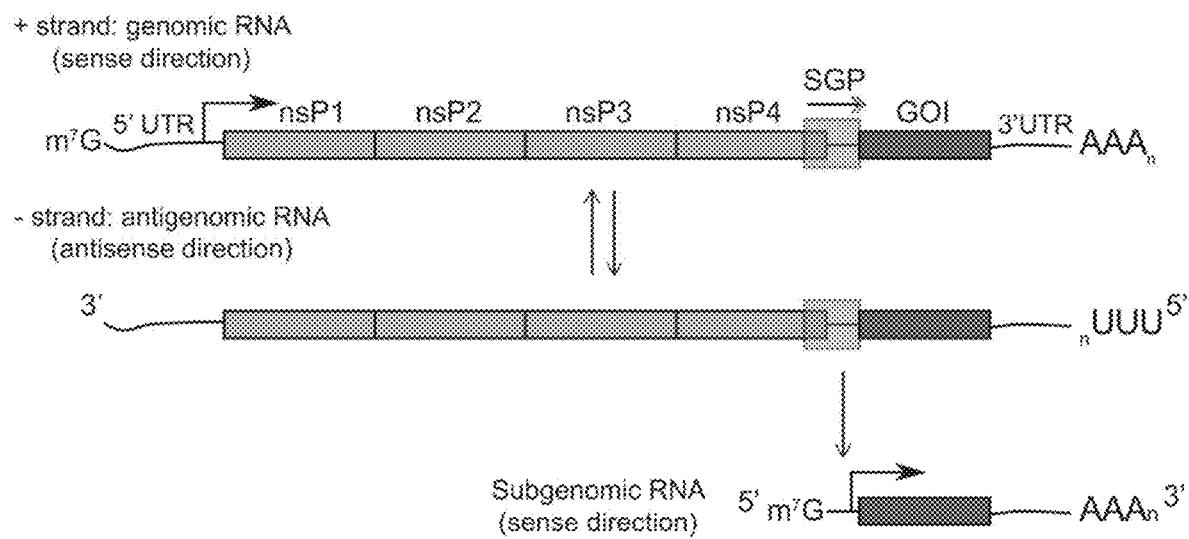
FIG. 21. Replicon life cycle. Replicon RNAs used in this study contain a 7-methylguanosine cap, a 5'UTR, an RNA-dependent RNA polymerase (RdRp) polyprotein P1234 (i.e. nonstructural proteins [nsPs]), a subgenomic promoter element (SGP), a variable region of interest from which a reporter protein or RNA binding protein is expressed (GOI), a 3'UTR, and a poly(A) tail (+strand). Once the replicon RNA (generated by in vitro transcription) is transfected into a cell, the polyprotein P1234 is translated. Alphaviral RNA synthesis occurs at the plasma membrane of a cell, where the nsPs, together with alphaviral RNA, form membrane invaginations (or "spherules" (42, 43)). These spherules contain dsRNA created by replication of "+" strand viral genomic RNA into "−" strand anti-genomic RNA. The "−" strand serves as a template from which additional "+" strand genomic RNA (synthesized from the 5'UTR) or a shorter subsequence of the genomic RNA (termed subgenomic RNA) is synthesized from the subgenomic promoter region located near the end of the nonstructural protein ORF. The "+" strand genomic RNA and the subgenomic RNA are exported out of the spherules into the cytoplasm where they are translated by endogenous ribosomes.
Figure 22A:
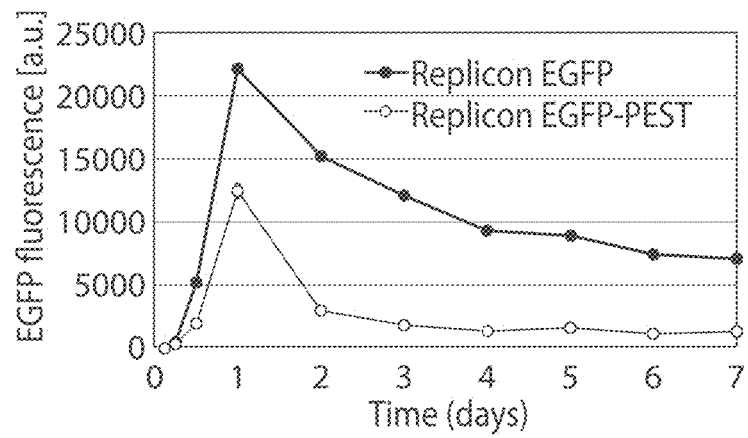
FIGS. 22A-22E. VEE replicon time-lapse flow cytometry and qPCR. (a,b) Replicons encoding constitutive EGFP or EGFP-PEST (41) were electroporated into BHK21 cells and EGFP fluorescence was measured by flow cytometry at 3 h, 6 h, 12 h, day 1, day 2, day 3, day 4, day 5, day 6, and day 7 (a [linear scale y-axis], b [log scale y-axis]). (c) The percentage of EGFP positive cells at the same time points as in (a) are plotted. (d,e) Replicon EGFP or EGFP-PEST genomic RNA levels in (a) were measured by qRT-PCR (d [linear scale y-axis], e [log scale y-axis]).
Figure 22B:
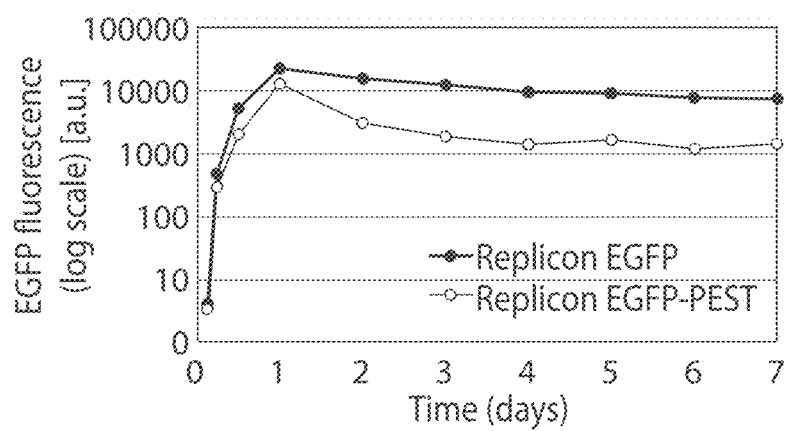
Figure 22C:
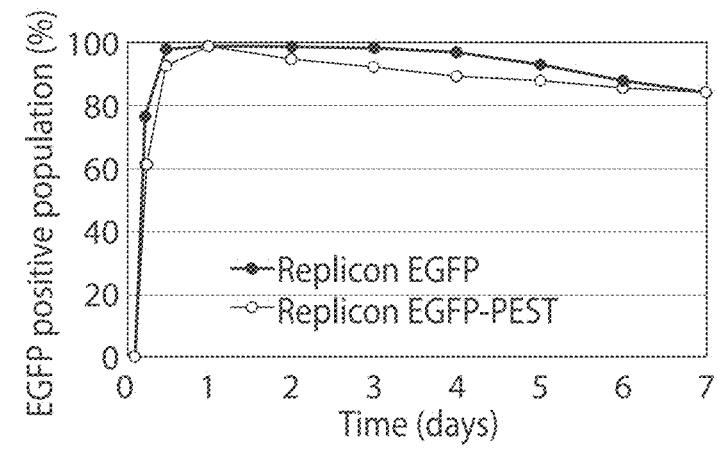
Figure 22D:
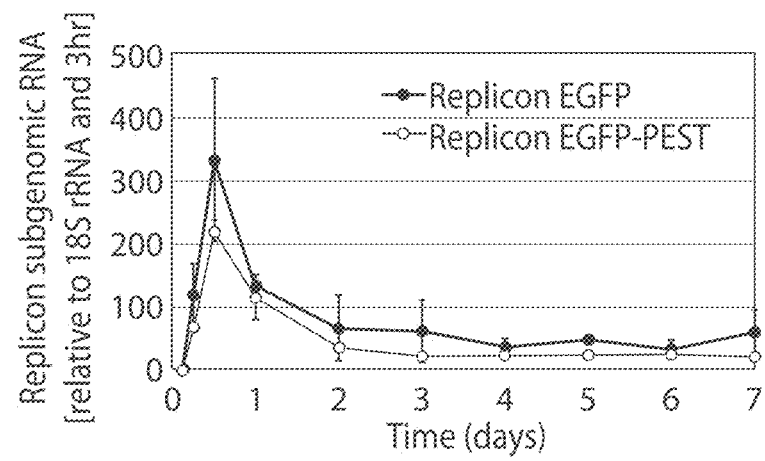
Figure 22E:
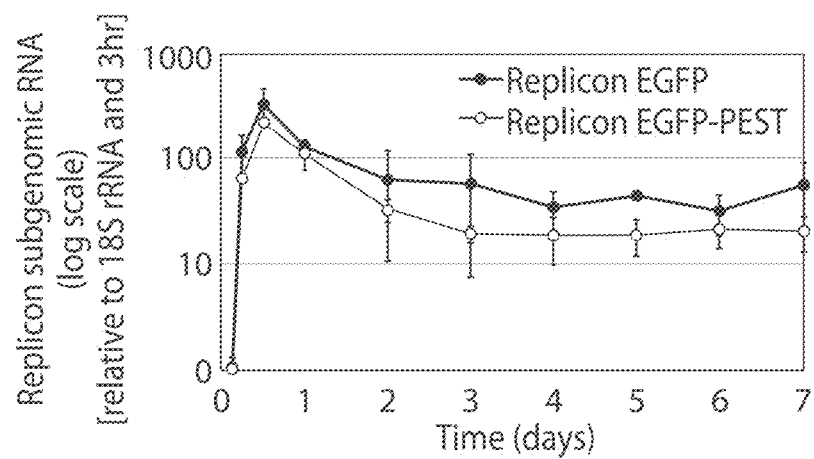
Figures 23A, 23B, 23C:
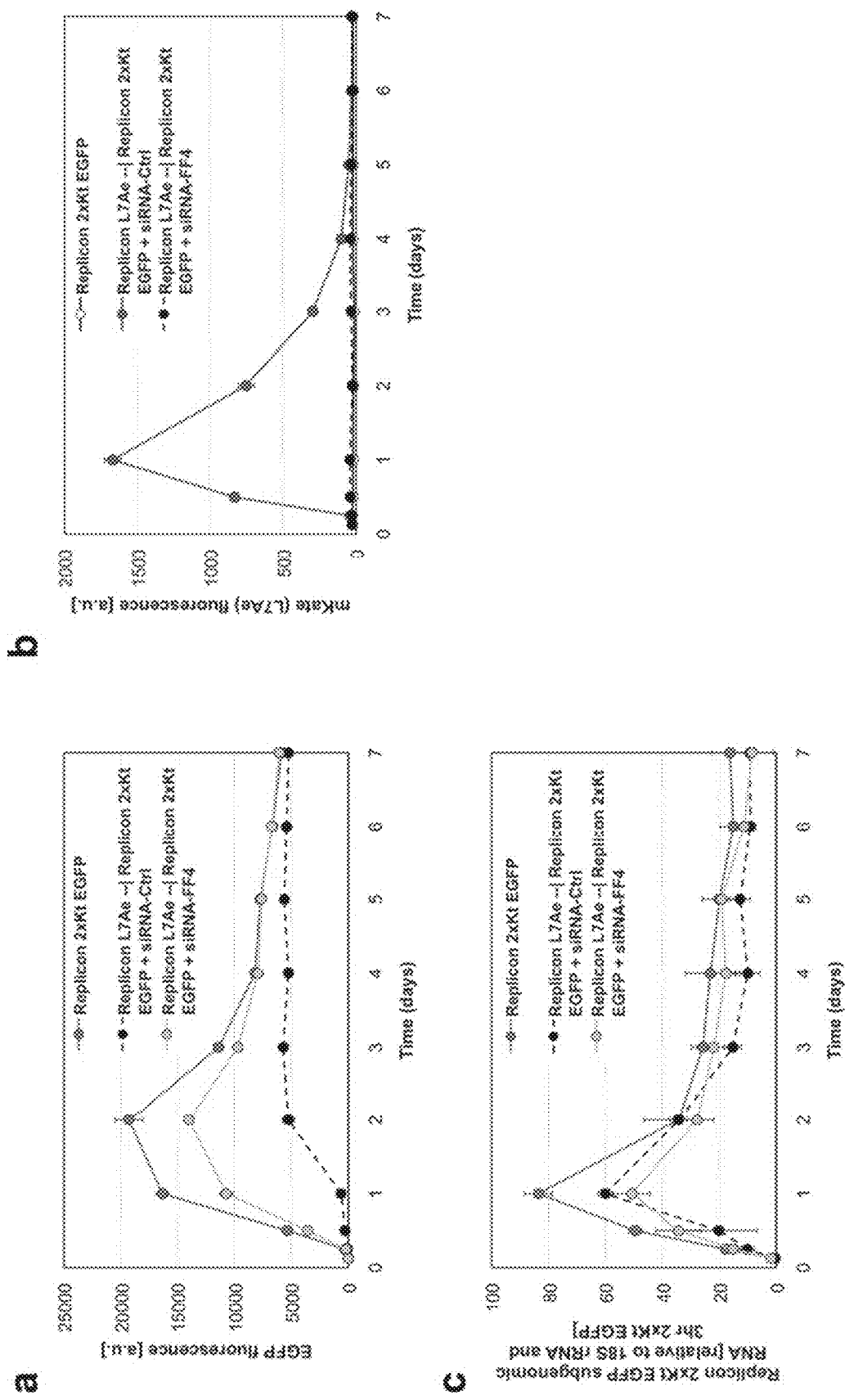
FIGS. 23A-23C. VEE replicon-based cascade time-lapse flow cytometry and qPCR. (a) Replicon encoding 2×Kt EGFP was electroporated into BHK21 cells with or without replicon encoding L7Ae, and EGFP fluorescence was measured by flow cytometry at 3 h, 6 h, 12 h, day 1, day 2, day 3, day 4, day 5, day 6, and day 7. Cells co-electroporated with 2×Kt EGFP and L7Ae were also electroporated with either siRNA-FF4 (to knock down replicon L7Ae) or siRNA-Ctrl. (b) mKate (L7Ae) fluorescence was measured by flow cytometry at the same time points as in (a). (c) Replicon 2×Kt EGFP genomic RNA levels in (a) were measured by qRT-PCR. Arbitrary units of EGFP or mKate fluorescence are plotted. qRT-PCR was normalized to genomic RNA levels 3 h post-electroporation. The reduced cascade performance over time may be attributed to potential competition between replicons (FIGS. 24A-24B) that needs to be evaluated with further studies (e.g. through creating multi-translation unit circuits encoded on a single RNA replicon).
Figure 24A:
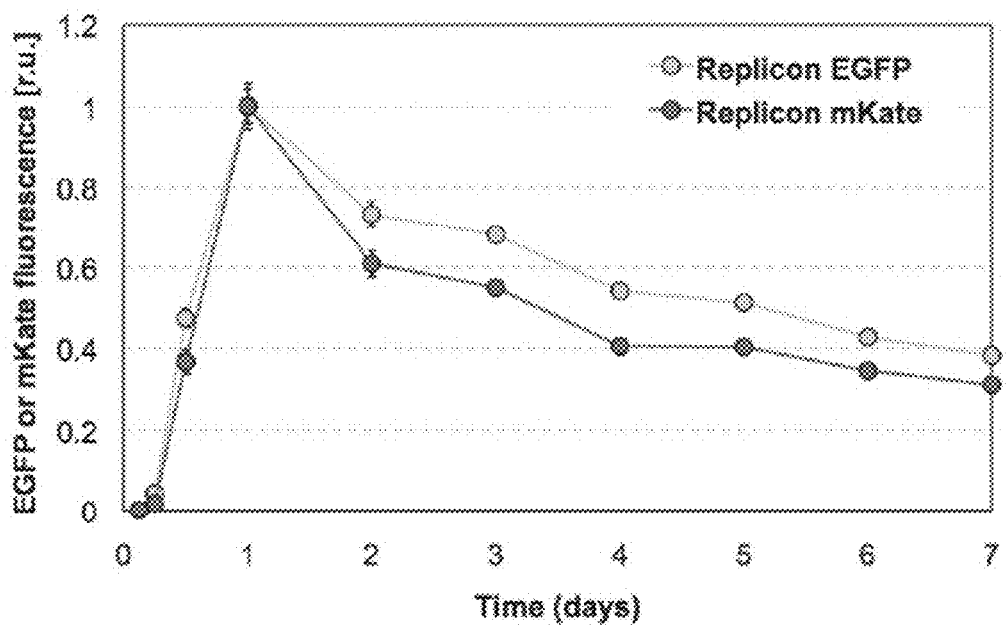
FIGS. 24A-24B. Expression kinetics of BHK21 cells transfected with two VEE replicons. (a) Replicons encoding constitutive EGFP and mKate were co-electroporated into BHK21 cells, and EGFP and mKate fluorescence levels were measured by flow cytometry at 3 h, 6 h, 12 h, day 1, day 2, day 3, day 4, day 5, day 6, and day 7. (b) The percentage of EGFP/mKate double positive, EGFP single positive, mKate single positive, and double negative cells at the time points in (a) are plotted.
Figure 24B:
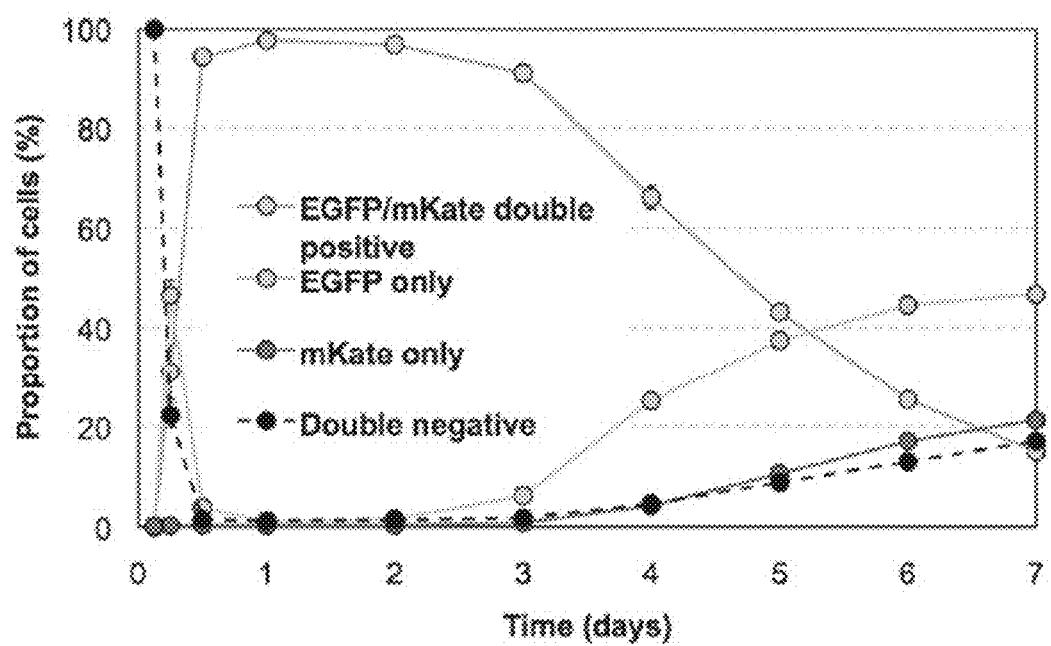

Self-replicating RNA (replicon). RNA replicons used in this study were derived from the single-strand positive-sense RNA viruses, Sindbis (52) or Venezuelan equine encephalitis (constructed here) viruses of the Alphavirus genus, Togaviridae family (30). The entire lifecycle of a positive strand RNA virus (and thus also the alphavirus) occurs in the cytoplasm of the cell (30) (FIG. 21). Replicon RNAs used in this study contain a 7-methylguanosine cap, a 5'UTR, an RNA-dependent RNA polymerase (RdRp) polyprotein P1234 (i.e. nonstructural proteins, nsPs), a subgenomic promoter element, a variable region of interest from which a reporter protein or RNA binding protein is expressed, a 3'UTR, and a poly(A) tail (+strand). Once the replicon RNA (generated by in vitro transcription) is transfected into a cell, the polyprotein P1234 is translated. Interestingly, P1234 contains an opal (UGA) stop codon between P123 and nsP4 (the catalytic subunit of the RdRp) so that ~90% of the time, translation terminates after synthesis of P12320. Readthrough of the stop codon and production of P1234 occurs at a frequency of ~10%. This regulates the stoichiometry of the components of the RdRp, which in turn affects the kinetics of viral RNA replication (30). P1234 is rapidly cleaved into P123 and nsP4 by autoproteolytic activity originating from the nsP2 (proteinase) portion of the polyprotein (30). Alphaviral RNA synthesis occurs at the plasma membrane of a cell, where the nsPs, together with alphaviral RNA, form membrane invaginations (or "spherules" (42, 43)). These spherules contain dsRNA created by replication of "+" strand viral genomic RNA into "−" strand antigenomic RNA. The "−" strand serves as a template from which additional "+" strand genomic RNA (synthesized from the 5'UTR) or a shorter subsequence of the genomic RNA (termed subgenomic RNA) is synthesized from the subgenomic promoter region located near the end of the nonstructural protein ORF. The "+" strand genomic RNA and the subgenomic RNA are exported out of the spherules into the cytoplasm where they are translated by endogenous ribosomes. The exported "+" strand genomic RNA can associate with nsPs and form additional spherules, thus resulting in exponential increase of replicon RNA. Several hours following RNA entry into the cell, the rate of genomic RNA replication drastically decreases as the catalytic activity of the majority of the existing RdRp complexes changes so that it is no longer able to synthesize "−" strand RNA (30). However, "non-cytopathic" mutant replicons such as those used in this study are capable of persistently replicating own RNA and expressing proteins(36, 38). While the reason for this is unknown, it is possible that nascent P1234 polyproteins produced during later stages of the alphaviral replicon lifecycle can confer "−" strand RNA synthesis activity to the cell.

Expression noise with pDNA, modRNA and replicon. Complex regulatory networks are subject to gene expression noise, resulting in cell populations exhibiting cell-to-cell variation in protein levels (56, 57). It has been shown that regulatory motifs, such as negative feedback loops, acting at transcriptional (58) or post-transcriptional level (59) may reduce noise in gene expression, thus conferring robustness to biological processes.

Since they avoid transcriptional bursting, which is often a major source of intrinsic noise (57), RNA encoded circuits might exhibit less variability in protein expression in comparison to their pDNA counterpart. For this, we analyzed the coefficient of variation (CV), that is the relative deviation of protein expression in each cell compared with the population average, which is used as a measure of noise (57, 59). We computed the CV for cells where constitutive expression of EGFP was delivered with pDNA, modRNA, or replicon. A smaller CV corresponds to a tight distribution centered around the mean, therefore a smaller cell-to-cell variability; a large CV corresponds to a wide distribution, indicating larger cell-to-cell variability (59). Indeed pDNA delivery shows higher CV than modRNA and replicon, suggesting that RNA based circuits might provide in this experimental setup more robust gene expression than DNA counterparts (FIGS. 36A-36B).

Finally, we created an RNA-based switch circuit in which two RBPs cross-repress each other to demonstrate two-way signal transmission and feedback regulation (FIGS. 8E-8H, FIGS. 9C and 27). The general topology of our switch is similar to previously described bacterial and mammalian transcriptional toggle switches (31, 32). The switch components include MS2-CNOT7 with two 5'UTR K-turn motifs and L7Ae with eight repeats of the MS2 binding site in the 3'UTR. To monitor switch behavior we additionally co-express (via 2A tags) a blue fluorescent protein (EBFP2) with MS2-CNOT7 and EYFP with L7Ae. The state of the system can be set with transient introduction of exogenous siRNA, or alternatively, endogenously expressed miRNA. We use two artificial and orthogonal siRNAs (FF4 and FF5). For pDNA transfection, when no specific siRNA is present, both repressors and associated reporters remain at intermediate levels after 48 hours (FIGS. 8F-8G, FIG. 28). siRNA-FF4 sets the state to high MS2-CNOT7 (EBFP2) and low L7Ae (EYFP), while siRNA-FF5 transfection results in the opposite state. The ON/OFF ratio between the two states is 56-fold for EBFP2 and 59-fold for EYFP. Since many potential applications of the switch require longer-term expression, we also encoded the circuit on self-replicating RNA (FIGS. 8F, 8H, FIGS. 28, 29A-29D, and 30A-30C). Similar to pDNA, siRNA-FF4 and FF5 set the state effectively, with ON/OFF ratios of 93-fold for EBFP2 and 1718-fold for EYFP. In the absence of specific siRNA, the replicon-encoded circuit had stronger bimodality than pDNA. We further explored this observation using a computational model of the pDNA and replicon-encoded switch circuits (FIGS. 31A-31B, 32A-32B, 33A-33B, 34, and 35A-35B). Based on literature (33) and our computational model we hypothesize that in the absence of specific siRNA, initial pDNA expression of the two switch branches (each encoding an RBP) is simultaneous (multiple plasmids delivered to the nucleus at the same time) and results in production of stable proteins. These remain in the cell at relatively high levels for the duration of the transfection experiment. In contrast, initial replicon RNA and replicon-encoded RBP production is more stochastic as single replicon species are rapidly amplified, typically leading to one of the two possible states.

In the absence of siRNA 1-1-4 or FF5, the replicon-based and plasmid-based switch systems exhibit different behaviors (FIG. 8F). The replicon-based system seems to fall into a more "mutually exclusive" distribution fairly soon after transfection, whereas the plasmid-based system appears to maintain a more unimodal population at an intermediate state for at least 48 hours.

To investigate these observations, simple computational models of the pDNA and replicon systems were implemented and analyzed. Stochastic simulations using the Gillespie Algorithm were performed in MATLAB27 using HTCondor queued computer cluster at MIT Computer Science and Artificial Intelligence Laboratory. The reaction equations and rates are reported below, and model schematic diagrams are displayed in FIGS. 31A-31B. Unless otherwise stated, 96 cell simulations were performed for each parameter set. To assess the bimodality, or "mutual exclusivity", of the population of cells that results from these simulations, a Mutual Exclusivity (MEx) score was developed (FIGS. 32A-32B). As demonstrated, this score provides useful information for the analysis of the two systems. The pDNA and replicon systems were simulated for 48 and 24 hours respectively with the parameter values listed in Table 6. These simulations resulted in populations that were qualitatively very similar to FIG. 8F (FIGS. 33A-33B).

TABLE 6

Theoretical model: reaction rates*

| Rate constant | Description | Value or range | Units | Source |
| --- | --- | --- | --- | --- |
| $k_{TS}$ | Transcription rate | 1 | $\text{min}^{-1}$ | Schwanhausser et al.[48] |
| $k_{TL}$ | Translation rate | 8 | $\text{min}^{-1}$ | Schwanhausser et al.[48], Mittal et al.[49] |
| $k_{ON,C}$ | MS2 binding rate | 4e−6 | $\text{molec}^{-1}\,\text{s}^{-1}$ | Assumed the same as L7Ae |
| $k_{ON,L}$ | L7Ae binding rate | 4e−6 | $\text{molec}^{-1}\,\text{s}^{-1}$ | Saito et al.[12]*a |
| $k_{OFF,C}$ | MS2 dissociation rate | 0.1 | $\text{min}^{-1}$ | Peabody[50]*b |
| $k_{OFF,L}$ | L7Ae dissociation rate | 0.01 | $\text{min}^{-1}$ | Saito et al.[12] |
| degR | RNA degradation rate | 0.002 | $\text{min}^{-1}$ | Schwanhausser et al.[48] |
| degP | Protein degradation rate | 5e−4 | $\text{min}^{-1}$ | Schwanhausser et al.[48] |
|  | CNOT7 degradation factor | 400 |  | This study (FIG. 10E)*c |
|  | L7Ae translational repression factor | 3e−3 |  | This study (FIG. 10C)*d |
| P0 | Starting pDNA copy number (each) | 100 | molec | Middleton et al.[51] |
| R0 | Starting replicon copy number (each) | $10^1 : 10^{2.5}$ | molec | Beal et al.[52] |
| $k_{TR}$ | Replicon transport and RF formation rate | $10^{-2.5} : 10^{-1}$ | $\text{min}^{-1}$ | *e |
|  | RF transport inhibition fraction (1 = no blocking, 0 = complete blocking) | 0:1 |  |  |
|  | Genomic fraction of positive synthesized strands | $10^{-3.5} : 10^{-2}$ |  | This study (FIGS. 22A-22E)*f |

*For all calculations involving molar to molecule conversions, the cell volume is assumed to be 3e−12 L.
*a$K_d$ of L7Ae binding is ~1e−9 $M^5$ and $k_{on} = k_{off}/K_d$.
*b$K_d$ of MS2 binding is 1e−8 $M^{13}$ and $k_{off} = K_d * k_{on}$.
*cFrom FIG. 10E, we have an expression decrease of ~35 fold at saturation. The degradation factor was tuned to achieve this fold expression decrease.
*dFrom FIG. 10C, one L7Ae bound reduces expression to ~0.3%
*e: Lower and upper bounds were picked so that fastest overall initial rates ($k_{TR}$ * R0) would be on the order of seconds and the slowest would be on the order of hours
*fUpper bound was calculated from qPCR data. The fraction of formation rate of genomic strands to subgenomic + genomic was found from fitting the qPCR curves after the point at which negative strand synthesis ceases.

First, to better understand the nature of the unimodal state achieved by the pDNA system, several of the parameter values were varied. The resulting behavioral trends are shown in FIG. 34. When either the starting copy number (P0) or the transcription rate (kTS) is set to lower values, the system becomes more mutually exclusive. This implies that this state might be due to a high and simultaneous burst of expression from both the L7Ae and MS2-CNOT7 plasmids, which express stable proteins. To investigate this, the variance-to-mean ratio (VMR), also known as the index of dispersion, of the distribution from which the starting plasmid copy number was selected was varied to allow for greater degree of initial bias. Since P0 follows a Poisson distribution with VMR=1, this was achieved by selecting from a Poisson distribution with mean=P0/VMR and then multiplying that value by the VMR. In this way, the mean of the distribution stays the same but the variance is increased. Increasing the VMR led to a higher degree of initial bias, causing a large increase in bimodality even when the initial copy number is kept high. In addition to the simultaneous burst of expression, this seemingly unstable state can be maintained for some time due to the slow switching rate, which is greatly influenced by the degradation rate of the proteins. To demonstrate this, we also increased the degradation rate, which causes an increased MEx score.

The next question to investigate was why the replicon system does not go through this high/high state. Based on the results from the pDNA analysis, we hypothesized that the replicon system either avoids the simultaneous burst of expression or it has a faster switching time due to the feedback mechanisms involved in the first few hours post-infection (ongoing negative strand synthesis). As depicted in FIGS. 31A-31B, the computational model of the replicon system essentially mirrors the pDNA system after the 4 hour time point when negative strand synthesis ceases. Therefore, for computational simplicity, we chose to simulate the replicon system for just 4 hours post-infection in our analysis. Sample simulations were also run for 24 hours to verify this simplification. In our simulations, we carefully analyzed the parameters involved in both of these hypotheses: the starting replicon copy number (R0), the transport rate (kTR), the transcription rate (kTS), positive feedback (6), and replication inhibition (8), and how the system responds to changes in each of these parameters.

Figure 30A:
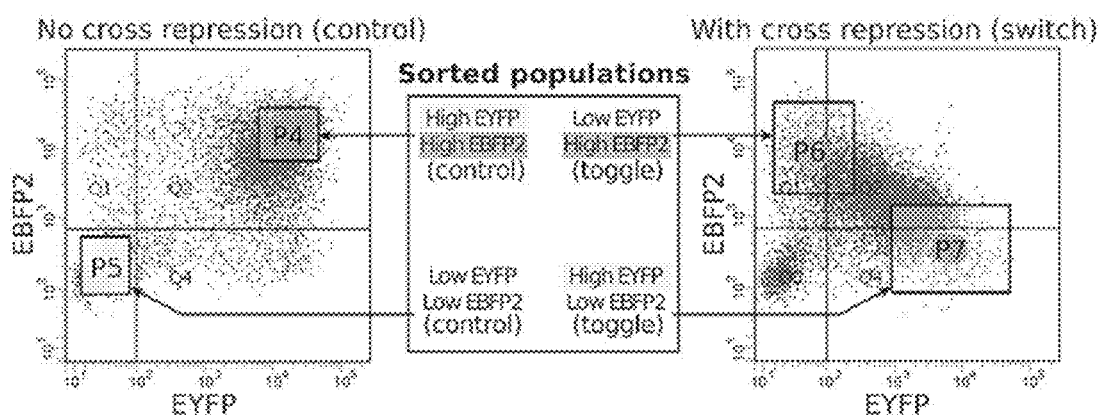
FIGS. 30A-30C. Sindbis replicon genomic RNA levels in FACS sorted populations from the post-transcriptional switch. Design of the Sindbis replicon post-transcriptional switch is as in FIG. 8E. BHK21 cells transfected with the switch circuit expressing low EYFP/high EBFP2 (P6) or high EYFP/low EBFP2 (P7) were sorted by FACS (a, right). Additionally, replicons lacking the aptamers that enable translational repression (2×Kt or MS2 binding site) were co-transfected as a "no cross-repression" control and FACS sorted for low EYFP/low EBFP2 (P5) or high EYFP/high EBFP2 (P4) (a, left). RNA from each sorted population was extracted and qRT-PCR was performed to measure the relative amounts of replicon genomic RNA in each population (b,c). The level of each replicon (Replicon L7Ae EYFP: b, Replicon MS2-CNOT7 EBFP2: c) was normalized to that in the high EYFP/high EBFP2 population. MS2-CNOT7 results in degradation of the targeted mRNA, thereby affecting replication (b, P6 in replicon L7Ae EYFP). L7Ae, on the other hand, does not significantly affect replication of replicon MS2-CNOT7 EBFP2 (c, P6 and P7).
Figure 30B:
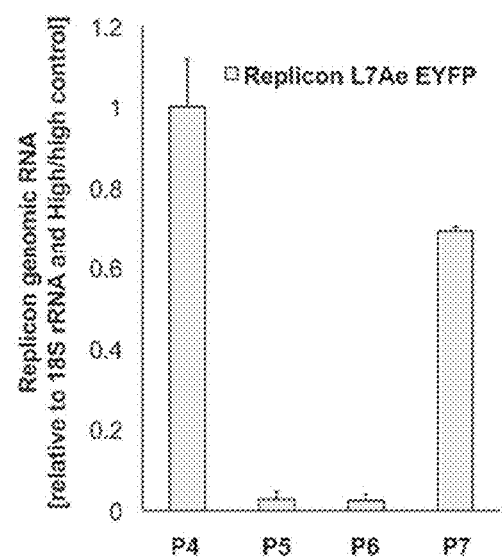
Figure 30C:
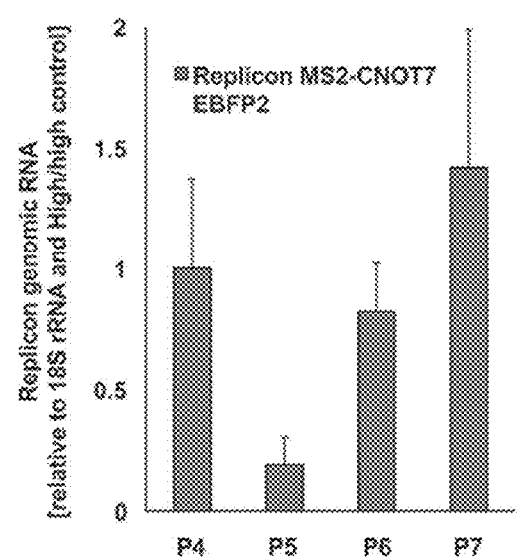

We performed global sensitivity analysis by randomly sampling 2000 parameter sets from the log-transformed realistic parameter space (Table 6). FIG. 35A shows the MEx scores when each of the parameters is varied 1.5 decades within its realistic set of values. Each point represents the distribution of 96 cell simulations for one random parameter set. FIG. 35B shows heat maps of the MEx scores for parameter pairs plotted together to identify parameter interactions. From these results, it appears that the stochasticity of replicon transport and spherule formation plays a major role in the dynamics of the system. In fact, the feedback mechanisms would not even be possible without the independent nature of this process, which distinguishes it from the pDNA system. However, FIG. 35B indicates that the system is fairly insensitive to the strength of the feedback mechanisms ((3 and c). Even at low kTR where replication inhibition (13) would have the most effect, we see no correlation with the MEx score. This is consistent with our experiments where we also find that L7Ae does not inhibit replication (FIGS. 30A-30C). To our knowledge there is no evidence that the binding of RBPs such as L7Ae to replicons affects formation of spherules. However, MS2-CNOT7 degradation of genomic RNA is likely. The positive feedback (c) due to +genomic strand synthesis also has no effect on the bimodality of the system in our simulations.

There is, however, a strong relationship between mutual exclusivity and both R0 and kTR, the initial replicon copy number and the transport rate. Both relate to the independent and stochastic nature of spherule formation. Decreasing either R0 or kTR leads to an increase in MEx score. This occurs because stochasticity in the transport reaction increases, allowing an initial bias in replication. As expected, their effects are also correlated (FIG. 35B). These results are also biologically relevant. The transport of replicons to the plasma membrane for spherule formation and negative strand synthesis is carried out by the nonstructural protein P1234, which is translated only when the opal codon is read thru (about 10% of the time). This low level of active protein could lead to initially slow and stochastic transport events, especially when the number of transported species is low. Additionally, our electroporation experiments indicate that there is a delay in protein expression, when delivered gene is encoded on replicon as compared to pDNA (assuming same delivery method, FIGS. 26A-26C), which implies that spherule formation may take a significant amount of time. Lastly, our qPCR results and a related publication (52) suggest that the starting number of replicons per cells in our electroporation experiments may be in the low tens while literature indicates that transfected pDNA copies are in the high tens to hundreds (61, 62). Additionally, bimodality is further amplified by an increase in transcription rate for the replicon system (which is in contrast to the pDNA case where higher transcription rate decreases bimodality). Here, however, increased transcription serves as an amplification of the initial bias caused by transport delay. In general, alphaviruses are able to replicate very quickly (30), so this computational result is biologically realistic.

Overall, these results suggest that the individualized and stochastic nature of spherule formation and transport results in an initial bias in replication. The resulting bimodality can be realized in the first four hours postinfection. The effects are amplified by an increase in stochasticity through a decrease in replicon copy number, and by a fast replication rate (kTS). These differences in dynamics are likely to have important implications when using replicons in synthetic biology circuits, especially when the expression timing of various species is important to circuit functionality.

To our knowledge no previous study has shown that complex cellular logic can be encoded exclusively at the post-transcriptional level in mammalian cells, offering potentially significant benefits for in vivo applications. This is made possible through the use of RBPs, which can act as both the input and the output of a regulatory device, and are promising candidates for creating scalable and modular control and information processing circuits. Our engineered circuits are functional when encoded either on modified mRNA (transient response) or self-replicating RNA (prolonged circuit operation). The inherently transient nature of RNA makes it an appealing platform for applications where safety is a primary concern, as RNA circuits could be programmed to act for a defined period of time and do not leave a long-term genetic footprint. Additionally, the different expression dynamics, lifetime (FIGS. 19A-19F, 20A-20F, 22A-22E, 23A-23C) and possibly noise properties (FIGS. 36A-36B) of modRNA and replicon delivery provide further potential for circuit design. Finally, the application of our RNA-only multi-input cell classifier circuit for specific induction of apoptosis, potentially concise formulation (two RNA species in case of the classifier) and its safety charac-

REFERENCES FOR EXAMPLES 1 AND 2

1. Van Tendeloo, V. F., Ponsaerts, P. & Berneman, Z. N. mRNA-based gene transfer as a tool for gene and cell therapy. *Current opinion in molecular therapeutics* 9, 423-431 (2007).
2. Tavernier, G. et al. mRNA as gene therapeutic: how to control protein expression. *Journal of controlled release: official journal of the Controlled Release Society* 150, 238-247 (2011).
3. Wang, Y. et al. Systemic delivery of modified mRNA encoding herpes simplex virus 1thymidine kinase for targeted cancer gene therapy. *Molecular therapy: the journal of the American Society of Gene Therapy* 21, 358-367 (2013).
4. Warren, L. et al. Highly efficient reprogramming to pluripotency and directed differentiation of human cells with synthetic modified mRNA. *Cell stem cell* 1, 618-630 (2010).
5. Kormann, M. S. et al. Expression of therapeutic proteins after delivery of chemically modified mRNA in mice. *Nature biotechnology* 29, 154-157 (2011).
6. Kramps, T. & Probst, J. Messenger RNA-based vaccines: progress, challenges, applications. *Wiley interdisciplinary reviews. RNA* (2013).
7. Yoshioka, N. et al. Efficient generation of human iPSCs by a synthetic self-replicative RNA. *Cell stem cell* 13, 246-254 (2013).
8. Geall, A. J., Mandi, C. W. & Ulmer, J.B. RNA: The new revolution in nucleic acid vaccines. *Seminars in immunology* 25, 152-159 (2013).
9. Khalil, A. S. & Collins, J. J. Synthetic biology: applications come of age. Nature reviews. Genetics 11, 367-379 (2010).
10. Aubel, D. & Fussenegger, M. Mammalian synthetic biology—from tools to therapies. *BioEssays: news and reviews in molecular, cellular and developmental biology* 32, 332-345 (2010).
11. Benenson, Y. Synthetic biology with RNA: progress report. *Current opinion in chemical biology* 16, 278-284 (2012).
12. Saito, H. et al. Synthetic translational regulation by an L7Ae-kink-turn RNP switch. *Nature chemical biology* 6, 71-78 (2010).
13. Weidmann, C. A. & Goldstrohm, A. C. *Drosophila* Pumilio protein contains multiple autonomous repression domains that regulate mRNAs independently of Nanos and brain tumor. *Molecular and cellular biology* 32, 527-540 (2012).
14. Endo, K., Stapleton, J. A., Hayashi, K., Saito, H. & Inoue, T. Quantitative and simultaneous translational control of distinct mammalian mRNAs. *Nucleic acids research* 41, e135 (2013).
15. Xie, Z., Wroblewska, L., Prochazka, L., Weiss, R. & Benenson, Y. Multi-input RNAi-based logic circuit for identification of specific cancer cells. *Science* 333, 1307-1311 (2011).
16. DD-Shield Domain Sequence Mammalian Codon Optimized and Adapted from: LA Banaszynski, et al. "A Rapid, Reversible, and Tunable Method to Regulate Protein Function in Living Cells Using Synthetic Small Molecules." *Cell*, 2006, 126, 995-1004.
17. Shield ligand (Clontech): clontech.com/US/Products/Inducible Systems/Inducible Prote in Stabilization/Shield1 Guard 1
18. DD-Guard Domain sequence: M Iwamoto et al. "A general chemical method to regulate protein stability in the mammalian central nervous system." Chemistry & Biology 2010, 17, 981-988.
19. Guard ligand (Trimethoprim) (Sigma Aldrich): sigmaaldrich.com/catalog/product/sigma/t7883?lang=en&region=US
20. Goldfless S. J., et al. Direct and specific chemical control of eukaryotic translation with a synthetic RNA-protein interaction. Nucl. Acids Res. (2012) Vol. 40, No 9.
21. Sahin, U., Karikó, K. & Türeci, Ö. mRNA-based therapeutics—developing a new class of drugs. *Nat Rev Drug Discov* 13, 759-780 (2014).
22. An, C. I. Artificial control of gene expression in mammalian cells by modulating RNA interference through aptamer-small molecule interaction. *RNA* 12, 710-716 (2006).
23. Culler, S. J., Hoff, K. G. & Smolke, C. D. Reprogramming cellular behavior with RNA controllers responsive to endogenous proteins. *Science* 330, 1251-1255 (2010).
24. Auslander, S. et al. A general design strategy for protein-responsive riboswitches in mammalian cells. *Nature Methods* 11, 1154-1160 (2014).
25. Rodrigo, G., Landrain, T. E. & Jaramillo, A. De novo automated design of small RNA circuits for engineering synthetic riboregulation in living cells. *Proc. Natl. Acad. Sci. U.S.A.* 109, 15271-15276 (2012).
26. Green, A. A., Silver, P. A., Collins, J. J. & Yin, P. Toehold switches: de-novo-designed regulators of gene expression. *Cell* 159, 925-939 (2014).
27. Qian, L. & Winfree, E. Scaling up digital circuit computation with DNA strand displacement cascades. *Science* 332, 1196-1201 (2011).
28. Ausländer, S., Auslander, D., Müller, M., Wieland, M. & Fussenegger, M. Programmable single-cell mammalian biocomputers. *Nature* 487, 123-127 (2012).
29. Van Etten, J. et al. Human *Pumilio* proteins recruit multiple deadenylases to efficiently repress messenger RNAs. *J. Biol. Chem.* 287, 36370-36383 (2012).
30. Strauss, J. H. & Strauss, E. G. The alphaviruses: gene expression, replication, and evolution. *Microbiol Rev* 58, 491-562 (1994).
31. Gardner, T. S., Cantor, C. R. & Collins, J. J. Construction of a genetic toggle switch in *Escherichia coli. Nature* 403, 339-342 (2000).
32. Kramer, B. P. et al. An engineered epigenetic transgene switch in mammalian cells. *Nat Biotechnol* 22, 867-870 (2004).
33. Mortimer, I. et al. Cationic lipid-mediated transfection of cells in culture requires mitotic activity. *Gene Ther.* 6, 403-411 (1999).
34. Azizgolshani, O., Garmann, R. F., Cadena-Nava, R., Knobler, C. M. & Gelbart, W. M. Reconstituted plant viral capsids can release genes to mammalian cells. *Virology* 441, 12-17 (2013).
35. Lustig, S. et al. Molecular basis of Sindbis virus neurovirulence in mice. *J. Virol.* 62, 2329-2336 (1988).
36. Frolov, I. et al. Selection of RNA replicons capable of persistent noncytopathic replication in mammalian cells. *J. Virol.* 73, 3854-3865 (1999).
37. Beal, J. et al. Model-driven engineering of gene expression from RNA replicons. *ACS Synth Biol* 4, 48-56 (2015).

38. Petrakova, O. et al. Noncytopathic replication of Venezuelan equine encephalitis virus and eastern equine encephalitis virus replicons in Mammalian cells. *J. Virol.* 79, 7597-7608 (2005).
39. Szymczak, A. L. et al. Correction of multi-gene deficiency in vivo using a single 'self-cleaving' 2A peptide-based retroviral vector. *Nat Biotechnol* 22, 589-594 (2004).
40. Stewart, S. A. et al. Lentivirus-delivered stable gene silencing by RNAi in primary cells. *RNA* 9, 493-501 (2003).
41. Rechsteiner, M. & Rogers, S. W. PEST sequences and regulation by proteolysis. Trends in Biochemical Sciences 21, 267-271 (1996).
42. Frolova, E. I., Gorchakov, R., Pereboeva, L., Atasheva, S. & Frolov, I. Functional Sindbis virus replicative complexes are formed at the plasma membrane. J. Virol. 84, 11679-11695 (2010).
43. Kallio, K. et al. Template RNA length determines the size of replication complex spherules for Semliki Forest virus. J. Virol. 87, 9125-9134 (2013).
44. Nechushtan, A., Smith, C. L., Hsu, Y. T. & Youle, R. J. Conformation of the Bax C-terminus regulates subcellular location and cell death. EMBO J. 18, 2330-2341 (1999).
45. Livet, J. et al. Transgenic strategies for combinatorial expression of fluorescent proteins in the nervous system. Nature 450, 56-62 (2007).
46. Ai, H.-W., Shaner, N. C., Cheng, Z., Tsien, R. Y. & Campbell, R. E.
Exploration of new chromophore structures leads to the identification of improved blue fluorescent proteins. Biochemistry 46, 5904-5910 (2007).
47. Shcherbo, D. et al. *Bright far—red fluorescent protein for whole—body imaging*. Nature Methods 4, 741-746 (2007).
48. Schwanhäusser, B. et al. Global quantification of mammalian gene expression control. Nature 473, 337-342 (2011).
49. Mittal, N., Roy, N., Babu, M. M. & Janga, S. C. Dissecting the expression dynamics of RNA—binding proteins in posttranscriptional regulatory networks. *Proc. Natl. Acad. Sci. U.S.A.* 106, 20300-20305 (2009).
50. Peabody, D. S. The RNA binding site of bacteriophage MS2 coat protein. *EMBO J.* 12, 595-600 (1993).
51. Middleton, T. & Sugden, B. Retention of plasmid DNA in mammalian cells is enhanced by binding of the Epstein—Barr virus replication protein EBNA1. J. Virol. 68, 4067-4071 (1994).
52. Beal, J. et al. Model—driven engineering of gene expression from RNA replicons. ACS Synth Biol 4, 48-56 (2015).
53. Pascolo, S. Vaccination with messenger RNA. DNA Vaccines, Methods Mol Med. 127, 23-40 (2006).
54. Gallie, D. R. The cap and poly(A) tail function synergistically to regulate mRNA translational efficiency. Genes Dev. 5, 2108-2116 (1991).
55. Anderson, B. R. et al. Incorporation of pseudouridine into mRNA enhances translation by diminishing PKR activation. Nucleic Acids Research 38, 5884-5892 (2010).
56. Pedraza, J. M. & van Oudenaarden, A. Noise propagation in gene networks. Science 307, 1965-1969 (2005).
57. Chalancon, G. et al. Interplay between gene expression noise and regulatory network architecture. Trends Genet. 28, 221-232 (2012).
58. Shimoga, V., White, J. T., Li, Y., Sontag, E. & Bleris, L. Synthetic mammalian transgene negative autoregulation. Molecular Systems Biology 9, 670 (2013).
59. Siciliano, V. et al. MiRNAs confer phenotypic robustness to gene networks by suppressing biological noise. Nat Commun 4, 2364 (2013).
60. MATLAB and Statistics Toolbox Release 2013b, The MathWorks, Inc., Natick, Mass., United States.
61. Cohen, R. N., van der Aa, M. A. E. M., Macaraeg, N., Lee, A. P. & Szoka, F. C. Quantification of plasmid DNA copies in the nucleus after lipoplex and polyplex transfection. Journal of controlled release 135, 166-174 (2009).
62. Bleris, L. et al. Synthetic incoherent feedforward circuits show adaptation to the amount of their genetic template. *Molecular Systems Biology* 7, 1-12 (2011).

Example 3. Synthetic RNA Circuits as a Vaccination Platform

The creation of a safe and cost-effective prophylactic/therapeutic vaccine which can induce potent broadly-neutralizing antibody (bNAb) and cytotoxic T lymphocyte (CTL) responses is urgently needed to end the global HIV/AIDS epidemic. Here we hypothesize that a programmable RNA replicon-based vaccination platform developed through a collaboration between the Weiss and Irvine groups may be used to effectively support this goal by precisely engineering and optimizing the kinetics of antigen/adjuvant expression.

Rationale and Preliminary Data

Figure 37A:
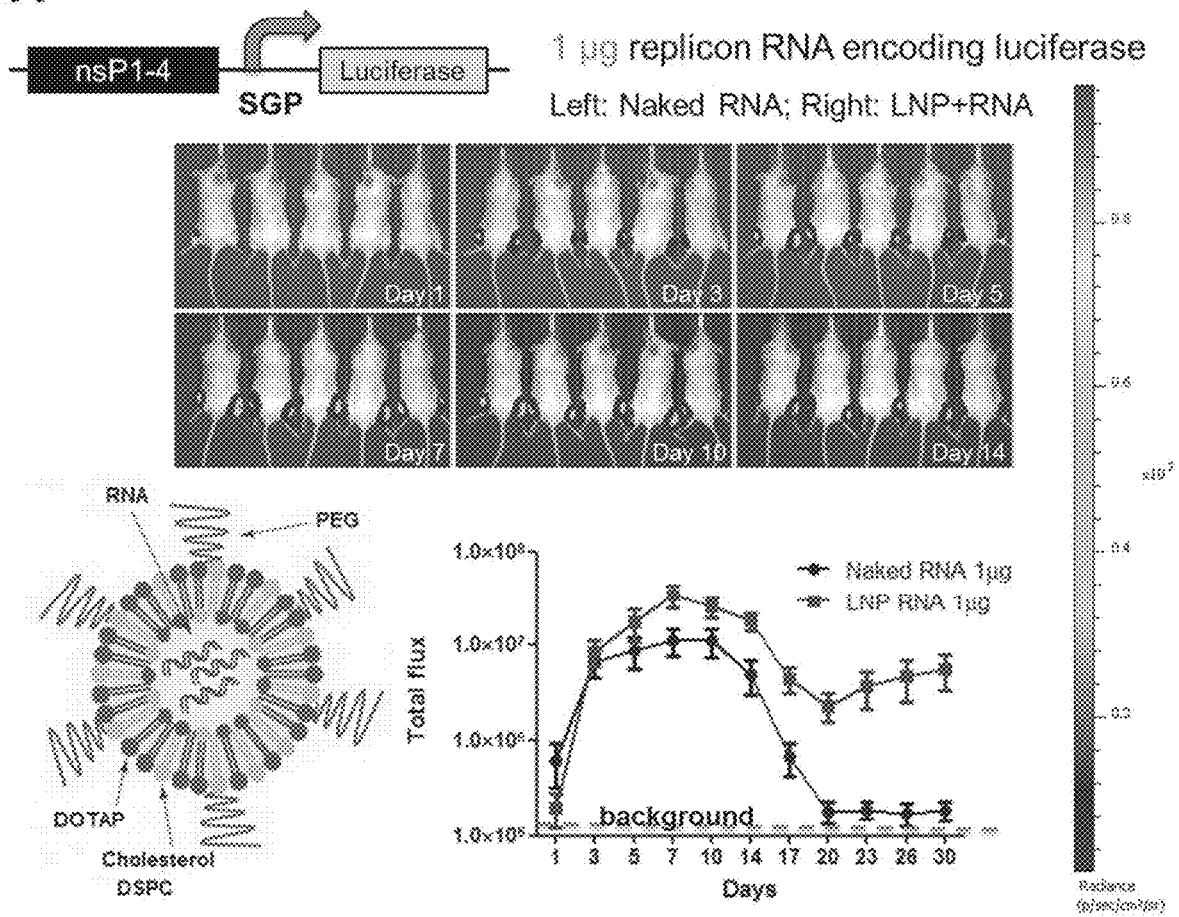
Figure 37B:
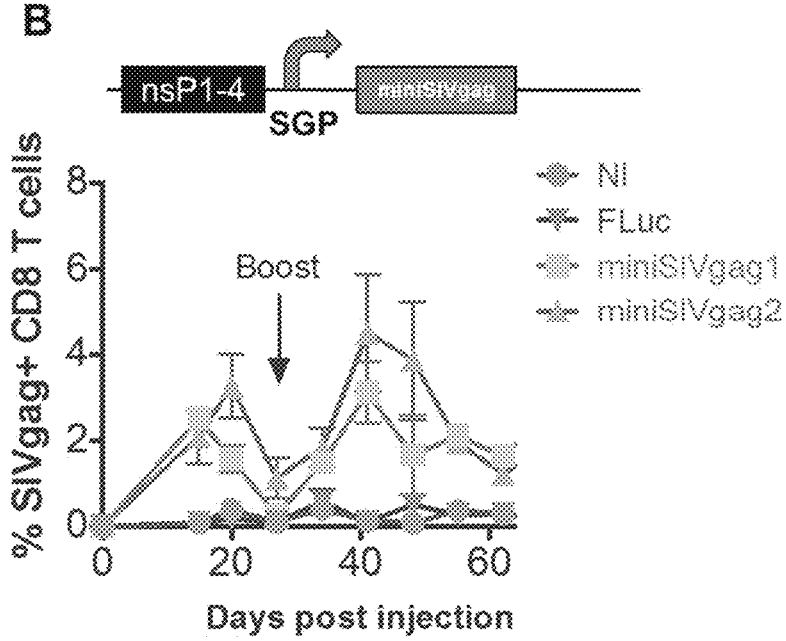
Figure 37E:
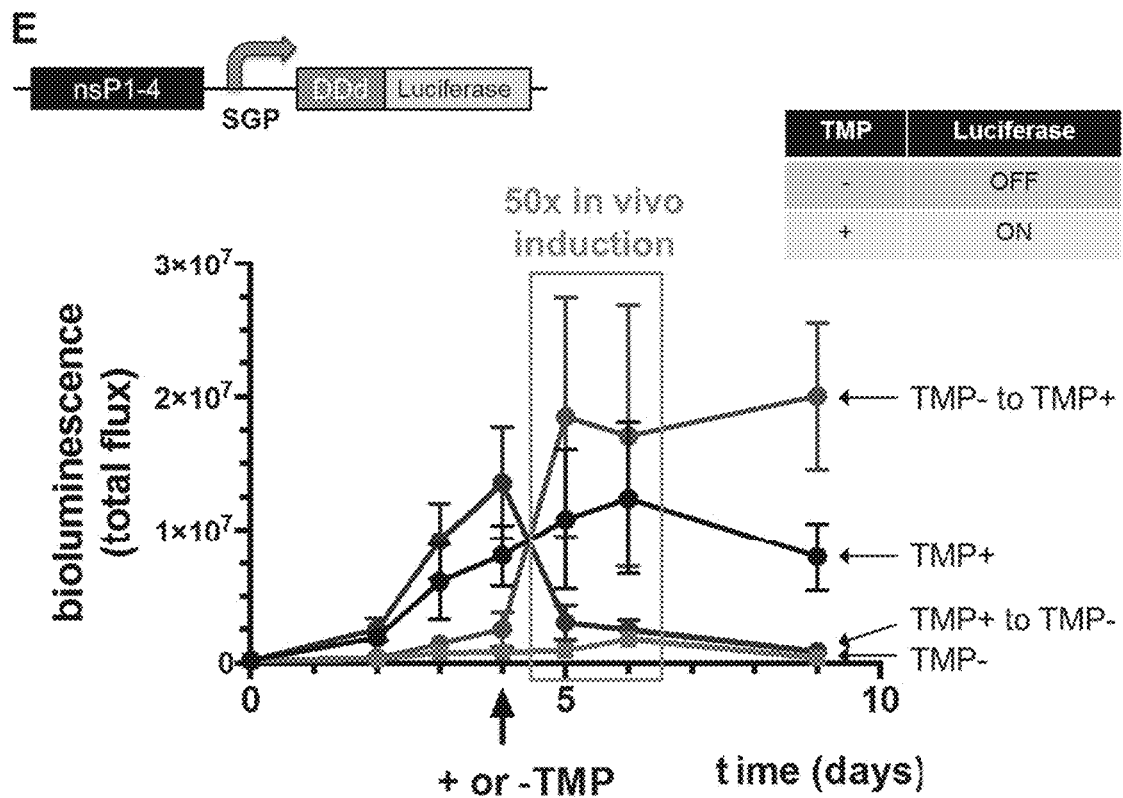
Figure 37F:
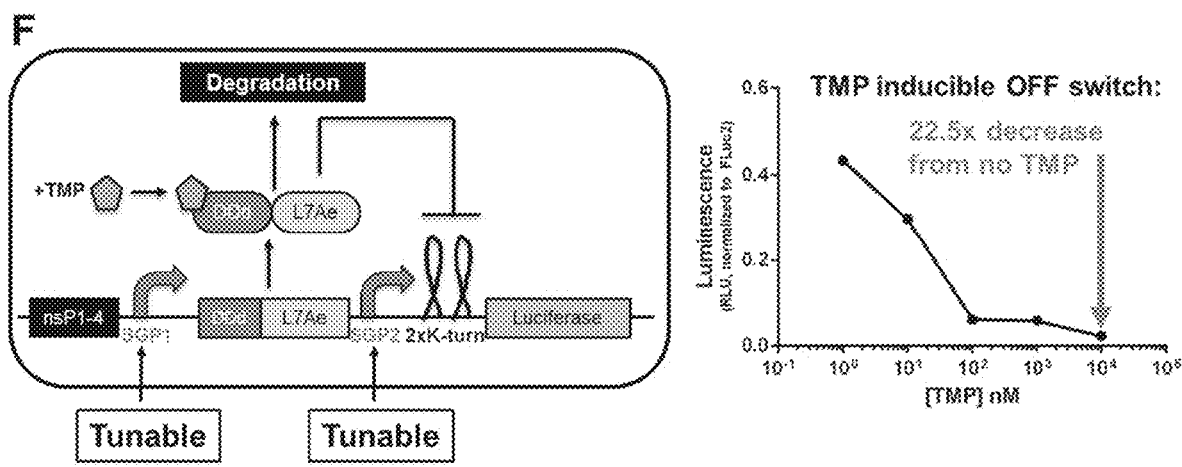

In vitro transcribed RNA as a vaccine platform is cheaper and easier to manufacture than recombinant proteins and safer than DNA to administer to patients due to the low risk of potentially harmful integration of the vector into the genome (Sahin et al. 2014). Furthermore, vaccination can be readily scaled-up to humans using synthetic lipid nanoparticle (LNP)-based delivery systems (Sahin et al. 2014). Previously, we demonstrated that the expression of a firefly luciferase (fluc) reporter gene from our Venezuelen Equine Encephalitis (VEE) Virus-based self-replicating RNA replicon vector can be prolonged by packaging it into a cationic LNP (FIG. 37A). Strikingly, we found that the sole injection of an LNP-packaged RNA replicon encoding a "long peptide" antigen derived from SIV gag elicited a strong CTL response in mice, likely due to the extended translational capability and "self-adjuvanting" properties of the replicon (FIG. 37B). Thus, our replicon platform is ideally suited to inducing cellular immune responses against rationally engineered peptide epitopes based on regions of HIV Gag in which mutations impose a high fitness cost according to "quantitative viral fitness landscape" models (Ferguson et al. 2013, Dahirel et al. 2011).

The quality and durability of immune responses elicited by vaccination can be dramatically impacted by the kinetics with which the immune system is exposed to antigen and adjuvant cues, yet vaccine kinetics are not typically engineered by immunization. For example, it had been previously shown that the augmentation of humoral responses against HIV-1 gp120 by expression of a cytokine (IL-2/Ig) requires the cytokine vector to be injected two to five days after injection of the antigen expressing vector and not before or coincident with the antigen vector (Barouch et al. 1998). Furthermore, we and others have shown that CTL and antibody responses can be drastically improved by exponential dosing and exposure of antigens to the immune system (Johansen et al. 2008 and unpublished results; FIG. 37C). Finally, it had been recently shown that sequential (as opposed to simultaneous) exposure of variant gp120 antigens to the immune system can prevent frustration of affinity maturation and induce cross-reactive HIV antibodies (Wang et al. 2015). One practical way to implement an actual vaccination scheme with such optimized antigen/adjuvant exposure patterns may be to program these behaviors onto an RNA replicon using our RNA binding protein (RBP)-based composable synthetic gene circuit platform. Using this platform, we previously created various synthetic gene circuits including toggle switches and small molecule-regulatable ON/OFF switches and cascades in vitro and/or in vivo (Wroblewska et al. in press and unpublished results; FIGS. 37D-37G). These results serve as the foundation for the engineering of programmable vaccines that may drastically improve the humoral/cellular immune response against HIV and provide protection against the virus as proposed below.

Engineering Delayed Expression of Adjuvants for Immune Response Augmentation

The expression of cytokines such as IL-2/Ig, IL-12/Ig, IL-15/Ig can be used to significantly enhance an immune response against an antigen, however, the timing of cytokine expression in relation to antigen expression must be carefully tuned. Here, we propose to program the optimal adjuvant expression kinetics (expression of adjuvant two to seven days after antigen expression) into our replicon vaccine using the small molecule-regulated OFF switch shown in FIG. 37F. Translation of the adjuvant is inhibited by binding of an RBP (L7Ae) to an RNA motif (K-turn) positioned in the 5'UTR of the adjuvant. A destabilizing domain (DDd), which confers instability to the protein of interest that it is fused to, is attached to L7Ae to target it for proteasome-mediated degradation. Degradation of L7Ae can be prevented by binding of trimethoprim (TMP), an FDA-approved small molecule drug, to DDd. Sustained local release of TMP is achieved by encapsulating TMP in PEG-b-PLGA, a surfactant-like amphiphilic block copolymer. TMP release kinetics can be tuned by adjusting the size of the PEG-b-PLGA nanoparticle by modifying the chain length and composition of the polymer. A schematic of the proposed programmed delayed adjuvant vaccine experiment is shown in FIG. 38A.

Engineering Exponential Prime/Boost Expression of Antigens for an Improved Immune Response Our programmable RNA replicon platform presents a practical means to provide the ideal (exponential) exposure pattern of an antigen (FIG. 37C) to the immune system of a patient. Using the TMP-regulated OFF switch described above (FIG. 37F), the prime and boost expression patterns of gag sequences which focus on "vulnerable regions" of the virus as described above (Ferguson et al. 2013, Dahirel et al. 2011) are modulated and CD4 binding site-presenting gp120 antigens are modeled by administering TMP through the drinking water of mice as show in FIG. 38B. T-cell and antibody responses are monitored over time. Promising results from this experiment as well as the nanoparticle-mediated TMP release experiment above justify future investment in the development of more sophisticated TMP release strategies to enable fully automated programmed exponential prime/boost expression of the gag peptide antigen.

Figure 37G:
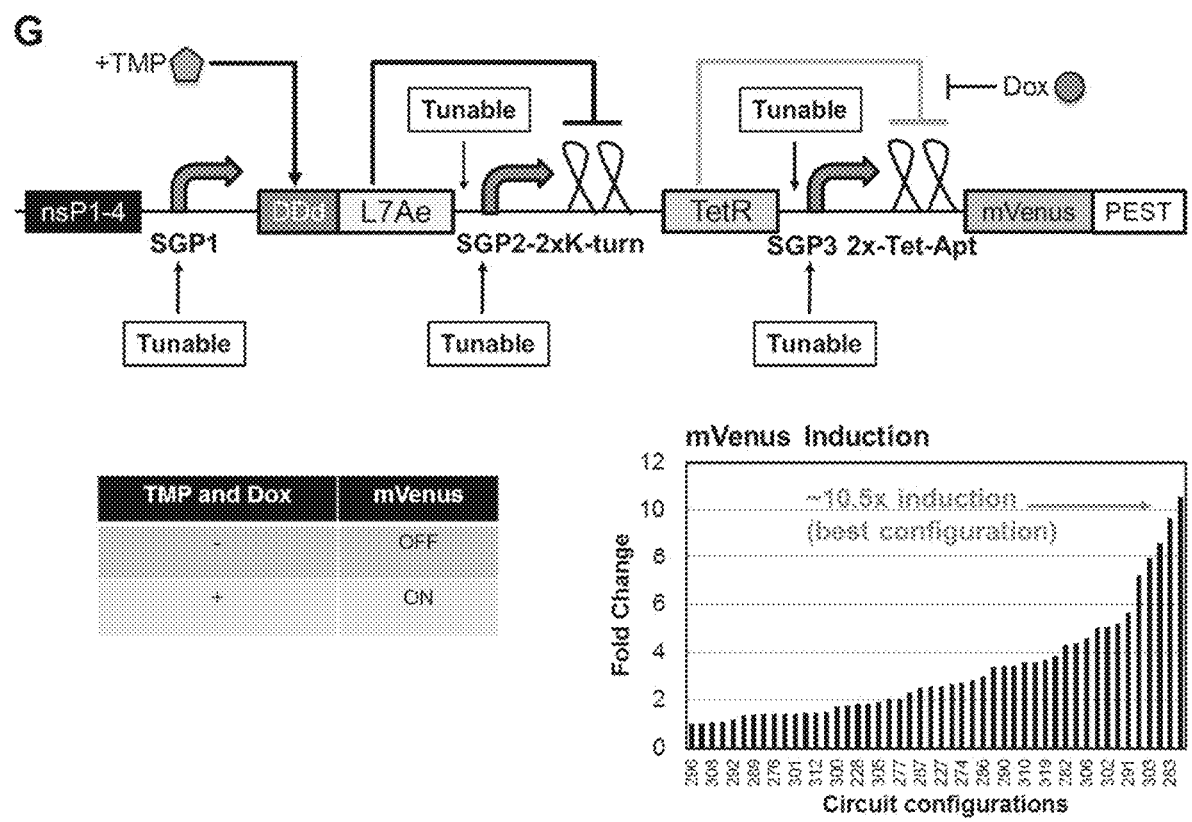

Engineering Sequential Expression of Antigens for Induction of Cross-Reactive Antibodies In order to test whether it is possible to program the sequential expression of rationally designed gp120 immunogens to guide the immune system to induce cross-reactive antibodies focused on the conserved CD4 binding site, a "stripped core" gp120 immunogen and a variant gp120 immunogen containing mutations outside of the CD4 binding site (Wang et al. 2015) are encoded on the small molecule-regulated replicon cascade shown in FIG. 37G. This cascade involves two small molecule-regulatable RBPs: DDd-L7Ae described above and the TetR protein designed to bind the TetR RNA aptamer sequence to repress translation. TetR binding to the aptamer can be derepressed using doxycycline (Dox). Therefore, administration of TMP and Dox first induces the expression of the stripped core gp120 immunogen and subsequent withdrawal of the two small molecules represses the translation of the stripped core and induces the expression of the variant gp120 immunogen as described in FIG. 38C. The successful implementation of this strategy leads to engineering more sophisticated replicon circuits that enable fully automated sequential expression of more gp120 variants to further expand the breadth of antibody cross-reactivity.

Example 4. High-Throughput Assembly Platform for Fine-Tuned Expression of Multiple Genes from RNA Replicons Using Multiple Subgenomic Promoters General Purpose Self-amplifying RNA replicons are an attractive alternative to traditional nucleic acid based expression platforms, providing relatively high, sustained expression compared to non-replicating RNA, without the risk of genomic integration associated with DNA-based therapies. When expressing multiple genes, encoding these genes on a single replicon is an attractive alternative to co-transfection. Here, we propose a comprehensive strategy for the assembly and characterization of multi-gene replicon. In order to control expression of multiple genes from a single Venezuelan Equine Encephalitis (VEE) replicon, we created a library of subgenomic promoters (SGPs) of varying strengths, both higher and lower than the wild type VEE SGP. We found that introducing additional 3'-UTR sequences between translational units also significantly increased expression. Finally, we adapted a Modular Cloning (MoClo) assembly strategy for VEE replicons, demonstrating controlled expression from one hundred and forty different two and three SGP variants expressing fluorescent proteins.

Technical Description

Interest has been growing in RNA replicons as an alternative to standard DNA-based gene delivery methods.[1] Replicons are not only self-amplifying, but are also regarded as safer than competing gene delivery technologies, making replicons attractive for medical applications such as vaccine delivery, gene therapy, and cellular reprogramming[2-4] Because they are self-amplifying, replicons can generate higher expression of a gene from a relatively low initial dose, compared to non-replicating RNA. Moreover, with regard to safety, replicons remain in the cytoplasm of the cell, so the risk of undesired integration into the genome is minimal.[5,6]

We have previously demonstrated that expression of multiple genes from co-transfected replicons can be modeled and predicted with a high degree of precision.[7] However, there are disadvantages associated with the use of multiple replicons for gene delivery. First, a cell must contain at least one copy of each replicon if more than one gene is required for a given therapy or any type of regulation. In addition, we have found that after three days, in those cells that are co-transfected with two replicons, there is a gradual decrease in the number of double positive cells, preventing sustained regulation using multiple replicons, as shown in FIGS. 47A-47B.

In order to have controlled expression of multiple genes from a single replicon, we needed to independently affect translation of each gene. At the RNA level, this was achieved creating a library of Venezuelan Equine Encephalitis (VEE)[8] subgenomic promoters (SGPs) of varying strengths, both higher and lower than the wild type VEE SGP. We also experimented with other means, such as introducing additional 3'-UTR sequences between translational units, which had a significant effect on expression. To truly characterize multi-gene replicons and understand how these components affect expression, we adapted a Modular Cloning (MoClo) assembly strategy for VEE replicons and generated all combinations of two and three SGP constructs expressing fluorescent proteins, using low, midrange, and high strength SGPs with and without 3'UTRs.

Controlling Expression Using Subgenomic Promoters and Additional 3'UTRS

A subgenomic promoter library was created for VEE replicon by truncating the full length SGP from either the plus or minus side. The SGP library was tested in a tandem format, depicted in FIG. 48, to prevent any deletions to nsP4, as the base pairs comprising the minus side of the SGP are located in the coding region of the nsP4 protein. The first SGP, governing expression of the fluorescent protein mVenus, was held constant at the full-length, −241/+30 SGP.[8] Our library of 27 truncated SGPs was placed before the second translational unit expressing mKate. As shown in FIG. 48 and enumerated in Table 7, modulation of the SGP can result in a 15-fold dynamic range in protein expression ranging from −241/+4 (weakest) to −241/+15 (strongest). The experiment was repeated using mKate under control of the first SGP and mVenus under control of the second, which gave the same outcome (data not shown), proving these results were not protein dependent. There are a few things to note regarding this data. First, some of our newly generated SGPs express higher than the wild type SGP. Second, a wide range of expressions can be gathered using only plus side deletions, meaning that these SGPs may also be used for single SGP constructs, as they would not interfere with nsP4 function. Finally SGP −241/+1 showed expression only two-fold above background, and was not considered when calculating the dynamic range of our library.

TABLE 7 mKate Fluorescence Levels using SGP Library

| SGP | mKate |
|---|---|
| 241-1 | 0.01 |
| 241-4 | 0.09 |
| 241-2 | 0.13 |
| 241-3 | 0.15 |
| 241-14 | 0.32 |
| 241-5 | 0.34 |
| 19-30 | 0.34 |
| 241-13 | 0.35 |
| 241-6 | 0.38 |
| 241-11 | 0.43 |
| 25-30 | 0.47 |
| 241-12 | 0.60 |
| 31-30 | 0.60 |
| 241-20 | 0.62 |
| 41-30 | 0.71 |
| 51-30 | 0.72 |
| 241-26 | 0.76 |
| 241-17 | 0.83 |
| 121-30 | 0.87 |
| 241-21 | 0.87 |
| 61-30 | 0.89 |
| 241-30 | 0.90 |
| 181-30 | 0.92 |
| 241-19 | 0.95 |
| mKate Ctrl | 1.00 |
| 241-18 | 1.02 |
| 241-16 | 1.14 |
| 241-15 | 1.48 |

Another particularly important finding from this experiment was the effect of position on expression, i.e. expression from the second unit is 8 times stronger than expression from the first unit when using two full-length −241/+30 SGPs. As a first attempt to overcome this disparity, an additional 3'UTR was inserted in between the translational units because it is known to play a role in minus strand RNA synthesis.[9] As shown in FIG. 49, expression from the first translational unit increased 8-fold, demonstrating that additional 3'UTRs could be another means of controlling expression.

Because the SGP library could be generated by mutating only the positive side of the SGP, we next set out to validate the results from the tandem library in a single SGP setting. We chose three SGPs with 5, 30, and 15 base pairs on the positive side, representing low, midrange, and high SGPs, respectively. However, our initial round of experiments did not show the same expression pattern as we observed in a tandem format. Specifically, SGP5, which was the weakest of the three in tandem, was now the strongest, as shown on the left side of FIG. 50. We hypothesized that the XbaI and attb1 sites, which were present for cloning purposes and immediately downstream of the SGP, were affecting expression. To test this hypothesis, we also designed two additional single SGP constructs. First, we added a 6 base pair AscI scar, a remnant from the tandem SGP library cloning process, upstream of the SGP. We also created a construct in which the SGP was followed immediately by the Kozak sequence. As shown in FIG. 48, both of these constructs showed a similar expression pattern to that observed using a tandem format, proving that the XbaI-attb1 sequence was directly influencing expression. The following MoClo assembly strategy allows our SGP library to be followed immediately by a Kozak, an orientation that gave us the largest dynamic range, and potentially limits variability.

MoClo Assembly of VEE Replicons

We have demonstrated that expression of multiple genes from a replicon can be modulated using SGPs, additional 3'UTRs, and position. However, to more comprehensively characterize expression of two or more genes launched from a single replicon, a more efficient, preferably scarless, assembly strategy was necessary. As shown in FIG. 51, a MoClo assembly method was adapted that divided each translational unit into three parts: a sub-genomic promoter (SGP), open reading frame (ORF), and 3'-untranslated region (3'UTR). Each of the parts was placed in a Level 0 vector and flanked by BsaI recognition sites. BsaI is a Type IIS restriction enzyme, so it recognizes a sequence but cleaves downstream of the recognition site, allowing for scarless assembly. The Level 0's are combined into a Level 1 vector to form a single translational unit, using conserved sequences in between the SGP, ORF, and 3'UTR. Finally, Level 1's are combined into the replicon backbone using a second Type IIS enzyme, SapI, to form the final Level 2 product, a functional multi-unit replicon.

The following is a sequence level description of the Replicon MoClo Assembly, beginning with the various Level 0 destination vectors. These Level 0 destination vectors were made for use with either of the following Type IIS enzymes: SapI or BbsI. SapI has a 7-base pair (bp) recognition site and a 3-bp overhang while BbsI has a 6-bp recognition site and a 4-bp overhang. Typically, we mutate BsaI and SapI sites within any new ORFs to make the Level 0→1 and Level 1→2 reactions more efficient, respectively, but this is not required if a final ligation step is added to the MoClo reaction. Our SGP library and the VEE 3'UTR do not contain recognition sites for either of these enzymes, so this problem most commonly arises with ORFs, although introduction of aptamer sequences or modified 3'UTRs should also be considered. The Level 0 destination vectors contain Ampicillin resistance, with the BsaI site in the AmpR gene mutated to facilitate a more efficient Level 0→1 reaction. In addition, we have mutated the BsaI site in the ccdB gene, allowing us to also create Level 0's via a digest/ligation reaction with BsaI, which is very efficient because the ccdB gene kills the cells that do not receive the insert.

Each Level 0 destination vector is shown below, along with an example of how to insert a given unit (SGP, ORF, or UTR).

Level 0 SapI Destination Vectors

SGP +/- Apatmer: TW196 (SapI)

BsaI → Cut Site ← SapI Insert SapI → Cut site ← BsaI

GGTCTCCGACTAGAAGAGC-ccdB-Cm-GCTCTTCACACCTGAGACC

↑                          ↑

SGP (-98 → -96)        Part of Kozak
SEQ ID NO: 26         SEQ ID NO: 27
ORF: TW197 (SapI)

BsaI → Cut Site ← SapI Insert SapI → Cut site ← BsaI

GGTCTCACACCGAAGAGC-ccdB-Cm-GCTCTTCAATAATGAGACC

↑                          ↑

Part of Kozak       Last bp of opal or ochre
SEQ ID NO: 28     stop codon + additional stop
3'UTR +/- Aptamer: TW198 (SapI)   SEQ ID NO: 29

BsaI → Cut Site ← SapI Insert SapI → Cut site ← BsaI

GGTCTCCATAAGAAGAGC-ccdB-Cm-GCTCTTCTTCATGAGACC

↑                         ↑

Last bp of opal or ochre   end of 3' UTR + A
stop codon + additional stop  SEQ ID NO: 31
SEQ ID NO: 30

Level 0 BsaI/BbsI Destination Vectors

SGP +/- Apatmer: TW063 (BsaI) or TW116 (BsaI or BbsI)

BsaI → Cut Site ← BbsI Insert BbsI → Cut site ← BsaI

GGTCTCCGACTAAGTCTTC-ccdB-Cm-GAAGACTTCACCTGAGACC

↑                          ↑

SGP (-98→-96)       Part of Kozak
SEQ ID NO: 32       SEQ ID NO: 33
ORF: TW064 (BsaI) or
TW117 (BsaI or BbsI)

BsaI → Cut Site ← BbsI Insert BbsI → Cut site ← BsaI

GGTCTCACACCAAGTCTTC-ccdB-Cm-GAAGACTTATAATGAGACC

↑                           ↑

Part of Kozak     Last bp of opal or ochre
SEQ ID NO: 34    stop codon + additional stop
3'UTR +/- Aptamer:   SEQ ID NO: 35

BsaI → Cut Site ← BbsI Insert BbsI → Cut site ← BsaI

GGTCTCCATAAAAGTCTTC-ccdB-Cm-GAAGACTTTTCATGAGACC

↑                            ↑

Last bp of opal or ochre   end of 3' UTR + A
stop codon + additional stop  SEQ ID NO: 37
SEQ ID NO: 36

Level 0 SapI SGP Example

SGP +/- Apatmer: TW196 (SapI)

BsaI → Cut Site ← SapI Insert SapI → Cut site ← BsaI

GGTCTCCGACTAGAAGAGC-ccdB-Cm-GCTCTTCACACCTGAGACC

↑                        ↑

SGP (-98→-96)      Part of Kozak
SEQ ID NO: 26      SEQ ID NO: 27

PCR Product    SapI → Cut Site Insert Cut site ← SapI
of gBlock
              GCTCTTCNACT-SGP +/- Aptamer-CACNGAAGAGC

SEQ ID NO: 38   ↑     SEQ ID NO: 39

Insert starts with SGP -95 and ends with
              GC (to restore Kozak = GCCACC)

Level 0 SGP Example

SGP +/- Apatmer: TW063 (BsaI) or TW116 (BsaI or BbsI)

BsaI → Cut Site ← BbsI Insert BbsI → Cut site ← BsaI

GGTCTCCGACTAAGTCTTC-ccdB-Cm-GAAGACTTCACCTGAGACC

↑                         ↑

SGP (-98→-96)      Part of Kozak
SEQ ID NO: 32      SEQ ID NO: 33

PCR Product       BsaI → Cut Site Insert Cut site ← BsaI
or gBlock   Using BsaI
                GGTCTCNGACT-SGP +/- Aptamer-CACCNGAGACC

SEQ ID NO: 40   ↑    SEQ ID NO: 41

Insert starts with SGP -95 and ends with
              GC (to restore Kozak = GCCACC)

BbsI → Cut Site Insert Cut site ← BbsI
        Using BbsI
               GAAGACNNGACT-SGP +/- Aptamer-CACCNNGTCTTC

SEQ ID NO: 42   ↑    SEQ ID NO: 43

Insert starts with SGP -95 and ends with
              GC (to restore Kozak = GCCACC)

Level 0 SapI ORF Example

ORF: TW197 (SapI)

BsaI → Cut Site ← SapI Insert SapI → Cut site ← BsaI

GGTCTCACACCGAAGAGC-ccdB-Cm-GCTCTTCAATAATGAGACC

↑                          ↑

Part of Kozak     Last bp of opal or ochre
SEQ ID NO: 28    stop codon + additional stop
                      SEQ ID NO: 29

SapI → Cut Site Insert Cut site ← SapI

PCR Product   GCTCTTCNCAC-C-Open Reading Frame-ATAAGAAGAGC
or gBlock
             SEQ ID NO: 44     ↑      SEQ ID NO: 45

Remember to include C before Insert, which starts with
ATG and ends with first 2 bp of stop codon
Make sure your ORF ends with either ochre → <u>TAATAA</u> or opal → <u>TGATAA</u>

Level 0 ORF Example

ORF:TW064 (BsaI) or TW117 (BsaI or BbsI)

BsaI → Cut Site ← BbsI  Insert  BbsI→ Cut site ← BsaI

GGTCTCACACCAAGTCTTC-ccdB-Cm-GAAGACTTATAATGAGACC

↑                                   ↑

Part of Kozak        Last bp of opal or ochre
     SEQ ID NO: 34      stop codon + additional stop
                                 SEQ ID NO: 35

BsaI → Cut Site Insert Cut site ← BsaI

PCR Product          GGTCTCNCACC-Open Reading Frame-ATAANGAGACC
or gBlock   Using BsaI

SEQ ID NO: 46    ↑    SEQ ID NO: 47

Insert starts with ATG and ends with
                        first 2 bp of stop codon (ochre → TAATAA, opal → TGATAA)

BbsI → Cut Site insert Cut site ← BbsI

Using BbsI  GAAGACNNCACC-Open Reading Frame-ATAANNGTCTTC

SEQ ID NO: 48    ↑    SEQ ID NO: 49

Insert starts with ATG and ends with
                        first 2 bp of stop codon (ochre → TAATAA, opal → TGATAA)

Level 0 SapI 3'UTR Example

Aptamer +/- 3'UTR: TW198 (SapI)

BsaI → Cut Site ← SapI Insert SapI→ Cut site ← BsaI

GGTCTCCATAAGAAGAGC-ccdB-Cm-GCTCTTCTTCATGAGACC

↑                              ↑

Last bp of opal or ochre    end of 3' UTR + A
stop codon + additional stop   SEQ ID NO: 31
     SEQ ID NO: 30

PCR Product      SapI → Cut Site Insert Cut site ← SapI
or gBlock

GCTCTTCNATA-A-3'UTR +/- Aptamer-T-TCAAGAAGAGC

SEQ ID NO: 50    ↑    SEQ ID NO: 51

Remember to insert an A before the 3'UTR +/- Aptamer
to restore ATAA cut site for BsaI and insert a T at the end
            to restore the TTCA cut site for BsaI

Level 0 UTR Example

ORF: TW065 (BsaI) or TW118 (BsaI or BbsI)

BsaI → Cut Site ← BbsI Insert BbsI→ Cut site ← BsaI

GGTCTCAATAAAAGTCTTC-ccdB-Dm-GAAGACTTTTCATGAGACC

↑                           ↑

Last bp of opal or ochre   end of 3' UTR + A
stop codon + additional stop  SEQ ID NO: 37
     SEQ ID NO: 52

BsaI → Cut Site Insert Cut site ← BsaI
          Using BsaI
PCR Product         GGTCTCNATAA 3'UTR +/- Aptamer-TTCANGAGACC
or gBlock

SEQ ID NO: 53    ↑    SEQ ID NO: 54

Insert 3'UTR sequence ending in TTCA

BbsI → Cut Site Insert Cut site ← BbsI

Using BbsI  GAAGACNNATAA-3'UTR +/- Aptamer-TTCANNGTCTTC

SEQ ID NO: 55    ↑    SEQ ID NO: 56

Insert 3'UTR sequence ending in TTCA

Once a library of SGPs, ORFs, and UTRs is established, one can combine Level 0's to make Level 1's, which are individual translational units. However, as we have shown, position on the replicon has a significant effect on expression, so the Level 1 destination vectors must also contain information on the translational unit's position in the final construct. In addition, some units have 3'UTR sequences while others do not. Finally, we have previously established (data not shown) that a truncated E1 structural protein is essential for replication, so the final (3'-most) translational unit must end with an E1-3'UTR sequence. These constraints leave us with the following seven Level 1 destination vectors (Table 8, FIG. 53):

TABLE 8

Level 1 destination vectors.

| Position | Type of Level 2 | 3'UTR (Y/N) | Destination Vector |
|---|---|---|---|
| P1 | Tandem or Triple SGP | Yes | TW322 |
| P1 | Tandem or Triple SGP | No | TW323 |
| P1 | Single SGP | Yes | TW324 |
| P2 | Triple | Yes | TW325 |
| P2 | Triple | No | TW326 |
| P2 | Tandem | Yes | TW327 |
| P3 | Triple | Yes | TW328 |

Level 1-Position 1 (P1)

P1 + 3'UTR (TW322)
    SapI → Cut Site ← BsaI ccdB replaced with BsaI → Cut site ← SapI
    GCTCTTCGACTAGAGACC-SGP + ORF + 3'UTR-GGTCTCCTTCACGCTGAAGAGC
          ↗       ↖                              ↗         ↖
    SapI cut site  SGP (-98→-96)      end of 3' UTR+A    SapI cut site P1 - 3'UTR (TW323)
    SapI → Cut Site ← BsaI ccdB replaced with BsaI → Cut site ← SapI
    GCTCTTCGACTAGAGACC-SGP + ORF-GGTCTCCATAACGCTGAAGAGC
          ↗       ↖                   ↗         ↖
    SapI cut site  SGP (-98→-96)   Stop codon   SapI cut site P1 - END (TW324)
    SapI → Cut Site ← BsaI ccdB replaced with BsaI → Cut site ← SapI
    GCTCTTCGACTAGAGACC-SGP + ORF + E1-3'UTR-GGTCTCCTTCACGAAGAGC
          ↗       ↖                              ↗         ↖
    SapI cut site  SGP (-98→-96)   end of 3' UTR + A    SapI cut site Level 1-P2

P2 + 3'UTR (TW325)
    SapI → Cut Site ← BsaI ccdB replaced with BsaI → Cut site ← SapI
    GCTCTTCACGC-CMV-GACTGGAGACC-SGP + ORF + 3'UTR-GGTCTCCTTCATAGGGAAGAGC
          ↗                ↖                              ↗         ↖
    SapI cut site       SGP (-98→-96)       end of 3' UTR + A    SapI cut site P2 - 3'UTR (TW326)
    SapI → Cut Site ← BsaI ccdB replaced with BsaI → Cut site ← SapI
    GCTCTTCACGC-CMV-GACTGGAGACC-SGP + ORF-GGTCTCCATAATAGGGAAGAGC
          ↗                ↖                     ↗         ↖
    SapI cut site       SGP (-98→-96)         Stop codon   SapI cut site P3 - END (TW327)
    SapI → Cut Site ← BsaI ccdB replaced with BsaI → Cut site ← SapI
    GCTCTTCACGC-CMV-GACTGGAGACC-SGP + ORF + E1-3'UTR-GGTCTCCTTCACGAAGAGC
          ↗                ↖                              ↗         ↖
    SapI cut site       SGP (-98→-96)       end of 3' UTR + A    SapI cut site Level 1-P3

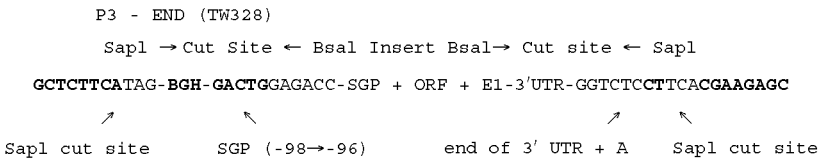

Finally the Level 1's are combined to generate Level 2's using the following destination vector:

Level 2

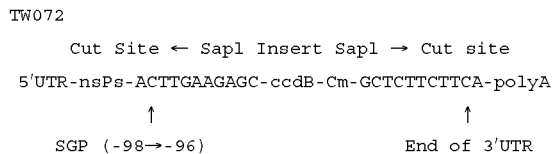

Notice that for a single translation unit, this strategy is cumbersome, requiring two rounds of reactions: first combining SGP, ORF, and E1-3'UTR into a Level 1 and then inserting this single translational unit into a Level 2. To speed up cloning for single gene replicon, we have also created Level 0S, as shown below. These Level 0S can be combined directly into a Level 2 to test the function of a specific ORF before more in depth characterization. After such characterization, the Level 0S can easily be transferred to Level 0 (using SapI) for use with the MoClo strategy above. Note that Level 0S have Kanamycin resistance similar to Level 1 vectors.

Level 0S

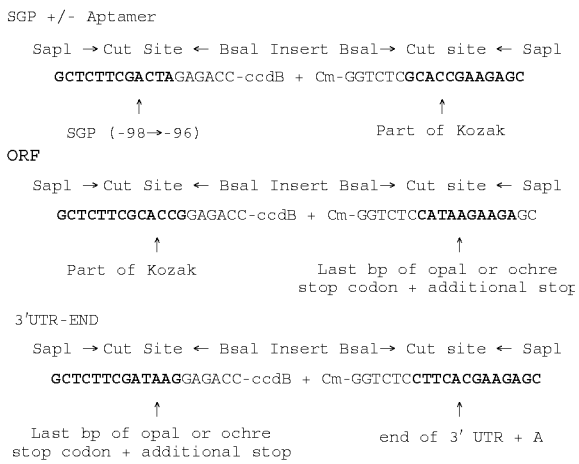

Characterization Strategy for Multi-Gene Expression

Using this MoClo-based assembly strategy, were able to construct over 250 different multi-unit replicons in under a month. Over 75% of the created constructs sequenced correctly from a single colony, with 100% correct after picking 3 colonies. One hundred and forty of these constructs, a fraction of which are shown in FIG. 52, were created to characterize constitutive expression from two and three subgenomic promoter systems. From this data, we see that physical position on the replicon is perhaps the most important consideration with regard to expression level, but expression can also be controlled via SGP strength and additional 3'UTR sequences. However, modulating SGP strength and introducing additional 3'UTR sequences can be used to control expression only to a certain extent. Presumably, as more SGPs are added, expression from the 5'-most translational units continues to decline.

Advantages and Improvements of Existing Methods, Devices, or Materials

We have demonstrated that we are able to modulate expression of multiple genes from a single replicon using position, a novel SGP library, and through incorporation of additional 3'UTR sequences. Coupled with our MoClo assembly strategy we are able to efficiently construct and characterize large libraries of construct. There has recently been a large amount of interest in self-replicating RNA, but such characterization has yet to occur for VEE or any other alphavirus replicon. Using this characterization, prediction and rational design of multi-gene replicons based upon the desired expression is provided.

REFERENCES FOR EXAMPLE 4

(1) Lundstrom, K. (2009) Alphaviruses in Gene Therapy. *Viruses* 1, 13-25.
(2) (2012) Alphavirus Vectors in Vaccine Development. *J Vaccines Vaccin* 3.
(3) (2000) Evaluation of recombinant alphaviruses as vectors in gene therapy. *Publ. Online* 7 Mar. 2000 Doi101038sjgt3301122 7.
(4) Yoshioka, N., Gros, E., Li, H.-R., Kumar, S., Deacon, D. C., Maron, C., Muotri, A. R., Chi, N. C., Fu, X.-D., Yu, B. D., and Dowdy, S. F. (2013) Efficient Generation of Human iPSCs by a Synthetic Self-Replicative RNA. *Cell Stem Cell* 13, 246-254.
(5) Robertson, J. S. (1994) Safety considerations for nucleic acid vaccines. *Vaccine* 12, 1526-1528.
(6) Klinman, D. M., Takeno, M., Ichino, M., Gu, M., Yamshchikov, G., Mor, G., and Conover, J. (1997) DNA vaccines: safety and efficacy issues. *Springer Semin. Immunopathol.* 19, 245-256.
(7) Beal, J., Wagner, T. E., Kitada, T., Azizgolshani, O., Parker, J. M., Densmore, D., and Weiss, R. (2015) Model-Driven Engineering of Gene Expression from RNA Replicons. *ACS Synthetic Biology* 4, 48-56.
(8) Kulasegaran-Shylini, R., Thiviyanathan, V., Gorenstein, D. G., and Frolov, I. (2009) The 5?UTR-specific mutation in VEEV TC-83 genome has a strong effect on RNA replication and subgenomic RNA synthesis, but not on translation of the encoded proteins. *Virology* 387, 211-221.
(9) Frolov, I., Hardy, R., and Rice, C. M. (2001) Cis-acting RNA elements at the 5' end of Sindbis virus genome RNA regulate minus- and plus-strand RNA synthesis. *RNA* 7, 1638-1651.

Example 5. Engineering Synthetic Self-Amplifying RNA Circuits for Therapeutic Applications Nucleic acids have shown promise as an alternative to protein therapeutics for many applications, including vaccination, cancer immunotherapy, genetic reprogramming, and protein-replacement therapies[3-5]. While tremendous strides have been made in protein engineering since the approval of recombinant human insulin, the cost of production, due to protein modification and purification, can discourage its use for some applications. Nucleic acid therapies avoid this cost by producing the desired protein within the target cells, allowing for correct folding and protein modifications, as well as longer exposure to the therapeutic protein[6]. In both cases, tissue-specific delivery and clearance rate are of great importance, leading to increased research in those areas. However, while targeted protein delivery is primarily extracellular via modified liposomes, nanoparticles or protein-protein interactions, nucleic acids have the ability to determine cell specificity inside the cell using genetic parts, such as tissue-specific promoters or microRNA (miRNA) target sites[-9]. This intracellular control, which can be coupled with extracellular modes of targeted delivery, is one of the key benefits of nucleic acid therapies, but is still very much in its infancy in a clinical setting.

DNA, the primary delivery platform for nucleic acid therapies, is generally introduced as either a viral vector or plasmid DNA (pDNA). Non-replicating RNA has recently emerged as a potential therapeutic platform, in part, due to the development of novel modifications that decrease immunogenicity and increase RNA half-life[6,14,22]. Unmodified mRNA has been shown to express in vivo as long as a week, but results in a significant innate immune response[23,24]. By incorporating modified bases, such as pseudouridine and 5-methylcytidine, into the mRNA, expression has been observed up to 4 weeks with a diminished innate immune response[25-29]. Additional optimization of the 5' cap, untranslated regions (UTRs), poly-A tail length, and open reading frame (ORF) have also been shown to affect mRNA stability and expression[6]. Unlike transcription of pDNA, translation of RNA occurs in the cytoplasm, making it possible in both dividing and non-dividing cells. However, because it cannot replicate, dilution becomes an issue in rapidly dividing cells. Additionally, modified RNA generally has lower expression levels than self-replicating RNA. Nonetheless, many of the genetic parts created for replicons can also be used with modified mRNA, and for some applications a much lower immune signature may be preferable.

Replicons are self-amplifying RNA, capable of producing high amounts of protein expression up to 7 weeks after administration in vivo, from relatively low initial doses compared to pDNA and non-replicating RNA[30]. Of the numerous replicon systems developed, two replicons derived from the alphavirus genus, Sindbis virus (SIN) and Venezuelan Equine Encephalitis virus (VEE) are used for the studies described herein. The invention is not limited to these examples. Replicons from both of these viruses are well-characterized and variants with reduced cytopathicity have been established[35-37]. Alphaviruses are a group of positive-strand RNA viruses with genomes between 11-12 kilobases. The genome is divided into two parts: the 5' two-thirds encodes four non-structural proteins used in RNA replication and the 3' one-third, or subgenomic RNA, encodes the structural proteins[38]. The genome is preceded by a 5'-7-methylguanosine cap and ends with a 3'-poly-A tail, mimicking cellular mRNA to facilitate translation of the non-structural proteins using host cell machinery.

As self-replicating RNA, replicons offer several advantages over other nucleic acid delivery systems. Because replication occurs outside of the nucleus and replicons do not reverse transcribe, there is minimal risk of integration, a major concern with viral particles. In addition, replicons have shown low vector immunity, expanding its applications to those requiring multiple doses. Replicons are also able to persist in both dividing and quiescent cells, presumably with lower dilution rates in rapidly dividing cells than non-replicating RNA. A high dose of a therapeutic protein can also be produced from as little as one replicon entering a target cell, minimizing the impact of delivery efficiency compared to pDNA and mRNA.

Self-amplifying nature of a replicon presents a major hurdle with respect to dosing. The majority of replicon-based technologies constitutively express a therapeutic protein without any regulation. It is demonstrated herein that protein production cannot be controlled by initial dose alone, as it can for pDNA and mRNA, but requires intracellular control of replicon expression. Control devices that not only govern output of the desired protein, but also determine tissue specificity using miRNA sensing, in a manner similar to tissue-specific promoters used in pDNA are described herein and provided as aspects of the invention. The external input for many of the genetic parts described herein are small molecules, as they are the simplest means to establish tunable and dose-dependent control after a replicon is inside a cell. However, other external inputs are also encompassed within the invention. Because it may not be optional for these drugs to be continuously administered to patients over long periods of time, we have focused the genetic circuits of the invention include ON/OFF switching in response to brief pulses of small molecule or other external inputs.

Many genetic parts for RNA have already been generated, including RNA binding proteins (RBPs), endoribonucleases, riboswitches, and RNA sensors. The examples described herein utilize two RBPs for the majority of the circuits, L7Ae and TetR. L7Ae is a ribosomal protein from *Archaeoglobus fulgidus* that has been shown to bind RNA motifs called kink-turns (K-turns) with high affinity, as well as K-loops to a lesser degree. The Tet repressor (TetR) protein derived from *Escherichia coli* is traditionally used for regulation of pDNA genetic circuits. However, using systematic evolution of ligands by exponential enrichment (SELEX), RNA aptamers were found to which TetR bound tightly. Placing either K-turns or TetR aptamers in the 5'UTR upstream of an ORF has been shown to repress expression of the output protein. In the case of TetR, this repression is relieved by the addition of a tetracycline derivative, such as doxycycline, showing small molecule regulation from RNA is possible. Another useful genetic part, Csy4, is a CRISPR-associated endoribonuclease found in *Pseudomonas aeruginosa*. The Csy4 protein recognizes a 28-nucleotide RNA repeat and cleaves between nucleotides 20 and 2146. Due to the inherent cytotoxicity of the replicon, a Csy4 site-specific "kill switch" is a very useful genetic part of the constructs described herein. Surprisingly, while L7Ae and TetR function in both replicon and modified RNA contexts, we have observed that Csy4 is unable to cleave modified RNA, presumably due to structural changes caused by the modified bases.

Single replicon circuits require multiple proteins to be expressed from a given RNA. Because these proteins must be independently regulated for predictable circuit design, and subgenomic promoter strength had been shown to be sequence dependent in Sindbis virus[59], we generated a subgenomic promoter library for VEE by truncating the full-length SGP from either the plus or minus side (FIG. 48). The SGP library was first tested in a tandem format to prevent any deletions to nsP4, as the base pairs comprising the minus side of the SGP are located in the coding region of the nsP4 protein. The first translational unit, expressing the fluorescent protein, mVenus, was held constant under the full-length −241/+30 SGP[60,61]. Our library of twenty-six truncated SGPs was placed before the second translational unit expressing mKate. FIG. 48 demonstrates that modulation of the SGP can result in a ten-fold dynamic range in protein expression ranging from −241/+3 (weakest) to −241/+15 (strongest). The experiment was repeated using mKate under control of the first SGP and mVenus under control of the second, and gave the same outcome, showing these results were not protein dependent.

Because a ten-fold range in expression was attainable by truncating only the plus side of the SGP, we were able to validate the results of our tandem experiment in a single SGP setting without risking mutations in nsP4. We chose three SGPs, representing low (SGPS), midrange (SGP30), and high (SGP15) expression in a tandem format, and placed them upstream of an mVenus reporter. These three SGPs exhibited the same pattern of expression strengths in a single SGP format, with a 22-fold range of expression (FIG. 54). From these results using one and two SGPs, we concluded that although the absolute strength of expression is context dependent, depending on the number of SGPs and position, the hierarchy of SGP strength remains unchanged.

During this experiment, we also found that cloning scars can have a profound impact on the range of expression of the SGP library. While cloning for the tandem SGP library left a minimal scar, initial cloning for the single SGP experiment was performed using standard Gateway® cloning (Life Technologies) techniques, resulting in a recombination scar that appeared to buffer expression and exhibited a low dynamic range. The maximal range of 22-fold was observed when the SGP was followed immediately by a Kozak sequence.

After establishing control of expression using an SGP library, additional 3'UTRs, and position on the replicon, a more in depth characterization of two and three SGP constructs was pursued. As we began testing the scalability of our approach in a three SGP format, it quickly became apparent that a large collection of SGP combinations, with and without additional 3'UTRs, would need to be tested to adequately characterize the system and understand positional effects. Due to the large number of combinatorial assemblies, as well as the need for scarless assembly, we adapted a Modular Cloning (MoClo)[63] assembly strategy for replicons, which was used to generate all two and three SGP constructs discussed hereafter.

RNA Binding Proteins, Destabilization Domains, and Endoribonucleases

A subset of RNA binding proteins (RBPs) can serve as translational repressors, recognizing specific RNA structures and blocking ribosome initiation. Many RBPs have been characterized, but for the following replicon circuits, we have chosen to focus on two RBPs with varying repressive capabilities, L7Ae and TetR. The archaeal protein L7Ae binds the kink-turn (K-turn) motif, repressing expression very strongly. We have enhanced this repression further by including multiple K-turn repeats (e.g. 2×K-turn). As shown in FIG. 54A, in BHK-21 cells, expression of L7Ae from the first translational unit of a replicon offers between 15- and 20,000-fold repression compared to the same construct with a dummy protein inserted in place of L7Ae. TetR, on the other hand, provided a weaker repression in the tested circuit, showing only 7-fold repression compared to the same construct with a mutant aptamer, even after increasing TetR expression by changing its position and placing it under the strongest SGP (FIG. 55B).

After characterizing these translational regulators, an input signal, either applied externally or in response to intracellular cues, was necessary to create a responsive replicon circuit. In has been demonstrated that destabilization domains (DDs) fused to proteins can promote reversible, dose-dependent small molecule regulation. These domains signal rapid degradation of the fusion protein unless the small molecule is present. We began by testing two orthogonal DDs engineered from *E. coli* dihydrofolate reductase (DDd) and human estrogen receptor ligand binding domain (DDe), which respond to trimethoprim (TMP) and 4-hydroxytamoxifin (4-OHT), respectively. The dose-response curves were produced by fusing each DD to a firefly luciferase (Fluc2) reporter and observing expression in C2C12 mouse myoblast cells (FIG. 56). These values were normalized to positive controls containing Fluc2 expressed under a wild type SGP30, revealing that the DDs decrease expression of the fusion protein even when the small molecule is present. This prevents the use of DDs directly fused to therapeutic proteins if large amounts of protein are required. Both N- and C-terminal fusions were explored, but in general, N-terminal fusions resulted in greater fold changes for both luciferase and RBP fusions.

After independently demonstrating the efficacy of both RBPs and DDs, we began to study DD-RBP fusions. It was observed in the previous experiment that DDs decrease protein expression, so focus was primarily on DD-L7Ae fusions, as weakening TetR would further decrease its fold repression. In these experiments, a 2×K-turn sequence was placed upstream of the reporter. If the small molecule was absent, DD-L7Ae would be degraded and the reporter would express. Alternatively, if the small molecule was present, DD-L7Ae would be stabilized and repress the output. Because L7Ae is such a strong repressor, initial experiments conducted in both BHK-21 and C2C12 cell lines used a relatively weak SGP driving DDd-L7Ae, and resulted in 18-fold and 22.5-fold repression, respectively, upon addition of TMP (FIGS. 57A-57B). These fold changes are higher than those attained by simply fusing the DD to Fluc2, providing evidence that DD-RBP circuits can be used to increase performance. The system was also transfected into mouse myotubes. Significant optimization was utilized to achieve comparable fold changes in myotubes, highlighting the need for an efficient assembly workflow. By shuffling SGPs, varying the number of K-turn repeats, and introducing protein kinase R (PKR) inhibitors to limit the interferon response, we achieved a 15-fold decrease in expression after addition of TMP (FIG. 57C). Because of the success of these small molecule induced "OFF" switches in vitro, this line of research is continued in vivo, specifically aiming to develop a "one-shot" prime/boost circuit for Respiratory Syncytial Virus (RSV) vaccination.

Another genetic part with potential for irreversible switching, Csy4 acts as a site-specific endoribonuclease. The 28-base pair Csy4 recognition site is relatively short, and a single recognition site inserted downstream of a reporter was able to decrease expression 23-fold. Because Csy4 can be used to cleave the poly-A tail off of a replicon, it has tremendous potential as a "kill-switch" and could be used to limit the immune response caused by the replicon over time. In order for this application to be feasible, DD-Csy4 fusions are designed to enable timed control of expression. Four constructs are co-transfected with a replicon containing mVenus and a Csy4 recognition site. Unlike TetR and L7Ae, Csy4 is irreversible, so a small amount of leaky expression would prevent proper circuit function. To prevent leaky expression, Csy4 expression is lowered by incorporating a second DDe or a PEST sequence, which decreases protein half-life[64]. These fusions are tested under a weak (SGPS) and wild type (SGP30) subgenomic promoter in both BHK-21 and C2C12 cell lines.

Characterize Replicon-Based Platforms for Expression of Multiple Genes

Co-Transfection of Multiple Replicons

Figures 58A, 58B, 58C, 58D:
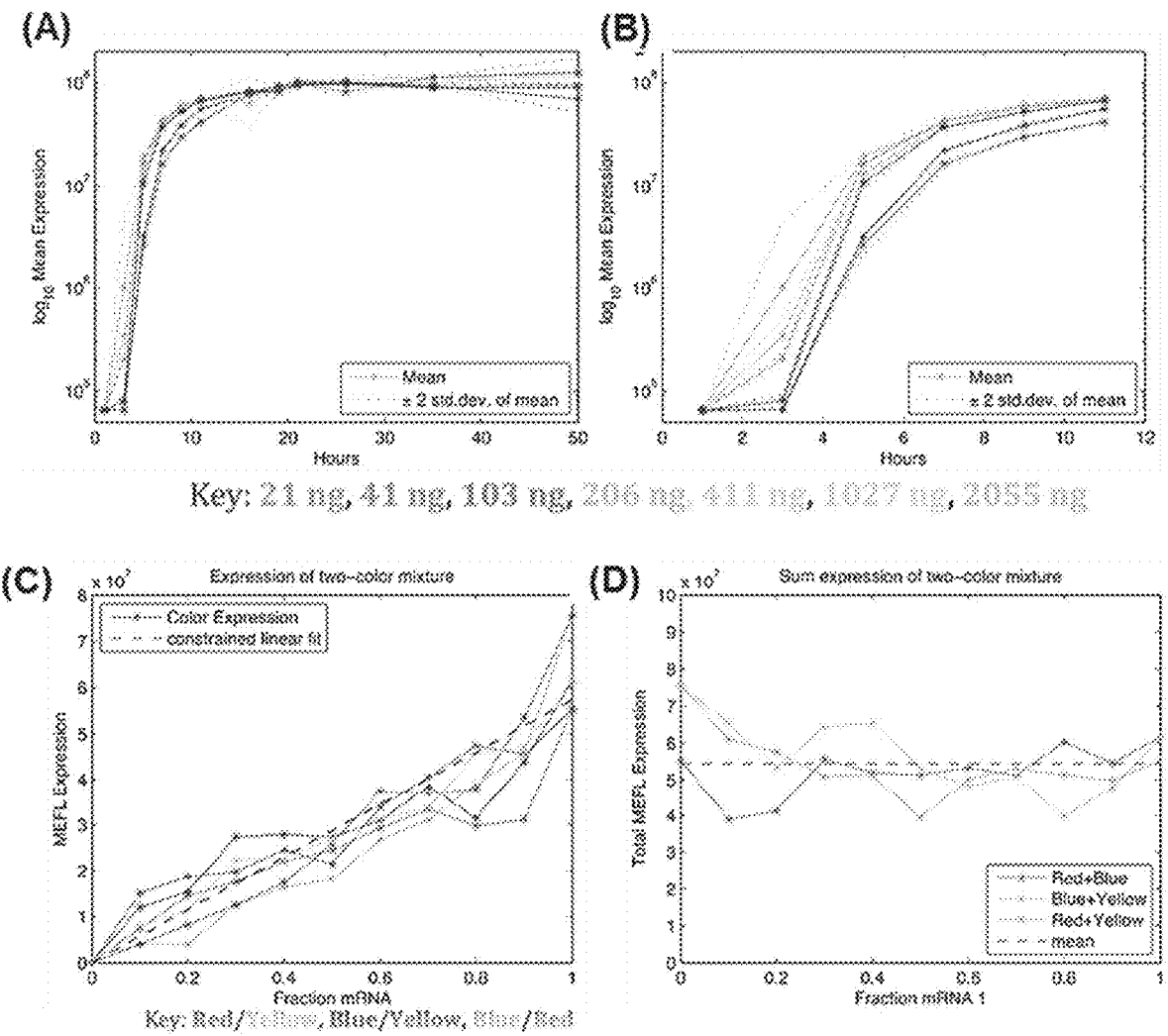

Before the SGP library was generated or destabilization domains were fused to RBPs, the most straightforward way to control the level of expression of a given protein was co-transfection with a second replicon species. As shown in FIGS. 58A-58B, while expression is dose-dependent for the first 12 hours using Sindbis replicons in BHK-21 cells, by 16 hours, protein expression converges and is independent of initial dose, precluding its use as a potential circuit input. Instead, the use of a "ballast" replicon can be used to predictably decrease expression of the desired protein. While the total fluorescence from two co-transfected replicons remains constant, a change in the initial ratio of the two transfected species results in a linear change in expression (FIGS. 58C-58D). These results indicate that a second "ballast" replicon can be added to a system to decrease the expression of a desired protein, in a linear, competition-dependent manner. In addition, we have proposed a mathematical model for the prediction of expression levels in multi-replicon systems for Sindbis replicons, and have also reparametrized this model to make it applicable for VEE replicons.

While co-transfection can be useful for the transfection of independent, constitutively expressed proteins, it presents some hurdles with regard to genetic circuits. As previously demonstrated, after three days the percentage of double positive BHK-21 cells transfected with VEE replicon gradually decreased, with one of the two replicon species gaining prominence. This behavior would pose problems for circuit design and functionality, as regulatory devices could be out-competed. Furthermore, with co-transfection, it can be difficult to ensure that each component of a genetic circuit or therapy is transfected into a given cell, which affects circuit performance or therapeutic efficacy. To avoid these drawbacks, we began to pursue single replicon platforms that could be used to express multiple genes.

Multi-SGP Replicons

After determining the elements governing expression from multi-SGP systems, namely position, SGP strength, and the presence of additional 3'UTR sequences, we planned to characterize constitutive expression from two and three SGP replicons using fluorescent reporters. It became clear that such characterization could not be completed without a high-throughput workflow, so a Modular Cloning (MoClo) assembly strategy was adapted for VEE replicons. As shown in FIG. 11, each translational unit was divided into three parts: a sub-genomic promoter (SGP), open reading frame (ORF), and 3'-untranslated region (3'UTR). Each of the parts was placed in a Level 0 vector and flanked by BsaI recognition sites. BsaI, a Type HS restriction enzyme, recognizes a sequence and cleaves downstream of it recognition site, allowing for scarless assembly. The Level 0's are combined into a Level 1 vector to form a single translational unit, using conserved sequences in between the SGP, ORF, and 3'UTR. Finally, Level 1's are combined into the replicon backbone using a second Type Hs enzyme, SapI, to form the final Level 2 product, a functional multi-unit replicon. This assembly strategy is extremely efficient, with respect to both reaction time (~1.25 hours for each step) and percentage of correct clones (~75% correct by picking one colony, ~100% correct by picking 3 colonies), and was used to generate the majority of the multi-SGP replicons.

Using this MoClo-based cloning strategy, we were able to generate all combinations of two and three SGP constructs containing low (SGPS), midrange (SGP30), and high (SGP15) subgenomic promoter strengths, with and without additional 3'UTRs. FIG. 52A shows the results for the two SGP configuration in BHK-21 cells, with mVenus expressed under the first SGP and mKate expressed under the second SGP. If the SGPs are identical and there is not an additional 3'UTR in between the translational units, then expression from the second translational unit is between 5- and 10-fold higher than the first. As shown, this difference in expression can be mitigated by strengthening the first SGP, weakening the second SGP, and by inserting an additional 3'UTR.

These results also indicate an additional parameter with a lesser impact on expression: SGP length. The results for mVenus expression from the first SGP behave as expected, with a systematic increase in expression from the weak SGPS to the strong SGP15, and slightly higher expression of each after including another 3'UTR. While mKate expression shows this same general increase from SGPS to SGP15 under the second SGP, notice that the first SGP in front of mVenus also affects mKate expression, but not in a strength-dependent manner We expect that higher mVenus expression may take resources away, leading to slightly lower mKate expression. However, when holding the second SGP constant, mKate expression is inversely correlated to the length of the first SGP. Replicon position, additional 3'UTRs, and SGP choice are most important when determining expression level (in that order).

Constructs with three SGPs were created to validate the results observed with two SGPs (FIG. 52B). Fluorescence was normalized against single SGP controls expressing each fluorescent protein under the wild type subgenomic promoter. As expected, the third translational unit dominates expression. Modulating SGP strength and introducing additional 3'UTR sequences can be used to control expression only to a certain extent. The influence of the first SGP length on subsequent SGPs becomes inconsequential. Presumably, as more SGPs are added, expression from the 5'-most translational units continues to decline, limiting the scalability of this approach, depending on the necessary expression levels required for circuit function.

Helper-Defective Interfering (DI) RNA Expression

Another platform that was explored along with co-transfection of replicons was expression from a defective interfering (DI) RNA using a helper replicon. A defective interfering viral genome is produced when large portions of the genome are deleted due to recombination, leaving the remaining fragment defective and incapable of replication on its own. Instead, the DI genome must be complemented by a "helper" virus in order to replicate, interfering with the helper's own replication through competitive inhibition.

Figures 59A, 59B, 59C:
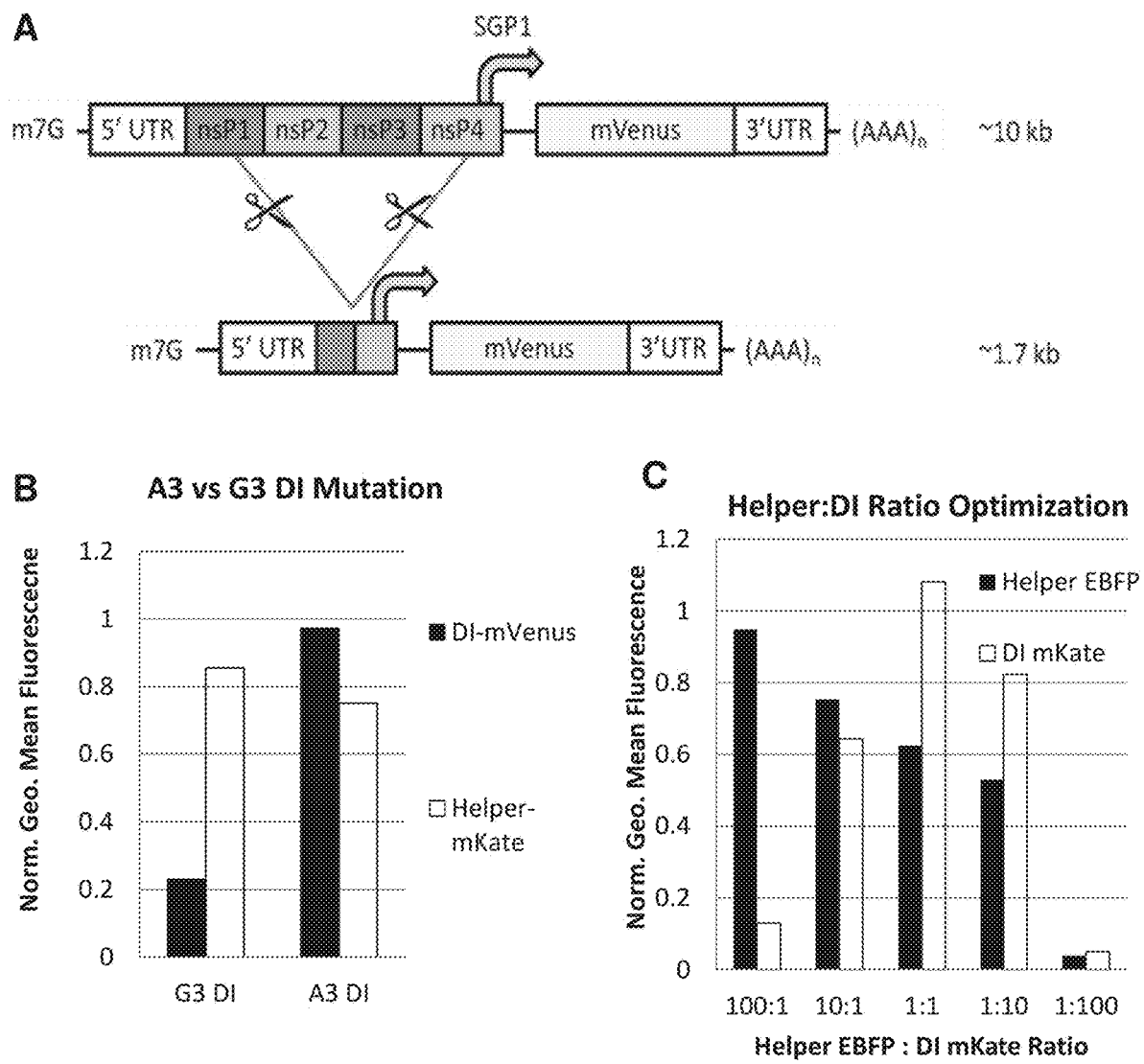

A VEE DI RNA was adopted for this study[60]. As shown in FIG. 59A, to create this DI RNA, deletions were made to remove the 3' portion of nsP1, the entirety of nsP2 and nsP3, and the 5' portion of nsP4. In this way, the structural cloverleaf element formed by the 5' of nsP1, which is involved in replication, remains intact, as well as the SGP located in the 3' of nsP4. This system was chosen because of the lack of full-length non-structural proteins, particularly nsP2 which has been reported to be involved in negative feedback of the replication, would increase DI RNA expression while limiting the host cell immune response.

Figure 59D:
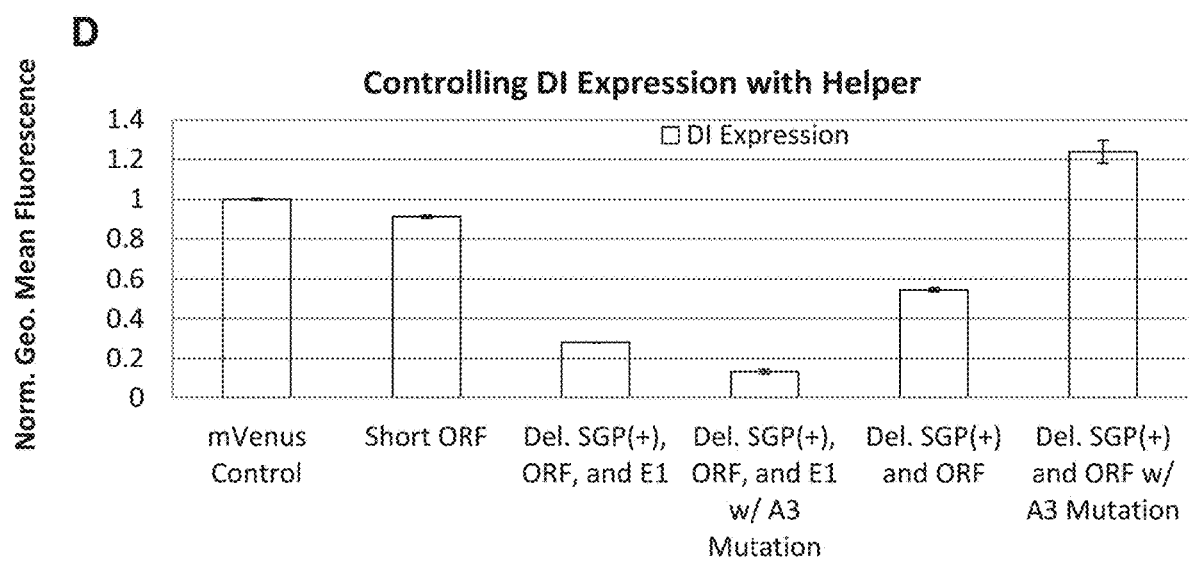

We have validated results reported by Kulasegaran-Shylini et al. that a G3→A mutation significantly increased DI RNA expression, even though this mutation increases the ratio of genomic to subgenomic RNA in a full-length replicon (FIG. 59B)[60]. We were also able to increase DI RNA expression ourselves by optimizing the helper. As shown in FIG. 59C, an optimal configuration for DI RNA expression is achieved by removing the positive side of the SGP and the entire ORF to prevent subgenomic translation, while introducing a G3→A mutation to generate more genomic RNA and thus more non-structural proteins. In addition, we were able to validate that the truncated E1 structural protein, though not functional, is necessary for high expression, most likely due to the RNA secondary structure involved in the interaction between the 5' and 3' ends of the genome during replication[62]. We next verified that the SGP library carried over into this new platform and that co-transfection of a helper with multiple DI species behaved in a predictable manner. As with co-transfected replicons, we observed constant total expression, with a linear response in expression based upon the initial ratio of the two DI species. Finally, we changed the ratio of helper to DI RNA, as multiple regimes of DI RNA interference have been reported against wild type viruses based on the amount of DI RNA present. Here, we see that while helper expression drops with decreasing initial dose, DI RNA expression does have a maximum in the tested system that is dependent on the helper-DI RNA ratio (FIG. 59D).

The helper-DI system may not experience the gradual decrease of double positive cells observed with co-transfection of multiple replicons. If the DI RNA begins to out-compete the helper, then the decrease in helper could lead to a decrease in non-structural proteins, and a subsequent decrease in DI RNA. If the helper begins to out-compete the DI RNA, then more non-structural proteins are produced, and more DI RNA is replicated. A helper-DI RNA time course is performed to determine if equilibrium exists in this system, preventing the domination of one species and averting one of the major obstacles of circuit function using co-transfection. In addition, because DI RNA replication is dependent on the presence of the helper, by encoding the circuit output on DI RNA and regulatory elements on a helper, it is possible to ensure that the output is always be regulated, even using co-transfection. There are three possible cases: (i) the DI RNA enters the cell alone, is not replicated, and the protein is not be expressed, (ii) the helper enters the cell alone, replicates, but does not contain the output protein, and (iii) both the helper and DI RNA are co-delivered, replicates, and permits desired circuit function. Using this format, a reversible and irreversible small molecule inducible OFF switch is created using DD-L7Ae and DD-Csy4, respectively.

To circumvent any co-delivery issues, we have proposed a novel self-cleaving helper-DI RNA platform (FIG. 60A). In this system the helper and DI RNA are delivered on a single strand of RNA. Csy4 is expressed from an internal ribosome entry site (IRES) shortly after the RNA enters the cell, preferably before RNA replication begins. Using a minimal Csy4 recognition site (CRS) located in between the helper and DI RNA, the two species are cleaved inside the cell. Because DI RNA is relatively short (~1.7 kb), this approach could be expanded to contain multiple DI RNAs. We expect this self-cleaving helper-CRS-DI RNA system to overcome limitations associated with transfection of multiple replicons, as well as those associated with multi-SGP replicons, such as uneven expression due to positional effects.

To test the validity of this approach, helper-CRS-DI RNA lacking an IRES-Csy4 was co-transfected with a replicon expressing either active or dead Csy4 (FIG. 60B). Replication was dramatically affected by additional base pairs on the 5' end of replicons, and we presumed this observation also applied to DI RNA, so both wild type CRS and a minimal 3' CRS were tested. The minimal 3' CRS limits the cleavage scar to a single cytosine, which we hypothesized would not dramatically reduce expression, as a guanine is added to the replicon during in vitro transcription (IVT) to facilitate m7G capping.

As shown, using dead Csy4 to prevent cleavage results in low helper and DI RNA expression. Expression still exists at low levels because the helper-CRS-DI RNA acts as a modified two SGP replicon. When active Csy4 is added, cleavage occurs, resulting in higher expression of mKate from the helper because it no longer experiences a positional effect. Here, we also observe the effect of the scar left by the full-length CRS compared to the minimal 3' CRS. The scar left by the full-length CRS makes DI RNA replication very inefficient, leading to low mVenus expression from the DI RNA. On the other hand, using the minimal 3' CRS results in substantial DI RNA expression. As a rapid test of the amount of Csy4 necessary, we also tested Csy4 expressed from a wild type VEE replicon. The wild type replicon produces higher levels of Csy4, enhancing cleavage and thus DI RNA expression, approaching levels comparable to the positive control of co-transfected helper-DI RNA.

As a next step, helper-CRS-DI RNA constructs containing Csy4 driven by an IRES from encephalomyocarditis virus (EMCV) is compared to co-transfection of a replicon expressing Csy4. These results indicate that optimization of the IRES sequence may produce higher expression of Csy4. Finally, we introduce ON/OFF switches that employ RNA degradation based regulation that would not be possible using a multi-SGP replicon.

Develop RNA-Only Circuits, with Emphasis on Small Molecule Inducible ON/OFF Switches Inducible Single Replicon Switch with Cascade Topology After characterizing our parts and expression platforms, we created a functional genetic circuit housed on a single replicon. While testing DDs fused to L7Ae, we effectively created an OFF switch, in which the addition of a small molecule stabilized L7Ae and repressed the output. Because we have not characterized any RBPs that act as translational activators, to create a single replicon ON switch required optimization of a three SGP system, containing a cascade of repressors (FIG. 61A). This circuit could have been created numerous ways using the available parts, so design constraints were necessary. Placing the reporter under the first or second SGP would prevent high expression during the ON state, so to allow the maximum range of output expression, our reporter was placed under the third SGP. Next, we had shown that L7Ae was the stronger of our two repressors, with higher fold changes when fused to DDs, and thus would be the first repressor in our cascade. Correspondingly, in this format the weaker repression exhibited by TetR would be conducive to switching the output from the OFF to the ON state. A range of expression levels were tested using position, SGP choice, and additional 3'UTRs.

In the circuit topology shown, if no TMP is present, DDd-L7Ae is destabilized, allowing TetR to repress mVenus-PEST. Alternatively, if TMP is present, DDd-L7Ae is stabilized, represses TetR, and mVenus-PEST is expressed.

The PEST sequence shortens the half-life of mVenus. This rapid turnover would allow for more sensitive studies of circuit dynamics in the future. Doxycycline (Dox) was added in conjunction with TMP to further decrease TetR binding and increase expression of the ON state. The 96 variants shown were constructed using the replicon MoClo assembly system and tested in BHK-21 cells. Flow cytometry was performed 48 hours post-transfection and the optimal construct resulted in an OFF (−TMP/−Dox) to ON (+TMP/+Dox) fold-change of 10.75-fold (FIG. 61B).

Surprisingly, the eight constructs with the highest fold changes all had TetR expressed under the first SGP and DDd-L7Ae expressed under the second SGP (Orientation 2). This result was unexpected because it was thought that not enough TetR would be translated under the first SGP to provide sufficient repression. However, expression of TetR in either the first or second position appears to result in similar OFF states. Therefore, the high fold changes observed are a product of high ON states, caused by increased amounts of DDd-L7Ae translated from the second SGP. While this switch functions, the OFF state has leaky expression due to incomplete repression by TetR.

To further decrease the OFF state of this circuit, repression enhancers fused to TetR using fluorescence activated cell sorting (FACS) are screened in conjunction with next generation RNA sequencing (RNA-seq). A library of 513 Dox-inducible TetR ON switches, testing multiple SGPs and 57 different repression enhancers, are constructed in a one-pot batch reaction using replicon MoClo assembly (FIG. 62). The entire library is transfected into C2C12 myoblasts at a low transfection efficiency, to ensure that the majority of cells receive only one variant of the circuit. Half of the transfected cells are plated with Dox, while the other half is not. After 24 hours, FACS is performed using mVenus as a transfection marker. Expression of mKate is grouped into 8 bins for both the +Dox and −Dox conditions. RNA-seq of extracted RNA reveals the circuit configurations present in each bin. Using this data, coupled with the mean fluorescence of each bin, fold-changes are calculated for each configuration.

Irreversible Switch Using Csy4

While the aforementioned switches are reversible by the addition or removal of small molecule, we have also devised an irreversible switch using Csy4 (FIG. 63A). This switch first takes advantage of positional effects, with low mVenus-PEST expression under the first SGP and higher mKate expression under the second SGP. When Csy4 is added, mKate is cleaved off, resulting in a single SGP replicon and higher mVenus expression. An additional E1-3'UTR sequence and poly-A tail were inserted in between the ORFs to facilitate continued replication and prevent degradation after cleavage occurs. The addition of the poly-A tail lowers mKate expression without active Csy4, so strong SGPs are used to counteract this effect. DDd-L7Ae is used to further decrease the OFF state of mVenus. Finally, DDe-Csy4 is incorporated onto the replicon, making the system a single replicon, small molecule inducible switch.

In State 1, to produce low mVenus and high mKate, TMP is added to stabilize DDd-L7Ae. Expression of mVenus should already be very low, as it is in the first position of a three SGP replicon, but the stabilized DDd-L7Ae should reduce expression further. No 4-OHT is present, so DDe-Csy4 is degraded, but also is repressed by DDd-L7Ae to prevent leaky expression and premature cleavage. In State 2, TMP is removed and 4-OHT is added. This combination of small molecules eliminates DDd-L7Ae repression and induce DDe-Csy4 cleavage, resulting in a single replicon with high mVenus expression.

Helper-CRS-DI miRNA High Sensor

RNA degradation-based regulation has remained elusive in a single replicon format because any degradation affects the entire replicon, and thus the entire circuit. However, using Csy4 to intracellularly split a single RNA into independently replicating components allows us to overcome this barrier. A microRNA (miRNA) high sensor, termed as such because when the target miRNA is present, the output has high expression is created (FIG. 64). In the circuit shown, the input is synthetic miR-FF4 and the output is mVenus. When miR-FF4 is absent, the DI RNA is not degraded and L7Ae is present to repress mVenus. However, when miR-FF4 is added to the system, the DI RNA degrades and mVenus freely expresses. In addition, because the DI RNA is no longer competing with the helper for replication machinery, mVenus expression could increase further using this helper-DI RNA configuration. It is crucial that Csy4 is expressed from an IRES to facilitate cleavage as early as possible. If miR-FF4 is present and the circuit is not cleaved, the entire helper-CRS-DI RNA strand is degraded.

Use of Replicon Circuits for Treating Duchenne Muscular Dystrophy (DMD).

Muscular Dystrophy Treatment

Unlike competing nucleic acid technologies, the replicon circuits of the invention utilize small molecule regulation rather than relying on integration or repeat administration of nucleic acids. Here, we propose a treatment for Duchenne muscular dystrophy (DMD) using a replicon switch to initially convert human dermal fibroblasts to a myogenic lineage to facilitate fusion, followed by expression of a therapeutic protein, follistatin.

DMD is a recessive X-linked disease characterized by continual degeneration and regeneration of muscle fibers. It is caused by a mutation in the dystrophin gene, which plays an important role in muscle stability by interacting with a dystrophin-glycoprotein complex at the muscle cell membrane. Over time the muscle tissue wastes away and is replaced by fibrotic and adipose tissue, leading to eventual paralysis and death. One in 3,500 males is born with DMD and those with the disease have a life expectancy of 25 years[65]. Because DMD is recessive and female carriers of the DMD allele retain muscle stability[66], initial therapies for DMD attempted to restore dystrophin to muscle tissue by implanting healthy donor myoblasts into dystrophic fibers. However, paternal biopsies used in clinical trials resulted in low engraftment efficiency and thus low dystrophin expression[67]. Additionally, using cells from a donor can lead to immune rejection of the implanted cells. Next, cell therapies were pursued to engineer a patient's own cells to express the therapeutic gene, follistatin. Unfortunately, a patient's pre-existing myogenic cells would have already undergone many cycles of degeneration and regeneration, making them difficult to expand[68]. Dermal fibroblasts are one of the most abundant and easily accessible cell types. They are also capable of myogenic conversion and fusion into myotubes using transient expression of MyoD, a transcription factor involved in skeletal muscle differentiation[69,70]. Initially, it was believed that MyoD alone can facilitate fibroblasts' conversion into myotubes. However, recent studies suggest that while MyoD is essential to initiate differentiation, Myogenin (MyoG) is required later to retain this fate[71].

A replicon circuit similar to that shown in FIG. 63 is used to sequentially express MyoD, followed by MyoG, in healthy human dermal fibroblasts. Myogenic conversion and fusion is detected by staining for myosin heavy chain (MHC). This task alone is therapeutically relevant, as these myotubes could then be implanted into dystrophic muscle, providing strength and stability. However, follistatin is also expressed, a secreted protein shown to improve muscle strength that is currently in clinical trials for Becker muscular dystrophy, also caused by a mutation in dystrophin[72].

Methods

RNA Preparation

Sindbis replicon plasmids were linearized using SacI-HF (NEB) prior to run-off in vitro transcription (IVT) using the mMESSAGE mMachine® SP6 Kit (Life Technologies). For experiments conducted in BHK-21 cells, VEE replicon plasmids were linearized using I-SceI (NEB) prior to in vitro transcription using the mMESSAGE mMachine® T7 Kit (Life Technologies). Following IVT, the resulting RNA was purified using the RNeasy® Mini Kit (Qiagen) and the concentration was measured using the NanoDrop™ 2000. For experiments conducted in C2C12 myoblasts or myotubes, IVT was performed using the MEGAscript® T7 Transcription Kit (Life Technologies), followed by purification using the RNeasy® Mini Kit (Qiagen). The resulting RNA was denatured at 65° C. and enzymatic capping was performed using the ScriptCap 2'-O-mehtyltrasnferase Kit (Cellscript) and ScriptCap m7G Capping System (Cellscript). A final purification step using the RNeasy® Mini Kit (Qiagen) was performed prior to transfection.

Transfection

BHK-21 cells (a kind gift from Dr. James H. Strauss) were cultured in EMEM (ATCC) supplemented with 10% FBS (PAA) at 37° C. and 5% $CO_2$. BHK-21 cells at approximately 70% confluence were electroporated using the Neon™ Transfection System (Life Technologies) following optimization, according to the manufacturers' instructions. In general, for a single well of a 24-well plate (Corning), approximately 100,000 cells were electroporated with 1,000 ng of RNA, unless otherwise stated.

C2C12 cells were cultured on gelatin coated plated in DMEM (ATCC) supplemented with 10% FBS (PAA) at 37° C. and 5% $CO_2$. The Neon™ Transfection System (Life Technologies) was independently optimized for C2C12 cells, following the manufacturer's instructions. In general, for a single well of a 24-well plate (Corning), approximately 50,000 cells were electroporated with 100 ng of RNA, unless otherwise stated.

To differentiate C2C12 cells into myotubes, 150,000 cells were plated per well in a 24-well plate and allowed to grow for one day in DMEM supplemented with 10% FBS. Once the cell population was confluent, the media was changed to DMEM supplemented with 2% horse serum (Thermo SH30074). The media was replaced each day for 4-5 days. After this time, the media was changed back to DMEM supplemented with 10% FBS and transfections were performed with Lipofectamine™ MessengerMAX™ Reagent (Life Technologies) using 100 ng of RNA.

Data Collection

For fluorescent reporters, cells for each time point were washed with 1× PBS, trypsinized, and resuspended in 1× PBS. Flow cytometry was performed using the BD LSR-Fortessa™ Flow Cytometer System (BD Biosciences), equipped with 405, 488, and 561 nm lasers. 20,000-40,000 events were collected per sample. FACSDiva software (BD Biosciences) was used for initial data collection and FlowJo was used for subsequent data analysis. For luciferase assays, 250 μL of Glo Lysis Buffer (Promega) was added to each well of a 24-well plate. 25 μL of lysate was mixed with 25 μL of Steady-Glo® reagent (Promega) in black 96-well clear bottom plates (Corning) and incubated at room temperature for 5 minutes. Luminescence was measured using a Tecan Safire² plate reader.

REFERENCES FOR EXAMPLE 5

1. Wolff, J. A. et al. Direct gene transfer into mouse muscle in vivo. *Science* 247, 1465-1468 (1990).
2. Beal, J. et al. Model-Driven Engineering of Gene Expression from RNA Replicons. *ACS Synth. Biol.* 4, 48-56 (2015).
3. Opalinska, J. B. & Gewirtz, A. M. Nucleic-acid therapeutics: basic principles and recent applications. *Nat. Rev. Drug Discov.* 1, 503-514 (2002).
4. Kay, M. A. State-of-the-art gene-based therapies: the road ahead. *Nat. Rev. Genet.* 12, 316-328 (2011).
5. Yin, H. et al. Non-viral vectors for gene-based therapy. *Nat. Rev. Genet.* 15, 541-555 (2014).
6. Sahin, U., Karikó, K. & Türeci, Ö. mRNA-based therapeutics—developing a new class of drugs. *Nat. Rev. Drug Discov.* 13, 759-780 (2014).
7. Wooddell, C. I., Reppen, T., Wolff, J. A. & Herweijer, H. Sustained liver-specific transgene expression from the albumin promoter in mice following hydrodynamic plasmid DNA delivery. *J. Gene Med.* 10, 551-563 (2008).
8. Haase, R. et al. Generation of a tumor- and tissue-specific episomal non-viral vector system. *BMC Biotechnol.* 13, 49 (2013).
9. Xie, Z., Wroblewska, L., Prochazka, L., Weiss, R. & Benenson, Y. Multi-input RNAi-based logic circuit for identification of specific cancer cells. *Science* 333, 1307-1311 (2011).
10. Bessis, N., GarciaCozar, F. J. & Boissier, M.-C. Immune responses to gene therapy vectors: influence on vector function and effector mechanisms. *Gene Ther.* 11 Suppl 1, S10-17 (2004).
11. Thomas, C. E., Ehrhardt, A. & Kay, M. A. Progress and problems with the use of viral vectors for gene therapy. *Nat. Rev. Genet.* 4, 346-358 (2003).
12. Inagaki, K., Piao, C., Kotchey, N. M., Wu, X. & Nakai, H. Frequency and spectrum of genomic integration of recombinant adeno-associated virus serotype 8 vector in neonatal mouse liver. *J. Virol.* 82, 9513-9524 (2008).
13. Rapti, K. et al. Neutralizing Antibodies Against AAV Serotypes 1,2,6, and 9 in Sera of Commonly Used Animal Models. *Mol. Ther.* 20, 73-83 (2012).
14. Geall, A. J., Mandl, C. W. & Ulmer, J. B. RNA: the new revolution in nucleic acid vaccines. *Semin. Immunol.* 25, 152-159 (2013).
15. Bouard, D., Alazard-Dany, N. & Cosset, F.-L. Viral vectors: from virology to transgene expression. *Br. J. Pharmacol.* 157, 153-165 (2009).
16. Miller, A. M. & Dean, D. A. Tissue-specific and transcription factor-mediated nuclear entry of DNA. *Adv. Drug Deliv. Rev.* 61, 603-613 (2009).
17. Jafari, M., Soltani, M., Naahidi, S., Karunaratne, D. N. & Chen, P. Nonviral approach for targeted nucleic acid delivery. *Curr. Med. Chem.* 19, 197-208 (2012).
18. Chen, Z.-Y., Riu, E., He, C.-Y., Xu, H. & Kay, M. A. Silencing of Episomal Transgene Expression in Liver by Plasmid Bacterial Backbone DNA Is Independent of CpG Methylation. *Mol. Ther.* 16, 548-556 (2008).
19. Chen, Z. Y., He, C. Y., Meuse, L. & Kay, M. A. Silencing of episomal transgene expression by plasmid bacterial DNA elements in vivo. *Gene Ther.* 11, 856-864 (2004).
20. Cohen, R. N., van der Aa, M. A. E. M., Macaraeg, N., Lee, A. P. & Szoka, F. C. Quantification of Plasmid DNA 20. Copies in the Nucleus after Lipoplex and Polyplex Transfection. *J. Control. Release Off. J. Control. Release Soc.* 135, 166-174 (2009).
21. Glover, D. J., Leyton, D. L., Moseley, G. W. & Jans, D. A. The efficiency of nuclear plasmid DNA delivery is a critical determinant of transgene expression at the single cell level. *J. Gene Med.* 12, 77-85 (2010).
22. Andries, O., Kitada, T., Bodner, K., Sanders, N. N. & Weiss, R. Synthetic biology devices and circuits for RNA-based 'smart vaccines': a propositional review. *Expert Rev. Vaccines* 14, 313-331 (2015).
23. Pascolo, S. Vaccination with messenger RNA. *Methods Mol. Med.* 127, 23-40 (2006).
24. Pollard, C., De Koker, S., Saelens, X., Vanham, G. & Grooten, J. Challenges and advances towards the rational design of mRNA vaccines. *Trends Mol. Med.* 19, 705-713 (2013).
25. Karikó, K., Buckstein, M., Ni, H. & Weissman, D. Suppression of RNA recognition by Toll-like receptors: the impact of nucleoside modification and the evolutionary origin of RNA. *Immunity* 23, 165-175 (2005).
26. Karikó, K. et al. Incorporation of pseudouridine into mRNA yields superior nonimmunogenic vector with increased translational capacity and biological stability. *Mol. Ther. J. Am. Soc. Gene Ther.* 16, 1833-1840 (2008).
27. Anderson, B. R. et al. Incorporation of pseudouridine into mRNA enhances translation by diminishing PKR activation. *Nucleic Acids Res.* 38, 5884-5892 (2010).
28. Anderson, B. R. et al. Nucleoside modifications in RNA limit activation of 2'-5'-oligoadenylate synthetase and increase resistance to cleavage by RNase L. *Nucleic Acids Res.* 39, 9329-9338 (2011).
29. Kormann, M. S. D. et al. Expression of therapeutic proteins after delivery of chemically modified mRNA in mice. *Nat. Biotechnol.* 29, 154-157 (2011).
30. Geall, A. J. et al. Nonviral delivery of self-amplifying RNA vaccines. *Proc. Natl. Acad. Sci. U.S.A* 109, 14604-14609 (2012).
31. Strauss, J. H. & Strauss, E. G. The alphaviruses: gene expression, replication, and evolution. *Microbiol. Rev.* 58, 491-562 (1994).
32. Wahlfors, J. J., Zullo, S. A., Loimas, S., Nelson, D. M. & Morgan, R. A. Evaluation of recombinant alphaviruses as vectors in gene therapy. *Gene Ther.* 7, 472-480 (2000).
33. Lundstrom, K. Alphaviruses in Gene Therapy. *Viruses* 1, 13-25 (2009).
34. Lundstrom, K. Alphavirus-Based Vaccines. *Viruses* 6, 2392-2415 (2014).
35. Frolov, I. et al. Selection of RNA replicons capable of persistent noncytopathic replication in mammalian cells. *J. Virol.* 73, 3854-3865 (1999).
36. Lustig, S. et al. Molecular basis of Sindbis virus neurovirulence in mice. *J. Virol.* 62, 2329-2336 (1988).
37. Petrakova, O. et al. Noncytopathic Replication of Venezuelan Equine Encephalitis Virus and Eastern Equine Encephalitis Virus Replicons in Mammalian Cells. *J. Virol.* 79, 7597-7608 (2005).
38. Jose, J., Snyder, J. E. & Kuhn, R. J. A structural and functional perspective of alphavirus replication and assembly. *Future Microbiol.* 4, 837-856 (2009).
39. Ljungberg, K. & Liljeström, P. Self-replicating alphavirus RNA vaccines. *Expert Rev. Vaccines* 14, 177-194 (2015).
40. Berglund, P., Fleeton, M. N., Smerdou, C. & Liljeström, P. Immunization with recombinant Semliki Forest virus induces protection against influenza challenge in mice. *Vaccine* 17, 497-507 (1999).
41. Uematsu, Y. et al. Lack of Interference with Immunogenicity of a Chimeric Alphavirus Replicon Particle-Based Influenza Vaccine by Preexisting Antivector Immunity. *Clin. Vaccine Immunol. CVI* 19, 991-998 (2012).
42. Dubensky, T. W., Liu, M. A. & Ulmer, J. B. Delivery systems for gene-based vaccines. *Mol. Med. Camb. Mass.* 6, 723-732 (2000).
43. Yoshioka, N. et al. Efficient generation of human iPSCs by a synthetic self-replicative RNA. *Cell Stem Cell* 13, 246-254 (2013).
44. Saito, H. et al. Synthetic translational regulation by an L7Ae-kink-turn RNP switch. *Nat. Chem. Biol.* 6, 71-78 (2010).
45. Belmont, B. J. & Niles, J. C. Engineering a direct and inducible protein-RNA interaction to regulate RNA biology. *ACS Chem. Biol.* 5, 851-861 (2010).
46. Haurwitz, R. E., Jinek, M., Wiedenheft, B., Zhou, K. & Doudna, J. A. Sequence- and structure-specific RNA processing by a CRISPR endonuclease. *Science* 329, 1355-1358 (2010).
47. Haurwitz, R. E., Sternberg, S. H. & Doudna, J. A. Csy4 relies on an unusual catalytic dyad to position and cleave CRISPR RNA. *EMBO J.* 31, 2824-2832 (2012).
48. Iwamoto, M., Björklund, T., Lundberg, C., Kirik, D. & Wandless, T. J. A general chemical method to regulate protein stability in the mammalian central nervous system. *Chem. Biol.* 17, 981-988 (2010).
49. Miyazaki, Y., Imoto, H., Chen, L. & Wandless, T. J. Destabilizing Domains Derived from the Human Estrogen Receptor. *J. Am. Chem. Soc.* 134, 3942-3945 (2012).
50. Hahn, C. S., Hahn, Y. S., Braciale, T. J. & Rice, C. M. Infectious Sindbis virus transient expression vectors for studying antigen processing and presentation. *Proc. Natl. Acad. Sci. U.S.A* 89, 2679-2683 (1992).
51. Frolov, I. et al. Alphavirus-based expression vectors: strategies and applications. *Proc. Natl. Acad. Sci. U.S.A* 93, 11371-11377 (1996).
52. Petrakova, O. et al. Noncytopathic replication of Venezuelan equine encephalitis virus and eastern equine encephalitis virus replicons in Mammalian cells. *J. Virol.* 79, 7597-7608 (2005).
53. Wiley, M. R., Roberts, L. O., Adelman, Z. N. & Myles, K. M. Double subgenomic alphaviruses expressing multiple fluorescent proteins using a *Rhopalosiphum padi* virus internal ribosome entry site element. *PloS One* 5, e13924 (2010).
54. Sanz, M. A., Castelló, A., Ventoso, I., Berlanga, J. J. & Carrasco, L. Dual mechanism for the translation of subgenomic mRNA from Sindbis virus in infected and uninfected cells. *PloS One* 4, e4772 (2009).
55. Firth, A. E. & Brierley, I. Non-canonical translation in RNA viruses. *J. Gen. Virol.* 93, 1385-1409 (2012).
56. Donnelly, M. L. et al. Analysis of the aphthovirus 2A/2B polyprotein 'cleavage' mechanism indicates not a proteolytic reaction, but a novel translational effect: a putative ribosomal 'skip'. *J. Gen. Virol.* 82, 1013-1025 (2001).
57. Thomas, J. M., Klimstra, W. B., Ryman, K. D. & Heidner, H. W. Sindbis virus vectors designed to express a foreign protein as a cleavable component of the viral structural polyprotein. *J. Virol.* 77, 5598-5606 (2003).
58. Kim, J. H. et al. High cleavage efficiency of a 2A peptide derived from porcine teschovirus-1 in human cell lines, zebrafish and mice. *PloS One* 6, e18556 (2011).
59. Wielgosz, M. M., Raju, R. & Huang, H. V. Sequence Requirements for Sindbis Virus Subgenomic mRNA Promoter Function in Cultured Cells. *J. Virol.* 75, 3509-3519 (2001).

60. Kulasegaran-Shylini, R., Thiviyanathan, V., Gorenstein, D. G. & Frolov, I. The 5'UTR-specific mutation in VEEV TC-83 genome has a strong effect on RNA replication and subgenomic RNA synthesis, but not on translation of the encoded proteins. Virology 387, 211-221 (2009).
61. Petrakova, O. et al. Noncytopathic Replication of Venezuelan Equine Encephalitis Virus and Eastern Equine Encephalitis Virus Replicons in Mammalian Cells. *J. Virol.* 79, 7597-7608 (2005).
62. Frolov, I., Hardy, R. & Rice, C. M. Cis-acting RNA elements at the 5' end of Sindbis virus genome RNA regulate minus- and plus-strand RNA synthesis. *RNA* 7, 1638-1651 (2001).
63. Weber, E., Engler, C., Gruetzner, R., Werner, S. & Marillonnet, S. A Modular Cloning System for Standardized Assembly of Multigene Constructs. *PLoS ONE* 6, e16765 (2011).
64. Rechsteiner, M. & Rogers, S. W. PEST sequences and regulation by proteolysis. *Trends Biochem. Sci.* 21, 267-271 (1996).
65. Nowak, K. J. & Davies, K. E. Duchenne muscular dystrophy and dystrophin: pathogenesis and opportunities for treatment. *EMBO Rep.* 5, 872-876 (2004).
66. Pegoraro, E. et al. Genetic and biochemical normalization in female carriers of Duchenne muscular dystrophy: evidence for failure of dystrophin production in dystrophin-competent myonuclei. *Neurology* 45, 677-690 (1995).
67. Karpati, G. et al. Myoblast transfer in Duchenne muscular dystrophy. *Ann. Neurol.* 34, 8-17 (1993).
68. Webster, C. & Blau, H. M. Accelerated age-related decline in replicative life-span of Duchenne muscular dystrophy myoblasts: implications for cell and gene therapy. *Somat. Cell Mol. Genet.* 16, 557-565 (1990).
69. Lattanzi, L. et al. High efficiency myogenic conversion of human fibroblasts by adenoviral vector-mediated MyoD gene transfer. An alternative strategy for ex vivo gene therapy of primary myopathies. *J. Clin. Invest.* 101, 2119-2128 (1998).
70. Gibson, A. J. et al. Dermal fibroblasts convert to a myogenic lineage in mdx mouse muscle. *J. Cell Sci.* 108 (Pt 1), 207-214 (1995).
71. Liu, Z., Fan, H., Li, Y. & Zheng, S. G. Experimental Studies on the Differentiation of Fibroblasts into Myoblasts induced by MyoD Genes in vitro. *Int. J. Biomed. Sci. IJBS* 4, 14-19 (2008).
72. Mendell, J. R. et al. A phase 1/2a follistatin gene therapy trial for becker muscular dystrophy. *Mol. Ther. J. Am. Soc. Gene Ther.* 23, 192-201 (2015).

Example 6. Self-Replicating RNA Prime/Boost Circuit Vaccine for Respiratory Syncytial Virus (RSV)

Comparison of Luciferase Expression Levels from Different RNA Platforms and Delivery Formats in Wild-Type and SCID Mice To obtain a general understanding of the relative performances (translational capacity and duration) of different mRNA (RNA replicon and modified mRNA [modRNA]) platforms for intramuscular (i.m.) delivery into mice using various non-viral delivery methods (lipid nanoparticles (LNP) and electroporation (e.p.)) is performed.

To this end, Venezuelan equine encephalitis (VEE) replicon RNA and modRNA encoding firefly luciferase (Fluc) is produced by in vitro transcription (IVT) using bacteriophage T7 RNA polymerase. DNA templates for run-off IVT of the VEE replicons (wildtype (WT) and non-cytopathic nsP2Q739L replicon (NCP)) and modRNA (containing the 5' and 3' UTRs of the VEE subgenomic RNA (sgRNA)) are prepared by plasmid linearization followed by removal of the 3' overhang by Klenow fragment. For modRNA IVT, N1-methylpseudouridine (m1Y) is incorporated into the RNA instead of uridine. Both mRNAs (replicon and modRNA) are capped co-transcriptionally using cap analogues (e.g. anti-reverse cap analogue (ARCA)) and subsequently treated with phosphatase to remove 5' triphosphates from uncapped RNA. ModRNA is purified by high performance liquid chromatography (HPLC) and RNA replicon is purified by denaturing urea polyacrylamide gel electrophoresis combined with electroelution to remove contaminating dsRNA or RNA/DNA hybrids from the sample. Quality control (QC) of the RNAs is performed by denaturing gel electrophoresis or capillary electrophoresis using an Agilent Bioanalyzer to quantify the amount of full length RNA in the sample. Furthermore, dot blot is performed using a dsRNA specific antibody to quantify the levels of contaminating dsRNA in the sample, if any. The RNAs are subsequently transfected into mouse myotubes using Lipofectamine MessengerMAX (Life Technologies). Myotubes are differentiated from a mouse myoblast cell line (C2C12) using differentiation medium containing donor equine serum.

The RNAs that pass the QC test, are used for bilateral injection (6 ug) into the gastrocnemius muscles of WT (Balb/c) or severe combined immunodeficiency (SCID) mice. The levels of Fluc reporter proteins expressed from the various RNAs are monitored in vivo by bioluminescence imaging (BLI) over the course of 77 days. Admisinitration occurs at day 0, (bilateral, i.m.) and assays of in vivo bioluminescence occurs at days 2, 4, 7, 10, 14, 21, 28, 35, 42, 49, 56, 63, 70, and 77. After the last BLI measurement, the mice are sacrificed and quantitative reverse transcription PCR (qRT-PCR) analysis is performed on RNA extracted from the gastrocnemius muscle to detect the levels of replicon RNA in the tissue. I.m. delivery of RNA is accomplished by packaging the RNAs into LNPs or by naked injection followed by e.p. using a Harvard Apparatus BTX ECM830 electroporator (100V, 3 pulses, 60 ms duration/100 ms delay). Experimental groups are summarized in Table 9. LNP packaging of the RNAs is performed using the ethanol dilution method by complexing RNA with a cationic lipid and fusogenic lipids via electrostatic interactions and subsequently grafting with DSPE-PEG. QC of LNP-packaged RNA is performed by measuring the zeta-potential and size of the particles using dynamic light scattering (DLS) and by checking the RNA packaging efficiency using a RiboGreen® (Life Technologies) assay. The formulated RNAs are transfected in vitro into C2C12 myotubes to measure protein expression. The RNA and LNP QC procedures described are used to verify the quality of the IVT RNA and LNP-packaged RNA for all subsequent tasks.

TABLE 9

Comparison of luciferase expression levels from different RNA platforms and delivery formats in wild-type and SCID mice.

| Group | RNA type | Delivery (i.m.) | Dose per limb (ug) | Mice |
|---|---|---|---|---|
| 1 | Mock (lacZ) | LNP | 6 | Balb/c (n = 2) |
| 2 | WT replicon | | | SCID (n = 2) |
| 3 | Fluc | LNP | 6 | Balbic (n = 8) |
| 4 | modRNA | | | SCID (n = 8) |

TABLE 9-continued

Comparison of luciferase expression levels from different RNA platforms and delivery formats in wild-type and SCID mice.

| Group | RNA type | Delivery (i.m.) | Dose per limb (ug) | Mice |
|---|---|---|---|---|
| 5 | Fluc WT | LNP | 6 | Balb/c (n = 8) |
| 6 | replicon | | | SCID (n = 8) |
| 7 | Fluc NCP | LNP | 6 | Balb/c (n = 8) |
| 8 | replicon | | | SCID (n = 8) |
| 9 | Mock (lacZ) WT replicon | e.p. | 6 | Balb/c (n = 2) |
| 10 | Fluc modRNA | e.p. | 6 | Balb/c (n = 8) |
| 11 | Fluc WT | e.p. | 6 | Balb/c (n = 8) |
| 12 | replicon | | | SCID (n = 8) |
| 13 | Fluc NCP Replicon | e.p. | 6 | Balb/c (n = 8) |

Comparison of Immune Responses by Homologous Prime/Boost Using Different RNA Platforms and Delivery Formats The capabilities of the various RNA expression platforms (replicon and modRNA) to induce an immune response against the RSV F antigen by homologous prime/boost when delivered i.m. using LNPs or by e.p. as described above are compared.

To this end, two doses (1.5 and 6 ug) of WT or NCP VEE replicon or m1Y modRNA encoding the RSV F antigen are unilaterally injected and delivered into the gastrocnemius muscles of Balb/c mice by e.p. or using LNPs (prime; day 0). Three weeks after this prime injection, the mice receive a unilateral i.m. booster shot of the same amount/type of RNA using the same delivery method (boost; day 21). An aluminum-adjuvanted RSV protein prime/boost group following the same injection schedule as the RNA groups is included as a benchmark for the immune response against RSV F protein. Prime-only groups of the above are also included as a control. At Day 0, prime unilaterial, i.m. is delivered, at day 21 a boost is administered, and on day 35, the mice are sacrificed, immune response is measured, and qRT-PCT is performed. See Table 10.

The immune responses against the RSV F antigen on day 35 (two weeks after the boost injection or five weeks after the prime injection for prime-only groups) for each experimental group is determined by measuring 1) the serum antibody (Ab) titers against RSV F, 2) serum virus-neutralizing Ab (VNA) titers against RSV, and 3) antigen specific activation and cytokine secretion (interferon (IFN)-y) of spleen CD4+ and CD8+ T cells upon RSV F peptide stimulation (quantified by an Enzyme-Linked ImmunoSpot (ELISpot) assay.

Furthermore, the immunogenicity of the VEE replicase proteins are evaluated by measuring the serum Ab levels against the replicase proteins as well as the replicase specific immune response of splenocytes by IFN-γ ELISPOT. Systemic toxicity induced by the different RNA platforms and delivery methods is determined by measuring blood markers of liver toxicity (including aspartate aminotransferase (AST), alanine aminotransferase (ALT), and alkaline phosphatase) as well as pro-inflammatory cytokines (using cytometric bead array (CBA) assays).

Finally, after sacrificing the mice, qRT-PCR analysis is performed on RNA extracted from the gastrocnemius muscle to detect the levels of replicon RNA in the tissue.

TABLE 10

Comparison of immune responses by homologous prime/boost using different RNA platforms and delivery formats.

| Group | Payload Type | Delivery (i.m.) | Dose per injection (ug) | Mice |
|---|---|---|---|---|
| Prime/boost | | | | |
| 1 | — | LNP | — | Balb/c(n = 8) |
| 2 | RSV F modRNA | LNP | 1.5 | Balb/c(n = 8) |
| 3 | | | 6 | Balb/c(n = 8) |
| 4 | RSV F WT | LNP | 1.5 | Balb/c(n = 8) |
| 5 | replicon | | 6 | Balb/c(n = 8) |
| 6 | RSV F NCP | LNP | 1.5 | Balb/c(n = 8) |
| 7 | replicon | | 6 | Balb/c(n = 8) |
| 8 | — | e.p. | — | Balb/c(n = 8) |
| 9 | RSV F modRNA | e.p. | 1.5 | Balb/c(n = 8) |
| 10 | | | 6 | Balb/c(n = 8) |
| 11 | RSV F WT | e.p. | 1.5 | Balb/c(n = 8) |
| 12 | replicon | | 6 | Balb/c(n = 8) |
| 13 | RSV F NCP | e.p. | 1.5 | Balb/c(n = 8) |
| 14 | replicon | | 6 | Balb/c(n = 8) |
| 15 | RSV F protein + Alum | — | 0.5 | Balb/c(n = 8) |
| Prime only | | | | |
| 16 | RSV F modRNA | LNP | 1.5 | Balb/c(n = 8) |
| 17 | | | 6 | Balb/c(n = 8) |
| 18 | RSV F WT | LNP | 1.5 | Balb/c(n = 8) |
| 19 | replicon | | 6 | Balb/c(n = 8) |
| 20 | RSV F NCP | LNP | 1.5 | Balb/c(n = 8) |
| 21 | replicon | | 6 | Balb/c(n = 8) |
| 22 | RSV F modRNA | e.p. | 1.5 | Balb/c(n = 8) |
| 23 | | | 6 | Balb/c(n = 8) |
| 24 | RSV F WT | e.p. | 1.5 | Balb/c(n = 8) |
| 25 | replicon | | 6 | Balb/c(n = 8) |
| 26 | RSV F NCP | e.p. | 1.5 | Balb/c(n = 8) |
| 27 | replicon | | 6 | Balb/c(n = 8) |
| 28 | RSV F protein + Alum | — | 0.5 | Balb/c(n = 8) |

Assays:
1. Serum RSV F Ab titers (Crucell)
2. Serum RSV VNA titers (Crucell)
3. Immune response against RSV F by splenocyte (CD4+, CD8+ T cell) cytokine (IFN-γ) ELISpot (MIT)
4. Immune response against VEE replicase by serumAb titers and splenocyte (CD4+, CD8+ T cell) cytokine (IFN-γ) ELISpot (MIT)
5. Liver toxicity markers and pro-inflammatory cytokine measurements from the blood (MIT)
6. qRT-PCR of replicon RNA from muscle (MIT)

Comparison of Immune Responses of Homologous Vs Heterologous Prime/Boost

The magnitude and quality of the immune responses against RSV F following homologous (RNA-prime/RNA-boost or protein-prime/protein-boost) or heterologous (RNA-prime(/RNA-boost)/protein boost) prime/boosting of the antigen is compared.

Based on the results of the above, the optimal RNA platform, delivery method, and two RNA doses to express the RSV F antigen are determined. For the homologous RNA prime/boost, using this optimal setup, RNA are unilaterally injected into the gastrocnemius muscles of Balb/c mice (prime; day 0). Three and six weeks after this prime injection, the mice receive a unilateral i.m. booster shot (boost; days 21, 42). As a homologous protein prime/boost control, aluminum-adjuvanted RSV F protein prime-only or prime (day 0)/boost (day 21) injections is performed. These RNA or protein homologous prime/boost groups are compared with heterologous prime/boost injection groups in which an aluminum-adjuvanted RSV F protein booster injection is administered following a single RNA prime injection (day 0) or RNA prime (day 0)/boost (day 21) injections. Prime-only groups for replicon (1.5 ug) as well as aluminum-adjuvanted protein are also included as a control (experimental groups and injection schedules are summarized in FIG. 72).

The immune responses against the RSV F antigen on days 14, and/or 35, and/or 56 depending on the experimental group (as described in FIG. 72) are assessed by measuring the serum Ab titers, serum VNA titers, and antigen specific T cell activation levels as described above. For the prime-only groups serum is drawn every 14 days to follow the antibody responses against RSV F. For these groups, the mice are sacrificed 56 days after the prime and humoral and cellular immune responses are measured.

Small Molecule-Regulatable RNA Replicons for "One Shot" Prime/Boost Vaccination

The magnitude and quality of an immune response against an antigen is established and may be improved by modulating the in vivo quantity of the antigen expressed from an RNA replicon.

To this end, we first establish whether it is possible to regulate the expression levels of a Fluc reporter protein in a manner that would be meaningful for the purpose of modulating the adaptive immune response. Regulation of target protein expression is done by adapting the L7Ae/K-turn translational repression system. The L7Ae repressor is fused to a destabilizing domain derived from the *E. coli* DHFR protein (DDd). When fused to a protein of interest, DDd targets the protein to the proteasome for degradation. However, targeting of the protein to the proteasome can be blocked by binding of the small molecule trimethoprim (TMP) to DDd. A set of configurations to identify an optimal TMP regulatable RNA replicon is screened (Circuit 1; "OFF switch") with tandem subgenomic promoters (SGPs). The first SGP expresses a (2×)DDd-L7Ae fusion protein and the second SGP expresses a Fluc reporter whose translation can be controlled by binding of DDd-L7Ae to K-turn motifs as follows:

SGP1(15)(2×)DDd-L7Ae SGP2(x)NxKt Fluc(IRES E3)

(X=16,30;N=2,3,4)

(+TMP:DDd-L7Ae binding to motif→Fluc OFF;

−TMP:DDd-L7Ae degradation and no binding to motif→Fluc ON) Circuit 1

The ON/OFF ratio (circuit performance) of each replicon in the Circuit 1 library is first evaluated in C2C12 myotubes. The most promising member (high ON/OFF ratio and low OFF state expression) is subsequently tested in vivo. For this, two doses (1 and 6 ug) of the optimal Circuit 1 replicon is packaged with LNPs and bilaterally injected into the gastrocnemius muscles of Balb/c mice. TMP is added to the drinking water of the mice in the following periodic pattern: (1 week −TMP [Fluc ON], 2 weeks+TMP [Fluc OFF])×3 to see whether it would be possible to induce three pulses of Fluc expression in vivo in mice. "No TMP" and "constant TMP" groups as well as a constitutively repressed replicon group expressing L7Ae are used as controls (experimental groups and BLI schedules are summarized in FIG. 70).

Based on the in vivo performance of the injected replicon circuit, up to two more attempts are made to reconfigure the replicon and improve the performance of the circuit (if necessary).

Once it has been established that it is possible to provide sequential pulses of the Fluc reporter using the DD-L7Ae TMP OFF switch in vivo, next, we regulate the expression of the RSV F antigen using a replicon with the optimal circuit topology identified above but encoding the antigen instead of Fluc (Circuit 2). The optimal dose (1 or 6 ug depending on the results of the optimization experiment above) of Circuit 2 are packaged with LNPs and unilaterally injected into the gastrocnemius muscles of Balb/c mice (day 0). TMP is added to the drinking water of the mice in the following pattern: (1 week −TMP [RSV F ON], 2 weeks +TMP [RSV F OFF])×3 in order to modulate the expression of RSV F in vivo. "No TMP" and "constant TMP" groups as well as a constitutively repressed L7Ae replicon group are included as controls. The immune responses against the RSV F antigen on days 21, 42, and 63 are assessed by measuring the serum Ab titers, serum VNA titers, and antigen specific T cell activation levels. Experimental groups and assay schedules are summarized in FIG. 71.

If the optimal TMP-based RSV F antigen OFF switch (Circuit 2) contains IRES E3, control groups using a replicon identical to Circuit 2 except in which the E3 protein is replaced with a "dummy" protein (e.g. mVenus) are included to make sure that the E3 innate immune inhibitor protein does not negatively affect the adaptive immune response elicited against the RSV F antigen.

Materials:

In Vitro Reagents

DNA synthesis (IDT, GenScript), oligonucleotides (IDT), restriction enzymes (NEB), PCR reagents (Agilent), T4 DNA ligase (Promega), VEE replicon DNA template (manuscript in press), plasmid DNA purification columns (Qiagen), DNA sequencing services (Quintara), IVT kit (Life Technologies), modified NTPs (TriLink), ARCA (TriLink), phosphatase (epicentre), RNA purification columns (Qiagen), in vitro lipid transfection reagents (Life Technologies), dsRNA-specific monoclonal Ab J2 (English & Scientific Consulting), C2C12 myoblasts (kind gift from Dr. Barbara J. Wold, Caltech), cell culture media (Life Technologies, ATCC), fetal bovine serum (Thermo Fisher Scientific), donor equine serum (Thermo Fisher Scientific), phosphate buffered saline (Corning), trypsin (Corning), pipette tips, plastic ware other basic reagents and supplies (VWR, Fisher, Westnet).

In Vivo Reagents

Anesthesia machine fee (Koch Institute), IVIS machine fee (Koch Institute), flow cytometry facility fee (Koch Institute), CBA assay FACS panel (BD Biosciences), dialysis device (Life Technologies), liver and kidney toxicity enzyme detection kit (Millipore), ELISpot reagents/plates (Millipore), ELISpot Abs (MAbTech), RiboGreen® kit (Life Technologies), lipids (Avanti Lipids), ACK lysis buffer (Sigma), isoflurane (MIT DCM Pharmacy), Balb/c mice (The Jackson laboratory), NOD.SCID mice (The Jackson laboratory), mouse facility charges (Koch Institute), pipette tips, buffers, syringes, needles, other basic reagents and supplies (VWR, Fisher, Westnet).

Equipment

Elutrap electroelution system (Whatmann), Qubit® 3.0 Fluorometer (Life Technologies), C18 HPLC column (Transgenomic), AKTA pure (GE Healthcare), Agilent 2100 Bioanalyzer, ELISpot reader (Zeiss)

Small molecule-inducible RNA replicon translational "ON switch"

Respiratory Syncytial Virus (RSV) Vaccination

Replicons have recently received attention as vaccine delivery vectors. Replicons can produce large quantities of an antigen with sustained expression over many weeks. Additionally, replicons have inherent adjuvant-like properties, stemming from their viral origin. However, constitutive expression of an antigen is often not enough to mount a sustained immune response. Most vaccination strategies require prime-boosting, or delivery of two different doses of antigen usually separated by several weeks. Prime-boosting results in increased humoral and cell-mediated immunity compared to a single dose of an antigen. Because replicons have been shown to persist up to seven weeks in vivo, replicon-encoded circuits may be used to create a single injection prime-boost vaccination platform. Such a platform would be extremely beneficial in areas of the world where it is difficult to make repeat visits to a clinic. Instead of receiving a second injection, the antigen could be regulated by a small molecule, taken orally by the patient at the correct time.

As previously mentioned, the optimal prime-boost circuit would be an ON switch, requiring two doses of a small molecule to turn on antigen production during the prime and boost phases. However, as we have shown, replicon-based ON switches are more complex and require multiple regulatory elements. On the other hand, OFF switches require only one DD-fused repressor, as shown in FIG. 65. In this circuit, the luciferase reporter, Fluc, is expressed in the absence of small molecule. This simpler OFF circuit would require patients to take the small molecule for an extended duration in between the prime and boost phases, but is an ample proof of concept as we plan to move in vivo. To this end, optimal configurations of this circuit are screened in myotubes differentiated from C2C12 mouse myoblasts. SGP strength and K-turn number are tested. How fold change is affected by the presence of vaccinia virus E3, a viral inhibitor of the protein kinase R (PKR) response is examined. The most promising configuration is then be packaged into lipid nanoparticles (LNPs) and tested in vivo. The LNPs are injected into the gastrocnemius muscles of Balb/c mice and TMP is added or removed via the drinking water. If adequate fold changes in luciferase are observed, RSV F antigen is substituted into the circuit, and the immune response is determined by measuring serum Ab titers and specific T cell activation levels.

An RNA replicon-encoded small molecule regulatable "ON switch" which functions robustly when injected i.m. into mice is developed. An RNA replicon is created with tandem SGPs expressing a TetR fusion protein (TetR-RE; RE=repression enhancer, to be identified using the screen described below) from the first SGP and a Fluc reporter whose translation can be controlled by binding of TetR-RE to TetR aptamers (TetR-Apt) from the second SGP in the following manner:

SGP1(15)TetR-RE SGP2($X$)NxTetR-Apt Fluc (RE=member of Table RE;$X$=5,15,30;$N$=2,3,4)

(+Doxycycline[Dox]:No TetR-RE binding to Apt Fluc ON;

−Dox:TetR-RE binding to Apt Fluc OFF)    Circuit 3

RNA (1 or 6 ug) for the optimal Circuit 3 (optimized as described below) is injected bilaterally into the gastrocnemius muscles of Balb/c mice. The mice injected with Circuit 3 receive either Dox or do not receive Dox in the drinking water and Fluc expression is monitored by BLI for two weeks. As a negative control, RNA identical to Circuit 3 except with TetR-RE replaced by a mock repressor (mVenus-RE) that does not bind TetR-Apt is injected into a different group of mice. Experimental groups are summarized in FIG. 66.

The optimal Circuit 3 to be tested in the in vivo experiment in FIG. 66 is determined by performing a fluorescence activated cell sorting (FACS)/next generation RNA sequencing (RNA-Seq)-based in vitro screen to identify a potent TetR-RE and an optimal circuit configuration. To this end, we assemble a library of circuits with each containing a unique "configuration barcodes" to facilitate subsequent identification (total theoretical library size=57 [RE]×3 [SGP2 variants]×3 [TetR-Apt repeat variants]=513) in the following format using the MoClo method (each step being a "one-pot" assembly reaction):

SGP1(15)mVenus-2A-TetR-RE(configuration barcode)SGP2(λNxTetR-Apt mKate (RE=member of Table RE;$X$=5,15,30;$N$=2,3,4)

(+Doxycycline[Dox]:No TetR-RE binding to Apt Fluc ON;

−Dox:TetR-RE binding to Apt Fluc OFF)    Circuit 4

Candidate REs to be screened and their functions related to translational regulation are described in Table RE.

In order to enhance the throughput and reduce the cost of the screen, cloning, DNA preparation, and IVT is performed in batch (in one-pot reactions) for the entire library. The entire Circuit 4 library is then transfected into C2C12 myoblasts at a predetermined low transfection efficiency by e.p. to ensure that the majority of the transfected cells received one RNA circuit from the Circuit 4 library. The transfected cells are then divided into two: one group is cultured in media containing Dox and the other group without Dox. 24 h later, each group is separately processed by FACS. For either group, cells that are mVenus negative are not collected as those cells do not contain replicons from the Circuit 4 library. The mVenus positive cells are then be sorted into eight different bins by FACS based on their mKate expression levels using predetermined cell standards (e.g. negative cells, cells harboring SGP(5) mKate, SGP(15) mKate, SGP(30) mKate, etc.) as guides for partitioning of the experimental sample. The RNA from each bin (2 [+/−Dox]×8 [expression levels]=16 total bins) are then extracted and barcoded in batch (per bin). Subsequently, the barcoded samples are pooled and processed for RNA-Seq to read the configuration barcodes and determine the identities of TetR-RE, SGP2(x), NxTetR-Apt, and the mKate expression level bin that the replicon originated from (each mKate expression level bin is assigned an intensity score of 1-8). For each unique replicon, the geometric mean of the associated mKate intensity scores are calculated (separately for +Dox and −Dox conditions). The strategy of this screen is summarized in FIG. 62.

Members of the library with the largest differences in the geometic means of the mKate scores under the two conditions (+/−Dox) are tested for follow-up transfection and evaluation in differentiated C2C12 myotubes. Promising TetR-RE and circuit configurations identified from the Circuit 4 library are used to construct Circuit 3 replicons for testing in vivo as described in FIG. 66.

We discovered that enhancers of general translation such as protein kinase R (PKR) inhibitors can increase the dynamic range of small molecule-based regulation of replicon circuits in C2C12 myotubes. Therefore, to further improve the performance of the best performing member of the Circuit 4 library, a screen to identify general translation enhancers (GTEs) including but not limited to IFN response antagonist proteins that may further boost the performance of the optimal member of the Circuit 4 library when expressed from an internal ribosomal entry site (IRES) sequence is performed. Since it has been shown that certain IRES sequences may be more resistant to PKR-induced translational inhibition than others, we first identify the optimal IRES sequence to use for cap-independent expression from VEE replicons. To this end, we test the ability of known viral and synthetic IRES sequences (benchmarked against the EMCV IRES) to drive the expression of a Fluc reporter protein. Furthermore, we determine whether the magnitude of the intracellular antiviral innate immune response triggered by each IRES sequence is different by looking at the expression of IFN-0, PKR, and IL-6 by quantitative reverse-transcription PCR (qRT-PCR). Various IRES sequences (28 total) are tested in the following format initially in myotubes and then in vivo in mice for promising candidates (FIG. 67):

SGP1(15)TetR SGP2(30)2×TetR-Apt mKate IRES Fluc (IRES=member of Table IRES)   Circuit 5

IRES candidates to be screened and their origins are described in Table IRES.

Once an optimal IRES sequence is determined above (Circuit 5), that IRES is used to express candidate GTEs to enhance the performance of Circuit 4. To this end, a library of circuits (216 total) is constructed in the following format and screen by FACS/RNA-seq as described below:

SGP1(15)mVenus SGP2(30)2×TetR-Apt mKate IRES GTE (GTE=member of Table GTE)   Circuit 6

Candidate GTEs to be used in this screen and their biological functions are described in Table GTE.

The workflow of this screen is similar to that of the screen for Circuit 4 in FIG. 62. Cloning, DNA preparation, IVT, and transfection into C2C12 cells for the GTE screen is performed in batch for the entire Circuit 6 library. The transfected (mVenus/mKate double positive) cells is sorted into eight different bins (or more bins if mVenus/mKate 2D sorting is to be performed) by FACS, the RNA is extracted, barcoded, sequenced and individual replicons are scored based on their mKate expression levels as described above. Alternatively, to identify potential synergistic GTE combinations, single cells from the most highly expressed bin (Bin 8) are cultured and GTEs being co-expressed in those cells are identified by RNA extraction, barcoding and sequencing. The strategy of this screen is summarized in FIG. 68.

Replicons of the Circuit 6 library containing the top GTE candidates (i.e. with the highest mKate scores) are evaluated further in C2C12 myotubes. The most promising GTEs are subsequently expressed from an IRES off of the best Circuit 4 replicon and tested for improved circuit performance in C2C12 myotubes. Secreted GTEs that are expected to have paracrine effects are not included in the FACS screen above but are individually cloned and tested directly in myotubes. Once improvement is confirmed, the specific circuit configuration is used to build a replicon in the Circuit 3 format for in vivo testing as described in FIG. 66.

A library of replicons(216 total) is constructed in the following format:

SGP1(15)mVenus-2A-TetR-RE SGP2(x)NxTetR-Apt mKate IRES GTE ($X$=5,15,30;$N$=2,3,4;GTE=member of Table GTE)   Circuit 7

The workflow of this screen is similar to that of the screen for Circuit 4 in FIG. 62: cloning, DNA preparation, IVT, and transfection into C2C12 cells for the screen are performed in batch for the entire Circuit 7 library. The transfected (mVenus positive) cells for each condition (+/−Dox) are separately sorted into eight different bins by FACS based on their mKate expression levels. The RNA for each condition/bin is extracted, barcoded, sequenced and individual replicons are scored based on their mKate expression levels for each condition as described above. The strategy of this screen is summarized in FIG. 69.

Members of the Circuit 7 library with the largest differences in the mKate scores under the two conditions (+/−Dox) are tested for follow-up transfection/evaluation in differentiated C2C12 myotubes. Promising circuit configurations identified from the Circuit 7 library are used to construct Circuit 3 replicons tested in vivo as described in FIG. 66.

Circuit optimization screens are found in FIGS. 73-76.

TABLE RE

RE protein candidates to screen to identify enhancers of TetR-mediated translational repression.

| | Origin | RE candidate | Function in translational regulation |
|---|---|---|---|
| 1 | African swine fever virus (ASFV) | g5R | m7G decapping |
| 2 | Coxsackievirus B3 (CVB3) | 2A protease | eIF4G cleavage |
| 3 | CVB3 | 3C protease | Cleavage of eIF5B |
| 4 | Encephalomyocarditis virus (EMCV) | 2A protein (without NLS) | Binds eIF4E |
| 5 | EMCV | 3C protease | Dephosphorylation of eIF4E and 4E-BP1 |
| 6 | Feline calicivirus (FCV) | 3C-like protease | PABP cleavage |
| 7 | Foot-and-mouth disease virus (FMDV) | 3C protease | eIF4A, PABP cleavage |
| 8 | FMDV | L protease | eIF4G cleavage |
| 9 | Group A rotavirus (RVA) | NSP3 | Competes with Pab1p for eIF4G binding |
| 10 | Hantavirus (HV) | N | Endonuclease that cleaves RNA |
| 11 | Human adenovirus 5 (Ad5) | 100K | Binds eIF4G and prevents Mnk1 recruitment/phosphorylation of eIF4E |

TABLE RE-continued

RE protein candidates to screen to identify enhancers of TetR-mediated translational repression.

| | Origin | RE candidate | Function in translational regulation |
|---|---|---|---|
| 12 | Human immunodeficiency virus 1 (HIV-1) | Protease | eIF4G, PABP cleavage |
| 13 | HIV-1 | Protease | Cleavage of eIF4GI |
| 14 | Human rhinovirus (HRV) | 2A protease | eIF4G cleavage |
| 15 | HRV | 3C protease | Cleavage of eIF5B |
| 16 | Human herpesvirus 1 (HSV) | vhs | mRNA degradation |
| 17 | Human T-cell leukemia virus (HTLV-1) | Protease | Cleavage of eIF4GI |
| 18 | Influenza A virus (FluAv) | Pol | Binds m7G cap and cleaves RNA |
| 19 | Human herpesvirus 8 (KSHV) | SOX | RNA cleavage |
| 20 | MD145-12 | 3C-like protease | PABP cleavage |
| 21 | Measles virus (MV) | N | Interacts with eIF3 and blocks translation |
| 22 | Poliovirus (PV) | 2A protease | eIF4G cleavage |
| 23 | PV | 3C protease | Cleavage of eIF5B, dephosphorylation of eIF4E and 4E-BP1 |
| 24 | Moloney murine leukemia virus (MMLV) | Protease 3C | Cleavage of eIF4GI and eIF4GII |
| 25 | Rabies virus (RV) | M | Interacts with eIF3 and blocks translation |
| 26 | SARS-CoV (SARS-CoV) | Nsp1 | Binds 40S ribosomal subunit and degrades RNA |
| 27 | SARS-CoV | S | Inhibits eIF3f |
| 28 | SARS-CoV | Spike | Interacts with eIF3 and blocks translation |
| 29 | Simian virus 40 (SV40) | Small T antigen | 4E-BP1 dephosphorylation |
| 30 | Vaccinia virus (VV) | D10 | m7G decapping |
| 31 | VV | D9 | m7G decapping |
| 32 | Mouse | 4E-BP1 (constitutive active) | Binds eIF4E and blocks initiation |
| 33 | Mouse | 4E-BP2 (constitutive active) | Binds eIF4E and blocks initiation |
| 34 | Mouse | 4E-BP3 (constitutive active) | Binds eIF4E and blocks initiation |
| 35 | Mouse | 4EHP | Competes with eIF4E for cap binding |
| 36 | Mouse | Ago1 | Component of the RNA-induced silencing complex |
| 37 | Mouse | Ago2 | Component of the RNA-induced silencing complex |
| 38 | Mouse | Ago3 | Component of the RNA-induced silencing complex |
| 39 | Mouse | Ago4 | Component of the RNA-induced silencing complex |
| 40 | Mouse | CPEB2 | Stalls elongation (can be recruited to 5' and/or 3') |
| 41 | Mouse | DDX6 | CNOT complex interaction, P-body component |
| 42 | Mouse | eIF4E | Dominant negative (cap binding only) |
| 43 | Mouse | eIF4E (S2094) | Dominant negative (cap binding only) |
| 44 | Mouse | eIF4E (S209D) | Dominant negative (cap binding only) |
| 45 | Mouse | eIF4E (S209E) | Dominant negative (cap binding only) |
| 46 | Mouse | eIF4G (N-term) | Dominant negative (eIF4E interaction only) |
| 47 | Mouse | FMRP | Stalls elongation (can be recruited to 5' and/or 3') |
| 48 | Mouse | GW182 | CNOT complex recruitment |
| 49 | Mouse | p54 | ISG that inhibits eIF3 activity |
| 50 | Mouse | p56 | ISG that inhibits eIF3 activity |
| 51 | Mouse | p60 | ISG that inhibits eIF3 activity |

TABLE RE-continued

RE protein candidates to screen to identify enhancers of TetR-mediated translational repression.

| | Origin | RE candidate | Function in translational regulation |
|---|---|---|---|
| 52 | Mouse | PABP (eIF4G binding domain) | Dominant negative PABP |
| 53 | Mouse | PDCD4 | Blocks eIF4A interaction with eIF4G |
| 54 | Mouse | RNase L (NΔ385: constitutive active) | |
| 55 | Mouse | Upf1 (constitutive active) | RNA degradation |
| 56 | Mouse | Me31B | CNOT complex interaction, P-body component |
| 57 | — | EBFP2 | None (negative control) |

TABLE IRES

IRES sequences for testing for optimal protein expression from an RNA replicon.

| | IRES viral family | IRES viral genus | IRES (viral) species | IRES group |
|---|---|---|---|---|
| 1 | Flaviviridae | Hepacivirus | Hepatitis C virus (HCV) | IRES Group II |
| 2 | Flaviviridae | Pestivirus | Bovine diarrhea virus (BVDV) | IRES Group II |
| 3 | Flaviviridae | Pestivirus | Classical swine fever virus (CSFV) | IRES Group II |
| 4 | Flaviviridae | Pegivirus | Hepatitis GB virus B (GBV-B) | IRES Group II |
| 5 | Flaviviridae | Pegivirus | Hepatitis GB virus A (GBV-A) | (Uncategorized) |
| 6 | Flaviviridae | Pegivirus | Hepatitis GB virus C (GBV-C) | (Uncategorized) |
| 7 | Picornaviridae | Tremovirus | Avian Encephalomyelitis Virus (AEV) | IRES Group II |
| 8 | Picornaviridae | Cardiovirus | EMCV | IRES Group III |
| 9 | Picornaviridae | Cardiovirus | Theiler's Murine Encephalomyelitis Virus (TMEV) | IRES Group III |
| 10 | Picornaviridae | Aphthovirus | FMDV | IRES Group III |
| 11 | Picornaviridae | Aphthovirus | Equine rhinitis A virus (ERAV) | IRES Group III |
| 12 | Picornaviridae | Erbovirus | Equine rhinitis B virus (ERBV) | IRES Group III |
| 13 | Picornaviridae | Enterovirus | PV | IRES Group IV |
| 14 | Picornaviridae | Enterovirus | CVB3 | IRES Group IV |
| 15 | Picornaviridae | Enterovirus | Human enterovirus 71 (EV71) | IRES Group IV |
| 16 | Picornaviridae | Enterovirus | Human rhinovirus-2 (HRV-2) | IRES Group IV |
| 17 | Picornaviridae | Hepatovirus | Hepatitis A virus (HAV) | IRES Group IV |
| 18 | Potyviridae | Potyvirus | Tobacco etch virus (TEV) | (Uncategorized) |
| 19 | Polyomaviridae | Polyomavirus | SV40 | (Uncategorized) |
| 20 | Retroviridae | Alpharetrovirus | Rous sarcoma virus | (Uncategorized) |
| 21 | Retroviridae | Betaretrovirus | Mouse mammary tumor virus (MMTV) | (Uncategorized) |
| 22 | Retroviridae | Gammaretrovirus | Murine leukemia virus (MLV) | (Uncategorized) |
| 23 | Retroviridae | Gammaretrovirus | Feline leukemia virus (FLV) | (Uncategorized) |
| 24 | Retroviridae | Gammaretrovirus | Avian reticuloendotheliosis virus type A (REV-A) | (Uncategorized) |
| 25 | Retroviridae | Deltaretrovirus | HTLV-4 | (Uncategorized) |
| 26 | Retroviridae | Lentivirus | HIV-1 | (Uncategorized) |
| 27 | — | — | *Homo sapiens* c-Src | (Cellular IRES) |
| 28 | — | — | $(Gtx_{133-141})_{10}(SI)_9\beta$ | (Synthetic IRES) |

TABLE GTE

GTE protein candidates for screening to identify enhancers of translation in myoblasts which may improve TetR-mediated translational repression.

| | Origin | GTE candidate | Cellular target | Function in translational |
|---|---|---|---|---|
| 1 | Guanarito virus (GTOV) | Z | RIG-I | Binds RIG-I; prevents association with MAVS |
| 2 | Junin virus (JUNV) | NP | IFN induction (general) | Prevents IRF3 translocation or upstream event |
| 3 | JUNV | Z | RIG-I | Binds RIG-I; prevents association with MAVS |
| 4 | Lymphocytic choriomeningitis virus (LCMV) | NP | IFN induction (general) | Prevents IRF3 translocation or upstream event |
| 5 | Lassa virus (LV) | NP | IFN induction (general) | Prevents IRF3 translocation or upstream event |
| 6 | Machupo virus (MACV) | NP | IFN induction (general) | Prevents IRF3 translocation or upstream event |
| 7 | MACV | Z | RIG-I | Binds RIG-I and prevents association with MAVS |
| 8 | Pichinde virus (PINV) | NP | IFN induction (general) | Prevents IRF3 translocation or upstream event |
| 9 | Sabia virus (SABV) | Z | RIG-I | Binds RIG-I and prevents association with MAVS |
| 10 | Whitewater Arroyo virus (WWAV) | NP | IFN induction (general) | Prevents IRF3 translocation or upstream event |
| 11 | Borna disease virus (BDV) | P | TBK1 | Inhibition of TBK1 activity (possible decay substrate) |
| 12 | Andes virus (ANDV) | M | STAT1, STAT2 | Not determined |
| 13 | ANDV | Gn | TRAF3 | Binds TRAF3; prevents interaction with TBK1 |
| 14 | Crimean-Congo hemorrhagic fever virus (CCHFV) | L (OTU) | ISG15 | Catalytic deconjugation from targets |
| 15 | La Crosse virus (LAV) (LACV) | NSs | IFN induction (general) | Not determined |
| 16 | Prospect Hill virus (PHV) | M | STAT1, STAT2 | STAT phosphorylation and translocation |
| 17 | Punta Toro virus (PTV) | NSs | IFN induction (general) | Not determined |
| 18 | Ebola virus (EBOV) | VP24 | STAT1 | Binds karyopherin α1/5/6; prevents STAT1 translocation |
| 19 | EBOV | VP35 | dsRNA, IKKε, PKR, IRF7 | dsRNA binding; functions proximal of IRF3; binds IKKε and inhibits function; prevents PKR activation; prevents PACT activation; binds and mediates SUMOylation |
| 20 | Marburgvirus (MARV) | VP40 | JAK1 | Prevents phosphorylation of JAK1 |
| 21 | FluAV | NS1 | PKR, OAS, mRNA processing and transport, mRNA export, TRIM25, JAK-STAT pathway | Binding dsRNA; PKR inhibition; PACT inhibition; binding prevents activation of OAS; binds CPSF30 and PABII; binds mRNA export machinery; binding prevents RIG-I ubiquitination; sOCS-1 and -3 upregulation |
| 22 | Influenza B virus (FluBV) | NS1 | PKR, ISG15, IFN transcription | Binding dsRNA-PKR complex; sequesters human ISG15; inhibits RIG-I signaling |
| 23 | Bovine parinfluenzavirus 3 (bPIV3) | V | MDA5 | Not determined |
| 24 | Bovine repiratory syncytial virus (bRSV) | NS1 | TRAF3/IKKε | Reduces protein levels |
| 25 | bRSV | NS2 | TRAF3 | Reduces protein levels |
| 26 | Hendra virus (HendraV) | V | STAT1, STAT2, MDA5 | Change sub-cellular localization by complex formation; prevents MDA5 homodimerization |
| 27 | Human metapneumovirus (hMPV) | G | RIG-I | Binds RIG-I and inhibits activation |

TABLE GTE-continued

GTE protein candidates for screening to identify enhancers of translation in myoblasts which may improve TetR-mediated translational repression.

| | Origin | GTE candidate | Cellular target | Function in translational |
|---|---|---|---|---|
| 28 | Human parainfluenza virus 2 (hPIV2) | V | STAT1, MDA5 | Prevents phosphorylation |
| 29 | Menangle virus (MENV) | V | MDA5 | Prevents MDA5 homodimerization |
| 30 | Mapuera virus (MPRV) | V | ISGF3, MDA5 | Inhibits ISGF3 formation; prevents MDA5 homodimerization |
| 31 | Mumps virus (MuV) | V | STAT1, STAT1, STAT3, MDA5 | Formation of V/RACK-1/STAT1 complex; proteasomal degradation |
| 32 | MV | C | IFN induction (general), JAK-STAT pathway | Complex formation IFNAR1; RACK1 and STAT1 |
| 33 | MV | P | JAK-STAT pathway | STAT1 phosphorylation and cytoplasmic retention |
| 34 | MV | V | MDA5, STAT1, STAT2, JAK-STAT pathway | Cytoplasmic sequestering and inhibition phosphorylation; complex formation IFNAR1; RACK1 and STAT1 |
| 35 | Nipah virus (NipahV) | P | STAT1 | Cytoplasmic sequestering |
| 36 | NipahV | V | STAT1 | Cytoplasmic sequestering |
| 37 | NipahV | W | STAT1 | Nuclear sequestering |
| 38 | Rinder pest virus (RPV) | C | IFN induction (general) | Not determined |
| 39 | RPV | P | STAT1, STAT2 | Not determined |
| 40 | RPV | V | STAT1, STAT2 | Not determined |
| 41 | Salem virus (SALV) | V | MDA5 | Prevents MDA5 homodimerization |
| 42 | Sendai virus (SeV) | C | IFN induction (general), STAT1, STAT2, STAT1 | Prevents IRF3 phosphorylation (or earlier); proteasomal degradation; complex formation |
| 43 | SeV | V | IFN induction (general) | Prevents IRF3 phosphorylation (or earlier) |
| 44 | SeV | V | MDA5 | Prevents MDA5 homodimerization |
| 45 | SeV | Y1 | IFN induction (general) | Prevents IRF3 phosphorylation (or earlier) |
| 46 | SeV | Y2 | IFN induction (general), JAK-STAT pathway | Prevents IRF3 phosphorylation (or earlier) |
| 47 | Simian parainfluenza virus 5 (SV5) | P | IFN induction (general) | Prevents IRF3 dimerization (or earlier) |
| 48 | SV5 | V | IFN induction (general), STAT1, MDA5 | Prevents IRF3 translocation (or earlier); proteasomal degradation; prevents MDA5 homodimerization |
| 49 | RV | N | IFN induction (general) | Not determined |
| 50 | RV | P | STAT1, IRF3, PML | Prevents nuclear STAT1 accumulation and DNA binding; interferes with TBK1 activity; binds to PML; retains it in the cytoplasm |
| 51 | Equine arteritis virus (EAV) | Nsp2 | ISG15 | Catalytic deconjugation from targets |
| 52 | Porcine reproductive and respiratory syndrome virus (PRRSV) | Nsp1a | IFN induction (general) | Not determined |
| 53 | PRRSV | Nsp1b | IFN induction (general), JAK-STAT pathway | Interference with MAVS |
| 54 | PRRSV | nsP11 | RLR evasion | Ribonuclease |
| 55 | Murine hepatitis virus (MHV) | N | IFN induction (general), RNaseL | Not determined |
| 56 | MHV | ns2 | OAS | 2',5'-phosphodiesterase |
| 57 | MHV | Nsp3 (Plpro) | IRF3 | Deubiquitinates IRF3 and prevents activation |

TABLE GTE-continued

GTE protein candidates for screening to identify enhancers of translation in myoblasts which may improve TetR-mediated translational repression.

| | Origin | GTE candidate | Cellular target | Function in translational |
|---|---|---|---|---|
| 58 | Middle east respiratory syndrome coronavirus (MERS-CoV) | ORF-4a | RIG-I/MDA5 signaling | PACT inhibition |
| 59 | MERS-CoV | ORF-4b | IFN induction | Not determined |
| 60 | MERS-CoV | Papain-like protein (PLP) | ISG15 | DeISGylation |
| 61 | SARS-CoV | M | TBK1/IKKε | Sequesters TRAF3/TANK/TBK1/IKKε |
| 62 | SARS-CoV | N | IFN induction (general) | Prevents activity; prevents RIG-I, MDA5 activation; possibly masks dsRNA |
| 63 | SARS-CoV | nsP3 (Plpro) | IFN induction (general), ISG15, IRF3 | Deconjugation of ISG15 from targets; binding to IRF3; prevents STING, RLR-mediated activation of MAVS; TRAF3; prevents STAT1 signaling |
| 64 | SARS-CoV | nsP14 | RLR evasion | 3' to 5' exonuclease |
| 65 | SARS-CoV | ORF3a | IFNAR1 | Degradation |
| 66 | SARS-CoV | ORF3b | IFN induction (general) | Possibly prevents RLR mediated MAVS signaling |
| 67 | SARS-CoV | ORF6 | STAT1 | Prevents STAT1 nuclear import (karyopherin α2 binding); possibly prevents RLR mediated MAVS signaling |
| 68 | BVDV | Erns | dsRNA | dsRNA binding and cleavage |
| 69 | BVDV | Npro | IRF3 | Proteasomal degradation |
| 70 | CSFV | Erns | IFN induction (general) | dsRNA binding |
| 71 | CSFV | Npro | IRF3, IκBα | Proteasomal degradation; binds |
| 72 | Dengue virus (DENV) | NS5 (proteolytically-processed) | STAT2 | Proteasomal degradation; binds and prevents phosphorylation/degradation |
| 73 | DENV | NS2A | STAT1 | Prevents translocation |
| 74 | DENV | NS2B/3 protease | STING, IRF3 | Cleaves STING, prevents translocation of IRF3 |
| 75 | DENV | NS4A | STAT1 | Prevents translocation |
| 76 | DENV | NS4B | STAT1 | Not determined |
| 77 | GBV-B | NS3/4a | MAVS | Cleavage |
| 78 | HCV | Core | JAK-STAT pathway | SOCS-3 activation; prevents IRF3 activation; inhibits STAT1 activation |
| 79 | HCV | E2 | PKR | PKR binding |
| 80 | HCV | NS2 | IRF3 | Prevents IRF3 activation |
| 81 | HCV | NS3 | TBK1 | Binding to TBK1 prevents association with IRF3 |
| 82 | HCV | NS3/4A | MAVS, TRIF | Cleavage |
| 83 | HCV | NS4B | JAK-STAT pathway | Inhibits signaling through STING |
| 84 | HCV | NS5A | IRF1, PKR, RNaseL, IFN induction (general), TLR signalling, STAT1 | IL-8 induction; Karyopherin β3; myD88 binding prevents IRAK1 association; binding prevents phosphorylation |
| 85 | Japanese encephalitis virus (JEV) | E | JAK-STAT pathway | Not determined |
| 86 | JEV | NS2A | PKR | Binds PKR and blocks activation |
| 87 | JEV | NS4A | DDX42/IFN signaling | Interaction with DDX42 |
| 88 | JEV | NS5 | STAT1, TYK2 | Activates phosphatase and prevents phosphorylation |
| 89 | Langat virus (LGTV) | NS5 | JAK1, TYK2 | Complex formation IFNAR1; complex formation IFNAR1 |
| 90 | Tick-borne encephalitis virus (TBEV) | NS5 | JAK-STAT pathway | Binds PDZ protein scribble and blocks STAT1 phosphorylation |
| 91 | West Nile virus (WNV) | NS1 | IRF3, NF-κB | Inhibits translocation |
| 92 | WNV | NS2A | JAK1, TYK2 | Prevents phosphorylation |
| 93 | WNV | NS2B | JAK1, TYK2 | Prevents phosphorylation |
| 94 | WNV | NS3 | JAK1, TYK2 | Prevents phosphorylation |
| 95 | WNV | NS4A | JAK1, TYK2 | Prevents phosphorylation |
| 96 | WNV | NS4B | JAK1, TYK2 | Prevents phosphorylation |

TABLE GTE-continued

GTE protein candidates for screening to identify enhancers of translation in myoblasts which may improve TetR-mediated translational repression.

| | Origin | GTE candidate | Cellular target | Function in translational |
|---|---|---|---|---|
| 97 | WNV | NS5 | JAK-STAT pathway | Not determined |
| 98 | Yellow fever virus (YFV) | NS4B | STING | Cleavage |
| 99 | ECMV | Leader protein | IRF3 | Prevents dimerization |
| 100 | Hepatitis A virus (HAV) | 3ABC precursor | MAVS | Protealytic cleavage |
| 101 | Human rhinovirus (HRV) | 2A | MAVS | Cleavage |
| 102 | HRV | 3C protease | MAVS | Cleavage |
| 103 | PV | RNaseL ciRNA (3C) | RNaseL | Competetively inhibits RNaseL |
| 104 | TMEV | Leader protein | IRF3 | Nucleo-cytoplasmic trafficking |
| 105 | Human adenovirus 5 (Ad5) | E1A | CBP/p300, STAT1 | Association cellular CBP/p300; binding STAT1; prevents phosphorylation (or earlier) |
| 106 | Ad5 | E4-ORF1 | PI3K | Activation |
| 107 | Ad5 | E4 ORF3 | JAK-STAT pathway, PML/Daxx | Redistrubution NBs; disruption nuclear bodies |
| 108 | Ad5 | E4-ORF4 | mTORC1 | Activation |
| 109 | Ad5 | VAI RNA | PKR, ADAR | Binding |
| 110 | ASFV | A238L | IκB | Competitive non-functional IκB homologue |
| 111 | ASFV | DP17L | eIF2α | Dephosphorylation by PP2A recruitment |
| 112 | A. californica multiply-embedded nuclear polyhedrosis virus (AcMNPV) | PK2 | PKR | Inhibition of PKR action |
| 113 | Bovine herpes virus 1 (BoHV-1) | ICP0 | IRF7, IRF3 | Binds and prevents trans-activation of promoter; mediates proteasomal degradation |
| 114 | Epstein-Barr virus (EBV) | BZLF-1 | IFN transcription | Not determined |
| 115 | EBV | EBER-1 RNA | PKR | Binding |
| 116 | EBV | EBER-2 RNA | PKR | Binding |
| 117 | EBV | LF2 | IRF7 | Binding prevents dimerization |
| 118 | EBV | LMP-1 | TYK2, STAT2 | Prevents phosphorylation; prevents phosphorylation |
| 119 | EBV | LMP2A | mTORC1 | Upregulation of mTORC1 signaling |
| 120 | EBV | SM | PKR | dsRNA binding; PKR binding |
| 121 | Human cytomegalovirus (HCMV) | IE1 | disassemble NBs, STAT2 | Alter SUMO-1 modification; sequestration of STAT2 |
| 122 | HCMV | IRS1 | PKR | Binds dsRNA and prevents PKR activation |
| 123 | HCMV | IE86 | NF-κB | Prevents NF-κB mediated transcription |
| 124 | HCMV | M27 | STAT2 | Not determined |
| 125 | HCMV | TRS1 | PKR | Binds dsRNA and prevents PKR activation |
| 126 | HCMV | UL38 | TSC2/mTORC1 | TSC2 inactivation and downstream mTORC1 activation |
| 127 | HCMV | UL69 | eIF4E | Binds eIF4A/PABP and releases 4E-BP1 from eIF4E |
| 128 | Human herpesvirus 6 (HHV-6) | 1E1 | IRF3 | Prevents IFN promoter binding |
| 129 | HSV | γ34.5 protein | eIF2α | Binds GADD34 (MyD116), recuits protein phosphatase 1 (PP1) and prevents phosphorylation |
| 130 | HSV | gB | PERK | Binding |
| 131 | HSV | ICP0 | IRF3 translocation, PML, disassemble NBs | Recruitment IRF3 and CBP/p300 to nuclear structures; proteasomal degradation PML; alter SUMO-1 modification |
| 132 | HSV | ICP6 | eIF4E | Facilitates eIF4E/eIF4G interaction during stress |

TABLE GTE-continued

GTE protein candidates for screening to identify enhancers of translation in myoblasts which may improve TetR-mediated translational repression.

| | Origin | GTE candidate | Cellular target | Function in translational |
|---|---|---|---|---|
| 133 | HSV | ICP27 | mRNA synthesis and splicing, JAK-STAT pathway | ICP27 induces soluble inhibitor of signaling |
| 134 | HSV | UL13 | JAK-STAT pathway | SOCS3 upregulation |
| 135 | HSV | UL41 | JAK-STAT pathway | SOCS3 upregulation |
| 136 | HSV | US3 | Akt substrates | Ser/thr kinase (Akt mimic) phorphoryaltes Akt substrates |
| 137 | HSV | US11 | PKR, 2'5'-OAS | dsRNA binding |
| 138 | Human herpesvirus 8 (KSHV) | ORF45 | IRF7 | Prevents phosphorylation |
| 139 | KSHV | RIF (ORF 10) | IFNAR/JAK1/TYK2/STAT2 | Sequesters signaling molecules in complex |
| 140 | KSHV | vGPCR | mTORC1 | Upregulation of mTORC1 signaling |
| 141 | KSHV | vIL-6 | TYK-2 | Activation cellular gp130 reduces phosphorylation |
| 142 | KSHV | vIRF1 (K9) | IRF1 mediated IFN transcription, p300 | Interference w/ cellular IRFs; Association cellular CBP/p300 |
| 143 | KSHV | vIRF2 | IRF1/2/3 reg. transcription, IRF3, p300, PKR | Interference w/ cellular IRFs; enhances caspase-3 mediated inactivation; association cellular CBP/p300; binding to PKR |
| 144 | KSHV | vIRF3 | IRF3, IRF5, IRF7 | Associates with IRFs and prevents DNA binding |
| 145 | KSHV | LANA2 | eIF2α | Inhibits eIF2α phosphorylation |
| 146 | Human herpesvirus 3 (Varicella-Zoster) (VZV) | IE63 | eIF2α (or earlier) | Prevents phosphorylation |
| 147 | VZV | ORF66 prot | JAK-STAT (or earlier) | Not determined |
| 148 | Human papilloma virus 16 (HPV-16) | E6 | IRF3 activation, STAT1, STAT2, TYK2, eIF2α | Binding to IRF3; binding/prevent phosphorylation; dephosphorylation |
| 149 | HPV-16 | E7 | IRF1 | Binding to IRF1 prevents association with IFNb promoter |
| 150 | Merkel cell polyomavirus (MCPyV) | Small T antigen | mTORC1 | Activation |
| 151 | Murine polyomavirus (MPyV) | Large T antigen | JAK1 | Binding |
| 152 | Monkeypox virus (MPXV) | B16 | Secreted IFN α/β | Soluble receptor decoy |
| 153 | Myxoma virus (MYXV) | M-T5 | Akt | Activation |
| 154 | Variola virus (VARV) | B17 | Secreted IFN α/β | Soluble receptor decoy |
| 155 | VARV | H1 | STAT1 | Dephosphorylation STAT1 |
| 156 | VV | A46R | TRIF | Decoy MyD88 and TRIF-like adaptors |
| 157 | VV | A46R | MyD88 | Decoy MyD88 and TRIF-like adaptors |
| 158 | VV | A52R | MyD88 | Decoy MyD88 and TRIF-like adaptors |
| 159 | VV | B18R | Secreted IFNα/β | Soluble receptor decoy |
| 160 | VV | B8R | Secreted IFNγ | Soluble receptor decoy |
| 161 | VV | BRLF1 | IFN induction (general) | Not determined |
| 162 | VV | C7L | Anti-viral effectors | Not determined |
| 163 | VV | E3L | IFN induction (general), PKR, ISG15 | dsRNA binding; sequesters ISG15 |
| 164 | VV | H1 | STAT1 | Dephosphorylation STAT1 |
| 165 | VV | K1L | Anti-viral effectors | Not determined |
| 166 | VV | K3L | PKR | eIF2α decoy |
| 167 | VV | N1L | TBK1/IKK complex | Physical interaction with TBK1; iKKα/β/ε and TANK |
| 168 | VV | VH1 | STAT1 | VH1 phosphatase reverts STAT1 phosphorylation |

TABLE GTE-continued

GTE protein candidates for screening to identify enhancers of translation in myoblasts which may improve TetR-mediated translational repression.

| | Origin | GTE candidate | Cellular target | Function in translational |
|---|---|---|---|---|
| 169 | Yaba-like disease virus (YLDV) | Y136 | Type I and III IFN receptor sign. | Binding to type I and III IFNs |
| 170 | Hepatitis B virus (HBV) | C | IFN induction (general), MxA | IFN transcription (or earlier steps); interaction core with MxA promoter region |
| 171 | HBV | HBsAg/HBeAg | IFN induction (general) | Not determined |
| 172 | HBV | Polymerase | TBK1/IKKε complex, STAT1 | Interferes with IRF3 activation by TBK1/IKKε; binds STAT1 and blocks transcriptional activity |
| 173 | RVA | VP3 | OAS | 2',5'-phosphodiesterase |
| 174 | (Porcine rotavirus (pRotaV) | NSP1 | IRF3, IRF5, IRF7, NF-κB | Proteasomal degradation; proteasomal degradation; proteasomal degradation; proteasomal degradation of β-TrCP |
| 175 | pRotaV | NSP3 | PKR | dsRNA binding |
| 176 | Avian reovirus (ReoV) | M1, S2, L2 | IFN induction (general) | Not determined |
| 177 | ReoV | μ2 | IRF9 | Modulates interaction IRF9 and STATs |
| 178 | ReoV | σ3 | PKR | dsRNA binding |
| 179 | ReoV | σA | PKR | dsRNA binding |
| 180 | HIV-1 | Vif | APOBEC3G | Mediates APOBEC3G proteasomal degradation |
| 181 | HIV-1 | gp120 | TLR9 | Not determined |
| 182 | HIV-1 | TAR RNA | PKR | Not determined |
| 183 | HIV-1 | Tat | PKR | competition with eIF2α |
| 184 | HIV-1 | Vpr | IFN induction (general) | Not determined |
| 185 | HIV-1 | Vpu | IRF3 | Degradation |
| 186 | HTLV-1 | Tax | CBP/p300 | Binding competion with STAT-2 |
| 187 | Torque Teno virus (TTV) | ORF2 | NF-κB | Inhibits IκB degradation and physical interaction with IKKα and IKKβ |
| 188 | Mouse | USP18 | IFN signaling | DeISGylation |
| 189 | Mouse | TAR RNA binding protein (TRBP) | PKR | Inhibits PKR |
| 190 | Mouse | p58IPK | PKR | Prevents PKR dimerization/activation |
| 191 | Mouse | p67 | eIF2α | Inhibits phosphorylation |
| 192 | Mouse | Nucleophosmin | PKR | Binds PKR and inhibits eIF2α phosphorylation |
| 193 | Mouse | IDO1 | Not determined | Tryptophan-catabolizing enzyme |
| 194 | Mouse | APOBEC3A | Not determined | Cytidine deaminase |
| 195 | Mouse | SOCS-1 | JAK/STAT1 | Inhibition |
| 196 | Mouse | SOCS-3 | JAK/STAT1 | Inhibition |
| 197 | Mouse | Hsp27 | eIF4F | Facilitates eIF4F formation during stress |
| 198 | Mouse | Polyadenylate-binding protein-interacting protein 1 (Paip1) | PABP | Activation of translation |
| 199 | Mouse | Ligatin (eIF2D) | Met-tRNAi | GTP independent delivery of Met-tRNAi to P site of ribosome |
| 200 | Mouse | eIF2α (constitutive active) | eIF2α | Increased translation |
| 201 | Mouse | eIF2Bδ/ε (constitutive active) | eIF2Bδ/ε | Increased translation |
| 202 | Mouse | eIF4E (constitutive active) | eIF4E | Increased translation |
| 203 | Mouse | GADD34 + PP1 | eIF2α | eIF2α dephosphorylation |
| 204 | Mouse | CReP + PP1 | eIF2α | eIF2α dephosphorylation |
| 205 | Mouse | Siglec-G | RIG-I | Degradation |
| 206 | Mouse | PI3K | 4EBP, eIF4B | Phosphorylation |
| 207 | Mouse | Myr-Akt | 4EBP, eIF4B | Phosphorylation |

TABLE GTE-continued

GTE protein candidates for screening to identify enhancers of translation in myoblasts which may improve TetR-mediated translational repression.

| | Origin | GTE candidate | Cellular target | Function in translational |
|---|---|---|---|---|
| 208 | Mouse | mTOR | 4EBP, eIF4B | Phosphorylation |
| 209 | Mouse | Follistatin | 4EBP, eIF4B | Phosphorylation |
| 210 | Mouse | Dominant negative PKR | PKR | Inhibition |
| 211 | Mouse | Dominant negative RIG-I | RIG-I | Inhibition |
| 212 | Mouse | Dominant negative MDA5 | MDA5 | Inhibition |
| 213 | Mouse | Dominant negative TLR3 | TLR3 | Inhibition |
| 214 | Mouse | Dominant negative TLR7 | TLR7 | Inhibition |
| 215 | Mouse | Dominant negative TLR8 | TLR8 | Inhibition |
| 216 | — | EBFP2 | — | None (negative control) |

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A synthetic RNA circuit comprising
(a) a first RNA molecule comprising a 5' cap, at least one target site specific for a first microRNA molecule, a sequence encoding an RNA binding protein, and a poly(A) tail; and
(b) a second RNA molecule comprising a 5' cap, at least one target site specific for a second microRNA molecule, at least one RNA motif that is capable of being bound by the RNA binding protein in (a), a sequence encoding an output molecule, and a poly(A) tail,
wherein the first microRNA molecule and the second microRNA molecule are different, wherein the first microRNA molecule is a microRNA that is present in a first cell type such that it reduces expression of the first RNA molecule in the first cell type and the second microRNA molecule is a microRNA that is present in a second cell type such that it reduces expression of the second RNA molecule in the second cell type but does not reduce expression of the second RNA molecule in the first cell type or reduces expression of the second RNA molecule less in the first cell type compared to the second cell type, wherein the first cell type and the second cell type are different, wherein the RNA binding protein inhibits production of the output molecule when bound to the at least one RNA motif, and wherein the synthetic RNA circuit is capable of being expressed in a eukaryotic cell.

2. The synthetic RNA circuit of claim 1, wherein the output molecule is a protein.

3. The synthetic RNA circuit of claim 2, wherein the output molecule protein is a therapeutic protein, a cell death protein, a fluorescent protein, an antigen, a selection protein, or an immunomodulator.

4. The synthetic RNA circuit of claim 1, wherein the RNA binding protein comprises a L7Ae protein or a fusion protein of a MS2 protein and a protein that inhibits protein production.

5. The synthetic RNA circuit of claim 1, wherein the second RNA molecule is capable of expressing the output molecule in the first cell type.

6. The synthetic RNA circuit of claim 1, wherein the at least one first microRNA molecule is a microRNA that is expressed in a cancer cell, and the at least one second microRNA molecule is a microRNA that is not expressed or is expressed at a low level in a cancer cell compared to a non-cancer cell.

7. The synthetic RNA circuit of claim 1, further comprising a sequence encoding a Csy4 protein and a Csy4 recognition site.

8. The synthetic RNA circuit of claim 1, wherein the second RNA molecule further comprises a target site for a third microRNA molecule, a target site for a fourth microRNA molecule, or a target site for a fifth microRNA molecule.

9. The synthetic RNA circuit of claim 1, which is present in a cell that expresses the at least one first microRNA molecule but does not express the at least one second microRNA molecule.

10. The synthetic RNA circuit of claim 1, wherein the first microRNA molecule is miR21.

11. The synthetic RNA circuit of claim 1, wherein the eukaryotic cell is a mammalian cell.

12. A synthetic RNA circuit comprising:
(a) a first RNA molecule comprising a 5' cap, at least one first RNA motif, a sequence encoding a second RNA binding protein that is capable of binding to a second RNA motif and that is capable of inhibiting protein production, at least one target site specific for a first siRNA molecule or first microRNA molecule, and a poly(A) tail; and
(b) a second RNA molecule comprising a 5' cap, at least one second RNA motif that is capable of being bound by the second RNA binding protein, a sequence encoding a first RNA binding protein that is capable of binding to the first RNA motif and inhibiting protein production, at least one target site specific for a second siRNA molecule or second microRNA molecule, and a poly(A) tail, wherein the first siRNA molecule or first microRNA molecule and the second siRNA molecule or second microRNA molecule are different, and wherein the first RNA motif and the second RNA motif are different wherein the first RNA binding protein, upon binding to the first RNA motif, inhibits expression of the second RNA binding protein, and wherein the second RNA binding protein, upon binding to the second RNA motif, inhibits expression of the first RNA binding protein, and wherein the synthetic RNA circuit is capable of being expressed in a eukaryotic cell.

13. The synthetic RNA circuit of claim 12, wherein the first RNA molecule and/or the second RNA molecule further comprises a sequence encoding an output molecule.

14. The synthetic RNA circuit of claim 13, wherein the output molecule comprises a therapeutic protein, a cell death protein, a fluorescent protein, an antigen, a selection protein, or an immunomodulator.

15. The synthetic RNA circuit of claim 12, wherein the eukaryotic cell is a mammalian cell.

* * * * *